(12) United States Patent
Boissel et al.

(10) Patent No.: US 12,109,238 B2
(45) Date of Patent: *Oct. 8, 2024

(54) CHIMERIC ANTIGEN RECEPTOR-MODIFIED NK-92 CELLS

(71) Applicant: ImmunityBio, Inc., Culver City, CA (US)

(72) Inventors: Laurent H. Boissel, Culver City, CA (US); Hans G. Klingemann, Culver City, CA (US)

(73) Assignee: ImmunityBio, Inc., Culver City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/812,264

(22) Filed: Jul. 13, 2022

(65) Prior Publication Data

US 2022/0401485 A1    Dec. 22, 2022
US 2024/0238623 A9    Jul. 18, 2024

Related U.S. Application Data

(63) Continuation of application No. 16/969,152, filed as application No. PCT/US2019/033411 on May 21, 2019, now Pat. No. 11,547,727.

(60) Provisional application No. 62/756,395, filed on Nov. 6, 2018, provisional application No. 62/756,402, filed on Nov. 6, 2018.

(51) Int. Cl.
| | | |
|---|---|---|
| *A61K 35/17* | (2015.01) | |
| *A61K 35/28* | (2015.01) | |
| *A61K 39/395* | (2006.01) | |
| *A61K 45/06* | (2006.01) | |
| *A61P 35/00* | (2006.01) | |
| *C07K 14/705* | (2006.01) | |
| *C07K 14/735* | (2006.01) | |
| *C07K 16/10* | (2006.01) | |
| *C07K 16/28* | (2006.01) | |
| *C07K 16/32* | (2006.01) | |
| *C12N 5/0783* | (2010.01) | |

(52) U.S. Cl.
CPC .............. *A61K 35/17* (2013.01); *A61K 35/28* (2013.01); *A61K 39/3955* (2013.01); *A61K 45/06* (2013.01); *A61P 35/00* (2018.01); *C07K 14/70517* (2013.01); *C07K 14/70521* (2013.01); *C07K 14/70535* (2013.01); *C07K 16/10* (2013.01); *C07K 16/1018* (2013.01); *C07K 16/1027* (2013.01); *C07K 16/1063* (2013.01); *C07K 16/109* (2013.01); *C07K 16/2803* (2013.01); *C07K 16/2827* (2013.01); *C07K 16/2863* (2013.01); *C07K 16/2866* (2013.01); *C07K 16/2878* (2013.01); *C07K 16/2887* (2013.01); *C07K 16/32* (2013.01); *C12N 5/0646* (2013.01); *C07K 2317/53* (2013.01); *C07K 2317/622* (2013.01); *C07K 2319/03* (2013.01); *C12N 2510/00* (2013.01)

(58) Field of Classification Search
CPC .... A61K 35/17; A61K 35/28; A61K 39/3955; A61K 45/06; A61P 35/00; C07K 14/70517; C07K 14/70521; C07K 14/70535; C07K 16/10; C07K 16/1018; C07K 16/1027; C07K 16/1063; C07K 16/109; C07K 16/2803; C07K 16/2827; C07K 16/2863; C07K 16/2866; C07K 16/2878; C07K 16/2887; C07K 16/32; C12N 5/0646

See application file for complete search history.

(56) References Cited

U.S. PATENT DOCUMENTS

| | | |
|---|---|---|
| 7,098,008 B2 | 8/2006 | Park et al. |
| 7,618,817 B2 | 11/2009 | Campbell |
| 8,034,332 B2 | 10/2011 | Klingemann |
| 8,313,943 B2 | 11/2012 | Campbell |
| 9,150,636 B2 | 10/2015 | Campbell |
| 9,181,322 B2 | 11/2015 | Campbell |
| 10,138,462 B2 | 11/2018 | Klingemann |
| 10,738,279 B2 | 8/2020 | Lee |
| 10,765,701 B2 | 9/2020 | Klingemann et al. |
| 11,077,143 B2 | 8/2021 | Klingemann et al. |
| 2002/0068044 A1 | 6/2002 | Klingemann |
| 2013/0189268 A1 | 7/2013 | Du et al. |
| 2013/0280285 A1 | 10/2013 | Schonfeld et al. |

(Continued)

FOREIGN PATENT DOCUMENTS

| | | |
|---|---|---|
| AU | 2019375375 A1 | 9/2020 |
| CA | 2 977 106 A1 | 9/2016 |

(Continued)

OTHER PUBLICATIONS

Eiseman, E. et al., Signal transduction by the cytoplasmic domains of Fct:RI-y and TCR-( in rat basophilic leukemia cells, The Journal of Biological Chemistry, Oct. 15, 1992, vol. 267, No. 29, pp. 21027-21032 See abstract.

(Continued)

*Primary Examiner* — Amy E Juedes
*Assistant Examiner* — Peter Johansen
(74) *Attorney, Agent, or Firm* — Martin Fessenmaier; Umberg Zipser LLP

(57) ABSTRACT

Provided are NK-92 cells expressing a chimeric antigen receptor (CAR). The CAR can comprise an intracellular domain of FcεRIγ. Also described are methods for treating a patient having or suspected of having a disease that is treatable with NK-92 cells, such as cancer or a viral infection, comprising administering to the patient NK-92-CAR cells.

17 Claims, 67 Drawing Sheets

Specification includes a Sequence Listing.

(56) References Cited

U.S. PATENT DOCUMENTS

| | | | |
|---|---|---|---|
| 2014/0242701 A1* | 8/2014 | Shiku | C07K 16/30 |
| | | | 435/325 |
| 2014/0274909 A1 | 9/2014 | Orentas et al. | |
| 2016/0067356 A1* | 3/2016 | Campbell | A61P 31/00 |
| | | | 435/372 |
| 2016/0347854 A1 | 12/2016 | Hombach et al. | |
| 2017/0260268 A1* | 9/2017 | Beatty | C07K 14/70539 |
| 2020/0038441 A1* | 2/2020 | Klingemann | C12N 15/625 |
| 2020/0129552 A1* | 4/2020 | Klingemann | C07K 14/4702 |
| 2021/0187024 A1 | 6/2021 | Klingemann et al. | |
| 2021/0260116 A1 | 8/2021 | Boissel | |

FOREIGN PATENT DOCUMENTS

| | | | |
|---|---|---|---|
| CA | 3 055 202 A1 | 9/2018 | |
| CA | 3 092 305 A1 | 5/2020 | |
| CN | 106176609 A | 12/2016 | |
| CN | 106701685 A | 5/2017 | |
| CN | 112352048 A | 2/2021 | |
| EP | 3 743 513 A4 | 11/2021 | |
| JP | 2017-504601 A | 2/2017 | |
| JP | 2018-513692 A | 5/2018 | |
| KR | 10-2018-0002604 A | 1/2018 | |
| KR | 10-2018-0008862 A1 | 1/2018 | |
| KR | 10-2020-0118904 A | 10/2020 | |
| WO | 1998/049268 A1 | 11/1998 | |
| WO | 1999/024566 A1 | 5/1999 | |
| WO | 2000/020460 A1 | 4/2000 | |
| WO | 2014/039523 A1 | 3/2014 | |
| WO | 2014/099671 A1 | 6/2014 | |
| WO | 2015/092024 A2 | 6/2015 | |
| WO | 2016138491 A1 | 9/2016 | |
| WO | WO-2016201304 A1 * | 12/2016 | A61K 35/17 |
| WO | 2017/172981 A2 | 10/2017 | |
| WO | 2017/192440 A1 | 11/2017 | |
| WO | 2018/064594 A2 | 4/2018 | |
| WO | 2018/076391 A1 | 5/2018 | |
| WO | 2020/091869 A1 | 5/2020 | |
| WO | 2020/096646 A1 | 5/2020 | |

OTHER PUBLICATIONS

Zhang, C. et al., Chimeric antigen receptor-engineered NK-92 cells: an off-the-shelf cellular therapeutic for targeted elimination of cancer cells and induction of protective antitumor immunity, Frontiers in Immunology, May 18, 2017, vol. 8, Article 533, pp. 1-17.
International Search Report with International Application No. PCT/US2019/033411 dated: May 21, 2019, pp. 1-6.
Oelsner et al., "Continuously expanding CAR NK-92 cells display selective cytotoxicity against B-cell leukemia and lymphoma," Cytotherapy, 2017; 19:235-249.
Haynes et al., "Redirecting Mouse CTL Against Colon Carcinoma: Superior Signaling Efficacy of Single-Chain Variable Domain Chimeras Containing TCR-ζ vs FcεRI-γ", The Journal of Immunology, 2001, vol. 166, pp. 182-187.
Cartellieri et al., "Chimeric Antigen Receptor-Engineered T Cells for Immunotherapy of Cancer", Journal of Biomedicine and Biotechnology, vol. 2010, No. 956304, pp. 1-13.
Hermanson et al., "Utilizing Chimeric Antigen Receptors to Direct Natural Killer Cell Activity", Frontiers in Immunology, 2015, vol. 6, No. 195, pp. 1-6.
Bruhns et al., "Specificity and affinity of human Fcγ receptors and their polymorphic variants for human IgG subclasses", Blood, 2009, vol. 113, No. 16, pp. 3716-3725.
Konstantinidis et al., "Targeting IL-2 to the endoplasmic reticulum confines autocrine growth stimulation to NK-92 cells", Exp Hematol., 2005, vol. 33, No. 2, pp. 159-164.
Sarcia-Sanchez et al., "Cytosine Deaminase Adenoviral Vector and 5-fluorocytosine Selectively Reduce Breast Cancer Cells 1 Million-Fold When They Contaminate Hemalopoielic Cells: A Potential Purging Method for Aulologous Transplantation", Blood, 1998, vol. 92, No. 2, pp. 672-682.
Touati et al., "A Suicide Gene Therapy Combining the Improvement of Cyclophosphamide Tumor Cytotoxicity and the Development of an Anti-Tumor Immune Response", Current Gene Therapy, 2014, vol. 14, pp. 236-246.
Stasi et al., "Inducible Apoptosis as a Safety Switch for Adoptive Cell Therapy", The New England journal of Medicine, 2011, vol. 365, No. 18, pp. 1673-1683.
Morgan Richard A, "Live and Let Die: A New Suicide Gene Therapy Moves to the Clinic", Molecular Therapy, Jan. 2012, vol. 20, No. 1, pp. 11-13.
Smith et al., "Comparison of biosequences", Advances in Applied Mathematics, Dec. 1981, vol. 2, No. 4, pp. 482-489.
Altschul et al., "Gapped BLAST and PSI-BLAST: a new generation of protein database search programs", Nucleic Acids Research, 1997, vol. 25, No. 17, 3389-3402.
Altschul et al., "Basic local alignment search tool", Journal of Molecular Biology, 1990, vol. 215, No. 3, pp. 403-410.
Henikoff et al., "Amino acid substitution matrices from protein blocks", PNAS, 1992, vol. 89, No. 22, pp. 10915-10919.
Yazawa et al., "Current progress in suicide gene therapy for cancer", World Journal of Surgery, 2002, vol. 26, pp. 783-789.
Gong et al., "Characterization of a human cell line (NK-92) with phenotypical and functional characteristics of activated natural killer cells", Leukemia, 1994, vol. 8, No. 4, pp. 652-658.
Bollino et al., "Chimeric antigen receptor engineered natural killer and natural killer T cells for cancer immunotherapy", 2017, vol. 187, 21 pages.
International Preliminary Report on Patentability Chapter I received for International PCT Application Serial No. PCT/US2019/033411 dated May 20, 2021, 8 pages.
Office Action received for Canadian Application Serial No. CA3092305, dated Aug. 27, 2021, 4 Pages.
Restriction requirement received for U.S. Appl. No. 16/969,152, dated Nov. 26, 2021, 73 Pages.
Extended European Search Report received for European Patent Application Serial No. 19882519.2, dated Oct. 21, 2021, 8 pages.
Examination Report received for Australian Patent Application Serial No. 2019375375, dated Nov. 12, 2021, 4 pages.
First Substantive Examination Report received for Israeli Patent Application Serial No. 277414 dated Nov. 4, 2021, 12 pages. (Including English Translation).
Non-Final Office Action received for U.S. Appl. No. 16/969,152 dated Feb. 11, 2022, 115 pages.
Final Office Action received for U.S. Appl. Serial No. 16/969,152 dated May 27, 2022, 22 pages.
Office Action received for Israel Patent Application Serial No. 277414 dated May 17, 2022, 10 pages. (Including English Translation).
Second Office Action received for Canadian Patent Application Serial No. 3092305 dated Jul. 29, 2022, 4 pages.
Request for the Submission of an Opinion received for Korean Patent Application Serial No. 10-2020-7028467 dated Aug. 16, 2022, 9 pages. (Including English Translation).
Examination Report No. 2 received for Australian Patent Application Serial No. 2019375375 dated Sep. 16, 2022, 4 pages.
Examination Report No. 3 received for Australian Patent Application Serial No. 2019375375 dated Oct. 19, 2022, 3 pages.
Notice of Acceptance received for Australian Patent Application Serial No. 2019375375 dated Nov. 17, 2022, 3 pages.
Office Action received for Israel Patent Application Serial No. 277414 dated Jan. 16, 2023, 12 pages. (Including English Translation).
Notice of Allowance received for U.S. Appl. No. 16/969,152 dated Sep. 14, 2022, 28 pages.
Notification of Reasons for Rejection received for Japanese Patent Application Serial No. 2020-554246 dated Jan. 13, 2023, 20 pages. (Including English Translation).
Clémenceau et al., "In Vitro and In Vivo Comparison of Lymphocytes Transduced with a Human CD16 or with a Chimeric Antigen Receptor Reveals Potential Off-Target Interactions due to the IgG2 CH2-CH3 CAR-Spacer", Hindawi, Journal of Immunology Research, vol. 3, Article ID 482089, 2015, pp. 1-13.

(56) References Cited

OTHER PUBLICATIONS

Examination Report No. 1 received for Australian Patent Application Serial No. 2022283619 dated May 30, 2023, 3 pages.
Examination Report No. 3 received for CA Application No. 3092305 dated Sep. 15, 2023, 03 pages.
Notice of Allowance received for KR Application No. 10-2023-7011716 dated May 25, 2023, 12 pages (including English Translation).
Decision of Rejection received for JP Application No. 2020-554246 dated Jul. 28, 2023, 22 pages (including English Translation).
First office Action received in CN Application No. 201980023758.8 dated Jul. 22, 2023, 15 pages (including English translation).
Notice of Allowance received for KR Application No. 10-2020-7028467 dated Feb. 24, 2023, 12 pages (including English Translation).
Office Action issued for IL Application No. 277414 dated Jul. 30, 2023, 10 pages (including English Translation).
Second office Action received for CN Application No. 201980023758.8 dated Jan. 27, 2024, 12 pages (including English translation).
Notice of Reasons for Rejection received for JP Application No. 2020-554246 dated Mar. 29, 2024, 09 pages (including English Translation).

* cited by examiner

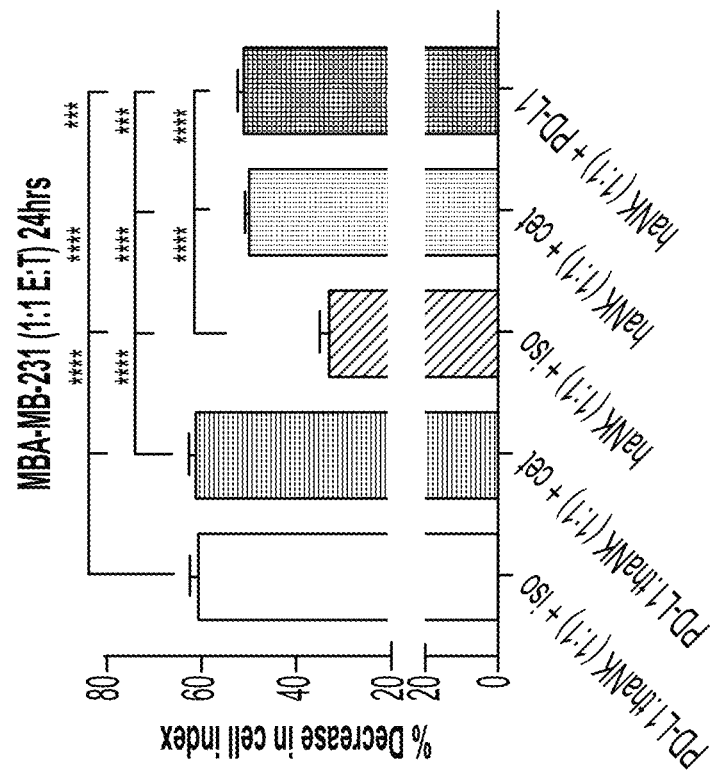
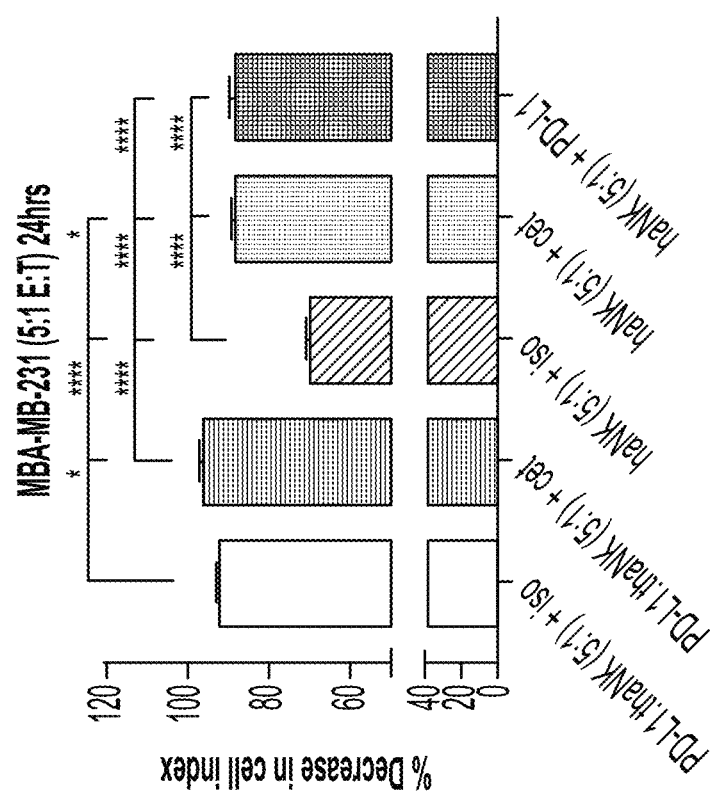
FIG. 24 CONTINUED

```
                              SEQUENCE LISTING

Sequence total quantity: 76
SEQ ID NO: 1            moltype = AA   length = 41
FEATURE                 Location/Qualifiers
REGION                  1..41
                        note = FceRIgamma Intracellular Domain peptide
source                  1..41
                        mol_type = protein
                        organism = synthetic construct
SEQUENCE: 1
LKIQVRKAAI TSYEKSDGVY TGLSTRNQET YETLKHEKPP Q                         41

SEQ ID NO: 2            moltype = DNA  length = 123
FEATURE                 Location/Qualifiers
misc_feature            1..123
                        note = FceRIgamma Intracellular Domain
source                  1..123
                        mol_type = other DNA
                        organism = synthetic construct
SEQUENCE: 2
ctgaagatcc aggtccgaaa ggccgccatc accagctacg agaagtctga tggcgtgtac      60
accggcctga gcaccagaaa ccaggaaacc tacgagacac tgaagcacga agccccccc     120
cag                                                                 123

SEQ ID NO: 3            moltype = AA   length = 398
FEATURE                 Location/Qualifiers
REGION                  1..398
                        note = CD19CAR FceRIgamma
source                  1..398
                        mol_type = protein
                        organism = synthetic construct
SEQUENCE: 3
MDWIWRILFL VGAATGAHSA QPADIQMTQT TSSLSASLGD RVTISCRASQ DISKYLNWYQ      60
QKPDGTVKLL IYHTSRLHSG VPSRFSGSGS GTDYSLTISN LEQEDIATYF CQQGNTLPYT    120
FGGGTKLELK RGGGGSGGGG SGGGGSGGGG SEVQLQQSGP GLVAPSQSLS VTCTVSGVSL    180
PDYGVSWIRQ PPRKGLEWLG VIWGSETTYY NSALKSRLTI IKDNSKSQVF LKMNSLQTDD    240
TAIYYCAKHY YYGGSYAMDY WGQGTTVTVS SAAALFVPVF LPAKPTTTPA PRPPTPAPTI    300
ASQPLSLRPE ACRPAAGGAV HTRGLDFACF WVLVVVGGVL ACYSLLVTVA FIIFWVRLKI    360
QVRKAAITSY EKSDGVYTGL STRNQETYET LKHEKPPQ                           398

SEQ ID NO: 4            moltype = AA   length = 259
```

| | | |
|---|---|---|
| FEATURE | Location/Qualifiers | |
| REGION | 1..259 | |
| | note = CD19CAR scFv | |
| source | 1..259 | |
| | mol_type = protein | |
| | organism = synthetic construct | |

SEQUENCE: 4

```
AATGAHSAQP ADIQMTQTTS SLSASLGDRV TISCRASQDI SKYLNWYQQK PDGTVKLLIY    60
HTSRLHSGVP SRFSGSGSGT DYSLTISNLE QEDIATYFCQ QGNTLPYTFG GGTKLELKRG   120
GGGSGGGGSG GGGSGGGGSE VQLQQSGPGL VAPSQSLSVT CTVSGVSLPD YGVSWIRQPP   180
RKGLEWLGVI WGSETTYYNS ALKSRLTIIK DNSKSQVFLK MNSLQTDDTA IYYCAKHYYY   240
GGSYAMDYWG QGTTVTVSS                                                259
```

| | | |
|---|---|---|
| SEQ ID NO: 5 | moltype = DNA  length = 1197 | |
| FEATURE | Location/Qualifiers | |
| misc_feature | 1..1197 | |
| | note = CD19CAR FceRIgamma DNA | |
| source | 1..1197 | |
| | mol_type = other DNA | |
| | organism = synthetic construct | |

SEQUENCE: 5

```
atggactgga tctggcggat cctgtttctc gtgggagctg ccacaggcgc tcattctgct     60
cagcctgccg atatccagat gacccagaca caagcagcc tgagcgcctc tctgggcgat    120
agagtgacaa tcagctgcag agccagccag gacatcagca gtacctgaa ctggtatcag    180
cagaaaccgc acggcaccgt gaagctgctg atctaccaca caagcagact gcacagcggc    240
gtgccaagca gattttctgg cagcggcagc ggcaccgatt acagcctgac catcagcaac    300
ctggaacagg aagatatcgc tacctacttc tgtcagcagg gcaacaccct gccttacacc    360
tttggcggcg gaacaaagct ggaactgaaa agaggcggcg gaggaagcgg aggcggagga    420
tctggggggcg gaggctctgg cggagggga tctgaagtgc agctgcagca gtctggacct    480
ggactggtgg ctccttctca gtccctgtct gtgacctgca cagtgtctgg cgtgtccctg    540
cctgattacg gcgtgtcctg gatcagacag cctcccagaa aaggcctgga atggctggga    600
gtgatctggg gcagcgagac aacctactac aacagcgccc tgaagtcccg gctgaccatc    660
atcaaggaca cagcaagag ccaggtgttc ctgaagatga cagcctgca gaccgacgac    720
accgccatct actactgcgc caagcactac tactacggcg gcagctacgc catggattat    780
tgggccagg gcaccaccgt gacagtgtca tctgctgctg ctctgttcgt gcctgtgttc    840
ctgcctgcca agcctacaac aacaccagcc cctagacctc caacccctgc ccctacaatt    900
gcctctcagc ctctgtctct gaggcccgaa gcttgtagac ctgctgctgg cggagctgtg    960
cacaccagag gactggattt cgcctgcttt tgggtgctgg tggtcgtggg cggagtgctg   1020
gcttgtattt ctctgctggt caccgtggcc ttcatcatct tttggtccg actgaagatc   1080
caggtccgaa aggccgccat caccagctac gagaagtctg atggcgtgta caccggcctg   1140
agcaccgaga accaggaaac ctacgagaca ctgaagcacg agaagccccc ccagtaa     1197
```

| | | |
|---|---|---|
| SEQ ID NO: 6 | moltype = AA  length = 54 | |
| FEATURE | Location/Qualifiers | |
| REGION | 1..54 | |
| | note = CD8 Hinge | |
| source | 1..54 | |
| | mol_type = protein | |
| | organism = synthetic construct | |

SEQUENCE: 6

```
KPTTTPAPRP PTPAPTIASQ PLSLRPEACR PAAGGAVHTR GLDFACFWVL VVVG          54
```

| | | |
|---|---|---|
| SEQ ID NO: 7 | moltype = AA  length = 20 | |
| FEATURE | Location/Qualifiers | |
| REGION | 1..20 | |
| | note = CD28 Transmembrane domain | |
| source | 1..20 | |
| | mol_type = protein | |
| | organism = synthetic construct | |

SEQUENCE: 7

```
GVLACYSLLV TVAFIIFWVR                                                20
```

| | | |
|---|---|---|
| SEQ ID NO: 8 | moltype = AA  length = 41 | |
| FEATURE | Location/Qualifiers | |
| REGION | 1..41 | |
| | note = CD28 signaling domain | |
| source | 1..41 | |
| | mol_type = protein | |
| | organism = synthetic construct | |

SEQUENCE: 8

```
RSKRSRLLHS DYMNMTPRRP GPTRKHYQPY APPRDFAAYR S                         41
```

| | | |
|---|---|---|
| SEQ ID NO: 9 | moltype = AA  length = 42 | |
| FEATURE | Location/Qualifiers | |
| REGION | 1..42 | |
| | note = 4-1BB signaling domain | |
| source | 1..42 | |
| | mol_type = protein | |
| | organism = synthetic construct | |

```
SEQUENCE: 9
KRGRKKLLYI FKQPFMRPVQ TTQEEDGCSC RFPEEEEGGC EL                                42

SEQ ID NO: 10              moltype = AA  length = 113
FEATURE                    Location/Qualifiers
REGION                     1..113
                           note = CD3 zeta signaling domain
source                     1..113
                           mol_type = protein
                           organism = synthetic construct
SEQUENCE: 10
RVKFSRSADA PAYQQGQNQL YNELNLGRRE EYDVLDKRRG RDPEMGGKPQ RRKNPQEGLY             60
NELQKDKMAE AYSEIGMKGE RRRGKGHDGL YQGLSTATKD TYDALHMQAL PPR                   113

SEQ ID NO: 11              moltype = DNA  length = 339
FEATURE                    Location/Qualifiers
misc_feature               1..339
                           note = Human CD3 zeta (codon optimized):
source                     1..339
                           mol_type = other DNA
                           organism = synthetic construct
SEQUENCE: 11
gtgaagttta gcagatctgc cgacgcccct gcctaccagc agggacagaa tcagctgtac             60
aacgagctga acctgggcag acggaagag tacgacgtgc tggataagag aagaggcaga            120
gatcccgaga tggcggcaa gccccagaga agaaagaatc cccaggaagg cctgtataac            180
gaactgcaga aagacaagat ggccgaggcc tacagcgaga tcggcatgaa gggcgagaga            240
agaagaggca agggccacga tggactgtac cagggactga gcacagccac caaggatacc            300
tacgatgccc tgcacatgca ggccctgcct ccaagataa                                   339

SEQ ID NO: 12              moltype = DNA  length = 339
FEATURE                    Location/Qualifiers
misc_feature               1..339
                           note = Human CD3 zeta (non-codon optimized)
source                     1..339
                           mol_type = other DNA
                           organism = synthetic construct
SEQUENCE: 12
gtgaagttca gcaggagcgc agacgccccc gcgtaccagc agggccagaa ccagctctat             60
aacgagctca atctaggacg aagagaggag tacgatgttt tggacaagag acgtggccgg            120
gaccctgaga tggggggaaa gccgcagaga aggaagaacc ctcaggaagg cctgtacaat            180
gaactgcaga agataagat ggcggaggcc tacagtgaga ttgggatgaa aggcgagcgc             240
cggaggggca agggcacga tggcctttac cagggtctca gtacagccac caaggacacc            300
tacgacgccc ttcacatgca ggccctgccc ctcgctaa                                    339

SEQ ID NO: 13              moltype = DNA  length = 1410
FEATURE                    Location/Qualifiers
misc_feature               1..1410
                           note = CD19CAR CD3z (DNA sequence)
source                     1..1410
                           mol_type = other DNA
                           organism = synthetic construct
SEQUENCE: 13
atggactgga tctggcggat cctgtttctc gtgggagctg ccacaggcgc tcattctgct             60
cagcctgccg atatccagat gacccagaca acaagcagcc tgagcgcctc tctgggcgat            120
agagtgacaa tcagctgcag agccagccag gacatcagca agtacctgaa ctggtatcag            180
cagaaacccg acggcaccgt gaagctgctg atctaccaca agcagact gcacagcggc             240
gtgccaagca gattttctgg cagcggcagc ggcaccgatt acagcctgac catcagcaac            300
ctgaacagg aagatatcgc tacctacttc tgtcagcaag caacaccct gccttacacc             360
tttggcggcg gaacaaagct ggaactgaaa agaggcggcg gaggaagcgg aggcggagga            420
tctggggggc gaggcgtctg cggaggggga gctgaagtgc agctgcagca gtctggaccc            480
ggactggtgg ctccttctca gtccctgtct gtgacctgta cagtgtctgg cgtgtccctg            540
cctgattacg gcgtgtcctg gatcagacag cctcccagaa aggcctgga atggctggga            600
gtgatctggg gcagcgagac aacctactac aacagcgccc tgaagtcccg gctgaccatc            660
atcaaggaca acagcaagag ccaggtgttc ctgaagatga acagcctgca gaccgacgac            720
accgccatct actactgcgc caagcactac tactacggcg gcagctacgc catggattat            780
tggggccagg gcaccaccgt gacagtgtca tctgctgctg ctctgttcgt gcctgtgttc            840
ctgcctgcca agcctacaac aacaccagcc ctagacctc caaccctgc ccctacaatt             900
gcctctcagc ctctgtctct gaggcccgaa gcttgtagac ctgctgctgg cggagctgtg            960
cacaccagag gactggattt cgcctgcttt tgggtgctgg tggtcgtggg cggagtgctg           1020
gcttgttatt ctctgctggt caccgtggcc ttcatcatct ttgggttccg agtgaagttc           1080
agcagatccg ccgatgcccc tgcttaccag cagggccaga atcagctgta caacgagctg           1140
aacctgggca gacgggaaga gtacgacgtg ctggataaga gaagaggcag agatcccgag           1200
atgggcggca gccccagag aagaaagaat cccaggaag gcctgtataa cgaactgcag             1260
aaagacaaga tggccgaggc ctacagcgag atcggcatga agggcgagag aagaagaggc           1320
aagggccacg atggactgta ccagggactg agcacagcca caaggatac ctacgatgcc            1380
ctgcacatgc aggccctgcc tccaagataa                                            1410

SEQ ID NO: 14              moltype = DNA  length = 1533
FEATURE                    Location/Qualifiers
```

| | | |
|---|---|---|
| misc_feature | 1..1533 | |
| | note = CD19CAR CD28/CD3z (DNA sequence) | |
| source | 1..1533 | |
| | mol_type = other DNA | |
| | organism = synthetic construct | |

SEQUENCE: 14

```
atggactgga tctggcggat cctgtttctc gtgggagctg ccacaggcgc tcattctgct   60
cagcctgccg atatccagat gacccagaca acaagcagcc tgagcgcctc tctgggcgat  120
agagtgacaa tcagctgcag agccagccag gacatcagca gtacctgaa ctggtatcag   180
cagaaacccg acggcaccgt gaagctgctg atctaccaca caagcagact gcacagcggc  240
gtgccaagca gattttctgg cagcggcagc ggcaccgatt acagcctgac catcagcaac  300
ctgaacagg aagatatcgc tacctacttc tgtcagcagg gcaacaccct gccttacacc   360
tttggcggcg aacaaagct ggaactgaaa agaggcggcg gaggaagcgg aggcggagga   420
tctggggcg aggctctgg cggaggggga tctgaagtgc agctgcagca gtctggacct   480
ggactggtgg ctccttctca gtccctgtct gtgacctgta cagtgtctgg cgtgtccctg  540
cctgattacg gcgtgtcctg gatcagacag cctcccagaa aggcctggaa tggctggga   600
gtgatctggg gcagcgagac aacctactac aacagcgccc tgaagtcccg gctgaccatc  660
atcaaggaca acagcaagag ccaggtgttc ctgaagatga acagcctgca gaccgacgac  720
accgccatct actactgcgc caagcactac tactacggcg gcagctacgc catggattat  780
tggggccagg gcaccaccgt gacagtgtca tctgctgctg ctctgttcgt gcctgtgttc  840
ctgcctgcca gcctacaac aacaccagcc ctagacctc aacccctgc ccctacaatt    900
gcctctcagc ctctgtctct gaggcccgaa gcttgtagac tgctgctggg cggagctgtg  960
cacaccagag gactggattt cgcctgcttt gggtgctgg tggtcgtggg cggagtgctg  1020
gcttgttatt ctctgctggt caccgtggcc ttcatcatct tttggtccg aagcaagcgg  1080
agcaggctgc tgcacagcga ctacatgaac atgaccccta aaggcctgg ccccaccaga  1140
aagcactatc agccttacgc ccctcccaga gacttcgccg cctacagatc cagagtgaag  1200
ttcagcagat ctgccgacgc ccctgcttac cagcagggcc agaatcagct gtacaacgag  1260
ctgaacctgg gcagacggga gagtacgac gtgctggata agagaagg cagagatccc   1320
gagatgggcg gcaagcccca gagaagaag aatcccagg aaggcctgta taggaactg    1380
cagaaagaca agatggccga ggcctacagc gagatcggca tgaagggcga gagaagaaga  1440
ggcaagggcc acgatggact gtaccaggga ctgagcacag ccaccaagga tacctacgat  1500
gccctgcaca tgcaggccct gcctccaaga taa                               1533
```

| | | |
|---|---|---|
| SEQ ID NO: 15 | moltype = DNA length = 1536 | |
| FEATURE | Location/Qualifiers | |
| misc_feature | 1..1536 | |
| | note = CD19CAR_4-1BB/CD3z (DNA sequence) | |
| source | 1..1536 | |
| | mol_type = other DNA | |
| | organism = synthetic construct | |

SEQUENCE: 15

```
atggactgga tctggcggat cctgtttctc gtgggagctg ccacaggcgc tcattctgct   60
cagcctgccg atatccagat gacccagaca acaagcagcc tgagcgcctc tctgggcgat  120
agagtgacaa tcagctgcag agccagccag gacatcagca gtacctgaa ctggtatcag   180
cagaaacccg acggcaccgt gaagctgctg atctaccaca caagcagact gcacagcggc  240
gtgccaagca gattttctgg cagcggcagc ggcaccgatt acagcctgac catcagcaac  300
ctgaacagg aagatatcgc tacctacttc tgtcagcagg gcaacaccct gccttacacc   360
tttggcggcg aacaaagct ggaactgaaa agaggcggcg gaggaagcgg aggcggagga   420
tctggggcg aggctctgg cggaggggga tctgaagtgc agctgcagca gtctggacct   480
ggactggtgg ctccttctca gtccctgtct gtgacctgta cagtgtctgg cgtgtccctg  540
cctgattacg gcgtgtcctg gatcagacag cctcccagaa aggcctggaa tggctggga   600
gtgatctggg gcagcgagac aacctactac aacagcgccc tgaagtcccg gctgaccatc  660
atcaaggaca acagcaagag ccaggtgttc ctgaagatga acagcctgca gaccgacgac  720
accgccatct actactgcgc caagcactac tactacggcg gcagctacgc catggattat  780
tggggccagg gcaccaccgt gacagtgtca tctgctgctg ctctgttcgt gcctgtgttc  840
ctgcctgcca gcctacaac aacaccagcc ctagacctc aacccctgc ccctacaatt    900
gcctctcagc tctgtctct gaggcccgaa gcttgtagac tgctgctgg cggagctgtg   960
cacaccagag gactggattt cgcctgcttt gggtgctgg tggtcgtggg cggagtgctg  1020
gcttgttatt ctctgctggt caccgtggcc ttcatcatct tttggtcaa gcggggcaga  1080
aagaagctgc tgtatatctt caagcagccc ttcatgaggc ccgtgcagac cacacaggaa  1140
gaggacggct gcagctgtag attccctgag aagaagaag gcgctgcga gctgagagtg   1200
aagtttagca gatctgccga cgcccctgcc taccagcagg acagaatca gctgtacaac   1260
gagctgaacc tgggcagacg gggaagagtac gacgtgctga taagagaag aggcagagat  1320
cccgagatgg gcggcaagcc ccagagaaga aagaatccca ggaaggcct gtataggaac   1380
ctgcagaaag acaagatggc cgaggcctac agcgagatcg gcatgaaggg cgagagaaga  1440
agaggcaagg gccacgatgg actgtaccag ggactgagca cagccaccaa ggataccac   1500
gatgccctgc acatgcaggc cctgcctcca agataa                            1536
```

| | | |
|---|---|---|
| SEQ ID NO: 16 | moltype = DNA length = 1659 | |
| FEATURE | Location/Qualifiers | |
| misc_feature | 1..1659 | |
| | note = CD19CAR_CD28/4-1BB/CD3z (DNA sequence) | |
| source | 1..1659 | |
| | mol_type = other DNA | |
| | organism = synthetic construct | |

SEQUENCE: 16

```
atggactgga tctggcggat cctgtttctc gtgggagctg ccacaggcgc tcattctgct   60
cagcctgccg atatccagat gacccagaca acaagcagcc tgagcgcctc tctgggcgat  120
agagtgacaa tcagctgcag agccagccag gacatcagca gtacctgaa ctggtatcag   180
```

```
cagaaacccg acggcaccgt gaagctgctg atctaccaca caagcagact gcacagcggc  240
gtgccaagca gattttctgg cagcggcagc ggcaccgatt acagcctgac catcagcaac  300
ctggaacagg aagatatcgc tacctacttc tgtcagcagg caacaccct gccttacacc   360
tttggcggcg aacaaagct ggaactgaaa agaggcggcg aggaagcgg aggcggagga    420
tctggggcg gaggctctgg cggaggggga tctgaagtgc agctgcagca gtctggacct   480
ggactggtgg ctccttctca gtccctgtct gtgacctgta cagtgtctgg cgtgtccctg  540
cctgattacg gcgtgtcctg gatcagacag cctcccagaa aggcctgga atggctggga    600
gtgatctggg gcagcgagac aacctactac aacagcgccc tgaagtcccg gctgaccatc  660
atcaaggaca acagcaagag ccaggtgttc tgaagatgaa acagcctgca gaccgacgac  720
accgccatct actactgcgc caagcactac tactacgcg gcagctagc catggattat    780
tggggccagg gcaccaccgt gacagtgtca tctgctgctg ctctgttcgt gcctgtgttc  840
ctgcctgcca agcctacaac aacaccagcc ctagacctc aaccctgc ccctacaatt    900
gcctctcagc tctgtctct gaggcccgaa gcttgtagac tgctgctgg cggagctgtg    960
cacaccagag gactggattt cgcctgcttt tgggtgctgg tggtcgtggg ggagtgctg  1020
gcttgttatt ctctgctggt caccgtggcc ttcatcatct tttgggtccg aagcaagcgg 1080
agcaggctgc tgcacagcga ctacatgaac atgaccccta aaggcctgg ccccaccaga 1140
aagcactatc agccttacgc ccctcccaga gacttcgccg cctatagatc caagcggggc 1200
agaaaggaag tgctgtacat cttcaagcag cccttcatga ggccccgtgca gaccacacag 1260
gaagaggacg gctgcagctg tagattccct gaggaagaag aaggcggctg cgagctgaga 1320
gtgaagttta gcagatctgc cgacgcccct gcctaccagc agggacagaa tcagctgtac 1380
aacgagctga acctgggcag acgggaagag tacgacgtgc tggataagag aagaggcaga 1440
gatcccgaga tgggcggcaa gccccagaga agaaagaatc caggaaggc cctgtataac 1500
gaactgcaga agacaagat ggccgaggcc tacagcgaga tcggcatgaa gggcgagaga 1560
agaagaggca agggccacga tggactgtac cagggactga gcacagccac caaggatacc 1620
tacgatgccc tgcacatgca ggccctgcct ccaagataa                        1659

SEQ ID NO: 17           moltype = DNA  length = 1659
FEATURE                 Location/Qualifiers
misc_feature            1..1659
                        note = CD19CAR_4-1BB/CD3z/CD28 (DNA sequence)
source                  1..1659
                        mol_type = other DNA
                        organism = synthetic construct
SEQUENCE: 17
atggactgga tctggcggat cctgtttctc gtgggagctg ccacaggcgc tcattctgct   60
cagcctgccg atatccagat gacccagaca caagcagcc tgagcgcctc tctgggcgat  120
agagtgacaa tcagctgcag agccagccag gacatcagca gtacctgaa ctggtatcag  180
cagaaacccg acggcaccgt gaagctgctg atctaccaca caagcagact gcacagcggc  240
gtgccaagca gattttctgg cagcggcagc ggcaccgatt acagcctgac catcagcaac  300
ctggaacagg aagatatcgc tacctacttc tgtcagcagg caacaccct gccttacacc   360
tttggcggcg aacaaagct ggaactgaaa agaggcggcg aggaagcgg aggcggagga    420
tctggggcg gaggctctgg cggaggggga tctgaagtgc agctgcagca gtctggacct   480
ggactggtgg ctccttctca gtccctgtct gtgacctgta cagtgtctgg cgtgtccctg  540
cctgattacg gcgtgtcctg gatcagacag cctcccagaa aggcctgga atggctggga    600
gtgatctggg gcagcgagac aacctactac aacagcgccc tgaagtcccg gctgaccatc  660
atcaaggaca acagcaagag ccaggtgttc tgaagatgaa acagcctgca gaccgacgac  720
accgccatct actactgcgc caagcactac tactacgcg gcagctagc catggattat    780
tggggccagg gcaccaccgt gacagtgtca tctgctgctg ctctgttcgt gcctgtgttc  840
ctgcctgcca agcctacaac aacaccagcc ctagacctc aaccctgc ccctacaatt    900
gcctctcagc tctgtctct gaggcccgaa gcttgtagac tgctgctgg cggagctgtg    960
cacaccagag gactggattt cgcctgcttt tgggtgctgg tggtcgtggg ggagtgctg  1020
gcttgttatt ctctgctggt caccgtggcc ttcatcatct tttgggtcaa gcggggcaga 1080
aagaagctgc tgtacatctt caagcagccc ttcatgaggc ccgtgcagac cacacaggaa 1140
gaggacggct gcagctgtag attccctgag gaagaagaag cggctgcga gctgagagtg 1200
aagtttagca gatctgccga cgcccctgcc taccagcagg gacagaatca gctgtacaac 1260
gagctgaacc tgggcagacg ggaagagtac gacgtgctgg ataagagaag gcagagat  1320
cccgagatgg gcggcaagcc cagagaaga agaatcccc aggaaggcct gtataacgaa  1380
ctgcagaaag acaagatggc cgaggcctac agcgagatcg gcatgaaggg cgagagaaga 1440
agaggcaagg gccacgatgg actgtaccag ggactgagca gccaccaa ggataccc     1500
gatgccctgc acatgcaggc cctgcctcca agaagaagc agagatctag actgctgcac 1560
agcgactaca tgaacatgac ccctagaagg cctggcccca ccagaaagca ctatcagcct 1620
tacgcccctc ccagagactt cgccgcctac agatcttga                        1659

SEQ ID NO: 18           moltype = AA  length = 153
FEATURE                 Location/Qualifiers
REGION                  1..153
                        note = Wild-Type IL-2 (amino acid sequence)
source                  1..153
                        mol_type = protein
                        organism = synthetic construct
SEQUENCE: 18
MYRMQLLSCI ALSLALVTNS APTSSSTKKT QLQLEHLLLD LQMILNGINN YKNPKLTRML   60
TFKFYMPKKA TELKHLQCLE EELKPLEEVL NLAQSKNFHL RPRDLISNIN VIVLELKGSE  120
TTFMCEYADE TATIVEFLNR WITFCQSIIS TLT                              153

SEQ ID NO: 19           moltype = AA  length = 160
FEATURE                 Location/Qualifiers
REGION                  1..160
                        note = IL-2-ER (amino acid sequence)
```

```
source                  1..160
                        mol_type = protein
                        organism = synthetic construct
SEQUENCE: 19
MYRMQLLSCI ALSLALVTNS APTSSSTKKT QLQLEHLLLD LQMILNGINN YKNPKLTRML    60
TFKFYMPKKA TELKHLQCLE EELKPLEEVL NLAQSKNFHL RPRDLISNIN VIVLELKGSE   120
TTFMCEYADE TATIVEFLNR WITFCQSIIS TLTGSEKDEL                         160

SEQ ID NO: 20           moltype = DNA  length = 765
FEATURE                 Location/Qualifiers
misc_feature            1..765
                        note = Polynucleotide Encoding the Low Affinity
                         Immunoglobulin Gamma FcRegion Receptor III-A
source                  1..765
                        mol_type = other DNA
                        organism = synthetic construct
SEQUENCE: 20
atgtggcagc tgctcctccc aactgctctg ctacttctag tttcagctgg catgcggact    60
gaagatctcc caaaggctgt ggtgttcctg gagcctcaat ggtacagggt gctcgagaag   120
gacagtgtga ctctgaagtg ccagggagcc tactcccctg aggacaattc cacacagtgg   180
tttcacaatg agagcctcat ctcaagccag gcctcgagct acttcattga cgctgccaca   240
gtcgacgaca gtgagagta caggtgaccag acaaacctct ccaccctgga tgacccggtg   300
cagctagaag tccatatcgg ctggctgttg ctccaggccc tcggtgggg gttcaaggag   360
gaagacccta ttcacctgag gtgtcacagc tggaagaaca ctgctctgca taaggtcaca   420
tatttacaga atggcaaagg caggaagtat tttcatcata attctgactt ctacattcca   480
aaagccacac tcaaagacag cggctcctac ttctgcagag ggcttttttgg gagtaaaaat   540
gtgtcttcag agactgtgaa catcaccatc actcaaggtt tggcagtgtc aaccatctca   600
tcattctttc cacctgggta ccaagtctct ttctgcttgg tgatggtact ccttttttgca   660
gtggacacag gactatattt ctctgtgaag acaaacattc gaagctcaac aagagactgg   720
aaggaccata aatttaaatg gagaaaggac cctcaagaca aatga                  765

SEQ ID NO: 21           moltype = DNA  length = 1455
FEATURE                 Location/Qualifiers
misc_feature            1..1455
                        note = CD19-CAR DNA sequence (murine)
source                  1..1455
                        mol_type = other DNA
                        organism = synthetic construct
SEQUENCE: 21
cccgggaatt cgccaccatg gactggatct ggcggatcct gttcctcgtg ggagccgcca    60
caggcgccca ttctgcccag cccgccgaca tccagatgac ccagaccacc agcagcctga   120
gcgccagcct gggcgacaga gtgaccatca gctgccgggc cagccaggac atcagcaagt   180
acctgaactg gtatcagcag aaacccgacg gcaccgtgaa gctgctgatc taccacacca   240
gccggctgca cagcggcgtg cccagcagat ttctggcag cggcagcggc accgactaca   300
gcctgaccat ctccaacctg aacaggaag atatcgctac ctacttctgt cagcaaggca   360
acaccctgcc ctacaccttc ggcggaggca ccaagctgga actgaagaga ggcggcggag   420
gctctggtgg aggcggatct gggggcggag gaagtggcag cggaggatct gaagtgcagc   480
tgcagcagag cggccctggc ctggtggccc tagccagag cctgtccgtg acctgtaccg   540
tgtccggcgt gtccctgccc gactacgcg tgtcctggat ccggcagccc cccagaaagg   600
gcctggaatg gctgggcgtg atctgggca gcgagacaac ctactacaac agcgccctga   660
agtcccggct gaccatcatc aaggacaaca gcaagagcgt ggtgttcctg aagatgaaca   720
gcctgcagac cgacgacacc gccatctact actgcgccaa gcactactac acgcgccgga   780
gctacgccat ggactactgg ggccagggca ccaccgtgac cgtgtccagc gccctgtcca   840
acagcatcat gtacttcagc cacttcgtgc cgtgtttct gccgccaag ccaccacca   900
ccctgcccc tagacctccc accccagccc aacaatgcc cagccagcct cgtgtccctgc    960
ggcccgaagc tagcagacct gctgccggcg gagccgtgca caccagaggc tggaccccca  1020
agctgtgcta cctgctggac ggcatcctgt tcatctatgg cgtgatcctg accgccctgt  1080
tcctgagagt gaagttcagc agaagcgccg acgccctgc ctaccagcag gccagaacc   1140
agctgtacaa cgagctgaac ctgggcagac gggaagagta cgacgtgctg gacaagcgga  1200
gaggcaggga ccccgagatg ggcggcaagc cagacgaaa gaaccccgga aggcctgtg   1260
ataacgaact gcagaaagac aagatggccg aggcctacag cgagatcggc atgaagggcg  1320
agcggcggag gggcaaggc cacgatggac tgtaccaggg cctgagcacc gccaccaagg  1380
acacctacga cgccctgcac atgcaggccc tgccccccag atgacagcca gggcatttct  1440
ccctcgagcg gccgc                                                  1455

SEQ ID NO: 22           moltype = AA  length = 468
FEATURE                 Location/Qualifiers
REGION                  1..468
                        note = CD19-CAR amino acids sequence (murine)
source                  1..468
                        mol_type = protein
                        organism = synthetic construct
SEQUENCE: 22
MDWIWRILFL VGAATGAHSA QPADIQMTQT TSSLSASLGD RVTISCRASQ DISKYLNWYQ    60
QKPDGTVKLL IYHTSRLHSG VPSRFSGSGS GTDYSLTISN LEQEDIATYF CQQGNTLPYT   120
FGGGTKLELK RGGGGSGGGG SGGGGSGGGG SEVQLQQSGP GLVAPSQSLS VTCTVSGVSL   180
PDYGVSWIRQ PPRKGLEWLG VIWGSETTYY NSALKSRLTI IKDNSKSQVF LKMNSLQTDD   240
TAIYYCAKHY YGGSYAMDY WGQGTTVTVS SALSNSIMYF SHFVPVFLPA KPTTPAPRP   300
PTPAPTIASQ PLSLRPEASR PAAGGAVHTR GLDPKLCYLL DGILFIYGVI LTALFLRVKF   360
```

```
SRSADAPAYQ QGQNQLYNEL NLGRREEYDV LDKRRGRDPE MGGKPRRKNP QEGLYNELQK    420
DKMAEAYSEI GMKGERRRGK GHDGLYQGLS TATKDTYDAL HMQALPPR                468

SEQ ID NO: 23              moltype = DNA   length = 813
FEATURE                    Location/Qualifiers
misc_feature               1..813
                           note = Codon-optimized CD19 scFv - DNA sequence
source                     1..813
                           mol_type = other DNA
                           organism = synthetic construct
SEQUENCE: 23
atggactgga tctggcggat tctgtttctc gtgggagctg ccacaggcgc tcattctgct    60
cagcctgccg atatccagat gacccagaca caagcagcc tgagcgcctc tctgggcgat    120
agagtgacaa tcagctgcag agccagccag gacatccaga ctacctgaa ctggtatcag    180
cagaaacccg acggcaccgt gaagctgctg atctaccaca caagcagact gcacagcggc    240
gtgccaagca gatttctgg cagcggcagc ggcaccgatt acagcctgac catcagcaac    300
ctggaacagg aagatatcgc tacctactc tgtcagcagg caacaccct gccttacacc    360
tttggcggcg gaacaaagct ggaactgaaa agaggcggc gaggaagcgg aggcggagga    420
tctgggggcg gaggctctgg cggaggggga tctgaagtgc agctgcagca gtctggacct    480
ggactggtgg ctccttctca gtccctgtct gtgacctgta cagtgtctgg cgtgtccctg    540
cctgattacg gcgtgtcctg gatcagacag cctcccagaa aggcctgga atggctggga    600
gtgatctggg gcagcgagac aacctactac aacagcgccc tgaagtcccg gctgaccatc    660
atcaaggaca cagcaagag ccaggtgttc ctgaagatga acagcctgca gaccgacgac    720
accgccatct actactgcgc caagcactac tactacggcg gcagctacgc catggattat    780
tggggccagg caccaccgt gacagtgtca tct                                 813

SEQ ID NO: 24              moltype = AA   length = 271
FEATURE                    Location/Qualifiers
REGION                     1..271
                           note = CD19 scFv - Protein sequence
source                     1..271
                           mol_type = protein
                           organism = synthetic construct
SEQUENCE: 24
MDWIWRILFL VGAATGAHSA QPADIQMTQT TSSLSASLGD RVTISCRASQ DISKYLNWYQ    60
QKPDGTVKLL IYHTSRLHSG VPSRFSGSGS GTDYSLTISN LEQEDIATYF CQQGNTLPYT    120
FGGGTKLELK RGGGGSGGGG SGGGGSGGGG SEVQLQQSGP GLVAPSQSLS VTCTVSGVSL    180
PDYGVSWIRQ PPRKGLEWLG VIWGSETTYY NSALKSRLTI IKDNSKSQVF LKMNSLQTDD    240
TAIYYCAKHY YYGGSYAMDY WGQGTTVTVS S                                  271

SEQ ID NO: 25              moltype = DNA   length = 807
FEATURE                    Location/Qualifiers
misc_feature               1..807
                           note = Codon-optimized CD20 scFv - DNA sequence
source                     1..807
                           mol_type = other DNA
                           organism = synthetic construct
SEQUENCE: 25
atggactgga tctggcgcat cctcttcctc gtcggcgctg ctaccggcgc tcattcggcc    60
cagccggcca tggcgcaagt aaaactccaa gaatctgggg cggagctggt gaaaccgggg    120
gcgtctgtga agatgagctg taaagcatca ggctacacct tcacctccta taatatgcac    180
tgggtgaaac aaacacccgg acagggcctc gaatggattg tgccatcta tcctggaaat    240
ggtgatacct catataatca gaagtttaag gcaaggcta cgcttactgc ggataaaagc    300
tcttccactg cttacatgca actgagcagt ctcacttcag aggactcagc cgattattat    360
tgtgcccgca gcaactacta ctggtagtta tactggttttt gacgtttg ggggcaaggt    420
accaccgtca cggtttcttc tggtgggggc ggaagcggg gtggaggatc tggggcggt    480
ggttcagaca ttgaactcac ccagagccct actattctga cgcgtctcc aggtgaaaaa    540
gttacgatga cgtgcagagc atcaagtagt gtgaattata tggattggta tcaaaagaag    600
ccaggctcat ccccaaaacc gtggatctat gcaactagca acctcgcgtc aggggtgcca    660
gcaagttttt ccggaagtgg ttctggcaca tcttatagtc tcaccatttc ccgagtggag    720
gctgaggatg cggccactta ttactgccag caatggtcat tcaatccccc aacatttggt    780
ggcggaacaa aactcgaaat taaacgg                                       807

SEQ ID NO: 26              moltype = AA   length = 269
FEATURE                    Location/Qualifiers
REGION                     1..269
                           note = CD20 scFv - Protein sequence
source                     1..269
                           mol_type = protein
                           organism = synthetic construct
SEQUENCE: 26
MDWIWRILFL VGAATGAHSA QPAMAQVKLQ ESGAELVKPG ASVKMSCKAS GYTFTSYNMH    60
WVKQTPGQGL EWIGAIYPGN GDTSYNQKFK GKATLTADKS SSTAYMQLSS LTSEDSADYY    120
CARSNYYGSS YWFFDVWGQG TTVTVSSGGG GSGGGGSGGG GSDIELTQSP TILSASPGEK    180
VTMTCRASSS VNYMDWYQKK PGSSPKPWIY ATSNLASGVP ARFSGSGSGT SYSLTISRVE    240
AEDAATYYCQ QWSFNPPTFG GGTKLEIKR                                     269

SEQ ID NO: 27              moltype = DNA   length = 795
FEATURE                    Location/Qualifiers
```

| | | |
|---|---|---|
| misc_feature | 1..795 | |
| | note = Codon-optimized CD33 scfV - DNA sequence: | |
| source | 1..795 | |
| | mol_type = other DNA | |
| | organism = synthetic construct | |

SEQUENCE: 27

```
atggactgga tctggcgcat cctcttcctc gtcggcgctg ctaccggcgc tcattcggcc   60
cagccggccg acattcaaat gactcagtcc ccttccagct tgtcagcctc agtaggggac  120
cgggtcacga tcacctgtcg agcgtctgag tcagtggata actacgggat ttctttcatg  180
aactggttcc agcagaagcc cggcaaagct cctaagctcc ttatatatgc agcctcaaat  240
caggggagcg tgttcctag tcgcttcagt ggaagcggta gcgtacggga cttttacgttg  300
acgataagta gccttcagcc agatgacttt gccacttatt attgtcagca gtctaaggaa  360
gttccttgga cgtttggcca aggaacgaag gtcgaaatca aggggaggg gggctcagga  420
ggggcggca gtggtggtgg aggctctcaa gtccaactcg tacagtctgg cgcggaggtt  480
aaaaagccgg gaagctccgt gaaagtatcc tgtaaggcaa gcggatacac ctttaccgat  540
tataacatgc actgggttag gcaggcgccc ggccaaggtc tggaatggat cggttatatt  600
tatccataca acggtggtac cggctataat cagaagttta gagtaaggc tactattaca  660
gcggatgagt caaccaatac tgcatacatg gagctctcct cactcaggag cgaagatacc  720
gcagtgtatt actgtgcccg agggagacca gccatggact actggggtca gggtacccttt  780
gtgacagtat ctagc                                                   795
```

| | | |
|---|---|---|
| SEQ ID NO: 28 | moltype = AA length = 265 | |
| FEATURE | Location/Qualifiers | |
| REGION | 1..265 | |
| | note = CD33 scfV - Protein sequence | |
| source | 1..265 | |
| | mol_type = protein | |
| | organism = synthetic construct | |

SEQUENCE: 28

```
MDWIWRILFL VGAATGAHSA QPADIQMTQS PSSLSASVGD RVTITCRASE SVDNYGISFM   60
NWFQQKPGKA PKLLIYAASN QGSGVPSRFS GSGSGTDFTL TISSLQPDDF ATYYCQQSKE  120
VPWTFGQGTK VEIKGGGSG GGGSGGGGSQ VQLVQSGAEV KKPGSSVKVS CKASGYTFTD  180
YNMHWVRQAP GQGLEWIGYI YPYNGGTGYN QKFKSKATIT ADESTNTAYM ELSSLRSEDT  240
AVYYCARGRP AMDYWGQGTL VTVSS                                       265
```

| | | |
|---|---|---|
| SEQ ID NO: 29 | moltype = DNA length = 840 | |
| FEATURE | Location/Qualifiers | |
| misc_feature | 1..840 | |
| | note = Codon-optimized CSPG4 scfV - DNA sequence | |
| source | 1..840 | |
| | mol_type = other DNA | |
| | organism = synthetic construct | |

SEQUENCE: 29

```
atggactgga tctggcgcat cctcttcctc gtcggcgctg ctaccggcgc tcattcggcc   60
cagccggccg atatcgagct cacccaatct ccaaaattca tgtccacatc agtaggagac  120
agggtcagct caccctgcaa ggccagtcag aatgtggata ctaatgtagc gtggtatcaa  180
caaaaaccag gcaatctcc tgaaccactg cttttcatcg catcctaccg ttacactgga  240
gtccctgatc gcttcacagg cagtggatct gggacagatt tcactctcac catcagcaat  300
gtgcagtctg aagactggc agagtatttc tgtcagcaat ataacagcta tcctctgacg  360
ttcggtggc gcaccaagct ggaaatcaaa cgggctgccg cagaaggtgg aggcggttca  420
ggtggcggag gttccggcgg aggtggctct ggcggtggcg gatcggccat ggccaggtg  480
aagctgcagc agtcaggagg gggcttggtg caacctggag gctccatgaa actctcctgt  540
gttgtctctg gattcacttt cagtaattac tggatgaact gggtccgcca gtctccagag  600
aaggggcttg agtggattgc agaaattaga ttgaaatcca ataattttgg aagatattat  660
gcggagtctg tgaagggag gttcaccatc tcaagagatg attccaaag tagtgcctac  720
ctgcaaatga tcaacctaag agctgaagat actggcattt attactgtac cagttatggt  780
aactacgttg ggcactattt tgaccactgg ggccaaggga ccacggtcac cgtatcgagt  840
```

| | | |
|---|---|---|
| SEQ ID NO: 30 | moltype = AA length = 280 | |
| FEATURE | Location/Qualifiers | |
| REGION | 1..280 | |
| | note = CSPG4 scfV - Protein sequence | |
| source | 1..280 | |
| | mol_type = protein | |
| | organism = synthetic construct | |

SEQUENCE: 30

```
MDWIWRILFL VGAATGAHSA QPADIELTQS PKFMSTSVGD RVSVTCKASQ NVDTNVAWYQ   60
QKPGQSPEPL LFSASYRYTG VPDRFTGSGS GTDFTLTISN VQSEDLAEYF CQQYNSYPLT  120
FGGGTKLEIK RAAAEGGGS GGGGSGGGGS GGGGSAMAQV KLQQSGGGLV QPGGSMKLSC  180
VVSGFTFSNY WMNWVRQSPE KGLEWIAEIR LKSNNFGRYY AESVKGRFTI SRDDSKSSAY  240
LQMINLRAED TGIYYCTSYG NYVGHYFDHW GQGTTVTVSS                        280
```

| | | |
|---|---|---|
| SEQ ID NO: 31 | moltype = DNA length = 807 | |
| FEATURE | Location/Qualifiers | |
| misc_feature | 1..807 | |
| | note = Codon-optimized EGFR scFv - DNA sequence | |
| source | 1..807 | |
| | mol_type = other DNA | |
| | organism = synthetic construct | |

```
SEQUENCE: 31
atggactgga tctggcggat tctgtttctc gtgggagctg ccacaggcgc tcattctgct   60
cagcctgccg atattcttct tactcaatct cccgttattt tgtcagtatc cccaggtgag  120
cgagtcagct tctcttgtcg agcgtcacaa tccattggca ccaacataca ttggtaccaa  180
cagcgcacca acgggtctcc ccggctcttg attaagtacg catcagaaag tatttctggg  240
ataccagta ggttctcagg gagcgggagt ggcactgact ttaccctgtc cataaacagc  300
gttgagtctg aggacatcgc ggactactat tgtcagcaga caacaattg gccgaccacg  360
tttggtgcgg gaacaaaact tgaactcaaa ggcggcggag gaagcggagg cggaggatct  420
gggggcggag gctctggcgg aggggatct caggtgcagc tcaaacagtc aggacctggc  480
ctcgttcagc caagccaatc actgagtata acgtgcacgg tgagcggctt tagcctgaca  540
aactatggtg tccactgggt ccgccaatct cctggaaaag gcttgagtg gctcggtgtt  600
atctggtccg gtggtaacac agactacaac acgccattca ccagtcgcct tagtattaac  660
aaggacaact ccaagtctca ggttttcttt aaaatgaact ctctgcagtc taatgatacc  720
gcaattact actgtgcgag gcactcacg tactatgact atgagttcgc gtattgggc  780
caagggactc tcgttactgt ctcagcg                                       807

SEQ ID NO: 32              moltype = AA  length = 269
FEATURE                    Location/Qualifiers
REGION                     1..269
                           note = EGFR scFv - Protein sequence
source                     1..269
                           mol_type = protein
                           organism = synthetic construct
SEQUENCE: 32
MDWIWRILFL VGAATGAHSA QPADILLTQS PVILSVSPGE RVSFSCRASQ SIGTNIHWYQ   60
QRTNGSPRLL IKYASESISG IPSRFSGSGS GTDFTLSINS VESEDIADYY CQQNNNWPTT  120
FGAGTKLELK GGGGSGGGGS GGGGSGGGGS QVQLKQSGPG LVQPSQSLSI TCTVSGFSLT  180
NYGVHWVRQS PGKGLEWLGV IWSGGNTDYN TPFTSRLSIN KDNSKSQVFF KMNSLQSNDT  240
AIYYCARALT YYDYEFAYWG QGTLVTVSA                                    269

SEQ ID NO: 33              moltype = DNA  length = 822
FEATURE                    Location/Qualifiers
misc_feature               1..822
                           note = Codon-optimized IGF1R scFv - DNA sequence
source                     1..822
                           mol_type = other DNA
                           organism = synthetic construct
SEQUENCE: 33
atggactgga tctggcggat tctgtttctc gtgggagctg ccacaggcgc tcattctgct   60
cagcctgccg atgttgtaat gacgcagtca cccctgtcac tcccggtcac acccggagaa  120
ccagcgtcaa ttagctgccg atctagccaa agtttgcttc attccaatgg ttacaattat  180
ctcgactggt acttgcagaa acccggccaa tcccctcagc tgctcatcta ccttgggtct  240
aatagggcat ctgggttcc cgataggttc tctggctccg ggagcggcac cgactttacg  300
ttgaaaatct ctagggttga ggcggaagac gtaggcgttt actattgcat gcaggggacc  360
cactggccgc tgaccttcgg ccagggcacc aaggttgaaa taaaaggcgg cggaggaagc  420
ggaggcggag gatctggggg cggaggctct ggcgagggg atctcaggt acagctccag  480
gaatcaggac ccggttttgg taagccctcc gggaccttt ccctcacgtg tgcagtctca  540
ggtgggtcaa ttagttcttc caattggtgg tcttgggtgc ggcaaccacc tggtaaaggt  600
ctcgagtgga taggggaaat ttatcatagt ggctccacca attataaccc ctcactcaag  660
tccagggtta cgatatctgt ggacaaaagt aaaaaccaat tctccctcaa acttagtagt  720
gtaacagcg cagacaccgc ggtgtactac tgcgcacgt ggacaggccg aactgatgcc  780
tttgacattt ggggacaggg aactatggtg actgtgtcat cc                     822

SEQ ID NO: 34              moltype = AA  length = 274
FEATURE                    Location/Qualifiers
REGION                     1..274
                           note = IGF1R scFv -Protein sequence
source                     1..274
                           mol_type = protein
                           organism = synthetic construct
SEQUENCE: 34
MDWIWRILFL VGAATGAHSA QPADVVMTQS PLSLPVTPGE PASISCRSSQ SLLHSNGYNY   60
LDWYLQKPGQ SPQLLIYLGS NRASGVPDRF SGSGSGTDFT LKISRVEAED VGVYYCMQGT  120
HWPLTFGQGT KVEIKGGGGS GGGGSGGGGS GGGGSQVQLQ ESGPGLVKPS GTLSLTCAVS  180
GGSISSSNWW SWVRQPPPKG LEWIGEIYHS GSTNYNPSLK SRVTISVDKS KNQFSLKLSS  240
VTAADTAVYY CARWTGRTDA FDIWGQGTMV TVSS                              274

SEQ ID NO: 35              moltype = DNA  length = 822
FEATURE                    Location/Qualifiers
misc_feature               1..822
                           note = Codon-optimized CD30 scFv - DNA sequence
source                     1..822
                           mol_type = other DNA
                           organism = synthetic construct
SEQUENCE: 35
atggactgga tctggcggat tctgtttctc gtgggagctg ccacaggcgc tcattctgct   60
cagcctgccg atatccaaat gactcaatct cctagttcac tgtcagcctc tgttggtgat  120
cgcgtgacca ttacctgcca agctagccag gatattgcca ctacttgaa ctggtatcag  180
cagaagcctg gcaaagcccc aaagctgttg atctacgatg taagtaactt ggaaactggc  240
```

```
gtcccaagcc gcttctctgg atctggttca ggcaccgact tcactttcac tatcagcagc   300
ctgcagcctg aagatatcgc aacctactat tgccagcagg ttgctaatgt tcctctgact   360
ttcggccaag gcaccaaggt ggagatcaag gccggcggag gaagcggagg cggaggatct   420
gggggcggag gctctggcgg aggggggatct gaagttcagc ttgtagaatc tggaggtgga   480
ttggttcaac ctggtggctc tcttcgcctg agttgtgcag cctctgtgtt tactttctct   540
agttactgga tgcattgggt tcgtcaggct cctgggaaag gcctggaatg ggtttcagct   600
attagttgga gtggagatag tacttactac gcagacagtg tgaaaggtcg cttcaccatc   660
agccgtgata attctaagaa cactttgtac ctgcaaatga actccttgcg cgcagaagac   720
acggctgtgt actattgtgc ccgtgatcgc tctgcgactt ggtattatct ggggcttggt   780
ttcgatgtat ggggacaagg taccctggta acggtttcta gc                      822

SEQ ID NO: 36           moltype = AA  length = 274
FEATURE                 Location/Qualifiers
REGION                  1..274
                        note = CD30 scFv - Protein sequence
source                  1..274
                        mol_type = protein
                        organism = synthetic construct
SEQUENCE: 36
MDWIWRILFL VGAATGAHSA QPADIQMTQS PSSLSASVGD RVTITCQASQ DISNYLNWYQ    60
QKPGKAPKLL IYDVSNLETG VPSRFSGSGS GTDFTFTISS LQPEDIATYY CQQVANVPLT   120
FGQGTKVEIK GGGGSGGGGS GGGGSGGGGS EVQLVESGGG LVQPGGSLRL SCAASGFTFS   180
SYWMHWVRQA PGKGLEWVSA ISWSGDSTYY ADSVKGRFTI SRDNSKNTLY LQMNSLRAED   240
TAVYYCARDR SATWYYLGLG FDVWGQGTLV TVSS                                274

SEQ ID NO: 37           moltype = DNA  length = 825
FEATURE                 Location/Qualifiers
misc_feature            1..825
                        note = Codon-optimized HER2/neu scFv - DNA sequence
source                  1..825
                        mol_type = other DNA
                        organism = synthetic construct
SEQUENCE: 37
atggactgga tctggcggat tctgtttctc gtgggagctg ccacaggcgc tcattctgct    60
cagcctgccg acatccagat gacccagagc cccagcagcc tgagcgccag cgtgggcgac   120
agagtgacca tcacctgcag agccagccag gacgtgaaca ccgccgtggc ctggtaccag   180
cagaagcccg gcaaggcccc caagctgctg atctacagcg ccagcttcct gtacagcggc   240
gtgcccagca gattcagcgg cagcagaagc ggcaccgact tcaccctgac catcagcagc   300
ctgcagcccg aggacttcgc cacctactac tgccagcagc actacacccc cccccccacc   360
ttcggccagg gcaccaaggt ggagatcaag tcctcagggg gcgggggaag tggtgggggc   420
ggcagcggcg gaggggggctc aggaggaggc ggatcaggcg gatcagaggt gcagctggtg   480
gagagcggcg gcggcctggt gcagcccggc ggcagcctga actgagctg cgccgccagc   540
ggcttcaaca tcaaggacac ctacatccac tgggtgagac aggcccccgg caagggcctg   600
gagtgggtgg ccagaatcta ccccaccaac ggctacacca gatacgccga cagcgtgaag   660
ggcagattca ccatcagcgc cgacaccagc aagaacaccg cctacctgca gatgaacagc   720
ctgagagccg aggacaccgc cgtgtactac tgcagcagat ggggcggcga cggcttctac   780
gccatggact actggggcca gggcaccctg gtgaccgtga gcagc                   825

SEQ ID NO: 38           moltype = AA  length = 275
FEATURE                 Location/Qualifiers
REGION                  1..275
                        note = HER2/neu scFv - Protein sequence
source                  1..275
                        mol_type = protein
                        organism = synthetic construct
SEQUENCE: 38
MDWIWRILFL VGAATGAHSA QPADIQMTQS PSSLSASVGD RVTITCRASQ DVNTAVAWYQ    60
QKPGKAPKLL IYSASFLYSG VPSRFSGSRS GTDFTLTISS LQPEDFATYY CQQHYTTPPT   120
FGQGTKVEIK SSGGGSGGG GSGGGGSGGG GSGGGSEVQL VESGGGLVQPG GSLRLSCAAS   180
GFNIKDTYIH WVRQAPGKGL EWVARIYPTN GYTRYADSVK GRFTISADTS KNTAYLQMNS   240
LRAEDTAVYY CSRWGGDGFY AMDYWGQGTL VTVSS                               275

SEQ ID NO: 39           moltype = DNA  length = 798
FEATURE                 Location/Qualifiers
misc_feature            1..798
                        note = Codon-optimized GD2 scFv - DNA sequence VL/VH
source                  1..798
                        mol_type = other DNA
                        organism = synthetic construct
SEQUENCE: 39
atggactgga tctggcggat tctgtttctc gtgggagctg ccacaggcgc tcattctgct    60
cagcctgcca gcatcgtgat gacccagact cctaagttcc tgctggtgtc tgccggcgac   120
agagtgacca tcacctgtaa agccagccag agcgtgtcca cgacgtggc ctggtatcag   180
cagaagcccg gacagagccc caagctgctg atctacagcg ccagcaacag atacaccggc   240
gtgcccgata gattcaccgg ctctggctac ggcaccgact tcaccttcac catcagcacc   300
gtgcaggccg aggatctggc cgtgtacttc tgccagcaag actacagctc tcccggcgga   360
ggcaccaagc tggaaatcaa aggcggcgga ggaagcggag cggaggatc tggggggcgga   420
ggctctggcg gaggggggatc tcaggtgcaa gtgaaagagt ctggccctgg actggtggcc   480
ccaagccagt ctctgagcat cacatgtacc gtgtccggct tcagcctgac caactatggc   540
```

```
gtgcactggg tccgacagcc tccaggcaaa ggactggaat ggctgggagt gatttgggct    600
ggcggcagca ccaactacaa cagcgccctg atgagccggc tgagcatctc caaggacaac    660
agcaagagcc aggtgttcct gaagatgaac agcctgcaga ccgacgacac cgccatgtac    720
tactgtgcta gcagaggcgg caactacggc tacgccctgg attattgggg ccagggcaca    780
agcgtgaccg tgtcatct                                                  798
```

| | | |
|---|---|---|
| SEQ ID NO: 40 | moltype = DNA  length = 798 | |
| FEATURE | Location/Qualifiers | |
| misc_feature | 1..798 | |
| | note = Codon-optimized GD2 scFv - DNA sequence VH/VL | |
| source | 1..798 | |
| | mol_type = other DNA | |
| | organism = synthetic construct | |

```
SEQUENCE: 40
atggactgga tctggcggat tctgtttctc gtgggagctg ccacaggcgc tcattctgct    60
cagcctgccc aggtgcaagt gaaagagtct ggccctggac tggtggcccc aagccagtct    120
ctgagcatca catgtaccgt gtccggcttc agcctgacca ctatgggcgt gcactgggtc    180
cgacagcctc caggcaaagg actggaatgc tgggagtgta tttggctgg cggcagcacc    240
aactacaaca gcgccctgat gagccggctg agcatctcca aggacaacag caagagccag    300
gtgttcctga gatgaacag cctgcagacc gacgacaccg ccatgtacta ctgtgctagc    360
agaggcggca actacggcta cgccctggat tattggggcc agggcacaag cgtgaccgtg    420
tcatctggcg gcggaggaag cggaggcgga ggatctggcg gcggaggagg ttcgatcgta    480
atgactcaga ccccccaggt tctgctctgg tctgcgggcg acagagtgac cattaccctg    540
aagcagctca gagcgttcaa acgacggcct ggtaatcagc aagcctggac agaaccccaa    600
gctgctgatc tacagcgcca acagatacac cggcgtg    660
cccgatagat tcaccggctc tggctacggc accgacttca cctttaccat cagcaccgtg    720
caggccgagg atctggccgt gtacttctgc cagcaagact acagctctct cggcggaggc    780
accaagctgg aaatcaaa                                                  798
```

| | | |
|---|---|---|
| SEQ ID NO: 41 | moltype = AA  length = 266 | |
| FEATURE | Location/Qualifiers | |
| REGION | 1..266 | |
| | note = GD2 scFv - Protein sequence VL/VH | |
| source | 1..266 | |
| | mol_type = protein | |
| | organism = synthetic construct | |

```
SEQUENCE: 41
MDWIWRILFL VGAATGAHSA QPASIVMTQT PKFLLVSAGD RVTITCKASQ SVSNDVAWYQ    60
QKPGQSPKLL IYSASNRYTG VPDRFTGSGY GTDFTFTIST VQAEDLAVYF CQQDYSSLGG    120
GTKLEIKGGG GSGGGGSGGG GSGGGGSQVQ VKESGPGLVA PSQSLSITCT VSGFSLTNYG    180
VHWVRQPPGK GLEWLGVIWA GGSTNYNSAL MSRLSISKDN SKSQVFLKMN SLQTDDTAMY    240
YCASRGGNYG YALDYWGQGT SVTVSS                                         266
```

| | | |
|---|---|---|
| SEQ ID NO: 42 | moltype = AA  length = 266 | |
| FEATURE | Location/Qualifiers | |
| REGION | 1..266 | |
| | note = GD2 scFv - Protein sequence VH/VL | |
| source | 1..266 | |
| | mol_type = protein | |
| | organism = synthetic construct | |

```
SEQUENCE: 42
MDWIWRILFL VGAATGAHSA QPAQVQVKES GPGLVAPSQS LSITCTVSGF SLTNYGVHWV    60
RQPPGKGLEW LGVIWAGGST NYNSALMSRL SISKDNSKSQ VFLKMNSLQT DDTAMYYCAS    120
RGGNYGYALD YWGQGTSVTV SSGGGGSGGG GSGGGGSGGG GSSIVMTQTP KFLLVSAGDR    180
VTITCKASQS VSNDVAWYQQ KPGQSPKLLI YSASNRYTGV PDRFTGSGYG TDFTFTISTV    240
QAEDLAVYFC QQDYSSLGGG TKLEIK                                         266
```

| | | |
|---|---|---|
| SEQ ID NO: 43 | moltype = AA  length = 254 | |
| FEATURE | Location/Qualifiers | |
| REGION | 1..254 | |
| | note = High Affinity Variant Ig gamma FcRIII-A amino acid sequence | |
| source | 1..254 | |
| | mol_type = protein | |
| | organism = synthetic construct | |

```
SEQUENCE: 43
MWQLLLPTAL LLLVSAGMRT EDLPKAVVFL EPQWYRVLEK DSVTLKCQGA YSPEDNSTQW    60
FHNESLISSQ ASSYFIDAAT VDDSGEYRCQ TNLSTLSDPV QLEVHIGWLL LQAPRWVFKE    120
EDPIHLRCHS WKNTALHKVT YLQNGKGRKY FHHNSDFYIP KATLKDSGSY FCRGLVGSKN    180
VSSETVNITI TQGLAVSTIS SFFPPGYQVS FCLVMVLLFA VDTGLYFSVK TNIRSSTRDW    240
KDHKFKWRKD PQDK                                                      254
```

| | | |
|---|---|---|
| SEQ ID NO: 44 | moltype = DNA  length = 765 | |
| FEATURE | Location/Qualifiers | |
| misc_feature | 1..765 | |
| | note = High Affinity Variant IgGamma FcRIII-A nucleic acid sequence | |
| source | 1..765 | |
| | mol_type = other DNA | |

```
                    organism = synthetic construct
SEQUENCE: 44
atgtggcagc tgctgctgcc tacagctctc ctgctgctgg tgtccgccgg catgagaacc    60
gaggatctgc ctaaggccgt ggtgttcctg aacccagt ggtacagagt gctggaaaag     120
gacagcgtga ccctgaagtg ccaggcgcc tacagcccg aggacaatag caccagtgg      180
ttccacaacg agagcctgat cagcagccag gccagcagct acttcatcga cgccgccacc    240
gtggacgaca cgcgcgagta tagatgccag accaacctga gcaccctgag cgaccccgtg    300
cagctggaag tgcacatcgg atggctgctg ctgcaggccc ccagatgggt gttcaaagaa    360
gaggacccca tccacctgag atgccactct tggaagaaca ccgccctgca caaagtgacc    420
tacctgcaga acgcaagggg cagaaagtac ttccaccaca acagcgactt ctacatcccc    480
aaggccaccc tgaaggactc cggctcctac ttctgcagag gcctcgtggg cagcaagaac    540
gtgtccagcg agacagtgaa catcaccatc cccagggcc tggccgtgtc taccatcagc    600
agcttttttc caccoggcta ccaggtgtcc ttctgcctcg tgatggtgct gctgttcgcc    660
gtggacaccg gcctgtactt cagcgtgaaa acaaacatca gaagcagcac ccgggactgg    720
aaggaccaca agttcaagtg gcggaaggac ccccaggaca agtga                    765

SEQ ID NO: 45        moltype = AA   length = 61
FEATURE              Location/Qualifiers
REGION               1..61
                     note = CD8 Hinge peptide (Human)
source               1..61
                     mol_type = protein
                     organism = synthetic construct
SEQUENCE: 45
LSNSIMYFSH FVPVFLPAKP TTTPAPRPPT PAPTIASQPL SLRPEACRPA AGGAVHTRGL    60
D                                                                    61

SEQ ID NO: 46        moltype = DNA   length = 183
FEATURE              Location/Qualifiers
misc_feature         1..183
                     note = CD8 Hinge DNA (Human)
source               1..183
                     mol_type = other DNA
                     organism = synthetic construct
SEQUENCE: 46
ctgagcaaca gcatcatgta cttcagccac ttcgtgcctg tgttcctgcc tgccaagcct    60
acaacaacac cagcccctag acctccaacc cctgccccta caattgcctc tcagcctctg    120
tctctgaggc ccgaagcttg tagacctgct gctggcggag ctgtgcacac cagaggactg    180
gat                                                                  183

SEQ ID NO: 47        moltype = AA   length = 135
FEATURE              Location/Qualifiers
REGION               1..135
                     note = Human T-cell surface glycoprotein CD3 zeta
source               1..135
                     mol_type = protein
                     organism = synthetic construct
SEQUENCE: 47
PKLCYLLDGI LFIYGVILTA LFLRVKFSRS ADAPAYQQGQ NQLYNELNLG RREEYDVLDK    60
RRGRDPEMGG KPRRKNPQEG LYNELQKDKM AEAYSEIGMK GERRRGKGHD GLYQGLSTAT   120
KDTYDALHMQ ALPPR                                                    135

SEQ ID NO: 48        moltype = DNA   length = 822
FEATURE              Location/Qualifiers
misc_feature         1..822
                     note = Codon-optimized CD123 scFv DNA
source               1..822
                     mol_type = other DNA
                     organism = synthetic construct
SEQUENCE: 48
atggactgga tctggcggat tctgtttctc gtgggagctg ccacaggcgc tcattctgct    60
cagcctgccc tgcccgtcct gacacagtcc gcaagtgtga gtggatcacc tggacaatca   120
attactatca gttgcacagg cacttcctca gacgtaggga ggtatgatta cgtgtcatgg   180
tatcaacagc atccaggcaa agctcctcag ctcatgttt atgatgtgtc caacagaccg    240
tccgagtat ctaatcgctt cagtggatct aaatccggta atactgcctc cctcaccata    300
tcagggctcc aggccgaaga tgaagcgac tactattgca gtagttacac tggttcaagt    360
acgctttacg tttttggcac ggggaccaag gtaacggtcc tgggccaacc caaaggcgga   420
ggagggtccg gtggcggtgg cagtggtgga ggggatcag aggtgcaatt ggttgagagc    480
gtggttaaac ctggcgggtc ctccgcttc cttgtgcgc aagcggttt                 540
acctttagta atgcgtggat gagctgggtg cgacaagcac ccggaaaggg cctggagtgg    600
gtcggtagga ttaaaagcaa aacagatggt ggaacaaccg attatgcggc cccagtcaag    660
ggaaggttca ctatttcaag agacgattcc aagaacactc tttacctcca aatgaatagt    720
ttgaaaacag aggatacagc agtgtactat tgcacaacga ctacgacttt tggagcgga    780
tattactact ggggccaagg taccctggtc acagtttcat ca                      822

SEQ ID NO: 49        moltype = AA   length = 274
FEATURE              Location/Qualifiers
REGION               1..274
                     note = CD123 scFv Protein sequence
```

```
source                     1..274
                           mol_type = protein
                           organism = synthetic construct
SEQUENCE: 49
MDWIWRILFL VGAATGAHSA QPALPVLTQS ASVSGSPGQS ITISCTGTSS DVGRYDYVSW    60
YQQHPGKAPQ LMIYDVSNRP SGVSNRFSGS KSGNTASLTI SGLQAEDEAD YYCSSYTGSS   120
TLYVFGTGTK VTVLGQPKGG GGSGGGGSGG GGSEVQLVES GGGLVKPGGS LRLSCAASGF   180
TFSNAWMSWV RQAPGKGLEW VGRIKSKTDG GTTDYAAPVK GRFTISRDDS KNTLYLQMNS   240
LKTEDTAVYY CTTDYDFWSG YYYWGQGTLV TVSS                               274

SEQ ID NO: 50              moltype = DNA  length = 807
FEATURE                    Location/Qualifiers
misc_feature               1..807
                           note = Codon-optimized PD-L1 scFvDNA
source                     1..807
                           mol_type = other DNA
                           organism = synthetic construct
SEQUENCE: 50
atggactgga tctggcggat tctgtttctc gtgggagctg ccacaggcgc tcattctgct    60
cagcctgcca catccagat gacccagtct ccatcttctg tgtctgcatc tgtaggagac   120
agagtcacca tcacttgtcg ggcgagtcag gatattagcc gctggttagc ctggtatcag   180
cagaaaccag ggaaagcccc taaactcctg atctatgctg catccagttt gcaaagtggg   240
gtcccatcga ggttcagcgg cagtggatct gggacagatt tcgctctcac tatcagcagc   300
ctgcagcctg aagattttgc aacttactat tgtcaacagg ctgacagtcg tttctcgatc   360
accttcggcc aagggacacg actggagatt aaaggcggcg aggaagcgg aggcggagga   420
tctggggagc tctgg cggaggggga tctgaggtgc agctggtgca gtctggggga   480
ggcttggtac agcctggggg gtccctgaga ctctcctgtg cagcctctgg attcaccttc   540
agtagctata gcatgaactg ggtccgccag gctccaggga aggggctgga gtgggtttca   600
tacattagta gtagtagtag taccatacag tacgcagact ctgtgaaggg ccgattcacc   660
atctccagag acaatgccaa gaactcactg tatctgcaaa tgaacagcct gagagacgag   720
gacacggctg tgtattactg tgcgagaggg gactactact acggtatgga cgtctggggc   780
caagggacca cggtcaccgt gagctca                                        807

SEQ ID NO: 51              moltype = AA  length = 269
FEATURE                    Location/Qualifiers
REGION                     1..269
                           note = PD-L1 scFv Protein
source                     1..269
                           mol_type = protein
                           organism = synthetic construct
SEQUENCE: 51
MDWIWRILFL VGAATGAHSA QPANIQMTQS PSSVSASVGD RVTITCRASQ DISRWLAWYQ    60
QKPGKAPKLL IYAASSLQSG VPSRFSGSGS GTDFALTISS LQPEDFATYY CQQADSRFSI   120
TFGQGTRLEI KGGGGSGGGG SGGGGSGGGG SEVQLVQSGG GLVQPGGSLR LSCAASGFTF   180
SSYSMNWVRQ APGKGLEWVS YISSSSSTIQ YADSVKGRFT ISRDNAKNSL YLQMNSLRDE   240
DTAVYYCARG DYYYGMDVWG QGTTVTVSS                                      269

SEQ ID NO: 52              moltype = DNA  length = 807
FEATURE                    Location/Qualifiers
misc_feature               1..807
                           note = Codon-optimized B7-H4 scFvDNA
source                     1..807
                           mol_type = other DNA
                           organism = synthetic construct
SEQUENCE: 52
atggactgga tctggcggat tctgtttctc gtgggagctg ccacaggcgc tcattctgct    60
cagcctgccg aagttcagct tgtagaatct ggaggtggat tggttcaacc tggtggctct   120
cttcgcctga gttgtgcagc tctggttttt actttcaata gttacgctat gcattgggtt   180
cgtcaggctc ctgggaaagg cctggaatgg gtttcagcta ttagtggtaa tggaggtagt   240
actcgttacg cagacagtgt gaaaggtcgc ttcaccatca gccgtgataa ttctaagaac   300
acttttgtacc tgcaaatgaa ctccttgcgc gcagaagaca cggctgtgta ctattgtgcc   360
cgtgatcgct tcggaaggt tcatggtttc gatgtatggg gacaaggtac cctggtaacg   420
gtttctagcg gaggtggtgg gagtggtgga ggcggctcgg gtggaggtgg ttcaggagga   480
ggcggagata tccaaatgac tcaatctcct gttcactgt cagcctctgt tggtgatcgc   540
gtgaccatta cctgccaagc tagccaggat attagcaact acttgaactg gtatcagcag   600
aagcctggca agcccccaaa gctgttgatc tacgatgcaa gtaacttgga aactggcgtc   660
ccaagccgct tctctggatc tggttcaggc accgacttca ctttcactat cagcagcctg   720
cagcctgaag atatcgcaac ctactattgc cagcaggatg ctacttttcc tttgactttc   780
ggccaaggca ccaaggtgga gatcaag                                        807

SEQ ID NO: 53              moltype = AA  length = 269
FEATURE                    Location/Qualifiers
REGION                     1..269
                           note = B7-H4 scFvProtein
source                     1..269
                           mol_type = protein
                           organism = synthetic construct
SEQUENCE: 53
MDWIWRILFL VGAATGAHSA QPAEVQLVES GGGLVQPGGS LRLSCAASGF TFNSYAMHWV    60
```

-continued

```
RQAPGKGLEW VSAISGNGGS TRYADSVKGR FTISRDNSKN TLYLQMNSLR AEDTAVYYCA  120
RDRFRKVHGF DVWGQGTLVT VSSGGGGSGG GGSGGGGSGG GGDIQMTQSP SSLSASVGDR  180
VTITCQASQD ISNYLNWYQQ KPGKAPKLLI YDASNLETGV PSRFSGSGSG TDFTFTISSL  240
QPEDIATYYC QQDATFPLTF GQGTKVEIK                                    269

SEQ ID NO: 54           moltype = DNA  length = 1188
FEATURE                 Location/Qualifiers
misc_feature            1..1188
                        note = Codon-optimized HIV-gp120 binding domain (CD4)DNA
source                  1..1188
                        mol_type = other DNA
                        organism = synthetic construct
SEQUENCE: 54
atgaaccggg gagtcccttt taggcacttg cttctggtgc tgcaactggc gctcctccca  60
gcagccactc agggaaagaa agtggtgctg ggcaaaaaag gggatacagt ggaactgacc  120
tgtacagctt cccagaagaa gagcatacaa ttccactgga aaaactccaa ccagataaag  180
attctgggaa atcagggctc cttcttaact aaaggtccat ccaagctgaa tgatcgcgct  240
gactcaagaa gaagcctttg ggaccaagga aactttcccc tgatcatcaa gaatcttaag  300
atagaagact cagatactta catctgtgaa gtggaggacc agaaggagga ggtgcaattg  360
ctagtgttcg gattgactgc caactctgac acccacctgc ttcaggggca gagcctgacc  420
ctgaccttgg agagcccccc tggtagtagc cctcagtgc aatgtaggag tccaaggggt  480
aaaaacatac aggggggaa gaccctctcc gtgtctcagc tggagctcca ggatagtggc  540
acctggacat gcactgtctt gcagaaccag aagaaggtgg agttcaaaat agacatcgtg  600
gtgctagctt tccagaaggc ctccagcata gtctataaga aagaggggga acaggtggag  660
ttctccttcc cactcgcctt tacagttgaa aagctgacgg gcagtggcga gctgtggtgg  720
caggcggaga gggcttcctc ctccaagtct tggatcacct ttgacctgaa gaacaaggaa  780
gtgtctgtaa aacgggttac ccaggaccct aagctccaga tgggcaagaa gctcccgctc  840
cacctcaccc tgccccaggc cttgcctcag tatgctggct ctggaaacct caccctggcc  900
cttgaagcga aaacaggaaa gttgcatcag gaagtgaacc tggtggtgat gagagccact  960
cagctccaga aaaatttgac ctgtgaggtg tggggaccca cctcccctaa gctgatgctg  1020
agtttgaaac tggagaacaa ggaggcaaag gtctcgaagc gggagaaggc ggtgtgggtg  1080
ctgaaccctg aggcggggat gtggcagtgt ctgctgagtg actcgggaca ggtcctgctg  1140
gaatccaaca tcaaggttct gcccacatgg tccaccccgg tgcagcca              1188

SEQ ID NO: 55           moltype = AA  length = 396
FEATURE                 Location/Qualifiers
REGION                  1..396
                        note = HIV-gp120 binding domain (CD4) Protein
source                  1..396
                        mol_type = protein
                        organism = synthetic construct
SEQUENCE: 55
MNRGVPFRHL LLVLQLALLP AATQGKKVVL GKKGDTVELT CTASQKKSIQ FHWKNSNQIK  60
ILGNQGSFLT KGPSKLNDRA DSRRSLWDQG NFPLIIKNLK IEDSDTYICE VEDQKEEVQL  120
LVFGLTANSD THLLQGQSLT LTLESPPGSS PSVQCRSPRG KNIQGGKTLS VSQLELQDSG  180
TWTCTVLQNQ KKVEFKIDIV VLAFQKASSI VYKKEGEQVE FSFPLAFTVE KLTGSGELWW  240
QAERASSSKS WITFDLKNKE VSVKRVTQDP KLQMGKKLPL HLTLPQALPQ YAGSGNLTLA  300
LEAKTGKLHQ EVNLVVMRAT QLQKNLTCEV WGPTSPKLML SLKLENKEAK VSKREKAVWV  360
LNPEAGMWQC LLSDSGQVLL ESNIKVLPTW STPVQP                            396

SEQ ID NO: 56           moltype = DNA  length = 840
FEATURE                 Location/Qualifiers
misc_feature            1..840
                        note = Codon-optimized FAP scFv VL/VH DNA
source                  1..840
                        mol_type = other DNA
                        organism = synthetic construct
SEQUENCE: 56
atggactgga tctggcggat tctgtttctc gtgggagctg ccacaggcgc tcattctgct  60
cagcctgccg acatcgtgat gacacagagc ccttctagcc tggccgtgtc cgtgggagag  120
aaagtgacca tgagctgcaa gagcagccag agcctgctgt actcccggaa ccagaagaac  180
tacctggcct ggttccagca gaagcccggc cagtctccta agctgctgat cttctgggcc  240
agcaccagag aaagcggcgt gcccgataga ttcaccggca gcggctttgg caccgacttc  300
aacctgacaa tcagcagcgt gcaggccgag gacctggctg tgtacgattg ccagcagtac  360
ttcagctacc ctctgacctt tggagccggc accaagctgg aactgagagg cggcggagga  420
agcggaggcg gaggatctgg gggcggaggc tctggcggag gggatctca ggttcagctg  480
cagcagtctg gacctgagct ggttaagcct ggcgcctccg tgaagatgag ctgcaagacc  540
agccggtaca ccttcaccga gtacaccatc cactgggtcc gacagagcca cggcaagagc  600
ctggaatgga tcggcggcat caaccccaac aacggcatcc ccaactacaa ccagaagttc  660
aagggcagag ccacactgac cgtgggcaag tctagcagca ccgcctacat ggaactgcgg  720
agcctgacaa gcgaggacag cgccgtgtac ttctgcgcca gaagaagaat cgcctacggc  780
tacgatgagg gccacgccat ggattattgg ggccagggaa caagcgtgac cgtgtctagt  840

SEQ ID NO: 57           moltype = DNA  length = 840
FEATURE                 Location/Qualifiers
misc_feature            1..840
                        note = Codon-optimized FAP scFv VH/VL DNA
source                  1..840
                        mol_type = other DNA
```

```
                        organism = synthetic construct
SEQUENCE: 57
atggactgga tctggcggat tctgtttctc gtgggagctg ccacaggcgc tcattctgct     60
cagcctgccc aggttcagct gcagcagtct ggacctgagc tggttaagcc tggcgcctcc    120
gtgaagatga gctgcaagac cagccggtac accttcaccg agtacaccat ccactgggtc    180
cgacagagcc acggcaagag cctggaatgg atcggcggca tcaacccaaa caacggcatc    240
cccaactaca accagaagtt caagggcaga gccacactga ccgtgggcaa gtctagcagc    300
accgcctaca tggaactgcg gagcctgaca agcgaggaca cgccgtgta cttctgcgcc     360
agaagaagaa tcgcctacgg ctacgatgag ggccacgcca tggattattg gggccaggga    420
acaagcgtga ccgtgtctag tggcggcgga ggaagcggag gcggaggatc tgggggcgga    480
ggctctggcg gaggggggatc tgacatcgtg atgacacaga gcccttctag cctggccgtg    540
tccgtgggag agaaagtgac catgagctgc aagagcagcc agagcctgct gtactcccgg    600
aaccagaaga actacctggc ctggttccag cagaagcccg gccagtctcc taagctgctg    660
atcttctggg ccagcaccag agaaagcggc gtgcccgata gattcaccgg cagcggcttt    720
ggcaccgact tcaacctgac aatcagcagc gtgcaggaca aggacctggc tgtgtacgat    780
tgccagcagt acttcagcta ccctctgacc tttggagccg gcaccaagct ggaactgaga    840

SEQ ID NO: 58              moltype = AA  length = 280
FEATURE                    Location/Qualifiers
REGION                     1..280
                           note = FAP scFvVL/VH protein
source                     1..280
                           mol_type = protein
                           organism = synthetic construct
SEQUENCE: 58
MDWIWRILFL VGAATGAHSA QPADIVMTQS PSSLAVSVGE KVTMSCKSSQ SLLYSRNQKN     60
YLAWFQQKPG QSPKLLIFWA STRESGVPDR FTGSGFGTDF NLTISSVQAE DLAVYDCQQY    120
FSYPLTFGAG TKLELRGGGG SGGGGSGGGG SGGGGSQVQL QQSGPELVKP GASVKMSCKT    180
SRYTFTEYTI HWVRQSHGKS LEWIGGINPN NGIPNYNQKF KGRATLTVGK SSSTAYMELR    240
SLTSEDSAVY FCARRRIAYG YDEGHAMDYW GQGTSVTVSS                          280

SEQ ID NO: 59              moltype = AA  length = 280
FEATURE                    Location/Qualifiers
REGION                     1..280
                           note = FAP scFvVH/VL protein
source                     1..280
                           mol_type = protein
                           organism = synthetic construct
SEQUENCE: 59
MDWIWRILFL VGAATGAHSA QPAQVQLQQS GPELVKPGAS VKMSCKTSRY TFTEYTIHWV     60
RQSHGKSLEW IGGINPNNGI PNYNQKFKGR ATLTVGKSSS TAYMELRSLT SEDSAVYFCA    120
RRRIAYGYDE GHAMDYWGQG TSVTVSSGGG GSGGGGSGGG GSGGGGSDIV MTQSPSSLAV    180
SVGEKVTMSC KSSQSLLYSR NQKNYLAWFQ QKPGQSPKLL IFWASTRESG VPDRFTGSGF    240
GTDFNLTISS VQAEDLAVYD CQQYFSYPLT FGAGTKLELR                          280

SEQ ID NO: 60              moltype = DNA  length = 1233
FEATURE                    Location/Qualifiers
misc_feature               1..1233
                           note = artificial sequence
source                     1..1233
                           mol_type = other DNA
                           organism = synthetic construct
SEQUENCE: 60
atggactgga tctggcggat tctgtttctc gtgggagctg ccacaggcgc tcattctgct     60
cagcctgccg acatccagat gacccagagc cccagcctga gcgccag cgtgggcgac       120
agagtgacca tcacctgcag agccagccag gacgtgaaca ccgccgtggc ctggtaccag    180
cagaagcccg gcaaggcccc caagctgctg atctacagcg ccagcttcct gtacagcggc    240
gtgcccagca gattcagcgg cagcagaagc ggcaccgact tcaccctgac catcagcagc    300
ctgcagcccg aggacttcgc cacctactac tgccagcagc actacaccac ccccccacc    360
ttcggccagg gcaccaaggt ggagatcaag tcctcaggcg gcggggaag tggtggcgga    420
ggcagcggcg gaggggctc aggaggaggc ggatcaggcg gatcagaggt gcagctggtg    480
gagagcggcg gcggcctggt gcagcccggc ggcagcctga ctgagctg cgccgccagc     540
ggcttcaaca tcaaggacac ctacatccac tgggtgagac aggccccgg caagggcctg    600
gagtgggtgg ccagaatcta ccccaccaac ggctacacca gatacgccga cagcgtgaag    660
ggcagattca ccatcagcgc cgacaccagc aagaacaccg cctacctgca gatgaacagc    720
ctgagagccg aggacaccgc cgtgtactac tgcagcagat ggggccggca cggcttctac    780
gccatggact actggggcca gggcaccctg gtgaccgtga gcagcgcggc cgcgctgagc    840
aacagcatca tgtacttcag ccacttcgtg cctgtgttcc tgcctgccaa gcctacaaca    900
acaccagccc ctagacctcc aacccctgcc cctacaattg cctctcagcc tctgtctctg    960
aggcccgaag cttgtagacc tgctgctggc ggagctgtgc acaccagagg actggatttc    1020
gcctgctttt gggtgctggt ggtcgtgggc ggagtgctgg cttgttattc tctgctggtc    1080
accgtggcct tcatcatctt tgggtccga ctgaagatcc aggtccgaaa ggccgccatc    1140
accagctacg agaagtctga tggcgtgtac accggcctga gcaccagaaa ccaggaaacc    1200
tacgagacac tgaagcacga gaagcccccc cag                                1233

SEQ ID NO: 61              moltype = DNA  length = 1230
FEATURE                    Location/Qualifiers
misc_feature               1..1230
                           note = artificial sequence
```

```
source                  1..1230
                        mol_type = other DNA
                        organism = synthetic construct
SEQUENCE: 61
atggactgga tctggcggat tctgtttctc gtgggagctg ccacaggcgc tcattctgct    60
cagcctgccg atatccaaat gactcaatct cctagttcac tgtcagcctc tgttggtgat   120
cgcgtgacca ttacctgcca agctagccag gatattagca actacttgaa ctggtatcag   180
cagaagcctg gcaaagcccc aaagctgttg atctacgatg taagtaactt ggaaactggc   240
gtcccaagcc gcttctctgg atctggttca ggcaccgact tcacttttca tatcagcagc   300
ctgcagcctg aagatatcgc aacctactat tgccagcagg ttgctaatgt tcctctgact   360
ttcggccaag gcaccaaggt ggagatcaag ggcggcggag gaagcggagg cggaggatct   420
ggggggcggag gctctggcgg aggggggatct gaagttcagc ttgtagaatc tggaggtgga   480
ttggttcaac ctggtggctc tcttcgcctg agttgtgcag cctctggttt tactttctct   540
agttactgga tgcattgggt tcgtcaggct cctgggaaag gcctggaatg ggtttcagct   600
attagttgga gtggagatag tacttactac gcagacagtg tgaaaggtcg cttcaccatc   660
agccgtgata attctaagaa cactttgtac ctgcaaatga actccttgcg cgcagaagac   720
acggctgtgt actattgtgc ccgtgatcgc tctgcgactt ggtattatct ggggcttggt   780
ttcgatgtat ggggacaagg tacccggta acggtttcta gcgcggccgc gctgagcaac   840
agcatcatgt acttcagcca cttcgtgcct gtgttcctgc ctgccaagcc tacaacaaca   900
ccagccccta gacctccaac ccctgcccct acaattgcct ctcagcctct gtctctgagg   960
cccgaagctt gtagacctgc tgctggcgga gctgtgcaca ccagaggact ggatttcgcc  1020
tgcttttggg tgctggtggt cgtggggcgga gtgctggctt gttattctct gctggtcacc  1080
gtggccttca tcatcttttg ggtccgactg aagatccagg tccgaaaggc cgccatcacc  1140
agctacgaga agtctgatgg cgtgtacacc ggcctgagca cagaaaccca ggaaacctac  1200
gagacactga agcacgagaa gccccccag                                     1230

SEQ ID NO: 62           moltype = DNA  length = 1215
FEATURE                 Location/Qualifiers
misc_feature            1..1215
                        note = artificial sequence
source                  1..1215
                        mol_type = other DNA
                        organism = synthetic construct
SEQUENCE: 62
atggactgga tctggcggat tctgtttctc gtgggagctg ccacaggcgc tcattctgct    60
cagcctgccg atattcttct tactcaatct cccgttattt tgtcagtatc cccaggtgag   120
cgagtcagct tctcttgtcg agcgtcacaa tccattggca ccaacataca ttggtaccaa   180
cagcgcacca acgggtctcc ccggctcttg attaagtacg catcagaaag tatttctggg   240
atcccagta ggttctcagg gagcgggagt ggcactgact ttaccctgtc cataaacagt   300
gttgagtctg aggacatcgc ggactactat tgtcagcaga caacaattg gccgaccacg   360
tttggtgcgg gaacaaaact gaaactcaaa ggcggcggag gaagcggagg cggaggatct   420
ggggggcggag gctctggcgg aggggggatct caggtgcagc tcaaacagtc aggacctggc   480
ctcgttcagc caagccaatc actgagtata acgtgcagt tcaggtggtc tagcctgaca   540
aactatggtg tccactgggt ccgccaatct cctggaaaag gcttggagtg gctcggtgtt   600
atctggtccg gtggtaacac agactacaac acgccattca ccagtcgcct tagtattaac   660
aaggacaact ccaagtctca ggttttcttt aaaatgaact ctctgcagtc taatgatacc   720
gcaatttact actgtgcgag ggcactcacg tactatgatg atgagttcgc gtattgggc   780
caagggactc tcgttactgt ctcagcggcg gccgcgctga gcaacagcat catgtacttc   840
agccacttcg tgcctgtgtt cctgcctgcc aagcctacaa caacaccagc cctagacct   900
ccaaccctg cccctacaat tgcctctcag cctctgtctc tgaggcccga agcttgtaga   960
cctgctgctg gcggagctgt gcacaccaga ggactggatt tcgcctgctt ttgggtgctg  1020
gtggtcgtgg gcggagtgct ggcttgttat tctctgctgg tcaccgtggc cttcatcatc  1080
ttttgggtcc gactgaagat ccaggtccga aaggccgcca tcaccagcta cgagaagtct  1140
gatggcgtgt acaccggcct gagcacagaa accaggaaa cctacgagac actgaagcac  1200
gagaagcccc ccag                                                    1215

SEQ ID NO: 63           moltype = DNA  length = 1230
FEATURE                 Location/Qualifiers
misc_feature            1..1230
                        note = artificial sequence
source                  1..1230
                        mol_type = other DNA
                        organism = synthetic construct
SEQUENCE: 63
atggactgga tctggcggat tctgtttctc gtgggagctg ccacaggcgc tcattctgct    60
cagcctgccg atgttgtaat gacgcagtca cccctgtcac tcccggtcac acccggagaa   120
ccagcgtcaa ttagctgccg atctagccaa agtttgcttc attccaatgg ttacaattat   180
ctcgactggt acttgcagaa acccggccaa tcccctcagc tgctcatcta ccttgggtct   240
aatagggcat ctggggttcc cgataggttc tctggctccg gaccgggcac cgactttacg   300
ttgaaaatct ctagggttga ggcggaagac gtaggcgttt actattgcat gcaggggacc   360
cactggccgc tgaccttcgg ccagggcacc aaggttgaaa taaaaggcgg cggaggaagc   420
ggaggcggag gatctggggg cggaggctct ggcgagggg atctcaggt acagctccag   480
gaatcaggac cggttggt taagcctcc gggacccttt ccctcacgtg tgcagtctca   540
ggtgggtcaa ttagttcttc caattggtgg tcttgggtgc agccaccc tggtaaaggt   600
ctcgagtgga taggggaaat ttatcatagt ggctccacca attataaccc ctcactcaag   660
tccagggtta cgatatctgt ggacaaaagt aaaaaccaat ctccctcaa acttagtagt   720
gtaacagcgc agacaccgc ggtgtactac tgcgcacggt ggacaggccg aactgatgcc   780
tttgacattt ggggacaggg aactatggtg actgtgtcat ccgcggccgc gctgagcaac   840
agcatcatgt acttcagcca cttcgtgcct gtgttcctgc ctgccaagcc tacaacaaca   900
```

```
ccagccccta gacctccaac ccctgcccct acaattgcct ctcagcctct gtctctgagg   960
cccgaagctt gtagacctgc tgctggcgga gctgtgcaca ccagaggact ggatttcgcc  1020
tgcttttggg tgctggtggt cgtgggcgga gtgctggctt gttattctct gctggtcacc  1080
gtggccttca tcatcttttg ggtccgactg aagatccagg tccgaaaggc cgccatcacc  1140
agctacgaga agtctgatgg cgtgtacacc ggcctgagca ccagaaacca ggaaacctac  1200
gagacactga agcacgagaa gccccccag                                    1230

SEQ ID NO: 64           moltype = DNA   length = 1203
FEATURE                 Location/Qualifiers
misc_feature            1..1203
                        note = artificial sequence
source                  1..1203
                        mol_type = other DNA
                        organism = synthetic construct
SEQUENCE: 64
atggactgga tctggcgcat cctcttcctc gtcggcgctg ctaccggcgc tcattcggcc    60
cagccggccg acattcaaat gactcagtcc ccttccagct tgtcagcctc agtagggac   120
cgggtcacga tcacctgtcg agcgtctgag tcagtggata actacgggat ttctttcatg   180
aactggttcc agcagaagcc cggcaaagct cctaagctcc ttatatatgc agcctcaaat   240
caggggagcg gtgttcctag tcgcttcagt ggaagcggta cgtacgga ctttacgttg    300
acgataagta gccttcagcc agatgacttt gccacttatt attgtcagca gtctaaggaa   360
gttccttgga cgtttggcca aggaacgaag gtcgaaatca aaggggagg tctgccagga   420
ggggccgga gtggtggtgg aggctctcaa gtccaactcg tacagtctgg cgcggaggtt   480
aaaaagccgg gaagctccgt gaaagtatcc tgtaaggcaa gcggatacac ctttaccgat   540
tataacatgc actgggttag gcaggcgccc ggccaaggtc tggaatggat cggttatatt   600
tatccataca acggtggtac cggctataat cagaagttta agagtaaggc tactattaca   660
gcggatgagt caaccaatac tgcatacatg gagctctcct cactcaggag cgaagatacc   720
gcagtgtatt actgtgcccg agggagacca gccatggact actggggtca gggtacctt   780
gtgacagtat ctagcgcggc cgcgctgagc aacagcatca tgtacttcag ccacttcgtg   840
cctgtgttcc tgcctgccaa gcctacaaca acaccagtcc ctagacctcc aaccctgcc   900
cctacaattg cctctcagcc tctgtctctg aggcccgaag cttgtagacc tgctgctggc   960
ggagctgtgc acaccagagg actggatttc gcctgctttt gggtgctggt ggtcgtgggc  1020
ggagtgctgc cttgttattc tctgctggtc accgtggcct tcatcatctt tgggtccga  1080
ctgaagatcc aggtccgaaa ggccgccatc accagctacg agaagtctga tggcgtgtac  1140
accggcctga gcaccagaaa ccaggaaacc tacgagacac tgaagcacga agagccccc  1200
cag                                                               1203

SEQ ID NO: 65           moltype = DNA   length = 1215
FEATURE                 Location/Qualifiers
misc_feature            1..1215
                        note = artificial sequence
source                  1..1215
                        mol_type = other DNA
                        organism = synthetic construct
SEQUENCE: 65
atggactgga tctggcggat tctgtttctc gtgggagctg ccacaggcgc tcattctgct    60
cagcctgcca acatccagat gacccagtct ccatcttctc tgtctgcatc tgtaggagac   120
agagtcacca tcacttgtcg ggcgagtcag gatattagcc gctggttagc ctggtatcag   180
cagaaaccag ggaaagcccc taaactcctg atctatgctg catccagttt gcaaagtggg   240
gtcccatcga ggttcagcgg cagtggatct gggacagatt tcgctctcac tatcagcagc   300
ctgcagcctg aagattttgc aacttactat tgtcaacagg ctgacagtcg tttctcgatc   360
accttcggcc aagggacacg actggagatt aaaggcggcg aggaagcgg aggcggagga   420
tctgggggcg gaggctctgg cggaggggga tctgaggtgc agctggtgca gtctggggga   480
ggcttggtac agcctggggg gtccctgaga ctctcctgtg cagcctctgg attcaccttc   540
agtagctata gcatgaactg ggtccgccag gctccaggga agggctga gtgggtttca   600
tacattagta gtagtagtag taccatacag tacgcagact ctgtgaaggg ccgattcacc   660
atctccagag acaatgccaa gaactcactg tatctgcaaa tgaacagcct gagagacgag   720
gacacggctg tgtattactg tgcgagaggg gactactact acggtatgga cgtctggggc   780
caagggacca cggtcaccgt gagctcagcg gccgcgctga acagcatcat gtacttc    840
agccacttcg tgcctgtgtt cctgcctgcc aagcctacaa caaccagcc cctagacct   900
ccaacccctg cccctacaat gcctctcag cctctgtctc tgaggcccga gcttgtaga   960
cctgctgctg gcggagctgt gcacaccaga ggactggatt tcgcctgctt tgggtgctgg  1020
tggtcgtggg cggagtgctg gcttgttat tctctgctgg tcaccgtggc cttcatcatc  1080
ttttggtcc gactgaagat caggtccga aaggccgcca tcaccagcta cgagaagtct  1140
gatggcgtgt acaccggcct gagcaccaga aaccaggaaa cctacgagac actgaagcac  1200
gagaagcccc cccag                                                   1215

SEQ ID NO: 66           moltype = DNA   length = 1203
FEATURE                 Location/Qualifiers
misc_feature            1..1203
                        note = artificial sequence
source                  1..1203
                        mol_type = other DNA
                        organism = synthetic construct
SEQUENCE: 66
atggactgga tctggcgcat cctcttcctc gtcggcgctg ctaccggcgc tcattcggcc    60
cagccggccg acattcaaat gactcagtcc ccttccagct tgtcagcctc agtagggac   120
cgggtcacga tcacctgtcg agcgtctgag tcagtggata actacgggat ttctttcatg   180
aactggttcc agcagaagcc cggcaaagct cctaagctcc ttatatatgc agcctcaaat   240
```

```
caggggagcg gtgttcctag tcgcttcagt ggaagcggta gcggtacgga cttttacgttg  300
acgataagta gccttcagcc agatgacttt gccacttatt attgtcagca gtctaaggaa  360
gttccttgga cgtttggcca aggaacgaag gtcgaaatca aagggggagg gggctcagga  420
gggggcggca gtggtggtgg aggctctcaa gtccaactcg tacagtctgg cgcggaggtt  480
aaaaagccgg gaagctccgt gaaagtatcc tgtaaggcaa gcggatacac cttttaccgat  540
tataacatgc actgggttag gcaggcgccc ggccaaggtc tggaatggat cggttatatt  600
tatccataca acggtggtac cggctataat cagaagttta agagtaaggc tactattaca  660
gcggatgagt caaccaatac tgcatacatg gagctctcct cactcaggag cgaagatacc  720
gcagtgtatt actgtgcccg agggagacca gccatgact actggggtca gggtaccctt  780
gtgacagtat ctagcgcggc cgcgctgagc aacagcatca tgtactttcag ccacttcgtg  840
cctgtgttcc tgcctgccaa gcctacaaca acaccagccc ctagacctcc aacccctgcc  900
cctacaattg cctctcagcc tctgtctctg aggcccgaag cttgtagacc tgctgctggc  960
ggagctgtgc acaccagagg actggatttc gcctgcttt gggtgctggt ggtcgtgggc 1020
ggagtgctgg cttgttattc tctgctggtc accgtgcct tcatcatctt ttgggtccga 1080
ctgaagatcc aggtccgaaa ggccgccatc accagctacg agaagtctga tggcgtgtac 1140
accggcctga gcaccagaaa ccaggaaacc tacgagacac tgaagcacga gaagccccccc 1200
cag 1203

SEQ ID NO: 67        moltype = DNA  length = 1596
FEATURE              Location/Qualifiers
misc_feature         1..1596
                     note = artificial sequence
source               1..1596
                     mol_type = other DNA
                     organism = synthetic construct
SEQUENCE: 67
atgaaccggg gagtcccttt taggcacttg cttctggtgc tgcaactggc gctcctccca  60
gcagccactc agggaaagaa agtggtgctg ggcaaaaaag gggatacagt ggaactgacc 120
tgtacagctt cccagaagaa gagcatacaa ttccactgga aaaactccaa ccagataaag 180
attctgggaa atcagggctc cttcttaact aaaggtccat ccaagctgaa tgatcgcatt 240
gactcaagaa gaagcctttg ggaccaagga aactttcccc tgatcatcaa gaatcttaag 300
atagaagact cagatactta catctgtgaa gtggaggacc agaaggagga ggtgcaattg 360
ctagtgttcg gattgactgc caactctgac acccaccctgc ttcaggggca gagcctgacc 420
ctgacctttgg agagccccccc tggtagtagc ccctcagtgc aatgtaggag tccaagggggt 480
aaaaacatac agggggggaa gaccctctcc gtgtctcaga tggagctcca ggatagtggc 540
acctggacat gcactgtctt gcagaaccag aagaaggtgg agttcaaaat agacatcgtg 600
gtgctagctt tccagaaggc ctccagcata gtctataaga agaggggggga acaggtggag 660
ttctcctttcc cactcgcctt tacagttgaa aagctgacgg gcagtggcga gctgtggtgg 720
caggcggaga gggcttcctc ctccaagtct tggatccact ttgacctgaa gaacaaggaa 780
gtgtctgtaa aacgggttac ccaggaccct aagctccaga tgggcaagaa gctcccgctc 840
cacctcaccc tgccccaggc cttgcctcag tatgctggct ctggaaacct cacccctggcc 900
cttgaagcga aaacaggaaa gttgcatcag gaagtgaacc tggtggtgat gagagccact 960
cagctccaga aaaatttgac ctgtgaggtg tgggacccca cctccccctaa gctgatgctg 1020
agtttgaaac tggagaacaa ggaggcaaag gtctcgaagc ggggagaaggc ggtgtgggtg 1080
ctgaaccctg aggcggggat gtggcagtgt ctgctgagtg actcgggaca ggtcctgctg 1140
gaatccaaca tcaaggttct gcccacatgg tccaccccgg tgcagccagc ggccgcgctg 1200
agcaacagca tcatgtactt cagccacttc gtgcctgttc tcctgcctgc caagcctaca 1260
acaacaccag cccctagacc tccaacccct gccctacaa ttgcctctca gcctctgtct 1320
ctgaggcccg aagcttgtag acctgctgct ggcggagctg tgcacaccag aggactggat 1380
ttcgcctgct ttgggtgtct ggtggtcgtg gcggagtgc tggcttgtta ttctctgctg 1440
gtcaccgtgg ccttcatcat cttttgggtc cgactgaaga tccaggtccg aaaggccgcc 1500
atcaccagct acgagaagtc tgatggcgtg tacaccggcc tgagcaccag aaaccaggaa 1560
acctacgaga cactgaagca cgagaagccc ccccag 1596

SEQ ID NO: 68        moltype = DNA  length = 1215
FEATURE              Location/Qualifiers
misc_feature         1..1215
                     note = artificial sequence
source               1..1215
                     mol_type = other DNA
                     organism = synthetic construct
SEQUENCE: 68
atggactgga tctggcggat tctgtttctc gtgggagctg ccacaggcgc tcattctgct  60
cagcctgccg aagttcagct tgtagaatct ggaggtgat tggttcaacc tggtggctct 120
cttcgcctga gttgtgcagc ctctggtttt actttcaata gttacgctat gcattgggtt 180
cgtcaggctc tgggaaaagg cctggaatgg gtttcagcta ttagtggtaa tggaggtagt 240
actcgttacg cagacagtgt gaaaggtcgc ttcaccatca gccgtgataa ttctaagaac 300
actttgtacc tgcaaatgaa ctccttgcgc gcagaagaca cggctgtgta ctattgtgcc 360
cgtgatcgct ttcggaaggt tcatggtttc gatgtatggg gacaaggtac cctggtaacg 420
gtttctagcg gaggtggtgg gagtggtgga ggcggctcgg gtgaggtgg ttcaggagga 480
ggcggagata tccaaatgac tcaatctcct agttcactgt cagcctctgt tggtgatcgc 540
gtgaccatta cctgccaagc tagccaggat attagcaact acttgaactg gtatcagcag 600
aagcctggca agcccccaaa gctgttgatc tacgatgcaa gtaacttgga aactggcgtc 660
ccaagccgct tctctggatc tggttcaggc accgacttca ctttcactat cagcagcctg 720
cagcctgaag atatcgcaac ctactattgc cagcaggatg ctactttttcc tttgactttc 780
ggccaaggca ccaaggtgga gatcaaggcg gccgcgctga gcaacagcat catgtacttc 840
agccacttcg tgcctgtgtt cctgcctgcc aagcctacaa caacaccagc cctagacct 900
ccaaccccctg ccctacaat tgcctctcag cctctgtctc tgaggcccga agcttgtaga 960
cctgctgctg gcggagctgt gcacaccaga ggactggatt tcgcctgctt tgggtgctg 1020
```

```
gtggtcgtgg gcggagtgct ggcttgttat tctctgctgg tcaccgtggc cttcatcatc    1080
ttttgggtcc gactgaagat ccaggtccga aaggccgcca tcaccagcta cgagaagtct    1140
gatggcgtgt acaccggcct gagcaccaga aaccaggaaa cctacgagac actgaagcac    1200
gagaagcccc cccag                                                     1215

SEQ ID NO: 69           moltype = DNA   length = 1194
FEATURE                 Location/Qualifiers
misc_feature            1..1194
                        note = artificial sequence
source                  1..1194
                        mol_type = other DNA
                        organism = synthetic construct
SEQUENCE: 69
atggactgga tctggcggat tctgtttctc gtgggagctg ccacaggcgc tcattctgct      60
cagcctgccg tccagctgca gcagtctgga cctgagctgg taaagcctgg ggcttcagtg    120
aagatgtcct gcaaggcttc tggatacaca ttcactagct atgttatgca ctgggtgaag    180
cagaagcctg gcagggcct tgagtggatt ggatatatta ttccttacaa tgatgctact    240
aagtactgtc agaagttcaa aggcaaggcc acactgactt cagacaaatc ctccagcaca    300
gcctacatgg agctcagcag cctgacctct gaggactctg cggtctatta ctgtgcacgc    360
tataattacg acgggtactt cgatgtctgg ggcgcaggga ccacggtcac cgtctcctca    420
ggcggcggag gaagcggagg cggaggatct ggggcggag gctctgacat tgtgatgact    480
cagtctccag ccaccctgtc tgtgactcca ggagatagaa tctctctttc ctgcagggcc    540
agccagagta ttagcgacta cttacactgg tatcaacaaa aatcacatga gtctccaagg    600
cttctcatca aatatgcttc caatccatc tctggaatcc cctccaggtt cagtggcagt    660
ggatcagggt cagatttcac tctcagtatc aacagtgtgg aacctgaaga tgttggagtg    720
tattactgtc aaaatggtca cagctttcct ccgacgttcg gtggaggcac caagctggaa    780
atcaaagcgg ccgcgctgag caacagcatc atgtacttca gccacttcgt gcctgtgttc    840
ctgcctgcca agcctacaac aaccaccagcc cctagacctc caacccctgc ccctacaatt    900
gcctctcagc ctctgtctct gaggcccgaa gcttgtagac ctgctgctgg cggagctgtg    960
cacaccagag gactggattt cgcctgcttt tgggtgctgg tggtcgtggg cggagtgctg   1020
gcttgttatt ctctgctggt caccgtggcc ttcatcatct ttttgggtcc gactgaagatc   1080
caggtccgaa aggccgccat caccagctac gagaagtctg atggcgtgta caccggcctg   1140
agcaccagaa accaggaaac ctacgagaca ctgaagcacg agaagccccc ccag           1194

SEQ ID NO: 70           moltype = DNA   length = 1206
FEATURE                 Location/Qualifiers
misc_feature            1..1206
                        note = artificial sequence
source                  1..1206
                        mol_type = other DNA
                        organism = synthetic construct
SEQUENCE: 70
atggactgga tctggcggat tctgtttctc gtgggagctg ccacaggcgc tcattctgct      60
cagcctgccc aggtgcaagt gaaagagtct ggccctggac tggtggcccc aagccagtct    120
ctgagcatca catgtaccgt gtccggcttc agcctgacca actatggcgt gcactgggtc    180
cgacagcctc caggcaaagg actggaatgg ctggagtga tttgggctgg cggcagcacc    240
aactacaaca cgcccctgat gagccggctg agcatctcca aggacaacag caagagccag    300
gtgttcctga agatgaacag cctgcagacc gacgacaccg ccatgtacta ctgtgctagc    360
agaggcggca actacggcta cgccctggat tattggggcc agggcacaag cgtgaccgtg    420
tcatctggcg gcgaggaag cggaggcgga ggatctgggg cgaggctc tggcggaggg    480
ggatctagca tcgtgatgac ccagactcct aagttcctgc tggtgtctgc cggcgacaga    540
gtgaccatca cctgtaaagc cagccagagc gtgtccaacg acgtggcctg gtatcagcag    600
aagcctggac agagcccaa gctgctgatc tacagcgcca gcaacagata caccggcgtg    660
cccgatagat tcaccggctc tggctacggc accgacttca cctttaccat cagcaccgtg    720
caggccgagg atctggccgt gtacttctgc cagcaagact acagtctct cggcggaggc    780
accaagctgg aaatcaaagc ggccgcgctg agcaacagca tcatgtactt cagccacttc    840
gtgcctgtgt tcctgcctgc caagcctaca acaaccaccag cccctagacc tcaacccct    900
gcccctacaa ttgcctctca gcctctgtct ctgaggcccg aagcttgtag acctgctgct    960
ggcggagctg tgcacaccag aggactggat ttcgcctgct tttgggtgct ggtggtcgtg   1020
ggcggagtgc tggcttgtta ttctctgctg gtcaccgtgg ccttcatcat ctttttgggt   1080
cgactgaaga tccaggtccg aaaggccgcc atcaccagct acgagaagtc tgatggcgtg   1140
tacaccggcc tgagcaccag aaaccaggaa acctacgaga cactgaagca cgagaagccc   1200
ccccag                                                               1206

SEQ ID NO: 71           moltype = DNA   length = 1248
FEATURE                 Location/Qualifiers
misc_feature            1..1248
                        note = artificial sequence
source                  1..1248
                        mol_type = other DNA
                        organism = synthetic construct
SEQUENCE: 71
atggactgga tctggcggat tctgtttctc gtgggagctg ccacaggcgc tcattctgct      60
cagcctgccc aggtttcagct gcagcagtct ggacctgagc tggttaagcc tggcgcctcc    120
gtgaagatga gctgcaagac cagccggtac accttcaccg agtacaccat ccactgggtc    180
cgacagagcc acggcaagag cctggaatgg atcggcggca tcaacccca acctgggcatc    240
cccaactaca accagaagtt caagggcaga gccacactga ccgtgggcaa gtctagcagc    300
accgcctaca tggaactgcg gagcctgaca agcgaggaca cgccgtgta cttctgcgcc    360
agaagaagaa tcgcctacgg ctacgatgag ggccacgcca tggattattg gggccaggga    420
```

```
acaagcgtga ccgtgtctag tggcggcgga ggaagcggag gcggaggatc tgggggcgga    480
ggctctggcg gagggggatc tgacatcgtg atgacacaga gcccttctag cctggccgtg    540
tccgtgggag agaaagtgac catgagctgc aagagcagcc agagcctgct gtactcccgg    600
aaccagaaga actacctggc ctggttccag cagaagcccg ccagtctcc taagctgctg    660
atcttctggg ccagcaccag agaaagcggc gtgcccgata gattcaccgg cagcggcttt    720
ggcaccgact tcaacctgac aatcagcagc gtgcaggccg aggacctggc tgtgtacgat    780
tgccagcagt acttcagcta ccctctgacc tttggagccg gcaccaagct ggaactgaga    840
gcggccgcgc tgagcaacag catcatgtac ttcagccact cgtgcctgt gttcctgcct    900
gccaagccta caacaacacc agcccctaga cctccaaccc ctgccctac aaattgcctct    960
cagcctctgt ctctgaggcc cgaagcttgt agacctgctg ctggcggagc tgtgcacacc   1020
agaggactgg atttcgcctg cttttgggtg ctggtggtcg tgggcggagt gctggcttgt   1080
tattctctgc tggtcaccgt ggccttcatc atctttgg tccgactgaa gatccaggtc   1140
cgaaaggccc ccatcaccag ctacgagaag tctgatggcg tgtacaccgg cctgagcacc   1200
agaaaccagg aaacctacga gacactgaag cacgagaagc ccccccag              1248

SEQ ID NO: 72           moltype = DNA  length = 510
FEATURE                 Location/Qualifiers
misc_feature            1..510
                        note = artificial sequence
source                  1..510
                        mol_type = other DNA
                        organism = synthetic construct
SEQUENCE: 72
atgcgcatca gcaagcccca cctgcgcagc atcagcatcc agtgctacct gtgcctgctg     60
ctgaacagcc acttcctgac cgaggccggc atccacgtgt tcatcctggg ctgcttcagc    120
gccggcctgc ccaagaccga ggccaactgg gtgaacgtga tcagcgacct gaagaagatc    180
gaggacctga tccagagcat gcacatcgac gccaccctgt acaccgagag cgacgtgcac    240
cccagctgca aggtgaccgc catgaagtgc ttcctgctgg agctgcaggt gatcagcctg    300
gagagcggca cgccagcat ccacgacacc gtggagaacc tgatcatcct ggccaacaac    360
agcctgagca gcaacggcaa cgtgaccgag agcggctgca aggagtgcga ggagctggag    420
gagaagaaca tcaaggagtt cctgcagagc ttcgtgcaca tcgtgcagat gttcatcaac    480
accagcggct ccgagaagga cgagctgtaa                                    510

SEQ ID NO: 73           moltype = AA  length = 169
FEATURE                 Location/Qualifiers
REGION                  1..169
                        note = artificial sequence
source                  1..169
                        mol_type = protein
                        organism = synthetic construct
SEQUENCE: 73
MRISKPHLRS ISIQCYLCLL LNSHFLTEAG IHVFILGCFS AGLPKTEANW VNVISDLKKI     60
EDLIQSMHID ATLYTESDVH PSCKVTAMKC FLLELQVISL ESGDASIHDT VENLIILANN    120
SLSSNGNVTE SGCKECEELE EKNIKEFLQS FVHIVQMFIN TSGSEKDEL                169

SEQ ID NO: 74           moltype = DNA  length = 1215
FEATURE                 Location/Qualifiers
misc_feature            1..1215
                        note = artificial sequence
source                  1..1215
                        mol_type = other DNA
                        organism = synthetic construct
SEQUENCE: 74
atggactgga tctggcgcat cctcttcctc gtcggcgctg ctaccggcgc tcattcggcc     60
cagccggcca tggcgcaagt aaaactccaa gaatctggcc cggagctggt gaaaccgggg    120
gcgtctgtga agatgagctg taaagcatca ggctacacct tcacctccta taatatgcac    180
tgggtgaaac aaacacccgg acaggggcctc gaatggattg tgccatcta tcctggaaat    240
ggtgatacct catataatca gaagtttaag ggcaaggcta cgcttactgc ggataaaagc    300
tcttccactg cttacatgca actgagcagt ctcacttcag aggactcagc cgattattat    360
tgtgcccgca gcaactacta tggtagttca tactggtttt tcgacgtttg ggggcaaggt    420
accaccgtca cggtttcttc tggtggggc ggaagcgggg gtggaggatc tgggggcggt    480
ggttcagaca ttgaactcac ccagagccct actattctga gcgcgtctcc aggtgaaaaa    540
gttacgatga cgtcagagc atcaagtagt gtgaattata tggattggta tcaaaagaag    600
ccaggctcat ccccaaaacc gtggatctat gcaactagca tccgcgtc agggtgtcca    660
gcaaggtttt ccggaagtgg ttctggcaca tcttatagtc tcaccatttc ccgagtggag    720
gctgaggatg cggccactta ttactgccag caatggtcat tcaatccccc aacatttggt    780
ggcggaacaa aactcgaaat taacgggcg ccgcgctga gcaacagcat catgtacttc    840
agccacttcg tgcctgtgtt cctgcctgcc aagcctacaa caacaccagc ccctagacct    900
ccaacccctg cccctacaat tgcctctcag cctctgtctc tgaggcccga agcttgtaga    960
cctgctgctg gcggagctgt gcacaccaga ggactggatt tcgcctgctt tgggtgctg   1020
gtggtcgtgg gcggagtgct ggcttgttat tctctgctgg tcaccgtggc cttcatcatc   1080
tttttgggtcc gactgaagat ccaggtccga aaggccgcca tcaccagcta cgagaagtct   1140
gatggcgtgt acaccggcct gagcaccaga aaccaggaaa cctacgagac actgaagcac   1200
gagaagcccc ccag                                                    1215

SEQ ID NO: 75           moltype = DNA  length = 1248
FEATURE                 Location/Qualifiers
misc_feature            1..1248
                        note = artificial sequence
```

```
source                      1..1248
                            mol_type = other DNA
                            organism = synthetic construct
SEQUENCE: 75
atggactgga tctggcgcat cctcttcctc gtcggcgctg ctaccggcgc tcattcggcc    60
cagccggccg atatcgagct cacccaatct ccaaaattca tgtccacatc agtaggagac   120
agggtcagcg tcacctgcaa ggccagtcag aatgtggata ctaatgtagc gtggtatcaa   180
caaaaaccag ggcaatctcc tgaaccactg cttttctcgg catcctaccg ttacactgga   240
gtccctgatc gcttcacagg cagtggatct gggacagatt tcactctcac catcagcaat   300
gtgcagtctg aagacttggc agagtatttc tgtcagcaat ataacagcta tcctctgacg   360
ttcggtggcg gcaccaagct ggaaatcaaa cgggctgccg cagaaggtgg aggcggttca   420
ggtggcggag gttccggcgg aggtggctct ggcggtggcg gatcggccat ggcccaggtg   480
aagctgcagc agtcaggagg gggcttggtg caacctggag ctccatgaa actctcctgt    540
gttgtctctg gattcacttt cagtaattac tggatgaact gggtccgcca gtctccagag   600
aaggggcttg agtggattgc agaaattaga ttgaaatcca ataattttgg aagatattat   660
gcggagtctg tgaaagggag gttcaccatc tcaagaatg attccaaaag tagtgcctac    720
ctgcaaatga tcaacctaag agctgaagat actggcattt attactgtac cagttatggt   780
aactacgttg ggcactattt tgaccactgg ggccaaggga ccacggtcac cgtatcggct   840
gcggccgcgc tgagcaacag catcatgtac ttcagccact tcgtgcctgt gttcctgcct   900
gccaagccta caacaacacc agccctaga cctccaaccc ctgccctac aattgcctct     960
cagcctctgt ctctgaggcc cgaagcttgt agacctgctg ctggcggagc tgtgcacacc  1020
agaggactgg atttcgcctg cttttgggtg ctggtggtgg tgggcggagt gctggcttgt  1080
tattctctgc tggtcaccgt ggccttcatc atctttgggt ccgactgaa gatccaggtc   1140
cgaaaggccg ccatcaccag ctacgagaag tctgatggcc tgtacaccgg cctgagcacc  1200
agaaaccagg aaacctacga gacactgaag cacgagaagc cccccag                1248

SEQ ID NO: 76               moltype = DNA  length = 6787
FEATURE                     Location/Qualifiers
misc_feature                1..6787
                            note = artificial sequence
source                      1..6787
                            mol_type = other DNA
                            organism = synthetic construct
SEQUENCE: 76
tgtatttaga aaaataaaca aatagggggtt ccgcgcacat ttccccgaaa agtgccacct   60
gacgtcgacg gatcgggaga tctcccgatc ccctatggtg cactctcagt acaatctgct  120
ctgatgccgc atagttaagc cagtatctgc tccctgcttg tgtgttggag gtcgctgagt  180
agtgcgcgag caaaatttaa gctacaacaa ggcaaggctt accgacaat tgcatgaaga   240
atctgcttag ggttaggcgt tttgcgctgc ttcgggatcc gctgaccaaa agagcaccaa  300
aggcgccctg accttcagcc cctacctgcg ctccggtgcc cgtcagtggg cagagcgcac  360
atcgcccaca gtccccgaga agtgggggg agggtcggc aattgaaccg gtgcctagag    420
aaggtggcgc ggggtaaact gggaaagtga tgtcgtgtac tggctccgcc ttttcccga   480
gggtggggga gaaccgtata taagtgcagt agtcgccgtg aacgttcttt ttcgcaacgg  540
gtttgccgcc agaacacagg taagtgccgt gtgtggttcc cgcgggcctg gcctcttttac  600
gggttatggc ccttgcgtgc cttgaattac ttccacctgg ctgcagtacg tgattcttga   660
tcccgagctt cgggttggaa gtgggtggga gagttcgagg ccttgcgctt aaggagcccc   720
ttcgcctcgt gcttgagttg aggcctggcc tgggcgccgg ctgcgaatctg              780
gtggcacctt cgcgcctgtc tcgctgcttt cgataagtct ctagccatttt aaaattttg    840
atgacctgct gcgacgcttt tttttctggca agatagtctt gtaaatgcgg gccaagatct   900
gcacactggt atttcggttt ttggggccgc gggcggcgac ggggcccgtg cgtcccagcg   960
cacatcgttcg gcgaggcggg gcctgcgagc gcggccacgc agaatcggac gggggtagtc  1020
tcaagctggc cggcctgctc tggtgcctgg cctcgcgccg ccgtgtatcg ccccgccctg   1080
ggcggcaagg ctgcccggt cggcaccagt tgcgtgagcg aaagatggc cgcttcccgg     1140
ccctgctgca gggagctcaa aatggaggac gcggcgctcg ggagagcggg cgggtgagtc  1200
acccacacaa aggaaaaggg ccttttccgtc ctcagccgtc gcttcatgtg actccacgga  1260
gtaccgggcg ccgtccaggc acctcgatta gttctcgagc ttttggagta cgtcgtcttt  1320
aggttggggg gaggggtttt atgcgatgga gtttccccac actgagtggg tggagactga  1380
agttaggcca gcttggcact tgatgtaatt ctccttggaa tttgcccttt ttgagtttgg   1440
atcttggttc attctcaagc ctcagacagt ggttcaaagt tttttttcttc catttcaggt  1500
gtcgtgataa tacgactcac tatagggaga cccaagctgg aattcgccac catggactgg  1560
atctggcgga ttctgtttct cgtgggagct gccacaggcg ctcattcgc tcagcctgcc   1620
gatgttgtaa tgacgcagtc accctgtca ctcccggtca cccggaga accagcgtca      1680
attagctgcc gatctagcca aagtttgctt cattccaatg ttacaatta tctcgactgg   1740
tacttgcaga aacccggcca atcccctcag ctgctcatct accttgggtc taataggca    1800
tctgggggttc ccgataggtt ctctggctcc gggagcggga ccgactttac gttgaaaatc  1860
tctaggggttg aggcggaaga cgtaggcgtt tactattgca tgcagggggac ccactggccg  1920
ctgaccttcg gccagggcac caaggttgaa ataaaaggcg gcggaggaag cggaggcgga  1980
ggatctgggg gcggaggctc tggcggaggg ggatctcagg tacagctcca ggaatcagga  2040
cccggtttgg ttaagccctc cgggacccctt tccctcacgt gtgcagtctc aggtgggtca  2100
attagttctt ccaattggtg gtcttgggtg cggcaaccac ctggtaaagg tctcgagtgg   2160
ataggggaaa tttatcatag tggctccacc aattataacc cctcactcaa gtccagggtt  2220
acgatatctg tggacaaaag taaaaccaa ttctccctca aacttagtag tgtaacagcg    2280
gcagacaccg cggtgtacta ctgcgcacgg tggacaggga gaactgatgc ctttgacatt  2340
tggggacagg gaactatggt gactgtgtca tccgcggccg ctgcgcaa cagcatcatg     2400
tacttcagcc acttcgtgcc tgtgttcctg cctgccaagc ctacaacaac accagcccct  2460
agacctccaa cccctgcccc tacaattgcc tctcagcctc tgtctctgag gcccgaagct  2520
tgtagacctg ctgctggcgg agctgtgcac accagaggac tggatttcgc ctgcttttgg  2580
gtgctggtgg tcgtgggcgg agtgctggct tgttattctc tgctggtcac cgtggccttc  2640
atcatctttt gggtccgact gaagatccag gtccgaaagg ccgccatcac cagctacgag  2700
```

```
aagtctgatg gcgtgtacac cggcctgagc accagaaacc aggaaaccta cgagacactg   2760
aagcacgaga agccccccca gggatctgga gctactaact tcagcctgct gaagcaggct   2820
ggagacgtgg aggagaaccc tggacctatg tggcagctgc tgctgcctac agctctcctg   2880
ctgctggtgt ccgccggcat gagaaccgag gatctgccta aggccgtggt gttcctggaa   2940
ccccagtggg acagagtgct ggaaaaggac agcgtgaccc tgaagtgcca gggcgcctac   3000
agccccgagg acaatagcac ccagtggttc acaacgaga gcctgatcag cagccaggcc   3060
agcagctact tcatcgacgc cgccaccgtg gacgacagcg gcgagtatag atgccagacc   3120
aacctgagca ccctgagcga ccccgtgcag ctggaagtgc acatcggatg gctgctgctg   3180
caggccccca gatgggtgtt caaagaagag gaccccatcc acctgagatg ccactcttgg   3240
aagaacaccg ccctgcacaa agtgacctac ctgcagaacg gcaagggcag aaagtacttc   3300
caccacaaca gcgacttcta catccccaag gccaccctga aggactccgg ctcctacttc   3360
tgcagaggcc tcgtgggcag caagaacgtg tccagcgaga cagtgaacat caccatcacc   3420
cagggcctgg ccgtgtctac catcagcagc ttttttccac ccggctacca ggtgtccttc   3480
tgcctcgtga tggtgctgct gttcgccgtg gacaccggcc tgtacttcag cgtgaaaaca   3540
aacatcagaa gcagcacccg ggactggaag gaccacaagt tcaagtggcg gaaggacccc   3600
caggacaagt gaaattccgc ccctctcccc ccccccctc tccctcccc ccctaacg   3660
ttactggccg aagccgcttg gaataaggcc ggtgtgcgtt tgtctatatg ttattttcca   3720
ccatattgcc gtcttttggc aatgtgaggg cccggaaacc tggccctgtc ttcttgacga   3780
gcattcctag gggtctttcc cctctcgcca aggaatgca aggtctgttg aatgtcgtga   3840
aggaagcagt tcctctggaa gcttcttgaa gacaaacaac gtctgtagcg accctttgca   3900
ggcagcggaa ccccccacct ggcgacaggt gcctctgcgg ccaaaagcca cgtgtataag   3960
atacacctgc aaaggcggca caaccccagt gccacgttgt gagttggata gttgtggaaa   4020
gagtcaaatg gctctcctca agcgtattca acaaggggc gaaggatgcc cagaaggtac   4080
cccattgtat gggatctgat ctggggcctc ggtgcacatg ctttacatgt gtttagtcga   4140
ggttaaaaaa acgtctaggc cccccgaacc acggggacgt ggttttcctt tgaaaaacac   4200
gataaccgcc accatgtacc ggatgcagct gctgagctgt atcgccctgt ctctggccct   4260
cgtgaccaac agcgccccta ccagcagcag caccaagaaa acccagctgc agctggaaca   4320
tctgctgctg gacctgcaga tgatcctgaa cggcatcaac aactacaaga accccaagct   4380
gacccggatg ctgaccttca gttctacat gcccaagaag gccaccgaac tgaaacatct   4440
gcagtgcctg gaagaggaac tgaagcccct ggaagaagtg ctgaacctgg cccagagcaa   4500
gaacttccac ctgaggccca gggacctgat cagcaacatc aacgtgatcg tgctggaact   4560
gaaaggcagc gagacaacct tcatgtgcga gtacgccgac gagacagcta ccatcgtgga   4620
atttctgaac cggtggatca ccttctgcca gagcatcatc agcaccctga ccggctccga   4680
gaaggacgag ctgtgagcgg ccgccgctg atcagcctcg aacgagattt cgattccacc   4740
gccgccttct atgaaaggtt gggcttcgga atcgttttcc gggacgccgg ctggatgatc   4800
ctccacgcg gggatctcat gctggagttc ttcgcccacc ccaactttgt tattgcagct   4860
tataatggtt acaaataaag caatagcatc acaaatttca caaataaagc attttttca   4920
ctgcattcta gttgtggttt gtccaaactc atcaatgtat cttatcatgt ctgtgcggtg   4980
ggctctatgg cttctgaggc ggaaagaacc agctggggct ctaggggta tccccggatc   5040
ctgagcaaaa ggccagcaaa aggccaggaa ccgtaaaaag gccgcgttgc tggcgttttt   5100
ccataggctc cgcccccctg acgagcatca aaaaatcga cgctcaagtc agaggtggcg   5160
aaacccgaca ggactataaa gataccaggc gtttccccct ggaagctccc tcgtgcgctc   5220
tcctgttccg accctgccgc ttaccggata cctgtccgcc tttctccctt cgggaagcgt   5280
ggcgctttct catagctcac gctgtaggta tctcagttcg gtgtaggtcg ttcgctccaa   5340
gctgggctgt gtgcacgaac ccccgttca gcccgaccgc tgcgccttat ccggtaacta   5400
tcgtcttgag tccaacccgg taagacacga cttatcgcca ctggcagcag ccactggtaa   5460
caggattagc agagcgaggt atgtaggcgg tgctacagag ttcttgaagt ggtggcctaa   5520
ctacggctac actagaagaa cagtatttgg tatctgcgct ctgctgaagc cagttacctt   5580
cggaaaaaga gttggtagct cttgatccgg caaacaaacc accgctggta gcggtggttt   5640
ttttgtttgc aagcagcaga ttacgcgcag aaaaaaagga tctcaagaag atcctttgat   5700
cttttctacg gggtctgacg ctcagtggaa cgaaaactca cgttaaggga ttttggtcat   5760
gagattatca aaaaggatct tcacctagat ccttttaaat taaaaatgaa gttttaaatc   5820
aatctaaagt atatatgagt aaacttggtc tgacagttac caatgcttaa tcagtgaggc   5880
acctatctca gcgatctgtc tatttcgttc atccatagtt gcctgactcc ccgtcgtgta   5940
gataactacg atacgggagg gcttaccatc tggccccagt gctgcaatga taccgcgaga   6000
accacgctca ccggctccag atttatcagc aataaaccag ccagccggaa gggccgagcg   6060
cagaagtggt cctgcaactt tatccgcctc catccagtct attaattgtt gccgggaagc   6120
tagagtaagt agttcgccag ttaatagttt cgcaacgttg ttgccattg ctacaggcat   6180
cgtggtgtca cgctcgtcgt ttggtatggc ttcattcagc tccggttccc aacgatcaag   6240
gcgagttaca tgatccccca tgttgtgcaa aaaagcggtt agctccttcg gtcctccgat   6300
cgttgtcaga agtaagttgg ccgcagtgtt atcactcatg gttatggcag cactgcataa   6360
ttctcttact gtcatgccat ccgtaagatg cttttctgtg actggtgagt actcaaccaa   6420
gtcattctga gaatagtgta tgcggcgacc gagttgctct tgcccggcgt caatacggga   6480
taataccgcg ccacatagca gaactttaaa agtgctcatc attggaaaac gttcttcggg   6540
gcgaaaactc tcaaggatct taccgctgtt gagatccagt tcgatgtaac ccactcgtgc   6600
acccaactga tcttcagcat cttttacttt caccagcgtt tctgggtgag caaaaacagg   6660
aaggcaaaat gccgcaaaaa agggaataag ggcgacacgg aaatgttgaa tactcatact   6720
cttcctttt caatattatt gaagcattta tcagggttat tgtctcatga gcggatacat   6780
atttgaa                                                             6787
```

CHIMERIC ANTIGEN RECEPTOR-MODIFIED NK-92 CELLS

This application is a continuation of U.S. patent application Ser. No. 16/969,152 filed on Aug. 11, 2020, which claims priority to U.S. provisional applications with the Ser. Nos. 62/756,395 and 62/756,402, both filed Nov. 6, 2018.

SEQUENCE LISTING

The content of the XML file of the sequence listing named 104077.0003US2 Sequence Listing ST26, which is 150 kb in size was created on 7/13/2022 and electronically submitted via EFS-Web along with the application is incorporated by reference in its entirety.

FIELD OF THE INVENTION

The field of the invention is genetically modified immune competent cells that express a chimeric antigen receptor (CAR), and particularly modified NK-92 cells expressing a CAR with an Fc epsilon receptor gamma (FcεRIγ) signaling domain.

BACKGROUND OF THE INVENTION

Natural killer (NK) cells are cytotoxic lymphocytes that constitute a significant component of the innate immune system. In most cases, NK cells represent about 10-15% of circulating lymphocytes, and bind and kill targeted cells, including virus-infected cells and many malignant cells. NK cell killing is non-specific with regard to particular antigens and can occur without prior immune sensitization. Killing of targeted cells is typically mediated by cytolytic proteins, including perforin, granzyme, and granulysin.

Autologous NK cells have been used as therapeutic entities. To that end, NK cells are isolated from the peripheral blood lymphocyte fraction of whole blood, expanded in cell culture to obtain sufficient numbers of cells, and then re-infused into a subject. Autologous NK cells have shown in at least some cases moderate effectiveness in both ex vivo therapy and in vivo treatment. However, isolation and growth of autologous NK cell is time and cost intensive. Moreover, autologous NK cell therapy is further limited by the fact that not all NK cells are cytolytic.

At least some of these difficulties can be overcome by use of NK-92 cells, which are a cytolytic cancer cell line which was discovered in the blood of a subject suffering from a non-Hodgkins lymphoma and then immortalized in vitro (Gong et al., *Leukemia* 8:652-658 (1994)). While NK-92 cells are NK cell derivatives, NK-92 cells lack the major of inhibitory receptors that are otherwise displayed by normal NK cells, and retain the majority of the activating receptors. NK-92 cells do not, however, attack normal cells nor do they elicit an unacceptable immune rejection response in humans. Due to these desirable characteristics, NK-92 cells were characterized in detail and explored as therapeutic agent in the treatment of certain cancers as is described, for example, in WO 1998/049268 or US 2002/068044.

Phenotypic changes distinguishing a tumor cell from normal cells derived from the same tissue are often associated with one or more changes in the expression of specific gene products, including the loss of normal cell surface components or the gain of others (i.e., antigens not detectable in corresponding normal, non-cancerous tissue). The antigens which are expressed in neoplastic or tumor cells, but not in normal cells, or which are expressed in neoplastic cells at levels substantially above those found in normal cells, have been termed "tumor-specific antigens" or "tumor-associated antigens." Such tumor-specific antigens may serve as markers for tumor phenotype. Tumor-specific antigens include cancer/testis-specific antigen (e.g. MAGE, BAGE, GAGE, PRAME and NY-ESO-1), melanocyte differentiation antigens (e.g. tyrosinase, Melan-A/MART, gp100, TRP-1 and TRP-2), mutated or aberrantly expressed antigens (e.g. MUM-1, CDK4, beta-catenin, gp100-in4, p15 and N-acetylglucos-aminyltransferase V), and antigens that are expressed at higher levels in tumors (e.g., CD19 and CD20).

Tumor-specific antigens have been used as targets for cancer immunotherapies. One such therapy utilizes chimeric antigen receptors (CARs) expressed on the surface of immune cells, including T cells and NK cells, to improve cytotoxicity against cancer cells. CARs comprise a single-chain variable fragment (scFv) linked to at least one intracellular signaling domain. The scFv recognizes and binds an antigen on the target cell (e.g., a cancer cell) and triggers effector cell activation. The signaling domains contain immunoreceptor tyrosine-based activation domains (ITAMs) that are important for intracellular signaling by the receptor.

The first generation of CARs used in T-cells contained one cytoplasmic signaling domain. For example, one version of a first-generation CAR in T-cells included a signaling domain from the Fc epsilon receptor gamma (FcεRIγ) which contained one ITAM, while another version contained the signaling domain from CD3ζ which contained three ITAMs. In vivo and in vitro studies showed that the CD3ζ CAR T-cells were more efficient at tumor eradication than FcεRIγ CAR T-cells (e.g., Haynes, et al. 2001, *J. Immunology* 166:182-187; Cartellieri, et al. 2010, *J. Biomed and Biotech*, Vol. 2010, Article ID 956304). Additional studies then revealed that certain costimulatory signals were required for full activation and proliferation of such recombinant T-cells, and second and third generation CARs combined multiple signaling domains in to a single CAR to enhance efficacy of the recombinant CAR T-cells. Due to their less desirable philological effects in the tested T-cells, first generation CARs and the FcεRIγ signaling domains were largely discarded in favor of the new, more efficient CARs using CD3ζ in combination with one or more additional signaling domains (e.g., Hermanson and Kaufman 2015, *Frontiers in Immunol.*, Vol. 6, Article 195).

More recently, selected CARs have also been expressed in NK cells. For example, CAR-modified NK-92 cells have used first generation CARs with only a CD3ζ intracellular signaling domain. Several antigens have been targeted by these first generation CAR-NK cells, including CD19 and CD20 for B cell lymphoma, ErbB2 for breast, ovarian, and squamous cell carcinoma, GD2 for neuroblastoma, and CD138 for multiple myeloma. Second generation CAR-NK cells from the NK-92 line have also been created for several antigens, including EpCAM for multiple carcinomas HLA-A2 EBNA3 complex for Epstein-Barr virus, CS1 for multiple myeloma, and ErbB2 for HER2 positive epithelial cancers. The most common intracellular costimulatory domain used alongside CD3ζ in second generation NK-92 CARs is CD28. However, the potential effect of the CD28 domain is unclear since NK cells do not naturally express CD28. Additional second generation CARs have incorporated the 4-1BB intracellular signaling domain along with CD3ζ to improve NK cell persistence. Others compared functionality of different intracellular domains using an ErbB2 scFv fused with CD3ζ alone, CD28 and CD3ζ, or 4-1BB and CD3ζ tested against breast cancer cells. They found that both of the second generation constructs improved killing compared to the first generation CARs and the CD28 and CD3ζ had 65% target lysis, the 4-1BB and CD3ζ lysed 62%, and CD3ζ alone killed 51% of targets. 4-1BB and CD28 intracellular domains were also compared in a recent study using anti-CD19 CARs expressed on NK-92 cells for B cell malignances. Still others found that CD3ζ/4-1BB constructs were less effective than CD3ζ/CD28 in cell killing and cytokine production, highlighting differential effects of CD28 and 4-1BB costimulatory domains.

Third generation NK-92 CARs were constructed of an anti-CD5 scFv with CD3ζ, CD28, and 4-1BB intracellular signaling domains and demonstrated specific and potent anti-tumor activity against a variety of T-cell leukemia and lymphoma cell lines and primary tumor cells. Such cells were also able to inhibit disease progression in xenograft mouse models of T cell Acute lymphoblastic leukemia (ALL) cell lines as well as primary tumor cells (*Transl Res.* 2017 September; 187: 32-43). In further examples, WO 2016/201304 and WO 2018/076391 teach use of third generation CD3ζ CARs expressed in NK cells and NK-92 cells.

However, NK cells (and particularly NK-92 cells) are often difficult to genetically modify as evidenced by numerous failures to engineer NK-92 cells to express an Fc receptor. Such difficulties are further compounded where NK-92 cells are transfected with multiple recombinant genes or relatively large recombinant nucleic acid payload for heterologous expression. Additionally, NK-92 cells also exhibit a significant lack of predictability with respect to recombinant expression of exogenous proteins (e.g., CD16). On a functional level, while exhibiting in most cases targeted cytotoxicity, most if not all CAR NK-92 cells require a high effector to target cell ratio.

Therefore, even though numerous recombinant NK-92 cells are known in the art, all or almost all of them suffer from various difficulties. Consequently, there remains a need for CAR-expressing NK-92 cells that express a high-activity CAR in significant quantities, and that can be readily cultivated in a simple and effective manner.

SUMMARY OF THE INVENTION

The inventors have discovered that NK-92 cells expressing an FcεRIγ-containing CAR unexpectedly exhibit superior cytolytic activity, typically at a relatively low effector to target cell ratio as compared to other constructs, and high levels of expression of the FcεRIγ-containing CAR. Moreover, such recombinant cells also expressed CD16 at desirable levels, and where further modified to express a stimulatory cytokine, recombinant NK-92 cells were also readily cultivated without the need for exogenous IL-2.

Therefore, in one aspect of the inventive subject matter, the inventors contemplate a genetically modified NK cell carrying a membrane bound recombinant chimeric antigen receptor (CAR) that comprises in a single polypeptide chain (i) an extracellular binding domain, (ii) a hinge domain, (iii) a transmembrane domain, and (iv) a FcεRIγ signaling domain. Most typically, but not necessarily, the NK cell is an NK-92 cell.

In some embodiments, the extracellular binding domain comprises a scFv, which may specifically bind to a tumor-specific antigen (e.g., CD19, CD20, GD2, HER-2, CD30, EGFR, FAP, CD33, CD123, PD-L1, IGF1R, CSPG4, or B7-H4), a tumor associated antigen (e.g., MUC-2, brachyury, CEA), or a patient- and tumor-specific antigen (e.g., neoepitope with high affinity to the patient's MHC I and/or MHC II). Alternatively, the extracellular binding domain may also specifically bind to a virus-specific antigen, and typical viruses contemplated herein include an HIV virus, an HPV virus, an RSV virus, an influenza virus, an ebolavirus, or an HCV virus. For example, suitable viral antigens include gp120 of an HIV virus.

In further embodiments, the hinge domain and/or the transmembrane domain comprise a CD8 hinge domain and/or a CD28 transmembrane domain, and/or the FcεRIγ signaling domain has an amino acid sequence of SEQ ID NO:1.

Additionally, it is contemplated that the genetically modified NK cell may further carry a membrane bound recombinant CD16 (and especially a high-affinity variant of CD16), and/or the genetically modified NK cell may express a recombinant cytokine with an endoplasmic retention sequence.

Therefore, and viewed from a different perspective, the inventors also contemplate a genetically modified NK cell that comprises a recombinant nucleic acid encoding a chimeric antigen receptor (CAR), wherein the CAR includes in a single polypeptide chain (i) an extracellular binding domain, (ii) a hinge domain, (iii) a transmembrane domain, and (iv) a FcεRIγ signaling domain. As noted before, it is generally preferred that the NK cell is an NK-92 cell. In some embodiments, the recombinant nucleic acid is an RNA, which may be a polycistronic RNA that further encodes a CD16 and/or a cytokine with an endoplasmic retention sequence. With respect to the various domains, the same considerations as noted above apply.

In a still further aspect of the inventive subject matter, the inventors also contemplate a method of treating cancer in a patient in need thereof that comprises a step of administering to the patient a therapeutically effective amount of the genetically modified NK cells presented herein, thereby treating the cancer. As will be readily appreciated, contemplated methods will further include a step of administering at least one additional therapeutic entity, including a viral cancer vaccine, a bacterial cancer vaccine, a yeast cancer vaccine, N-803, an antibody, a stem cell transplant, and/or a tumor targeted cytokine.

For example, cancers treated by contemplated methods include leukemia, acute lymphocytic leukemia, acute myelocytic leukemia, chronic leukemias, chronic myelocytic (granulocytic) leukemia, chronic lymphocytic leukemia, polycythemia vera, lymphomas, Hodgkin's disease, non-Hodgkin's disease, multiple myeloma, Waldenstrom's macroglobulinemia, heavy chain disease, solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyo sarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma and retinoblastoma.

Likewise, the inventors contemplate a method of treating a viral infection in a patient in need thereof that includes a step of administering to the patient a therapeutically effective amount of the genetically modified NK cells presented herein (having an extracellular binding domain may also specifically bind to a virus-specific antigen), thereby treating the viral infection. Of course, contemplated methods may further include a step of administering an antiviral drug.

Regardless of the type of treatment, it is contemplated that about $1\times10^8$ to about $1\times10^{11}$ cells per m$^2$ of body surface area of the patient are administered to the patient.

Therefore, the inventors also contemplate use of genetically modified NK cells as presented herein in the treatment of cancer or a viral infection.

Various objects, features, aspects and advantages of the inventive subject matter will become more apparent from the following detailed description of preferred embodiments along with the accompanying drawing figures in which like numerals represent like components.

DETAILED DESCRIPTION OF THE INVENTION

Figure 1:
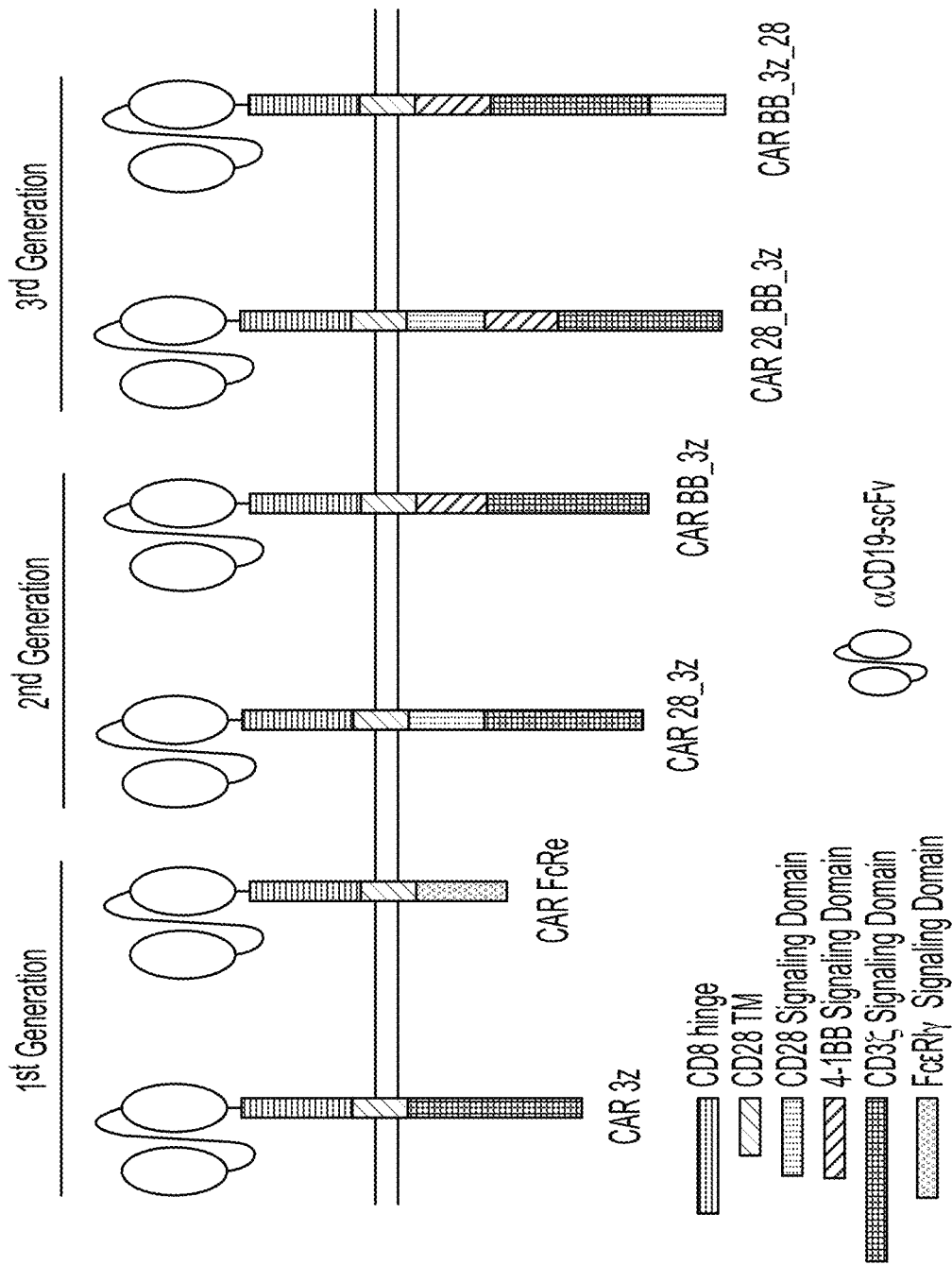
FIG. 1 is a schematic representation of exemplary CD19-CARs tested. All of the CD19-CAR variants contained an extracellular domain comprising an anti-CD19 scFv region (αCD19-scFv), a hinge region from CD8 (CD8 hinge), and a transmembrane domain from CD28 (CD28 TM). The intracellular domains of the CD19CARs were varied as indicated.

To date, FcεRIγ-containing CARs have not been utilized in NK-92 cells, other NK cell lines, or endogenous NK cells because as signaling domains (e.g., CD3ζ) were deemed more efficient, especially when combined with additional signaling domains (in second and third generation CARs). The inventors have now made the unexpected and surprising finding that NK-92 cells expressing a first-generation CAR comprising an intracellular domain from FcεRIγ, which has only one ITAM domain, have equal or higher cytotoxic activity against cancer cells expressing the antigen recognized by the CAR than NK-92 cells expressing CARs with a CD3ζ signaling domain, which has three ITAM domains, even where these ITAM domains were combined with other signaling domains (i.e., second or third generation CARs). Notably, the IgE receptor (FcεRI) in its native context includes two gamma chains coupled to each other via a disulfide bond and is normally expressed only in eosinophils, basophils, and epidermal Langerhans cells. The inventors also made the unexpected finding that a CAR comprising an intracellular domain from FcεRIγ was expressed at higher levels on the surface of NK-92 cells than other CARs, especially those comprising the CD3ζ signaling domain.

Therefore, the inventive subject matter is directed to a genetically modified NK-92 cell or NK cell line engineered to express a chimeric antigen receptor (CAR) on a cell surface. Most typically, the CAR comprises an intracellular domain from the Fc epsilon receptor gamma (FcεRIγ), however, in other embodiments the CAR may also comprise a T cell receptor (TCR) CD3 zeta (CD3ζ) intracellular domain. As will be readily appreciated, the CAR may be transiently or stably expressed by the NK-92 cell from a recombinant DNA or RNA molecule.

Consequently, in one aspect of the inventive subject matter, an NK cell, an NK-92 cell or NK/NK-92 cell line expresses a chimeric antigen receptor (CAR) on the surface of the NK-92 cell that comprises a cytoplasmic domain of FcεRIγ (e.g., having amino acid sequence of SEQ ID NO:1). Alternatively, or additionally, the CAR may also comprise a cytoplasmic domain of CD3 zeta (e.g., having amino acid sequence of SEQ ID NO: 10, which may be encoded by a nucleic acid of SEQ ID NO:11 (codon optimized) or SEQ ID NO:12 (non-codon-optimized); full-length sequence is shown in SEQ ID NO:47). In another aspect, an NK or NK-92 cell line is contemplated that is transformed with a nucleic acid encoding a chimeric antigen receptor (CAR). For example, preferred nucleic acids encode a cytoplasmic domain of FcεRIγ (e.g., comprising or consisting of SEQ ID NO:2). Alternatively, or additionally, the nucleic acid encodes a cytoplasmic domain of CD3 zeta (e.g., comprising or consisting of SEQ ID NO:11 (human, codon optimized) or SEQ ID NO:12 (human)). As will be readily appreciated, the CAR may target a cancer-associated or a virus-associated antigen via its extracellular binding domain as is described in more detail below.

In further contemplated embodiments, the NK or NK-92 cell can be modified to express at least one cytokine or variant thereof. For example, the cytokine may be transiently or stably expressed by the recombinant cell, and the cytokine may include an endoplasmic retention signal. Where desired, the NK or NK-92 cell may also be modified to express a suicide gene (e.g., suicide gene is thymidine kinase). Without being bound by any theory, it is believed that expression of a suicide gene can prevent uncontrolled proliferation of the NK-92 cells by providing a mechanism for selectively killing the cells upon introduction of a suitable stimulus.

In another aspect of the inventive subject matter, the inventors also contemplate a method of treating cancer in a patient in need thereof that includes a step of administering to the patient a therapeutically effective amount of modified NK/NK-92 cells or an NK/NK-92 cell line engineered to express a chimeric antigen receptor (CAR) as described herein. Viewed form a different perspective, the inventors also contemplate a modified NK/NK-92 cell or a NK/NK-92 cell line that expresses a chimeric antigen receptor (CAR), preferably comprising a cytoplasmic domain of FcεRIγ, for use in treating a tumor in a subject. In some embodiments, the use comprises administering to the subject an effective amount of modified cells or the cell line described herein to treat the tumor. In yet other embodiments, an in vitro method for killing tumor cells is contemplated and may include a step of contacting a tumor cell with a modified NK-92 cell or NK-92 cell line described herein. In some embodiments, the modified NK-92 cell or NK-92 cell line expresses a CAR that binds to an antigen on the tumor cell. In some embodiments, the CAR preferably comprises an intracellular domain from the Fc epsilon receptor gamma (FcεRIγ). Alternatively, or additionally, the CAR comprises a T cell receptor (TCR) CD3 zeta (CD3ζ) intracellular domain.

In still other embodiments, a method of treating a viral infection in a patient in need thereof is described, the method comprising administering to the patient a therapeutically effective amount of CAR-expressing NK-92 cells as described herein.

After reading this description, it will become apparent to one skilled in the art how to implement the invention in various alternative embodiments and alternative applications. However, not all embodiments of the present invention are described herein. It will be understood that the embodiments presented here are presented by way of an example only, and not limitation. As such, this detailed description of various alternative embodiments should not be construed to limit the scope or breadth of the present invention as set forth below.

Before the present invention is disclosed and described, it is to be understood that the aspects described below are not limited to specific compositions, methods of preparing such compositions, or uses thereof as such may, of course, vary. It is also to be understood that the terminology used herein is for the purpose of describing particular aspects only and is not intended to be limiting.

Titles or subtitles may be used in the specification for the convenience of a reader, which are not intended to influence the scope of the present invention. Additionally, some terms used in this specification are more specifically defined below.

With respect to suitable NK cells, it should be noted that all NK cells are deemed suitable for use herein and therefore include primary NK cells (preserved, expanded, and/or fresh cells), secondary NK cells that have been immortalized, autologous or heterologous NK cells (banked, preserved, fresh, etc.), and modified NK cells as described in more detail below. In some embodiments, it is preferred that the NK cells are NK-92 cells. The NK-92 cell line is a unique cell line that was discovered to proliferate in the presence of interleukin 2 (IL-2) (see e.g., Gong et al., *Leukemia* 8:652-658 (1994)). NK-92 cells are cancerous NK cells with broad anti-tumor cytotoxicity and predictable yield after expansion in suitable culture media. Advantageously, NK-92 cells have high cytolytic activity against a variety of cancers.

The original NK-92 cell line expressed the $CD56^{bright}$, CD2, CD7, CD11a, CD28, CD45, and CD54 surface markers and did not display the CD1, CD3, CD4, CD5, CD8, CD10, CD14, CD16, CD19, CD20, CD23, and CD34 markers. Growth of such NK-92 cells in culture is dependent upon the presence of interleukin 2 (e.g., rIL-2), with a dose as low as 1 IU/mL being sufficient to maintain proliferation. IL-7 and IL-12 do not support long-term growth, nor have various other cytokines tested, including IL-1α, IL-6, tumor necrosis factor α, interferon α, and interferon γ. Compared to primary NK cells, NK-92 typically have a high cytotoxicity even at relatively low effector:target (E:T) ratios, e.g. 1:1. Representative NK-92 cells are deposited with the American Type Culture Collection (ATCC), designation CRL-2407.

Therefore, suitable NK cells may have one or more modified KIR that are mutated such as to reduce or abolish interaction with MHC class I molecules. Of course, it should be noted that one or more KIRs may also be deleted or expression may be suppressed (e.g., via miRNA, siRNA, etc.). Most typically, more than one KIR will be mutated, deleted, or silenced, and especially contemplated KIR include those with two or three domains, with short or long cytoplasmic tail. Viewed from a different perspective, modified, silenced, or deleted KIRs will include KIR2DL1, KIR2DL2, KIR2DL3, KIR2DL4, KIR2DL5A, KIR2DL5B, KIR2DS1, KIR2DS2, KIR2DS3, KIR2DS4, KIR2DS5, KIR3DL1, KIR3DL2, KIR3DL3, and KIR3DS1. Such modified cells may be prepared using protocols well known in the art. Alternatively, such cells may also be commercially obtained from NantKwest as aNK cells ('activated natural killer cells). Such cells may then be additionally genetically modified to a CAR as further described in more detail below.

In another aspect of the inventive subject matter, the genetically engineered NK cell may also be an NK-92 derivative that is modified to express the high-affinity Fcγ receptor (CD16). Sequences for high-affinity variants of the Fcγ receptor are well known in the art (see e.g., *Blood* 2009 113:3716-3725; SEQ ID NO:43 and 44), and all manners of generating and expression are deemed suitable for use herein. Expression of such receptor is believed to allow specific targeting of tumor cells using antibodies that are specific to a patient's tumor cells (e.g., neoepitopes), a particular tumor type (e.g., her2neu, PSA, PSMA, etc.), or that are associated with cancer (e.g., CEA-CAM). Advantageously, such antibodies are commercially available and can be used in conjunction with the cells (e.g., bound to the Fcγ receptor). Alternatively, such cells may also be commercially obtained from NantKwest as haNK cells. Such cells may then be additionally genetically modified to a CAR as further described in more detail below.

Therefore, NK cells suitable for use herein include NK-92 cells (which may be transfected with a tricistronic construct encoding a CAR, a CD16 or variant thereof, and a cytokine or variant thereof), a genetically modified NK cell or NK-92 cell that expresses a CD16 or variant thereof or a cytokine or variant thereof (which may be transfected with a nucleic acid encoding a CAR and a CD16 or variant thereof or a cytokine or variant thereof), and a genetically modified NK cell or NK-92 cell that expresses a CD16 or variant thereof and a cytokine or variant thereof (which may be transfected with a nucleic acid encoding a CAR)

Genetic modification of the NK cells contemplated herein can be performed in numerous manners, and all known manners are deemed suitable for use hereon. Moreover, it should be recognized that NK cells can be transfected with DNA or RNA, and the particular choice of transfection will at least in part depend on the type of desired recombinant cell and transfection efficiency. For example, where it is desired that NK cells are stably transfected, linearized DNA may be introduced into the cells for integration into the genome. On the other hand, where transient transfection is desired, circular DNA or linear RNA (e.g., mRNA with polyA+ tail) may be used.

Similarly, it should be appreciated that the manner of transfection will at least in part depend on the type of nucleic acid employed. Therefore, viral transfection, chemical transfection, mechanical transfection methods are all deemed suitable for use herein. For example, in one embodiment, the vectors described herein are transient expression vectors. Exogenous transgenes introduced using such vectors are not integrated in the nuclear genome of the cell; therefore, in the absence of vector replication, the foreign transgenes will be degraded or diluted over time.

In another embodiment, the vectors described herein allow for stable transfection of cells. In one embodiment, the vector allows incorporation of the transgene(s) into the genome of the cell. Preferably, such vectors have a positive selection marker and suitable positive selection markers include any genes that allow the cell to grow under conditions that would kill a cell not expressing the gene. Non-limiting examples include antibiotic resistance, e.g. geneticin (Neo gene from Tn5).

Alternatively, or additionally, the vector is a plasmid vector. In one embodiment, the vector is a viral vector. As would be understood by one of skill in the art, any suitable vector can be used, and suitable vectors are well-known in the art.

In still other embodiments, the cells are transfected with mRNA encoding the protein of interest (e.g., the CAR). Transfection of mRNA results in transient expression of the protein. In one embodiment, transfection of mRNA into NK-92 cells is performed immediately prior to administration of the cells. In one embodiment, "immediately prior" to administration of the cells refers to between about 15 minutes and about 48 hours prior to administration. Preferably, mRNA transfection is performed about 5 hours to about 24 hours prior to administration. In at least some embodiments as described in more detail below, NK cell transfection with mRNA resulted in unexpectedly consistent and strong expression of the CAR at a high faction of transfected cells. Moreover, such transfected cells also exhibited a high specific cytotoxicity at comparably low effector to target cell ratios.

With respect to contemplated CARs it is noted that the NK/NK-92 cells will be genetically modified to express the CAR as a membrane bound protein exposing a portion of the CAR on the cell surface while maintaining the signaling domain in the intracellular space. Most typically, the CAR will include at least the following elements (in order): an extracellular binding domain, a hinge domain, a transmembrane domain, and a FcεRIγ signaling domain.

In preferred embodiments, the cytoplasmic domain of the CAR comprises or consists of a signaling domain of FcεRIγ. For example, the FcεRIγ signaling domain comprises or consists of or consists essentially of the amino acid sequence of SEQ ID NO:1. In some embodiments, the FcεRIγ cytoplasmic domain is the sole signaling domain. However, it should be appreciated that additional elements may also be included, such as other signaling domains (e.g., CD28 signaling domain, CD3ζ signaling domain, 4-1BB signaling domain, etc.). These additional signaling domains may be positioned downstream of the FcεRIγ cytoplasmic domain and/or upstream of the FcεRIγ cytoplasmic domain.

In some embodiments, the FcεRIγ signaling domain comprises or consists of or consists essentially of an amino acid sequence having at least about 85%, 90%, 95%, 96%, 97%, 98%, or 99% sequence homology to the amino acid sequence of SEQ ID NO:1.

As noted above, in some embodiments, the cytoplasmic domain of the CAR comprises a signaling domain of CD3 zeta (CD3ζ). In one embodiment, the cytoplasmic domain of the CAR consists of a signaling domain of CD3 zeta. In one embodiment, the CD3 zeta signaling domain comprises or consists of or consists essentially of the amino acid sequence of SEQ ID NO:10. In some embodiments, the CD3 zeta signaling domain comprises or consists of or consists essentially of an amino acid sequence having at least about 85%, 90%, 95%, 96%, 97%, 98%, or 99% sequence homology to the amino acid sequence of SEQ ID NO:10.

The CAR may comprise any suitable transmembrane domain. In one aspect, the CAR comprises a transmembrane domain of CD28. In one embodiment, the CD28 transmembrane domain comprises or consists of or consists essentially of the amino acid sequence of SEQ ID NO:7. In one embodiment, the CD28 transmembrane domain comprises or consists of or consists essentially of an amino acid sequence having at least about 85%, 90%, 95%, 96%, 97%, 98%, or 99% sequence homology to the amino acid sequence of SEQ ID NO:7. In one embodiment, the transmembrane domain is selected from a CD28 transmembrane domain, 4-1BB transmembrane domain, or FcεRIγ transmembrane domain.

The CAR may comprise any suitable hinge region. In one aspect, the CAR comprises a hinge region of CD8. In one embodiment, the CD8 hinge region comprises or consists of or consists essentially of the amino acid sequence of SEQ ID NO:6. In one embodiment, the CD8 hinge region comprises or consists of or consists essentially of an amino acid sequence having at least about 85%, 90%, 95%, 96%, 97%, 98%, or 99% sequence homology to the amino acid sequence of SEQ ID NO:6.

Most typically, but not necessarily, the extracellular binding domain of the CAR will be a scFv or other natural or synthetic binding portion that specifically binds an antigen of interest. Especially suitable binding portions include small antibody fragments with single, dual, or multiple target specificities, beta barrel domain binders, page display fusion proteins, etc. Among other suitable extracellular binding domains, preferred domains will specifically bind to a tumor-specific antigen, a tumor associated antigen, or a patient- and tumor-specific antigen. For example, contemplated antigens include CD19, CD20, GD2, HER-2, CD30, EGFR, FAP, CD33, CD123, PD-L1, IGF1R, CSPG4, or B7-H4. Further tumor-specific antigens are described, by way of non-limiting example, in US2013/0189268; WO 1999024566 A1; U.S. Pat. No. 7,098,008; and WO 2000020460, each of which is incorporated herein by reference in its entirety. Likewise, other preferred domains will specifically bind to a (pathogenic) virus-specific antigen, such as an antigen of an HIV virus (e.g., gp120), an HPV virus, an RSV virus, an influenza virus, an ebolavirus, or an HCV virus.

With respect to the construction of contemplated CARs it should be recognized that CARs can be engineered in numerous manners as described, for example, in WO 2014/039523; US 2014/0242701; US 2014/0274909; US 2013/0280285 and WO 2014/099671, each of which is incorporated herein by reference in its entirety.

Therefore, and viewed from a different perspective, contemplated CARs target an antigen associated with a specific cancer type. In one embodiment, the cancer is leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyo sarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, or retinoblastoma.

Therefore, contemplated CARs will generally have a structure of an extracellular binding domain that is (directly) coupled to a hinge domain, which is (directly) coupled to a transmembrane domain, which is (directly) coupled to an FcεRIγ signaling domain. In still further contemplated aspects, contemplated CARs may also include one or more signaling domains in addition to or replacing the FcεRIγ signaling domain, and especially contemplated signaling domains include CD3ζ signaling domains, 4-1BB signaling domains, and CD28 signaling domains. For example, contemplated CARs may therefore include any one of the binding domains having SEQ ID NO:4, 23-42, and 48-59 that is coupled to a hinge domain (e.g., CD8 hinge as in SEQ ID NO:6), which is in turn coupled to a transmembrane domain (e.g., CD28 TM as in SEQ ID NO:7), which is coupled to a signaling domain (e.g., FcεRIγ signaling domain as in SEQ ID NO:1, CD28 signaling domain as in SEQ ID NO:8, 4-1BB signaling domain as in SEQ ID NO:9, CD3ζ signaling domain as in SEQ ID NO:10)

In still further contemplated aspects, NK cells may be further genetically modified to express one or more cytokines to so provide a selection marker where the cytokine and the CAR are encoded on the same recombinant nucleic acid and/or to render the recombinant cells independent of exogenous IL-2. Therefore, in some embodiments, NK-92 cells are modified to express at least one cytokine. In particular, the at least one cytokine is IL-2, IL-12, IL-15, IL-18, IL-21, or a variant thereof. In preferred embodiments, the cytokine is IL-2 or a variant thereof and especially preferred variants include endoplasmic retention signals (e.g., human IL-2 as in SEQ ID NO:18, or with ER retention signal as in SEQ ID NO:19). For example, the IL-2 gene is cloned and expressed with a signal sequence that directs the IL-2 to the endoplasmic reticulum. This permits expression of IL-2 at levels sufficient for autocrine activation, but without releasing IL-2 extracellularly (e.g., *Exp Hematol.* 2005 February; 33(2): 159-64.) Alternatively, expression of a cytokine (and especially IL-15) may also be such that the cytokine will be expressed in sufficient quantities to provide an autocrine growth signal to the recombinant cells, but also to allow at least some of the expressed IL-15 to be released from the cell, which will so provide an immune stimulatory signal. For example, such expression may be achieved using a human IL-15 sequence that includes both the signal peptide and an endoplasmic retention sequence. An exemplary DNA and protein sequence for an endoplasmic retained IL-15 is shown in SEQ ID NO:72 and SEQ ID NO:73, respectively.

Where desired, contemplated cells may also express a suicide gene. The term "suicide gene" refers to a transgene that allows for the negative selection of cells expressing the suicide gene. A suicide gene is used as a safety system, allowing cells expressing the gene to be killed by introduction of a selective agent. This is desirable in case the recombinant gene causes a mutation leading to uncontrolled cell growth, or the cells themselves are capable of such growth. A number of suicide gene systems have been identified, including the herpes simplex virus thymidine kinase (TK) gene, the cytosine deaminase gene, the varicella-zoster virus thymidine kinase gene, the nitroreductase gene, the *Escherichia coli* gpt gene, and the *E. coli* Deo gene. Typically, the suicide gene encodes for a protein that has no ill effect on the cell but, in the presence of a specific compound, will kill the cell. Thus, the suicide gene is typically part of a system.

In one embodiment, the suicide gene is active in NK-92 cells. In one embodiment, the suicide gene is the thymidine kinase (TK) gene. The TK gene may be a wild-type or mutant TK gene (e.g., tk30, tk75, sr39tk). Cells expressing the TK protein can be killed using ganciclovir. In another embodiment, the suicide gene is cytosine deaminase, which is toxic to cells in the presence of 5-fluorocytosine. Garcia-Sanchez et al. "Cytosine deaminase adenoviral vector and 5-fluorocytosine selectively reduce breast cancer cells 1 million-fold when they contaminate hematopoietic cells: a potential purging method for autologous transplantation." *Blood.* 1998 Jul. 15; 92(2):672-82. In a further embodiment, the suicide gene is cytochrome P450, which is toxic in the presence of ifosfamide or cyclophosphamide. See, e.g. Touati et al. "A suicide gene therapy combining the improvement of cyclophosphamide tumor cytotoxicity and the development of an anti-tumor immune response." *Curr Gene Ther.* 2014; 14(3):236-46. In yet another embodiment, the suicide gene is iCasp9. Di Stasi, (2011) "Inducible apoptosis as a safety switch for adoptive cell therapy." *N Engl J Med* 365: 1673-1683. See also Morgan, "Live and Let Die: A New Suicide Gene Therapy Moves to the Clinic" *Molecular Therapy* (2012); 20: 11-13. iCasp9 induces apoptosis in the presence of a small molecule, AP1903. AP1903 is biologically inert small molecule, that has been shown in clinical studies to be well tolerated, and has been used in the context of adoptive cell therapy.

Of course, it should be noted that all of the recombinant proteins can be expressed from individual recombinant sequences. However, it is generally preferred that where multiple recombinant sequences are expressed (e.g., CAR, CD16, cytokine), coding regions may be arranged in a polycistronic unit with at least two or at least three coding regions encoding the recombinant proteins. Therefore, transgenes can be engineered into an expression vector by any mechanism known to those of skill in the art. Where multiple transgenes are to be inserted into a cell, transgenes may be engineered into the same expression vector or a different expression vector. In some embodiments, the cells are transfected with mRNA encoding the transgenic protein to be expressed. In some embodiments, the cells are transfected with DNA encoding the transgenic protein to be expressed. Transgenes, mRNA and DNA can be introduced into the NK-92 cells using any transfection method known in the art, including, by way of non-limiting example, infection, viral vectors, electroporation, lipofection, nucleofection, or "gene-gun."

In preferred embodiments, it should therefore be noted that the genetically modified NK cell (especially where the cell expresses a CAR and CD16 or variant thereof) will exhibit three distinct modes of cell killing: General cytotoxicity which is mediated by activating receptors (e.g., an NKG2D receptor), ADCC which is mediated by antibodies bound to a target cell, and CAR mediated cytotoxicity. As will be readily apparent, contemplated genetically modified cells can be used for treatment of various diseases, and especially of various cancers and viral infections where a diseased cell presents a disease-specific or disease-associated antigen. Consequently, the inventors contemplate methods of treating patients with modified NK or NK-92 cells as described herein. In one embodiment, the patient is suffering from cancer (e.g., a tumor) and the modified NK-92 cell or cell line expresses a CAR specific for an antigen expressed on the surface of a cell from the cancer or tumor. In one embodiment, the patient is suffering from a viral infection and the modified NK-92 cell or cell line expresses a CAR specific for an antigen expressed on the surface of a cell that has been infected by the virus. In one embodiment, the patient is suffering from a bacterial infection and the modified NK-92 cell or cell line expresses a CAR specific for an antigen expressed on the surface of a bacterial cell causing the infection.

In some embodiments, the cancer is selected from the group consisting of leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyo sarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma and retinoblastoma.

Contemplated modified NK or NK-92 cells can be administered to an individual by absolute numbers of cells. For example, the individual can be administered from about 1000 cells/injection to up to about 10 billion cells/injection, such as at about, at least about, or at most about, $1\times10^8$, $1\times10^7$, $5\times10^7$, $1\times10^6$, $5\times10^6$, $1\times10^5$, $5\times10^5$, $1\times10^4$, $5\times10^4$, $1\times10^3$, $5\times10^3$ (and so forth) modified NK-92 cells per injection, or any ranges between any two of the numbers, end points inclusive. In other embodiments, modified NK-92 cells can be administered to an individual by relative numbers of cells, e.g., said individual can be administered about 1000 cells to up to about 10 billion cells per kilogram of the individual, such as at about, at least about, or at most about, $1\times10^8$, $1\times10^7$, $5\times10^7$, $1\times10^6$, $5\times10^6$, $1\times10^5$, $5\times10^5$, $1\times10^4$, $5\times10^4$, $1\times10^3$, $5\times10^3$ (and so forth) modified NK-92 cells per kilogram of the individual, or any ranges between any two of the numbers, end points inclusive. In other embodiments, the total dose may calculated by $m^2$ of body surface area, including about $1\times10^{11}$, $1\times10^{10}$, $1\times10^9$, $1\times10^8$, $1\times10^7$, per $m^2$, or any ranges between any two of the numbers, end points inclusive. The average person is about 1.6 to about 1.8 $m^2$. In a preferred embodiment, between about 1 billion and about 3 billion NK-92 cells are administered to a patient.

The modified NK-92 cells, and optionally other anti-cancer or anti-viral agents can be administered once to a patient with cancer or infected with a virus or can be administered multiple times, e.g., once every 1, 2, 3, 4, 5, 6, 7, 8, 9, 10, 11, 12, 13, 14, 15, 16, 17, 18, 19, 20, 21, 22 or 23 hours, or once every 1, 2, 3, 4, 5, 6 or 7 days, or once every 1, 2, 3, 4, 5, 6, 7, 8, 9, 10 or more weeks during therapy, or any ranges between any two of the numbers, end points inclusive.

In one embodiment, where the modified NK-92 cells express a suicide gene, the patient is administered an agent to trigger modified NK-92 cell death. In one embodiment, the agent is administered at a time point after administration of the modified NK-92 cells that is sufficient for the NK-92 cells to kill target cells.

In one embodiment, the modified NK-92 cells are irradiated prior to administration to the patient. Irradiation of NK-92 cells is described, for example, in U.S. Pat. No. 8,034,332, which is incorporated herein by reference in its entirety. In one embodiment, modified NK-92 cells that have not been engineered to express a suicide gene are irradiated.

Furthermore, it should be appreciated that contemplated treatments will also include administration of other immune therapeutic entities, and especially preferred immune therapeutic entities include a viral cancer vaccine (e.g., adenoviral vector encoding cancer specific antigens), a bacterial cancer vaccine (e.g., non-pyrogenic E. coli expressing one or more cancer specific antigens), a yeast cancer vaccine, N-803 (also known as ALT-803, ALTOR Biosciences), an antibody (e.g., binding to a tumor associated antigen or patient specific tumor neoantigen), a stem cell transplant (e.g., allogeneic or autologous), and a tumor targeted cytokine (e.g., NHS-IL12, IL-12 coupled to a tumor targeting antibody or fragment thereof).

EXAMPLES

The following examples are for illustrative purposes only and should not be interpreted as limitations of the claimed invention. There are a variety of alternative techniques and procedures available to those of skill in the art which would similarly permit one to successfully perform the intended invention.

Example 1: CAR mRNA Preparation

DNA sequences encoding each variant of CD19CAR schematically depicted in FIG. 1 were designed in silico, synthesized de novo, and subcloned into the mRNA expression vector, pXT7 (GeneArt, Life Technologies). Ten micrograms (μg) of plasmid were linearized by digestion with the SalI restriction enzyme (New England Biolabs) and purified using a QIAgen gel purification kit (QIAgen) according to manufacturer's instructions.

The linearized DNA was used as template for in vitro synthesis of mRNA using a T7 mMessage mMachine Ultra transcription kit (ThermoFisher Scientific, Waltham, MA) according to the manufacturer's instructions. This kit includes a polyadenylation extension step that increases the length of the polyA tail of the mRNA and thus enhances stability in vivo.

mRNA for six CD19-CAR variants was prepared, with a green fluorescent protein (GFP) mRNA prepared as a negative control. All of the CD19-CAR polypeptide variants contained an extracellular domain comprising an anti-CD19 scFv region (αCD19-scFv) (SEQ ID NO:4), a hinge region from CD8 (SEQ ID NO:6), and a transmembrane domain from CD28 (SEQ ID NO:7). The intracellular domains of the CD19CARs were as follows and schematically shown in FIG. 1: CAR 3z contained a CD3ζ signaling domain; CAR FcεRIγ contained a FcεRIγ signaling domain (SEQ ID NO: 1); CAR 28_3z contained a CD28 signaling domain fused to a CD3ζ signaling domain; CAR BB_3z contained a 4-1BB signaling domain fused to a CD3ζ signaling domain; CAR 28_BB_3z contained a CD28 signaling domain fused to a 4-1BB signaling domain fused to a CD3ζ signaling domain; CAR BB_3z_28 contained a 4-1BB signaling domain fused to a CD3ζ signaling domain fused to a CD28 signaling domain.

More particularly, the 1st generation CAR with CD3ζ signaling domain of FIG. 1 had a nucleic acid sequence of SEQ ID NO:13 (human) and SEQ ID NO:21 (murine), which translated to an amino acid sequence of SEQ ID NO:22. The $1^{st}$ generation CAR with a FcεRIγ signaling domain nucleic had a nucleic acid sequence of SEQ ID NO:5 and an amino acid sequence of SEQ ID NO:3. The $2^{nd}$ generation CAR with CD28/CD3ζ signaling domain had a nucleic acid sequence of SEQ ID NO:14 and the $2^{nd}$ generation CAR with 4-1BB/CD3ζ signaling domain had a nucleic acid sequence of SEQ ID NO:15. The $3^{rd}$ generation CAR with CD28/4-1BB/CD3ζ signaling domain had a nucleic acid sequence of SEQ ID NO:16 and the $3^{rd}$ generation CAR with 4-1BB/CD3ζ/CD28 signaling domain had a nucleic acid sequence of SEQ ID NO:17.

Further $1^{st}$ generation CARs with a FcεRIγ signaling domain were prepared as described in more detail below in which the hinge region was a CD8 hinge (SEQ ID NO:6 or SEQ ID NO:45 (human), encoded by SEQ ID NO:46), in which the transmembrane domain was a CD28 transmembrane domain (SEQ ID NO:7), and in which the signaling domain was a FcεRIγ signaling domain (SEQ ID NO:1, encoded by nucleic acid SEQ ID NO:2).

Target specificity was then imparted against a variety of tumor-associated targets using selected scFv portions as follows (all in a sequential arrangement as shown in FIG. 1, CAR FcRe): CD19 (using anti-CD19 scFv of SEQ ID NO:4 or SEQ ID NO:24, encoded by codon-optimized SEQ ID NO:23), CD20 (using anti-CD20 scFv of SEQ ID NO:26, encoded by codon-optimized SEQ ID NO:25), CD33 (using anti-CD33 scFv of SEQ ID NO:28, encoded by codon-optimized SEQ ID NO:27), CSPG4 (using anti-CSPG4 scFv of SEQ ID NO:30, encoded by codon-optimized SEQ ID NO:29), EGFR (using anti-EGFR scFv of SEQ ID NO:32, encoded by codon-optimized SEQ ID NO:31), IGF1R (using anti-IGF1R scFv of SEQ ID NO:34, encoded by codon-optimized SEQ ID NO:33), CD30 (using anti-CD30 scFv of SEQ ID NO:36, encoded by codon-optimized SEQ ID NO:35), HER2/neu (using anti-HER2/neu scFv of SEQ ID NO:38, encoded by codon-optimized SEQ ID NO:37), GD2 (using anti-GD2 scFv or SEQ ID NO:40 or SEQ ID NO:42, encoded by codon-optimized SEQ ID NO:39 or SEQ ID NO:41), CD123 (using anti-CD123 scFv of SEQ ID NO:49, encoded by codon-optimized SEQ ID NO:48), PD-L1 (using anti-PD-L1 scFv of SEQ ID NO:51, encoded by codon-optimized SEQ ID NO:50), B7-H4 (using anti-B7-H4 scFv of SEQ ID NO:53, encoded by codon-optimized SEQ ID NO:52), and FAP (using anti-FAP scFv of SEQ ID NO:58 or SEQ ID NO:59, encoded by codon-optimized SEQ ID NO:56 or SEQ ID NO:57).

Likewise, target specificity was imparted against a variety of virus-associated targets using selected scFv portions as follows (all in a sequential arrangement as shown in FIG. 1, CAR FcRe): HIV gp120 (using anti-gp120 scFv of SEQ ID NO:55, encoded by codon-optimized SEQ ID NO:54).

All constructs as prepared above expressed well in NK-92 cells and exemplary results are shown for the physiological activity of the so modified NK-92 cells.

Example 2: Electroporation of NK-92 Cells with CD19CAR mRNA

NK-92 cells were grown in X-Vivo10 medium (Lonza, Basel, Switzerland) supplemented with 5% Human AB Serum (Valley Biomedical, Winchester, VA) and 500 IU/mL IL-2 (Prospec, Rehovot, Israel). Cells were electroporated with mRNA using the Neon™ electroporation device (Life Technologies, Carlsbad, CA), following the manufacturer's parameters for NK-92 cells (1250 V, 10 ms, 3 pulses) and using 5 μg of mRNA per $10^6$ cells in a volume of 100 μl. Electroporated cells were maintained in medium (same as above) for 20 hours (h).

Figure 2A:
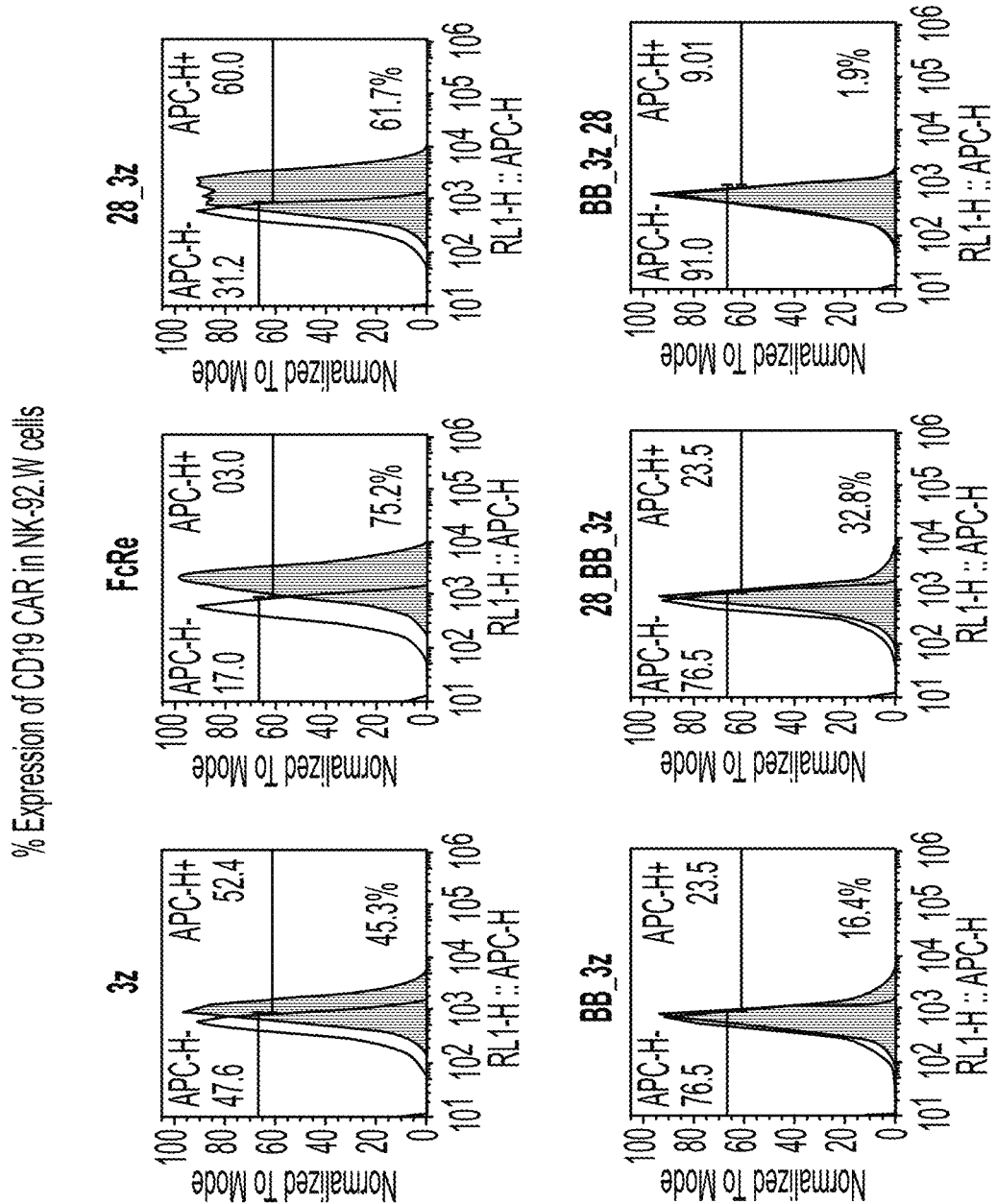
FIG. 2A are exemplary results for the percentage of NK-92 cells expressing the CD19-CAR of FIG. 1 after transfection with CD19-CAR mRNA as determined by flow cytometry with an anti-scFv antibody labeled with eF660.
Figure 2B:
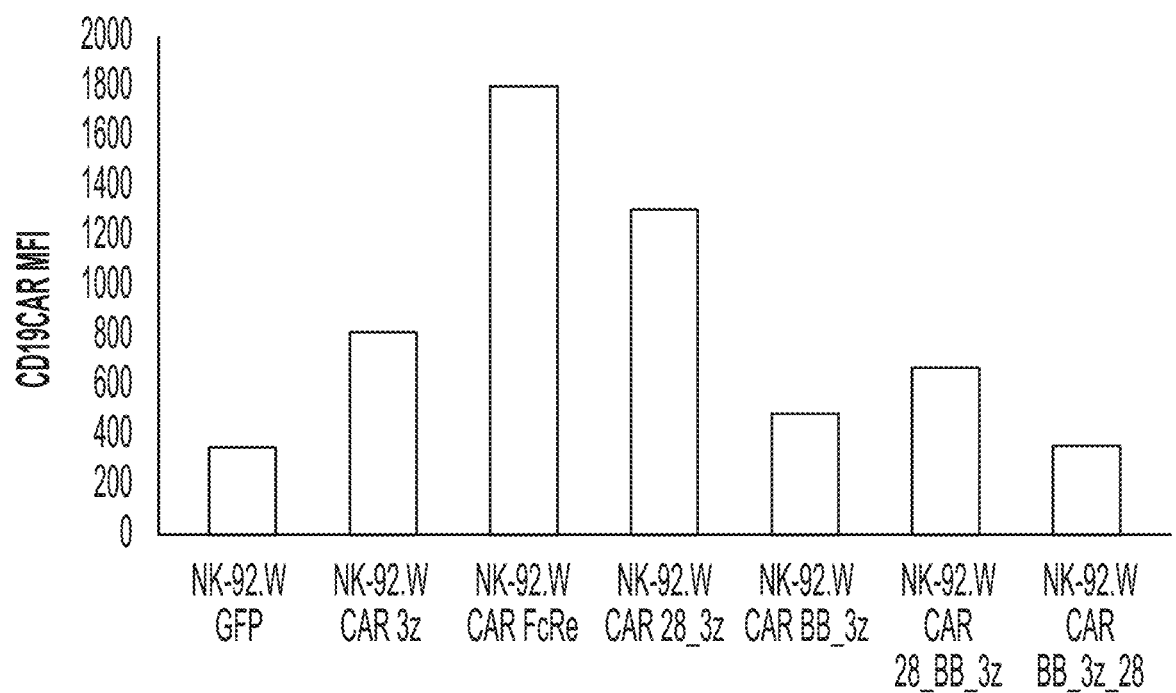
FIG. 2B are exemplary results for the median fluorescent intensity (MFI) minus background for CD19-CAR-expressing NK-92 cells labeled with an anti-scFv antibody labeled with eF660.

The CD19CAR expression on the NK-92 cell surface was determined by flow cytometry using anti-scFv antibody labeled with eF660 (eBioscience, San Diego, CA). FIG. 2A shows the % expression of the indicated CD19CAR in the NK-92 cell population. FIG. 2B shows the median fluorescence intensity (MFI, minus background) of cells electroporated with the indicated CD19CAR. As can be taken from FIGS. 2A and 2B, CAR FcRe unexpectedly had the highest percentage of cells (75.2%) expressing CD19CAR at the cell surface, as well as the highest MFI (quantity of expressed CAR on a recombinant cell), followed by 28_3z (61.7%).

Example 3: Cytotoxicity of NK-92 Cells Expressing CD19CAR Against Cancer Cell Lines The efficacy of CAR-expressing NK-92 cells to target cancer cells in vitro was tested 20 hours post-electroporation using a flow-based in vitro cytotoxicity assay. Effector cells (NK-92 expressing CD19CAR or GFP) were mixed with PKHGL67-labeled (Sigma-Aldrich, St. Louis, MO) target cells (K562; or SUPB15, B-ALL, CD19+) at different effector to target ratios (5:1 to 0.3:1) in a 96-well plate and incubated 4 h at 37° C. Propidium Iodide (PI) (Sigma Aldrich, St. Louis, MO) was added to the cells and samples were analyzed within 2 h using an Attune flow cytometer (Life Technologies, Carlsbad, CA). The cytotoxicity was determined by the % of PI-positive cells within the PKH-positive target population.

Figure 3A:
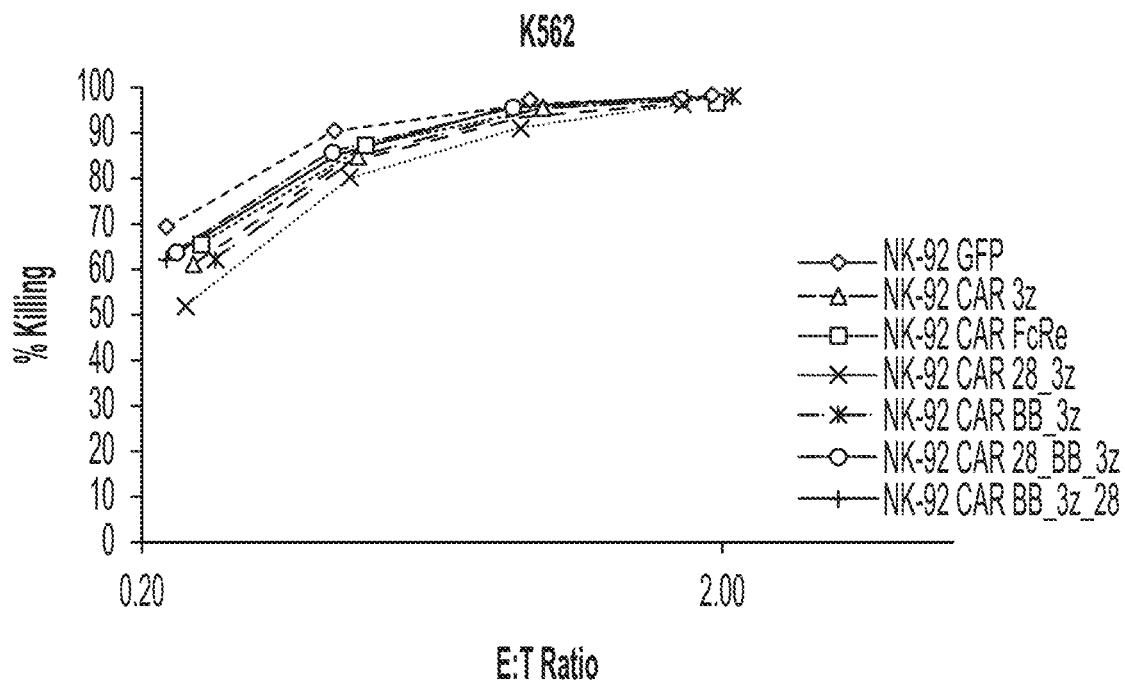
FIG. 3A shows exemplary results for the percentage of NK-92 cell-sensitive target cancer cells (K562) that were killed by NK-92 cells (effector) expressing the CD19CARs at effector:target ratios of from 5:1 to 0.3:1.
Figure 3B:
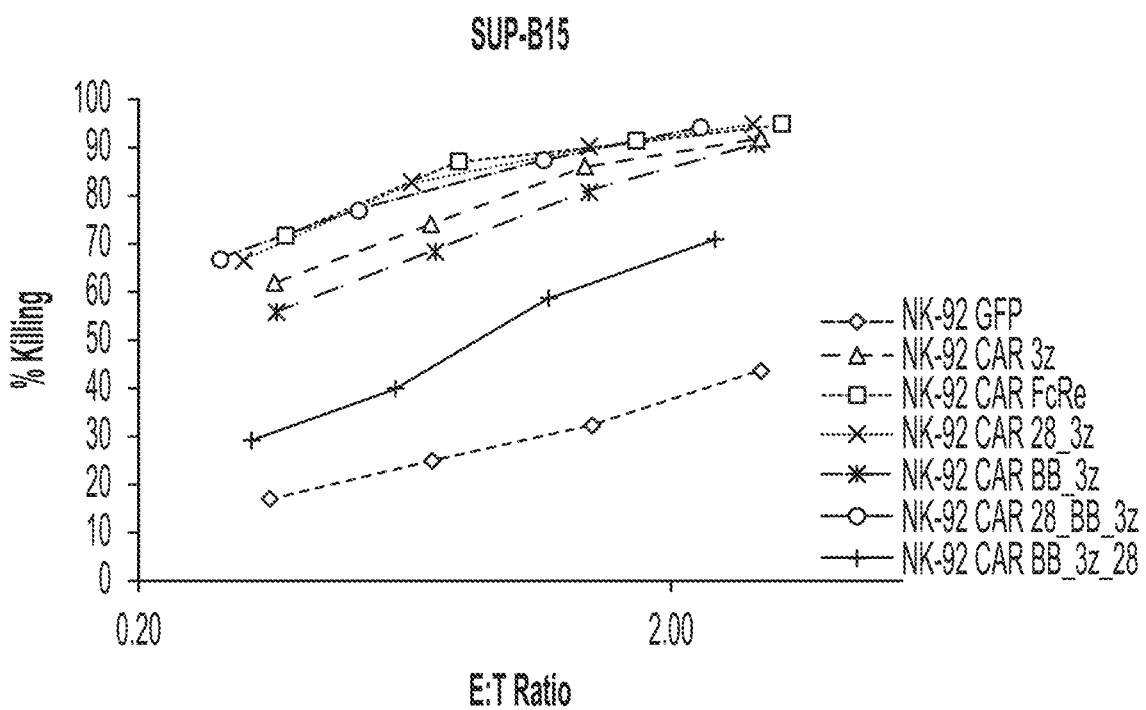
FIG. 3B shows exemplary results for the percentage of NK-92 cell-resistant, CD19-positive target cancer cells (SUP-B15) that were killed by NK-92 cells (effector) expressing the CD19CARs at effector:target ratios of from 5:1 to 0.3:1.

Exemplary results are provided in FIGS. 3A and 3B. NK-92 cells are effective at killing K562 cells regardless of CD19CAR expression as can be seen from FIG. 3A. Thus, it should be noted that recombinant cells will not lose cytotoxicity. In contrast, GFP-expressing NK-92 cells were inefficient at killing the cancer cell line SUP-B15. SUP-B15 is an acute lymphoblastic leukemia cell line that is CD19-positive and resistant to NK-92-mediated cytotoxicity. Expression of any CD19CAR tested provided increased cytotoxic activity against the SUP-B15 cell line compared to control (GFP-expressing NK-92 cells) as can be readily taken from FIG. 3B. Surprisingly, CAR FcRe exhibited cytotoxicity similar or superior to the $2^{nd}$ and $3^{rd}$ generation CARs. Such finding is particularly unexpected as the FcεRIγ signaling domain was present only as a single unit and not combined with other signaling domains. Such arrangement, when used in CAR T-cells failed to provide desirable targeted cytotoxicity. Advantageously, tricistronic mRNA constructs were able to produce substantial quantities of desired CARs with excellent functional activity. Such constructs are especially beneficial where the CAR expression should be transient.

Figure 4:
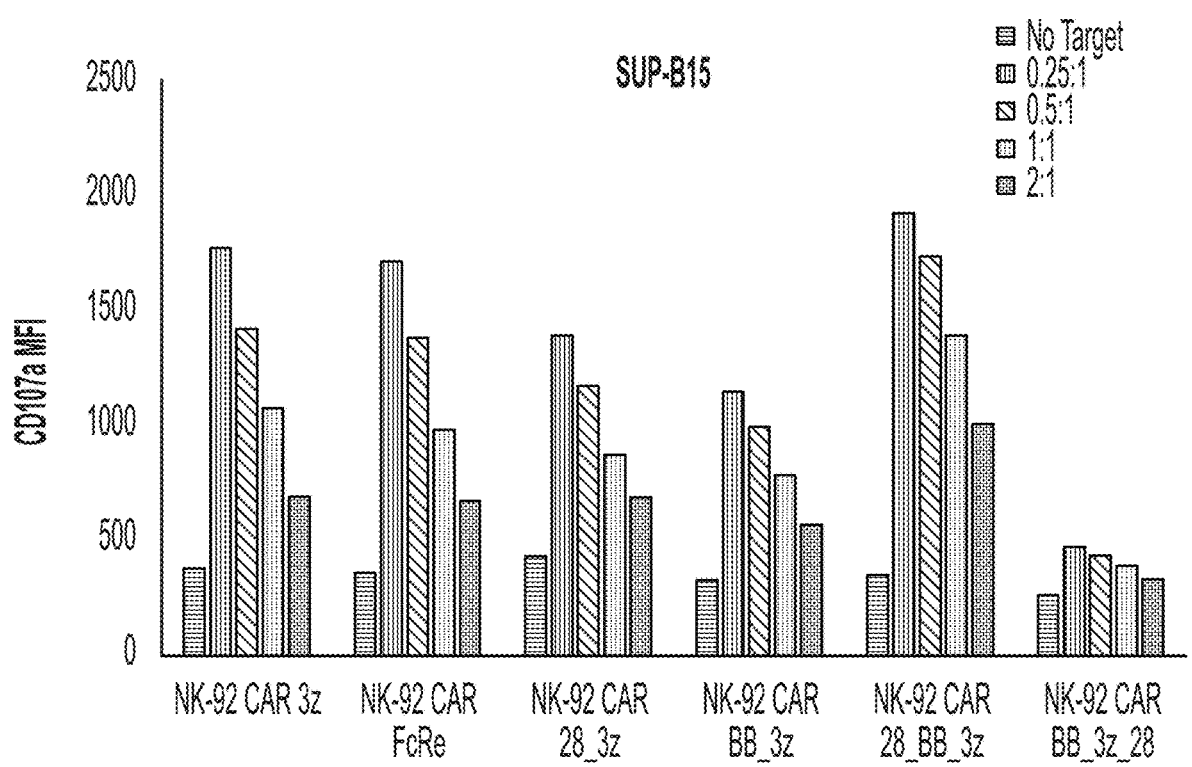
FIG. 4 shows exemplary results for the MFI of CD19-CAR-expressing NK-92 cells (effector) labeled with anti-CD107a antibody in a degranulation assay with SUP-B15 target cells at effector:target ratios of from 2:1 to 0.25:1.

Degranulation is a critical step required for the release of the lytic proteins (e.g., perforin and granzyme) from secretory granules in the NK-92 cells. Degranulation is initiated by recognition of a target cell by NK-92. To test degranulation in the constructs, effector cells (NK-92) were mixed with unlabeled target cells (SUP-B15) at different effector to target ratios (5:1 to 0.3:1) in a 96-well plate, and anti-CD107a (FITC-conjugated, BD Pharmingen, San Jose, CA) was added to each well. Plates were incubated at 37° C. in a $CO_2$ incubator and after 1 h monensin (Golgi-stop) was added to the wells. The plates were incubated for another 3 h at 37° C. and the samples were analyzed by flow cytometry (Attune, Life technologies, Carlsbad, CA). Percentage degranulation was determined by subtracting the % CD107a positive in NK-92 cells alone to the % CD107a positive in the effector+target samples, and exemplary results are provided in FIG. 4.

Example 4: CD19 t-haNK Cells Significantly Improved Animal Survival in a Raji Tumor Xenograft Model CD19 t-haNK cells (clone 19.6) comprising the Fc Epsilon intracellular signaling domain. CD19 t-haNK cells were cultured in X-VIVO™ 10 medium supplemented with 5% heat inactivated human AB serum.

Test Animals: Animal Strain/Species: NOD.Cg-Prkdc scid Il2rgtm1Wjl/SzJ (NSG) mice; Age: 9-10 weeks at study initiation (after quarantine); Sex: Female; Body Weight: 20-27 grams at study initiation. Number of Animals: 20 for the IV tumor model; 12 for the SC tumor model. Supplier: The Jackson Laboratory (610 Main Street Bar Harbor, ME 04609 US).

Raji Tumor Model: Raji Cancer Cell Line: Raji cells were originally purchased from ATCC (Catalog #CCL-86TM; Lot #61723871) and then expanded and prepared for administration.

Cell Culture Medium: ATCC-formulated RPMI-1640 medium supplemented with 10% fetal bovine serum with penicillin (100 U/mL), streptomycin (100 µg/mL).

Cell Harvest: Raji cells (passage 12) in exponential phase were collected by centrifugation. Cells were washed and re-suspended in serum free medium at the concentration of $5 \times 10^5$ viable cells/mL for IV inoculations, and in medium/Matrigel (1:1 v/v) at the concentration of $2.5 \times 10^6$ viable cells/mL for SC implantations. Cells were stored on ice prior to animal injection. Cells used in the in vivo study had a viability of 96%.

Raji Cell Inoculation: Raji IV Model. 20 animals were injected IV via the lateral tail vein with 0.2 mL of Raji cell suspension with 27 gauge needles ($1 \times 10^5$ cells inocula). Raji SC Model. 12 animals were implanted SC on both flanks with 0.1 mL of Raji cell suspension with 25-gauge needles ($2.5 \times 10^5$ cells inocula).

Other Reagents: RPMI-1640 media, X-VIVO™ 10 media; Heated-inactivated human male AB serum (Access Cell Culture (Access Biologicals LLC); Fetal Bovine Serum (FBS); Pen Strep Glutamine (100×) (Life Technologies, Catalog #10378, Lot #1881463, Expiration date: May 2018); Matrigel Basement Membrane Matrix; Pluronic(R) F-68, 10% Solution.

Experimental Procedures

IV Raji Model—Randomization: Within 24 hours after cancer cell inoculation, which was defined as Day 1, 20 animals were pseudo-randomized into 2 groups of 10 according to body weight to achieve similar average body weight between the groups.

Test Article Administration: On Days 2, 5, 8, 10, 12, and 17, CD19 t-haNK cells grown in the exponential phase were harvested by centrifugation and formulated in X-VIVO™ 10 at the concentration of $5 \times 10^7$ cells/mL for IV administration at the dose of $1 \times 10^7$ cells per mouse with an injection volume of 200 µL. Animals in Group A received the vehicle control, while animals in Group C received CD19 t-haNK cells.

Body Weight: Animals were weighed prior to tumor cell injection and twice weekly.

Clinical Observations: Animals were observed daily for mortality/morbidity (G0 to G4) and clinical signs of toxicity. Paralyzed or moribund animals were euthanized.

Euthanasia: Animals were euthanized with $CO_2$ inhalation followed by cervical dislocation. Mortality events (euthanasia or spontaneous) were recorded in Death Log (Appendix 6) and tallied to calculate the survival curve.

SC Raji Model—Tumor Volume Measurement: After SC tumor implantation, animals were examined at least twice a week for tumor establishment. When tumors became palpable, tumor volumes (TV) were measured with a digital hand held caliper once to twice weekly, and calculated using this formula: TV=Length×Width 2/2 [Length being the greatest diameter and Width being the shortest diameter of the tumor].

Randomization: When the average tumor volume reached an injectable size (195 mm3 in this case; 24 days post-implantation), the 12 tumor-bearing animals were pseudo-randomized into 2 groups of 6 to achieve similar tumor volumes between the groups. This was defined as Day 0.

Test Article Administration: On Days 1, 4, 7, 9, 11, and 13, CD19 t-haNK cells grown in the exponential phase were harvested by centrifugation, subjected to 1000 cGy gamma irradiation, and formulated in X-VIVO™ 10 medium at the concentration of $5 \times 10^7$ cells/mL for IV administration at the dose of $1 \times 10^7$ cells per mouse with an injection volume of 200 µL. As shown in Table 1, animals in Group D received the vehicle solution, while animals in Group F received CD19 t-haNK cells.

Body Weight. Animals were weighed prior to tumor cell injection and then twice weekly.

Clinical Observations. Animals were observed daily for mortality/morbidity (G0 to G4) and clinical signs of toxicity (T1 to T12). Paralyzed or moribund animals were euthanized.

Endpoint and Euthanasia. While moribund animals were euthanized as soon as they showed morbidity, surviving animals were subjected to scheduled euthanasia for tissue collection. Specifically, half of the surviving animals (up to 3 mice/group) were euthanized on Day 13 at 6 hours post the last dose of test article administration. The rest of the animals were euthanized on Day 15 at 48 hours post the last dosing.

Necropsy and Tumor and Tissue Collection. Upon termination, a necropsy was performed and organs with visible gross lesions were collected, fixed in 10% formalin, and submitted to a contract pathology laboratory (Seventh Wave Laboratories) for histological evaluation of tumor/metastatic disease burden.

TABLE 1

| Group | N | Tumor Model | Treatment | Tx Route | NK Cell Dose | Treatment Days | Endpoint |
|---|---|---|---|---|---|---|---|
| A | 10 | IV | Vehicle | IV | / | 2, 5, 8, 10, 12, and 17 | Moribund |
| C | 10 | IV | CD19 t-haNK, non-IR | IV | $1 \times 10^7$ | 2, 5, 8, 10, 12, and 17 | Moribund |
| D | 6 | SC, bilateral | Vehicle | IV | / | 1, 4, 7, 9, 11, and 13 | Days 13 and 15 or Moribund |
| F | 6 | SC, bilateral | CD19 t-haNK, IR | IV | $1 \times 10^7$ | 1, 4, 7, 9, 11, and 13 | Days 13 and 15 or Moribund |

IR, irradiated (1000 cGy); non-IR, non-irradiated; IV, intravenous; SC, subcutaneous; Tx, treatment.

Data Analysis

Tumor Volume Calculation: Tumor volume=Length× Width 2/2 (Length and Width being the longest and shortest diameters of the tumor, respectively); Tumor Growth Inhibition (TGI) Calculation: TGI=(TC−Tt)/ΔTC×100%, where TC and Tt is the average tumor volume for control and treatment groups at the end of the study, respectively, and ΔTC is the change in average tumor volume in the control group.

Statistical Analysis—Tumor Growth Curves: Tumor growth curves were analyzed by 2-way ANOVA followed by multiple comparison by Tukey test. Survival Curves: Survival curves were analyzed by Log-rank (Mantel-Cox) test.

Liver Metastasis Estimation: Differences in liver metastatic disease burden on individual days were analyzed by unpaired 2-tailed t test. Statistical Significance: $P<0.05$ is considered statistically significant. All statistical analyses were performed using GraphPad Prism version 7.

Results

Figure 5:
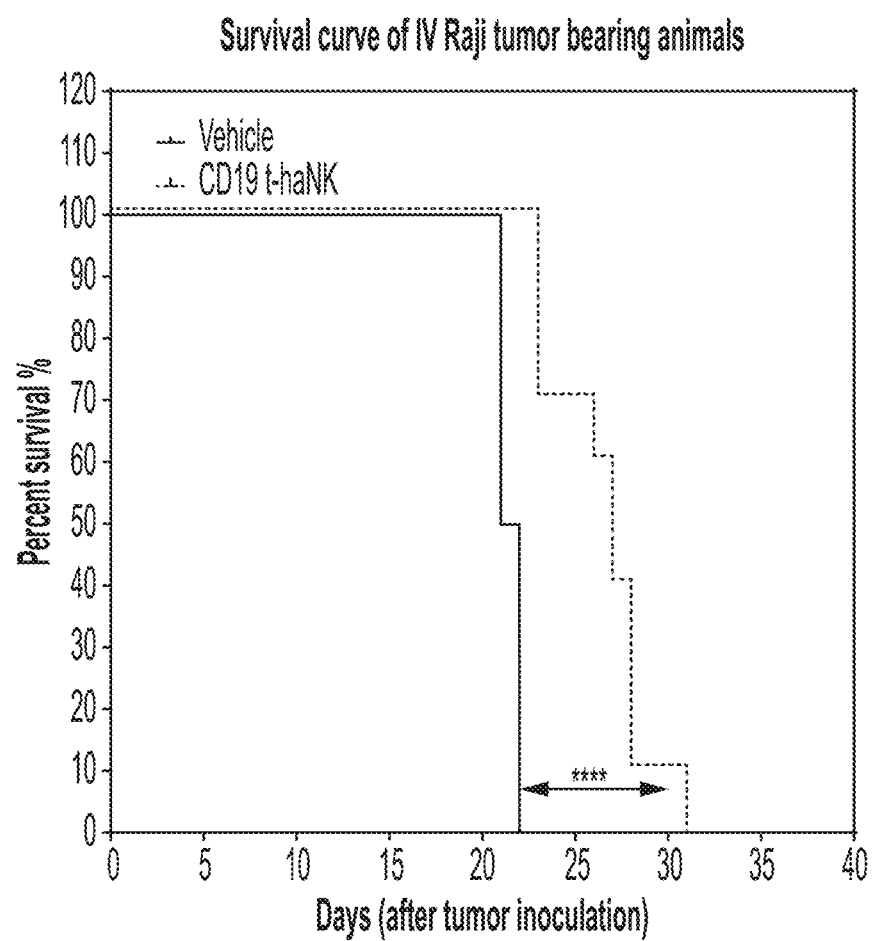
FIG. 5 shows an exemplary survival curve of IV Raji tumor bearing animals, as described in the Examples. Statistical analysis was Log-rank (Mantel-Cox) test. ****, P<0.0001.

IV Raji Model: The main readout in the IV tumor model was animal survival. A death event was counted when an animal was found dead or was euthanized due to disease-related morbidity and/or paralysis. As shown in FIG. 5, compared to vehicle control, CD19 t-haNK cell treatment was able to significantly improve the animals' rate of survival, resulting in a median survival of 27 days versus 21.5 days in the vehicle control group ($P<0.0001$).

Figure 6:
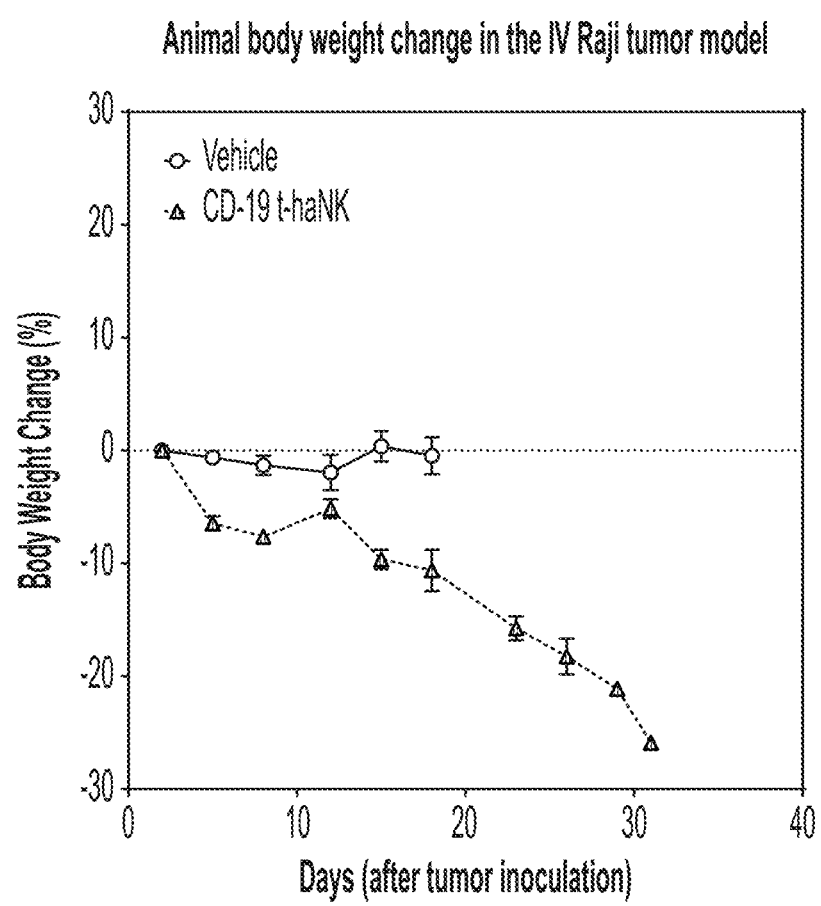
FIG. 6 shows exemplary results for animal body weight change in the IV Raji tumor model. Data are mean±SEM. SEM was calculated as Standard Deviation divided by the square root of N.

Animal body weight change was also monitored throughout the study. As shown in FIG. 6, CD19 t-haNK treated animals demonstrated a moderate (less than 10%) and short-term body weight loss when treatment was first initiated, which is not an uncommon phenomenon in animals receiving IV NK infusions, and not specific to the CD19 t-haNK cells (Reference study: LABC-TX01701). Their body weight was able to recover after the first week of treatment before decreasing again due to disease progression.

Figure 7:
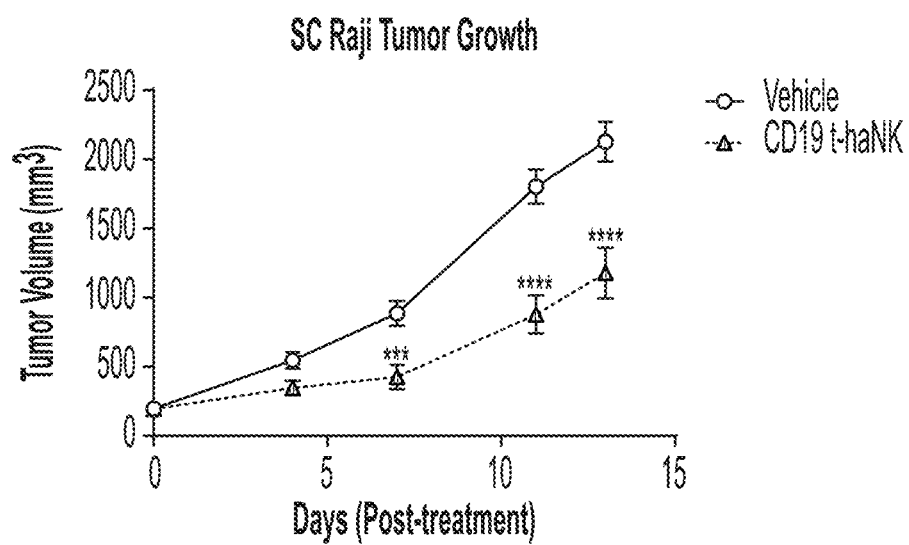
FIG. 7 shows an exemplary tumor growth curve for the SC Raji model. Data are Mean±SEM. Statistical analyses were done using 2-way ANOVA followed by multiple comparison by Tukey test; *, P<0.001; **, P<0.0001.

SC Raji Model: The primary readout in the SC tumor model was tumor growth. As shown in FIG. 7, CD19 t haNK cells demonstrated evident and statistically significant tumor growth inhibition on and after Day 7 compared to the vehicle control group, with a 49% TGI at the end of the study (Day 13).

Further, as Raji is an aggressive lymphoma model, even when inoculated SC, the cancer cells were able to disseminate and develop multiple sites of metastases that eventually led to animal morbidity and/or death. There were a total of 3 animals (50%) that were moribund between Days 11 and 13 and therefore were euthanized in the vehicle group. In contrast, there was no unscheduled death event in the CD19 t-haNK cells group (Table 3).

Figure 8:
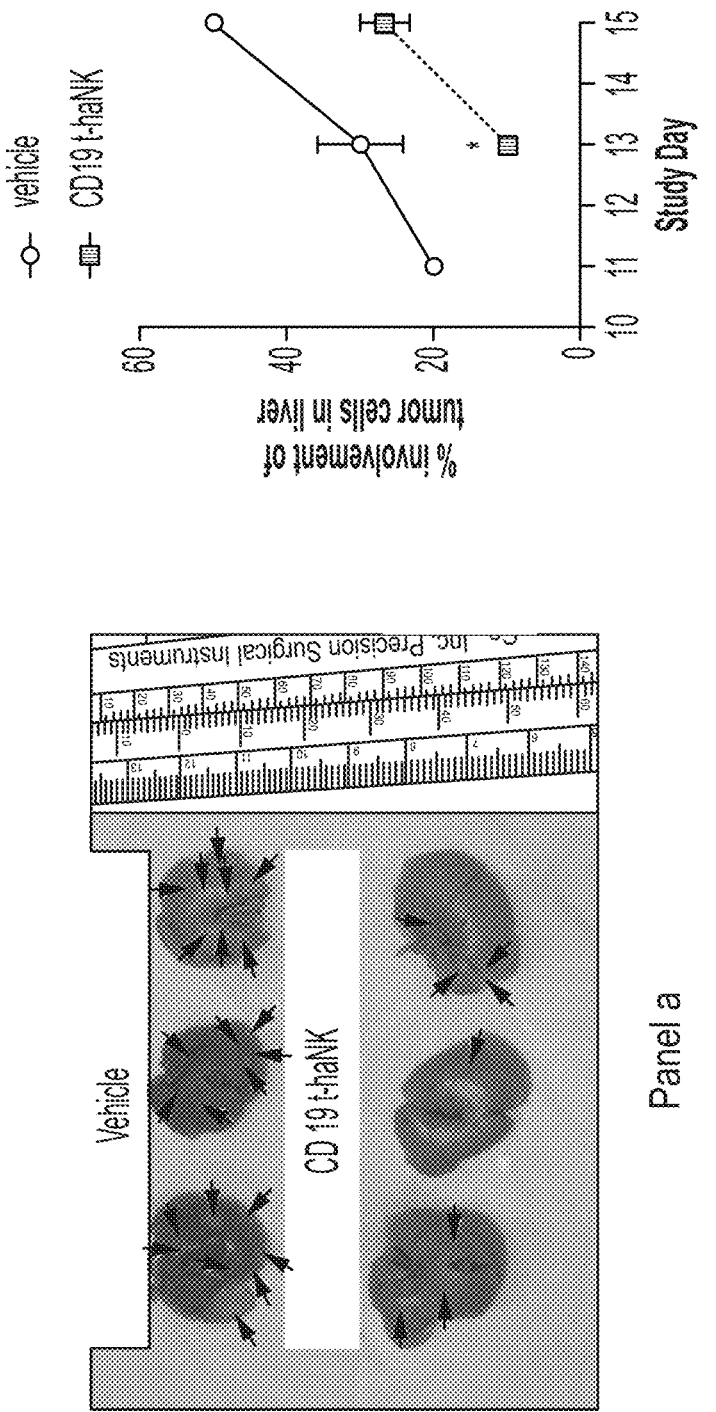
FIG. 8 shows exemplary data indicating CD19 t-haNK reduced metastatic disease burden in the livers of SC Raji tumor-bearing mice. Panel a: Whole liver images of animals from indicated treatment groups on Day 13. Arrows indicate metastatic lesions. Livers were fixed in 10% formalin for at least 24 hours prior to photography. Panel b: Quantification of percentage involvement of tumor cells in the liver (evaluated by H&E staining) on indicated days. On Day 13: *, P=0.0257 by unpaired 2-tailed t test. Statistical analyses for Days 11 and 15 could not be performed due to limited sample size. See Table 4 for raw data.

In addition, a qualitative reduction of liver metastases was observed in CD19 t-haNK treated animals during necropsy (FIG. 8A). A semi-quantitative estimation of the disease burden was performed by a contract pathology lab (Seventh Wave Laboratories) on H&E stained liver sections that were representatively sampled. As summarized in FIG. 8B and Table 4, there was a clear trend of increasing disease burden as the study advanced. Livers of CD19 t-haNK treated animals exhibited a remarkably lower percentage of cancer infiltrated areas compared to the vehicle control. Due to the small sample number and unscheduled early mortality in the control group, statistical analysis could only be performed on the Day 13 data. This analysis showed a significant difference in disease burden, with an average of 10% infiltration in CD19 t-haNK treated animals versus 30% in the control group.

Figure 9:
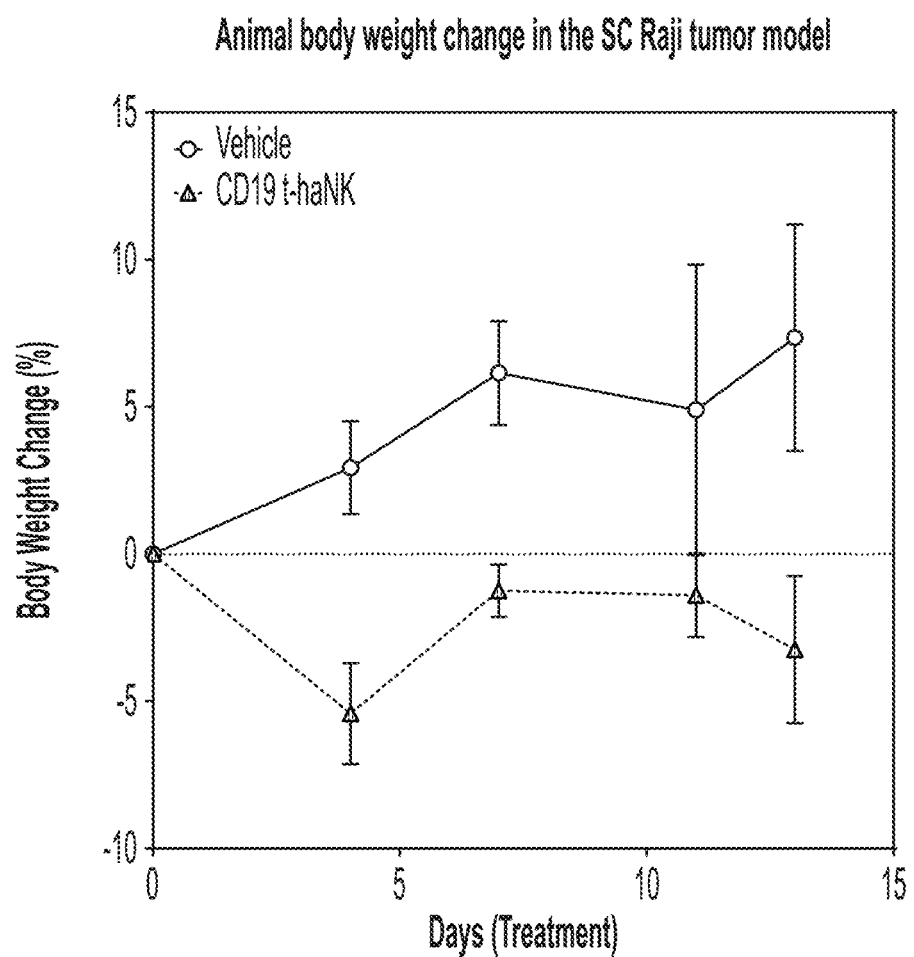
FIG. 9 shows exemplary results for animal body weight change in the SC Raji tumor model. Data are mean±SEM.

Body weight change was monitored throughout the study, and similar to the IV Raji model, CD19 t-haNK treated animals demonstrated a moderate (less than 10%) and transient body weight loss in the beginning of the treatment regimen as can be taken from FIG. 9.

TABLE 2

| Group | Initial N | Day 11 | Day 13 | Day 15 |
|---|---|---|---|---|
| D (Vehicle) | 6 | 2 × Moribund | 1 × Moribund | |
| | | | 2 × Scheduled | 1 × Scheduled |
| F (CD19 t-haNK) | 6 | | 3 × Scheduled | 3 × Scheduled |

Scheduled: scheduled euthanasia for tissue collection.

TABLE 3

| Group (Treatment) | Animal Number | Collection Day | Estimated % Tumor | Mean |
|---|---|---|---|---|
| D (Vehicle) | 503 | 11 | 20 | 20 |
| | 520 | 11 | 20 | |
| | 487 | 13 | 40 | 30 |

TABLE 3-continued

| Group (Treatment) | Animal Number | Collection Day | Estimated % Tumor | Mean |
|---|---|---|---|---|
| | 488 | 13 | 20 | |
| | 497 | 13 | 30 | |
| | 502 | 15 | 50 | 50 |
| F (CD19 t-haNK) | 495 | 13 | 10 | 10 |
| | 505 | 13 | 10 | |
| | 507 | 13 | 10 | |
| | 512 | 15 | 30 | 27 |
| | 522 | 15 | 30 | |
| | 525 | 15 | 20 | |

To assess the anti-tumor efficacy of CD19 t-haNK cells in repeated IV dosing regimens, 2 variations of the Raji xenograft model with IV and SC tumor inoculations, respectively, were utilized in this study.

In the IV tumor model, CD19 t-haNK cells were able to significantly improve animal survival, prolonging median survival by 5.5 days (a 26% increase) compared to the vehicle control group. In the SC tumor model, CD19 t-haNK cells were able to significantly suppress tumor growth, resulting in a 49% TGI at the end of the study. Furthermore, CD19 t-haNK treatment was able to reduce the number of animal morbidity/death events (0/6 in CD19 t-haNK treated animals versus 3/6 in the control group), and markedly decrease metastatic disease burden in the liver of SC Raji-tumor bearing animals.

As can be seen from the above data, CD19 t-haNK cells displayed significant therapeutic efficacy compared to vehicle control in both variations of the Raji xenograft model.

Example 5. Treatment of Mice Having L1210 Tumors with CD19-CAR-NK-92 Cells Increased Survival, and Mice that Completely Responded to Treatment Rejected L1210 Tumor Allografts when Re-Challenged Experimental Design: Thirty (30) male DBA/2J mice aged 6-8 weeks (Jackson Laboratories) were enrolled following randomization on Day 0. All animals were housed under standard environmental conditions and maintained on LabDiet 5053 irradiated rodent chow and sterile water provided ad libitum. On arrival, animals were identified by ear punch and housed in cages of ten (10) and acclimated in place for a minimum of three days prior to commencement of the study. Following acclimation, the injection area of each mouse was shaved and cleaned with sterile EtOH swab. On Day PR0 (pre-randomization Day 0), animals were anesthetized with isoflurane for tumor cell injection. All animals were injected with $2 \times 10^5$ L1210-Luc tumor cells subcutaneously (s.c.) into the right flank in a volume of 0.1 mL serum-free DMEM on Day PR0. Beginning on Day PR 7, all animals had tumors measured daily by digital caliper. On ~Day PR7 when tumor volumes were measured at ~50-150 mm$^3$, and mean tumor volume was measured at ~100 mm$^3$, the twenty (20) animals bearing tumors nearest to ~100 mm$^3$ were selected for enrollment in the study; these animals were randomized into two (2) groups consisting of ten (10) animals each. Randomization day was considered Day 0 of the study, and administration of treatments commenced on this day. Animals not enrolled on study were immediately euthanized by $CO_2$ overdose. Animals in Group 1 were administered vehicle (serum free DMEM) as an intratumoral (i.t.) injection of 50 µl. Animals in Group 2 were administered $2 \times 10^6$ mCD19-CAR-aNK cells i.t. in a volume of 50 µl. Identical treatments were administered on Days 0, 2 and 4 of the study.

Animals were weighed and monitored for general health daily. Following randomization, tumors were measured by digital caliper three times each week (3×/week). Any animal bearing a tumor >2500 mm$^3$ or a tumor that has ulcerated; that lost >30% of its initial body weight (on Day 0); or was found moribund, distressed or paralyzed was euthanized by $CO_2$ overdose with cause of death/sacrifice noted. On Day 30, completely responding animals and five (5) naïve additional male DBA/2J mice aged ~10 weeks (Jackson Laboratories; Barrier) comprising Group 4 were administered a rechallenge tumor cell inoculation of 2×105 L1210-Luc tumor cells subcutaneously (s.c.) into the left flank in a volume of 0.1 mL serum-free DMEM. All animals continued to be weighed and monitored daily and tumor measurements continued 3×/week through Day 60.

Results

Animal Survival to Welfare Thresholds—Initial Tumor Challenge: Animals were monitored for survival daily. Animals requiring euthanasia according to animal health and welfare thresholds, including loss of greater than 30% of their initial body weight, tumors exceeding 2500 mm$^3$, inability to obtain food/water, or found moribund, were included for survival analysis. Animals requiring euthanasia due to ulcerated tumors were not included in survival analysis.

Figure 10:
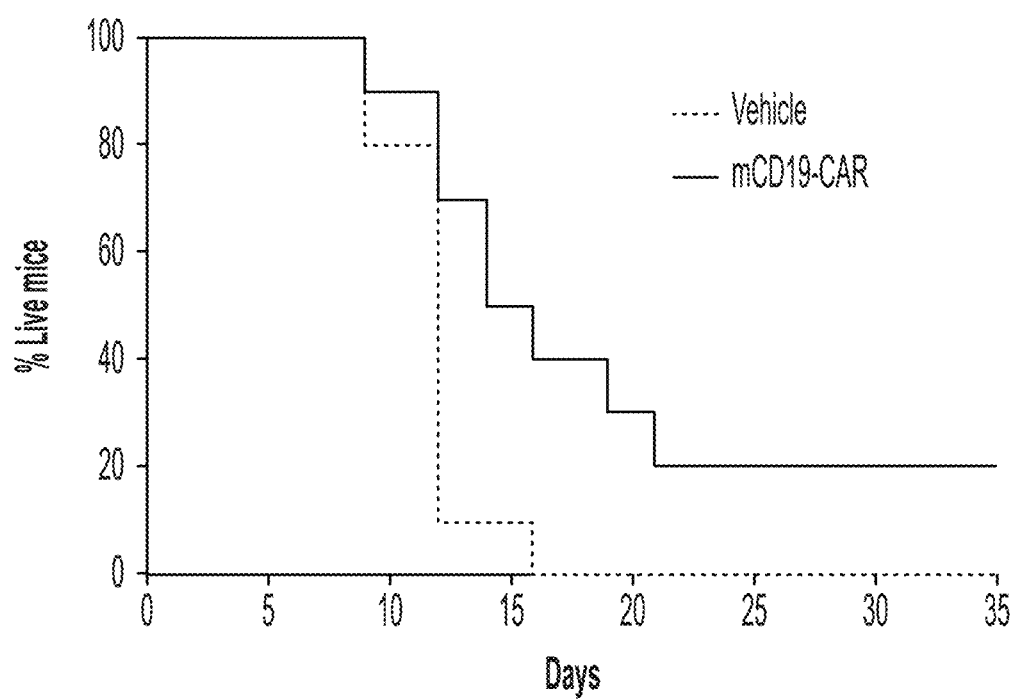
FIG. 10 shows an exemplary Kaplan-Meier survival curve of mice injected with L1210-Luc tumor cells following intratumoral treatment with mCD19-CAR NK-92 cells vs. vehicle control, as described in the Examples.

Cumulative survival to animal welfare thresholds over time is shown in FIG. 10. L1210 is an extremely fast-growing, aggressive tumor cell line and 0% of vehicle treated control animals survived further than twenty-three (23) days post tumor challenge. In contrast, treatment with CD19-CAR-aNK cells enhanced survival compared to treatment with vehicle. Indeed, 25% (2/8) of animals treated with CD19-CAR-aNK cells survived through study completion at Day 61 through tumor graft challenge.

The statistical significance of the observed survival enhancements provided by the test treatments was assessed by Log-rank (Mantel-Cox) and Gehan-Breslow Wilcoxon tests. Treatment with mCD19-CAR-aNK cells produced a statistically significant enhancement of survival, (p=0.05 (Mantel-Cox); p=0.04 (Gehan-Breslow-Wilcoxon). These results indicate that treatment with CD19-CAR-aNK produced statistically significant improvement of survival to welfare threshold compared to vehicle in this preclinical subcutaneous model of murine lymphocytic leukemia.

Tumor Re-challenge of Complete Responders: On Day 33, the two (2) complete responding animals from Group 2, along with five (5) age-matched naïve animals were challenged/rechallenged with a second inoculum of $2 \times 10^5$ L1210-Luc cells, injected into the opposite (left) flank (primary tumor was seeded into the right flank). Animals were monitored for survival daily. Animals requiring euthanasia according to animal health and welfare thresholds, including loss of greater than 30% of their initial body weight, tumors exceeding 2500 mm$^3$, inability to obtain food/water, or found moribund, were included for survival analysis. Animals requiring euthanasia due to ulcerated tumors were not included in survival analysis.

All (5 of 5) survival analysis eligible naïve animals required euthanization due to tumor volume by Day 52; in contrast, all completely responding animals previously treated with 2M CD19-CAR-aNK (N=2) cells survived through study completion (Day 62). The statistical significance of the observed survival enhancement provided by the test treatments was assessed by Log-rank (Mantel-Cox) and Gehan-Breslow Wilcoxon tests, however the enhancement in survival was not statistically distinguishable, most likely to due to small sample sizes.

Figure 11:
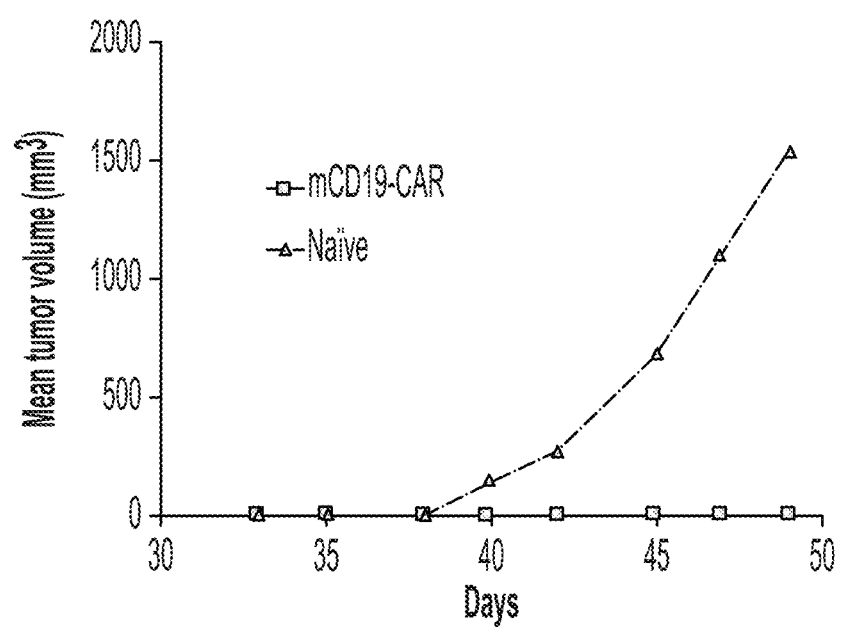
FIG. 11 shows exemplary results for tumor size of complete responders vs. naïve controls re-challenged with L1210-Luc tumor cells, as described in the Examples.

Tumors continued to be measured three times each week (3×/week) during the rechallenge phase. The mean tumor volume+SEM for each group from administration of challenge/rechallenge L1210-Luc cells to 0% control group survival (Day 52) are displayed in FIG. 11.

Tumors of naïve animals were first detectable about seven days after administration (on study Day 40) and increased steadily and rapidly. In contrast, no tumors were detected following rechallenge into completely responding animals previously treated with 2M CD19-CAR-aNK cells at any point over the full course of the rechallenge phase (Day 33-61).

The data provided in this example suggest that completely responding animals previously treated with 2M CD19-CAR-aNK cells may have developed an effective immune response to L1210 tumor cells.

Example 6: Treatment of Mice Having A20 Tumors with mCD19-CAR-NK-92 Cells Increased Survival, and Mice that Completely Responded to Treatment Rejected A20 Tumor Allografts when Re-Challenged Experimental Design Part A: Forty (40) 5-7 week old BALB/c mice (20 males and 20 females) were sourced Taconic Biosciences to serve Part A. On pre-randomization (PR) Day 0, animals were injected subcutaneously (s.c.) into the left flank with $2.5 \times 10^6$ A20 murine lymphoma cells in 100 μL volume of serum free media. Beginning on Day PR7, tumors were measured daily. Ten (10) days after tumor cell implantation (Day PR10; Day 0), mice were randomized into treatment groups, such that each group contained animals bearing tumors of similar volume and range. The day of randomization was considered Day 0 of the study. Tumors were measured three times each week (3×/week) by digital caliper to monitor tumor growth until completion of Part A on Day 26.

On Day 0, Day 3, and Day 5, mice were injected intratumorally (i.t.) with test cells or vehicle in 50 μl volume of serum free media into the tumor mass of each animal according to pre-established i.t. procedure (see Experimental Procedures). Briefly, animals were administered vehicle only or were administered $5 \times 10^6$ mCD19-CAR-NK-92. On Day 26, animals that did not develop a tumor of volume >40 mm³ were unenrolled from the study and euthanized by $CO_2$ asphyxiation; enrolled animals that displayed a complete response to treatment (CR; tumors >40 mm³ regressing so as to be undetectable (0 mm³) over multiple days without relapse prior to Day 26) were enrolled in Part B.

Part B: Part B began on Day 26. Animals from Part A without tumors were enrolled in Part B, along with twelve (12) naïve animals (6 males and 6 females). All Part B animals were administered $2.5 \times 10^6$ A20 cells into the right flank. Tumors were measured 2 times/week. Animals were euthanized on Day 57.

Figure 12:
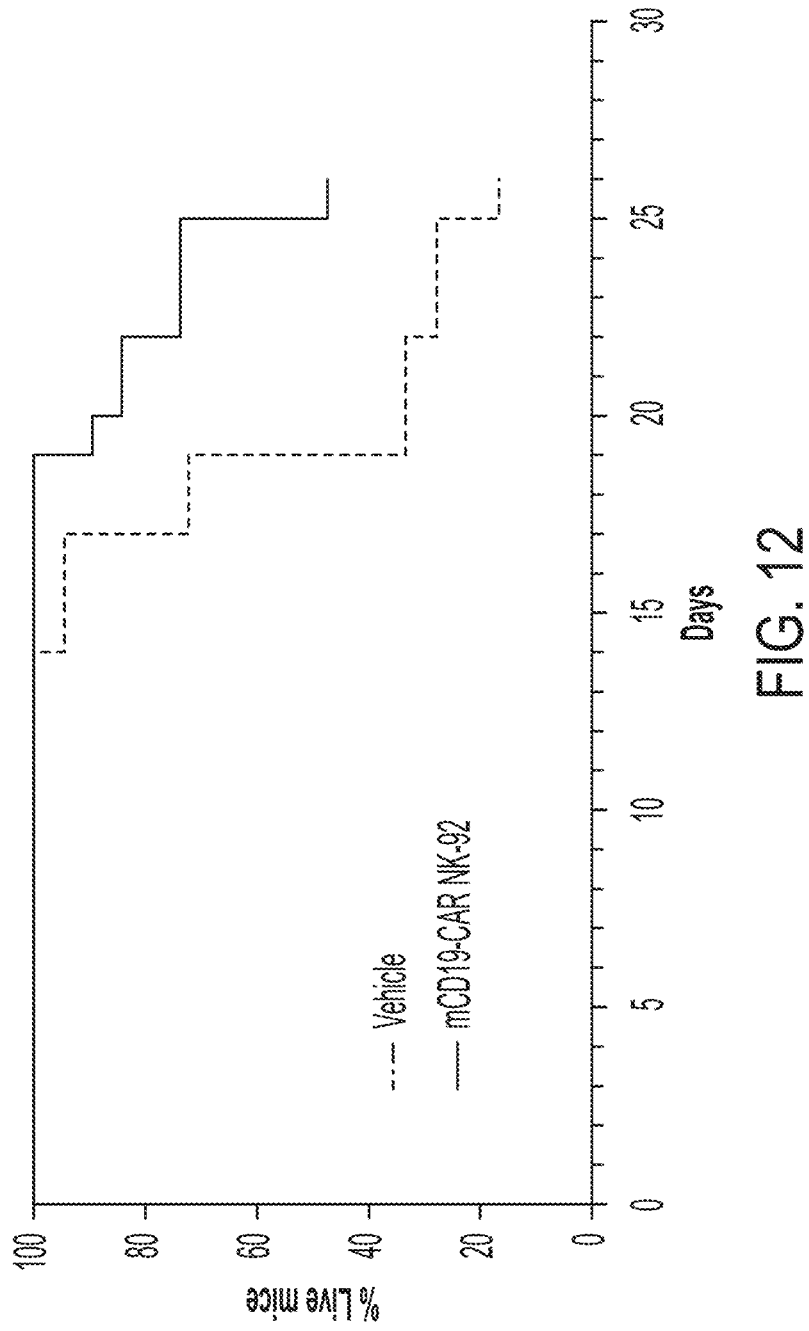
FIG. 12 shows an exemplary Kaplan-Meier survival curve of mice injected with A20 tumor cells following intratumoral treatment with mCD19-CAR NK-92 cells vs. vehicle control, as described in the Examples.

Results: Part A—Animal Survival: Animals were monitored for general health and survival daily. Animals requiring euthanasia according to animal health and welfare thresholds, including loss of greater than 30% of their initial body weight, tumors exceeding 1500 mm³, inability to obtain food/water or found moribund were included for survival analysis. Animals requiring euthanasia due to ulcerated tumors were not included in survival analysis. In this study, all animals considered in survival analysis were euthanized due to tumor burden exceeding 1500 mm³. As a subcutaneous tumor burden threshold represents an arbitrary cut-off point, the analysis of "survival" in this case must be considered only as an indicator of relative tumor growth. Cumulative survival over time for all animals considered is displayed in FIG. 12.

Of control animals administered vehicle intratumorally (i.t.) on Days 1, 3, and 5: 0 of 15 animals (0%) survived to Part A completion on Day 26. Survival through Day 26 was increased for animals for all animals receiving treatment: 9 out 18 (50%) animals administered 5M mCD19-CAR-NK92 cells. All groups were intercompared by log-rank (Mantel-Cox) test. Compared to animals administered vehicle, a statistically significant enhancement of survival was observed for animals administered 5M mCD19-CAR-NK92 cells (p=<0.0001). These results suggest that all treatments improved survival through Day 26 compared to treatment with vehicle.

Figure 13:
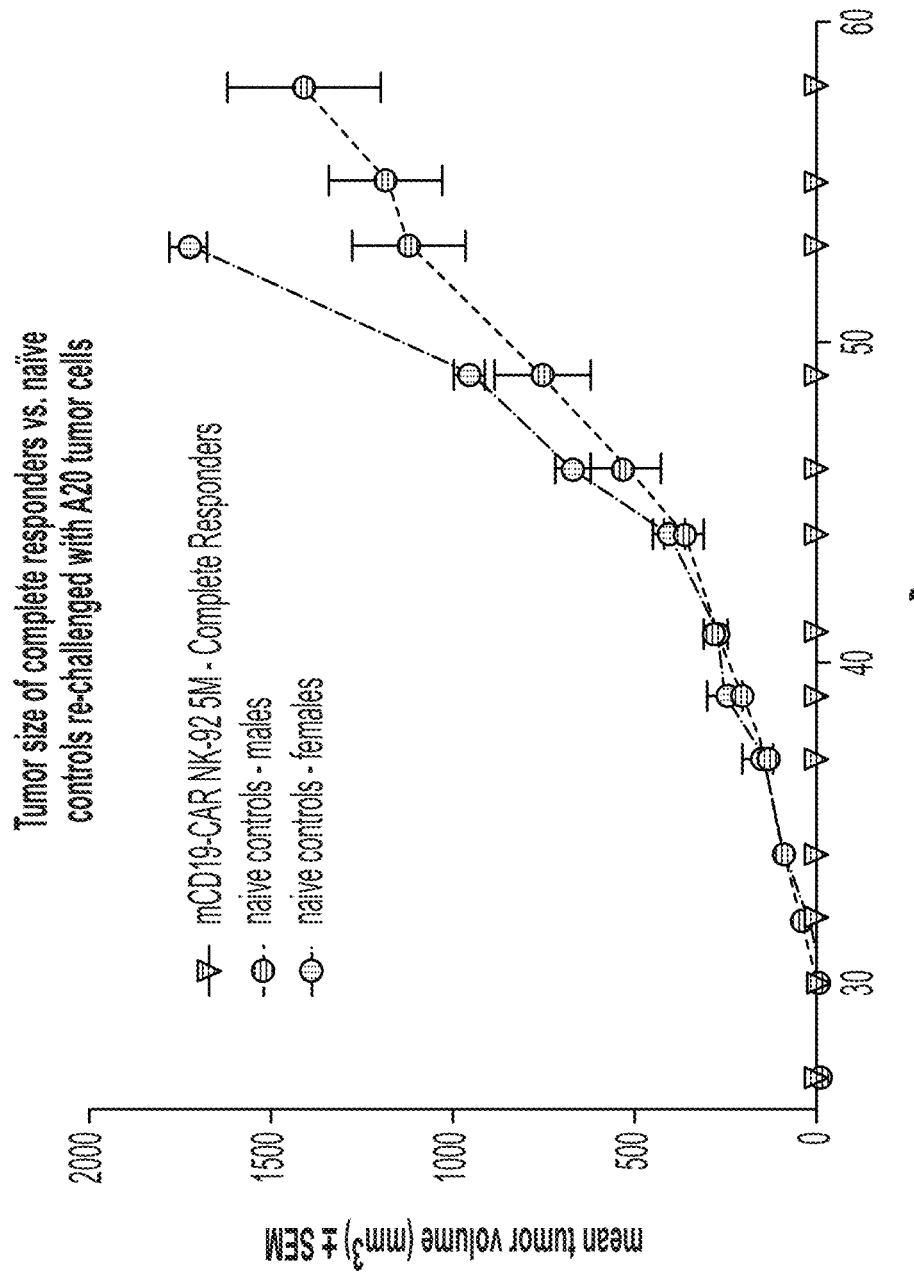
FIG. 13 shows exemplary results for tumor size of complete responders vs. naïve controls re-challenged with A20 tumor cells, as described in the Examples.

Part B—Tumor Re-challenge of Complete Responders: Animals that completely responded to treatment (bearing a tumor >40 mm³ that responded to treatment over the course of Day 0-26 (Part A) such that the tumor volume measured 0.00 mm³ through Day 26 without regrowth or relapse) were re-challenged with a second subcutaneous inoculation into the flank (opposite side from the first graft), with $2.5 \times 10^6$ A20 tumor cells in 0.1 mL serum free RPMI-1640 media on Day 27; the rechallenge portion of the study was designated as Part B. An additional twelve animals were enrolled into Part B the study to serve as naïve controls; six (6) male and six (6) female age-matched BALB/c mice sourced at the same time and vendor as Part A mice were administered $2.5 \times 10^6$ A20 tumor cells on Day 27. Tumors were measured 3 times/week for all animals through Day 57. Mean tumor volumes+SEM of each Part A treatment group and naïve controls are shown in FIG. 13. Tumors derived from cell inoculations into naïve animals grew steadily as expected; whereas re-challenge tumor cell inoculations into complete responder animals did not produce viable tumors (>40 mm³).

In summary, the data presented in this example indicates that, in contrast to naïve mice, previously treated mice that completely responded to treatment were able to reject A20 tumor allografts applied as re-challenge regardless of the treatment, and suggests that that these animals developed a memory response to tumor antigens.

The following examples for targeted CAR constructs and associated functional data were from linearized DNA vector constructs, which allowed transfected cells to integrate the linearized DNA into the genome and to so provide an avenue for non-transient expression of the specific CARs.

Example 7: HER2-CAR with FcεRIγ Signaling Domain

In this example, the inventors constructed a $1^{st}$ generation CARs with a FcεRIγ signaling domain that included an anti-HER2 scFv coupled to a CD8 hinge, that in turn was coupled to a CD28 transmembrane domain, which was coupled to a FcεRIγ signaling domain. The so constructed HER2-CAR had a nucleic acid sequence of SEQ ID NO:60.

Figure 14:
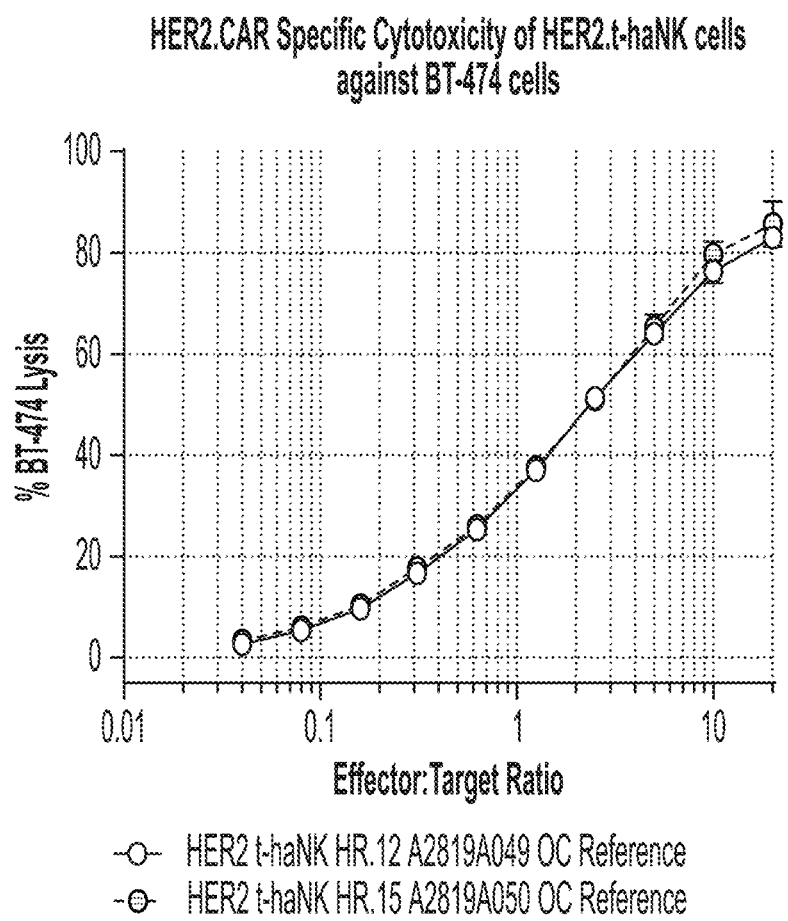
FIG. 14 shows exemplary results for cytotoxicity of HER2.CAR-t-haNK cells against BT-474 cells.

Functionality of the so constructed HER2.CAR-t-haNK cells was tested against BT-474 cells using a standard cytotoxicity assay and exemplary results are shown in FIG. 14. As can be readily seen from the data, the HER2.CARt-haNK cells expressing the CAR with the FcεRIγ signaling domain exhibited significant cytotoxicity against the BT-474 target cells.

Figure 40:
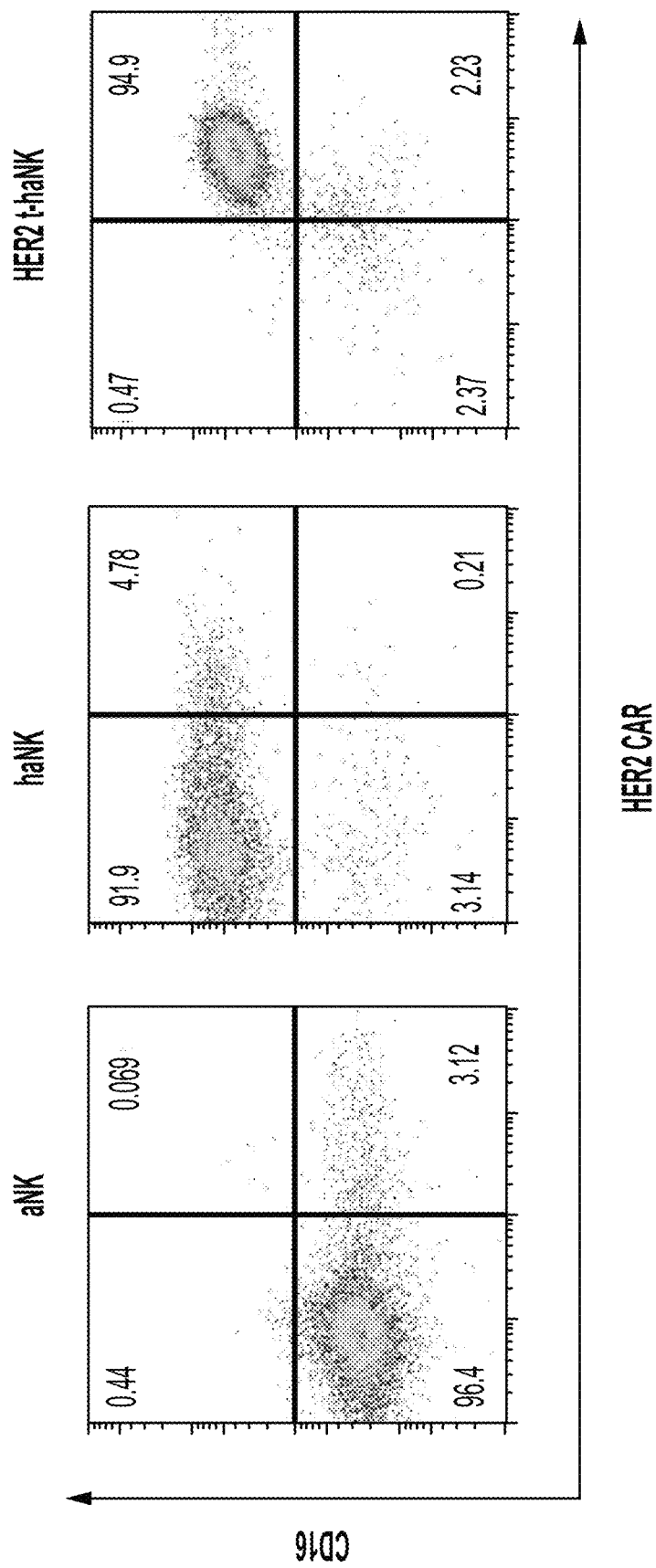
FIG. 40 shows exemplary results for expression of CD16 and HER2.CAR.
Figure 41:
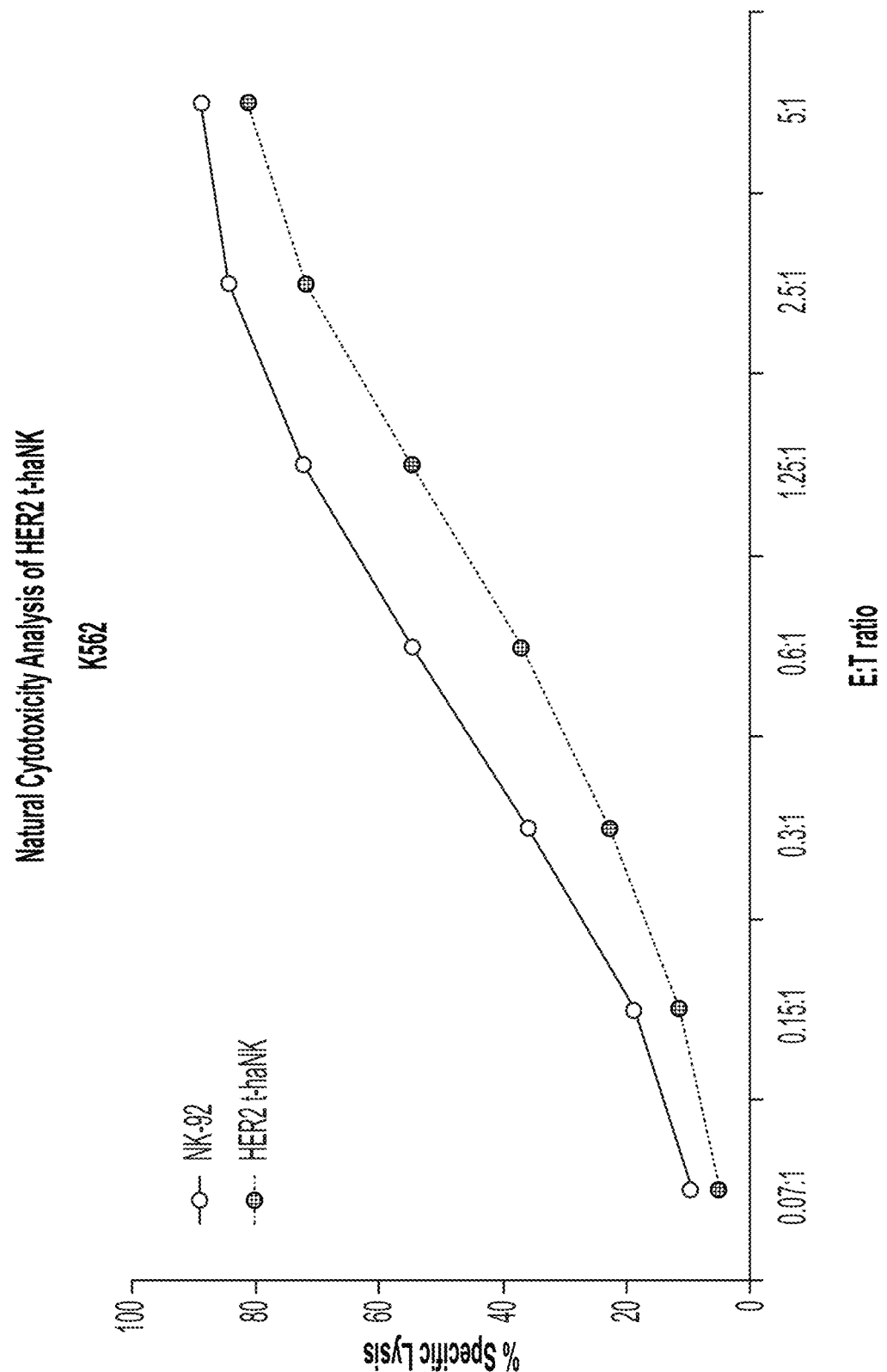
FIG. 41 shows exemplary results for natural cytotoxicity of HER2.CAR-t-haNK cells.
Figure 42:
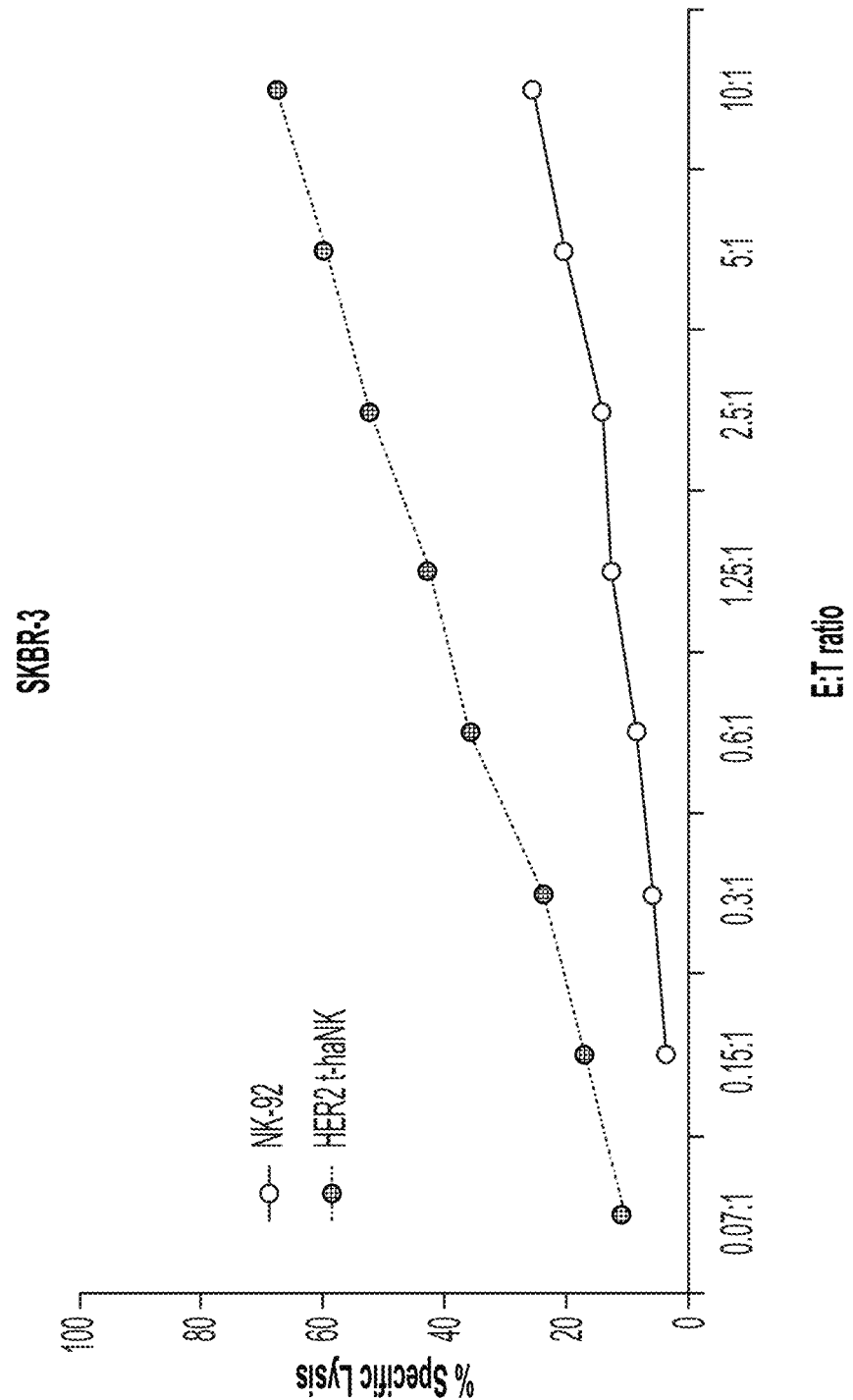
FIG. 42 shows exemplary results for CAR mediated cytotoxicity of HER2.CAR-t-haNK cells.
Figure 43:
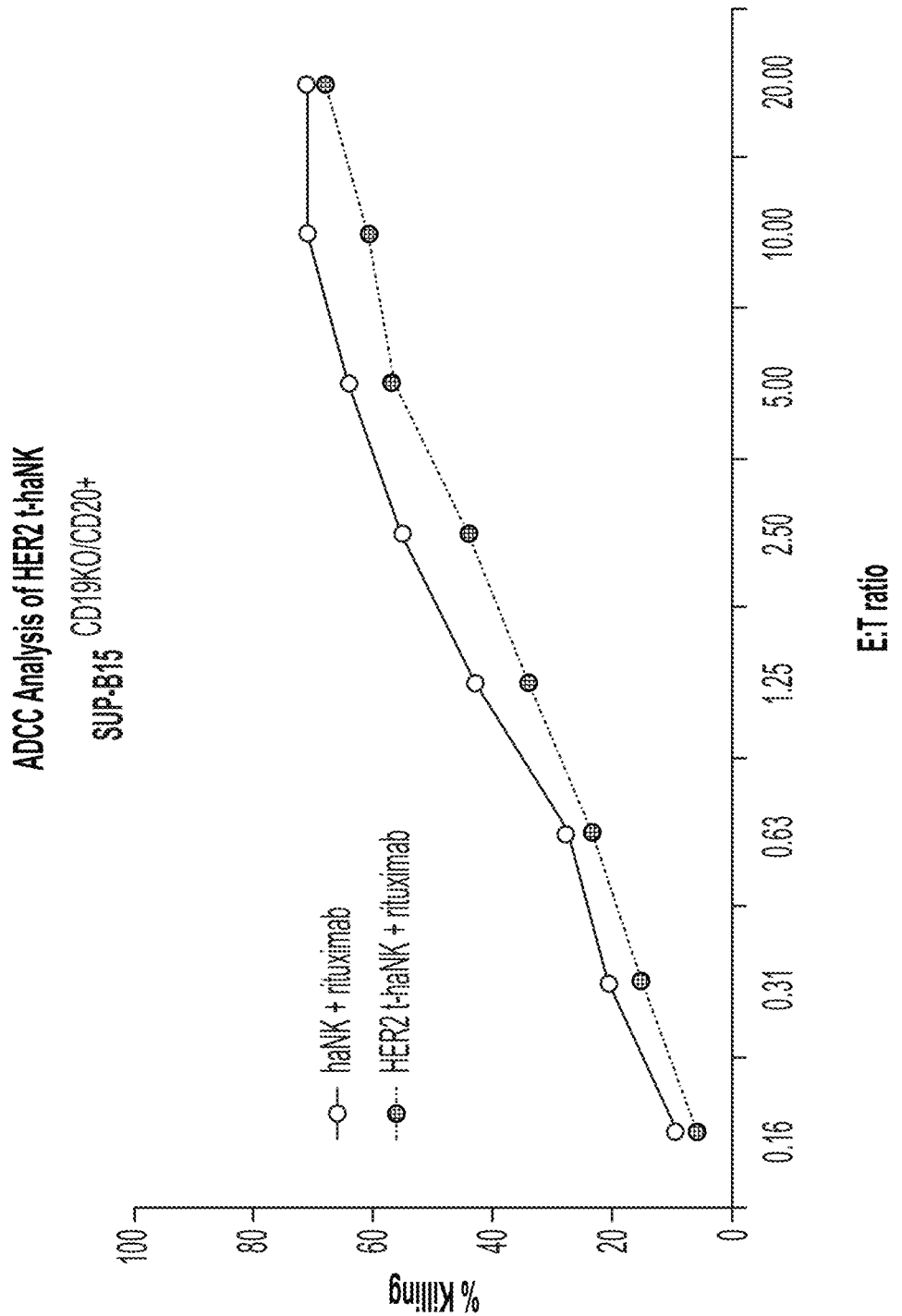
FIG. 43 shows exemplary results for ADCC of HER2.CAR-t-haNK cells.

In further experiments, the inventor demonstrated expression of the HER2.CAR in HER2.CAR-t-haNK cells as is illustrated in FIG. 40. Natural cytotoxicity of the HER2.CAR-t-haNK cells is shown in the results of FIG. 41, while results for CAR mediated cytotoxicity are shown in FIG. 42. Exemplary data for ADCC of HER2.CAR-t-haNK cells are shown in the graph of FIG. 43.

Example 8: CD30-CAR with FcεRIγ Signaling Domain

Figure 50:
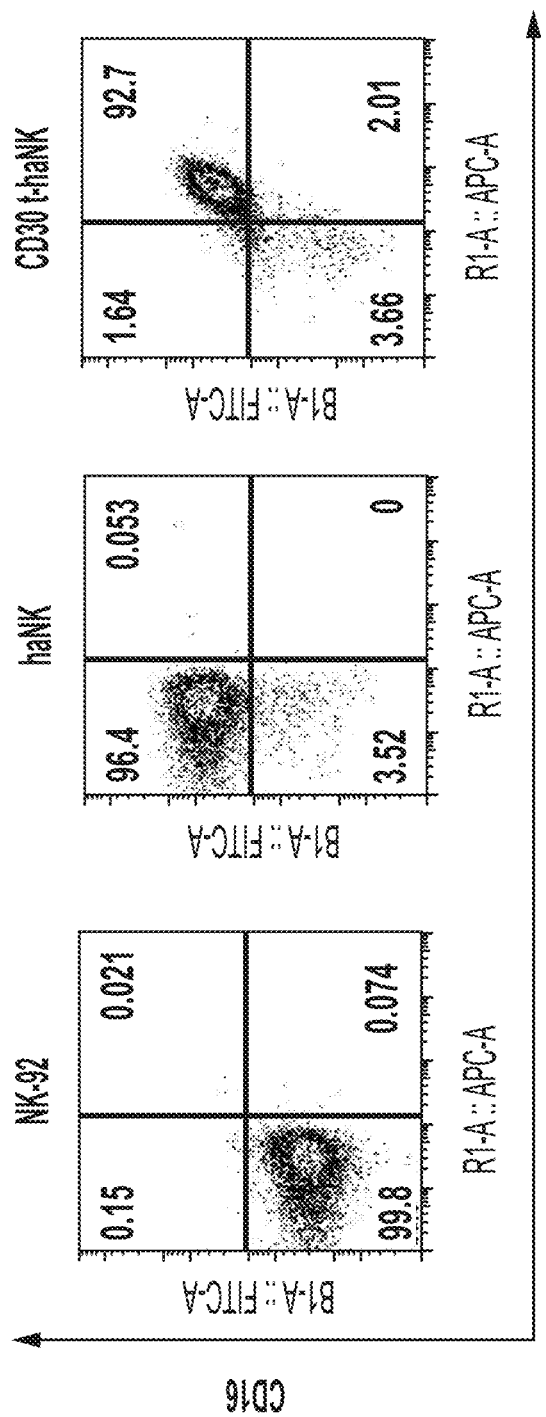
FIG. 50 shows exemplary results for expression of CD16 and CD30.CAR.
Figure 51:
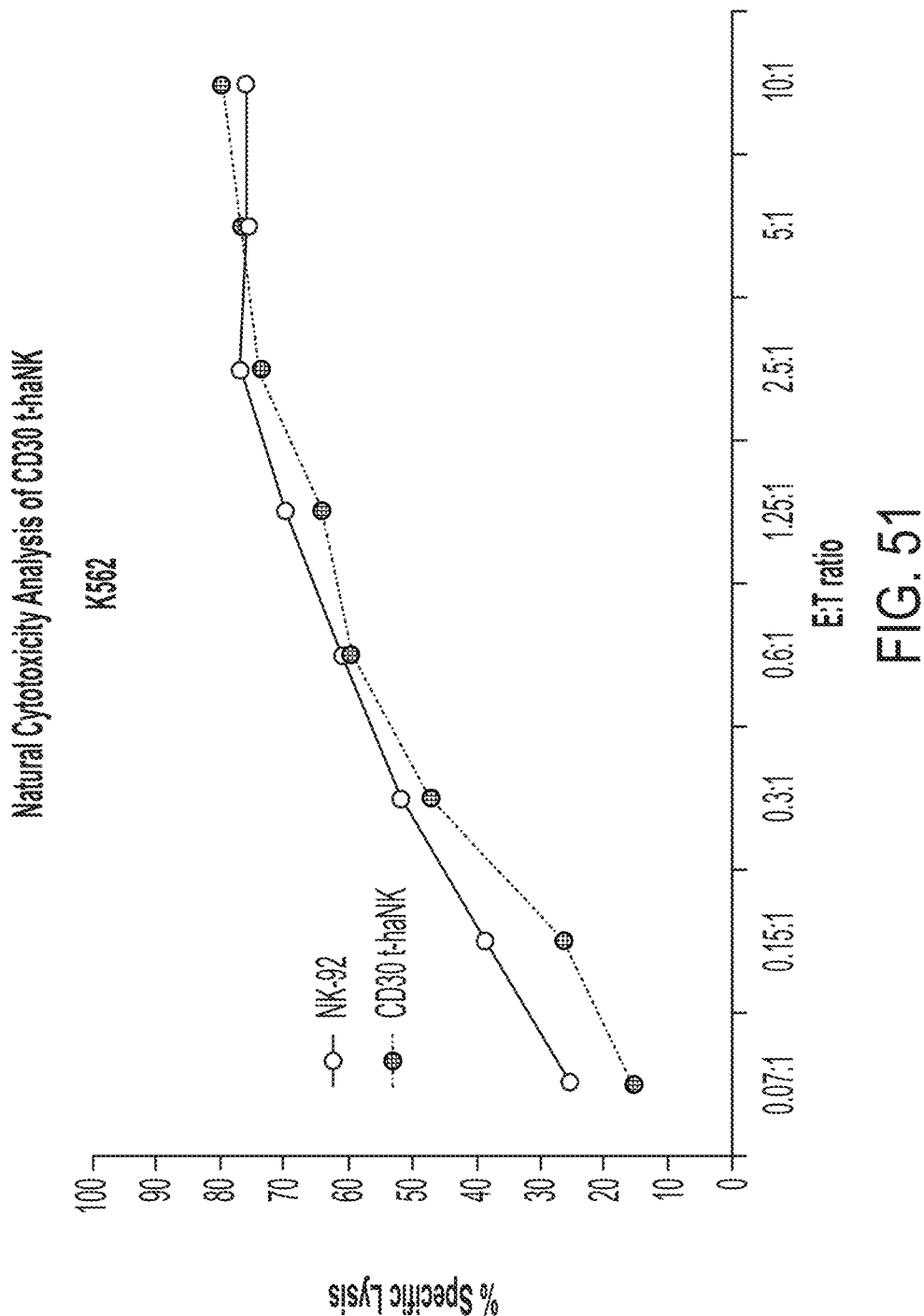
FIG. 51 shows exemplary results for natural cytotoxicity of CD30.CAR-t-haNK cells.
Figure 52:
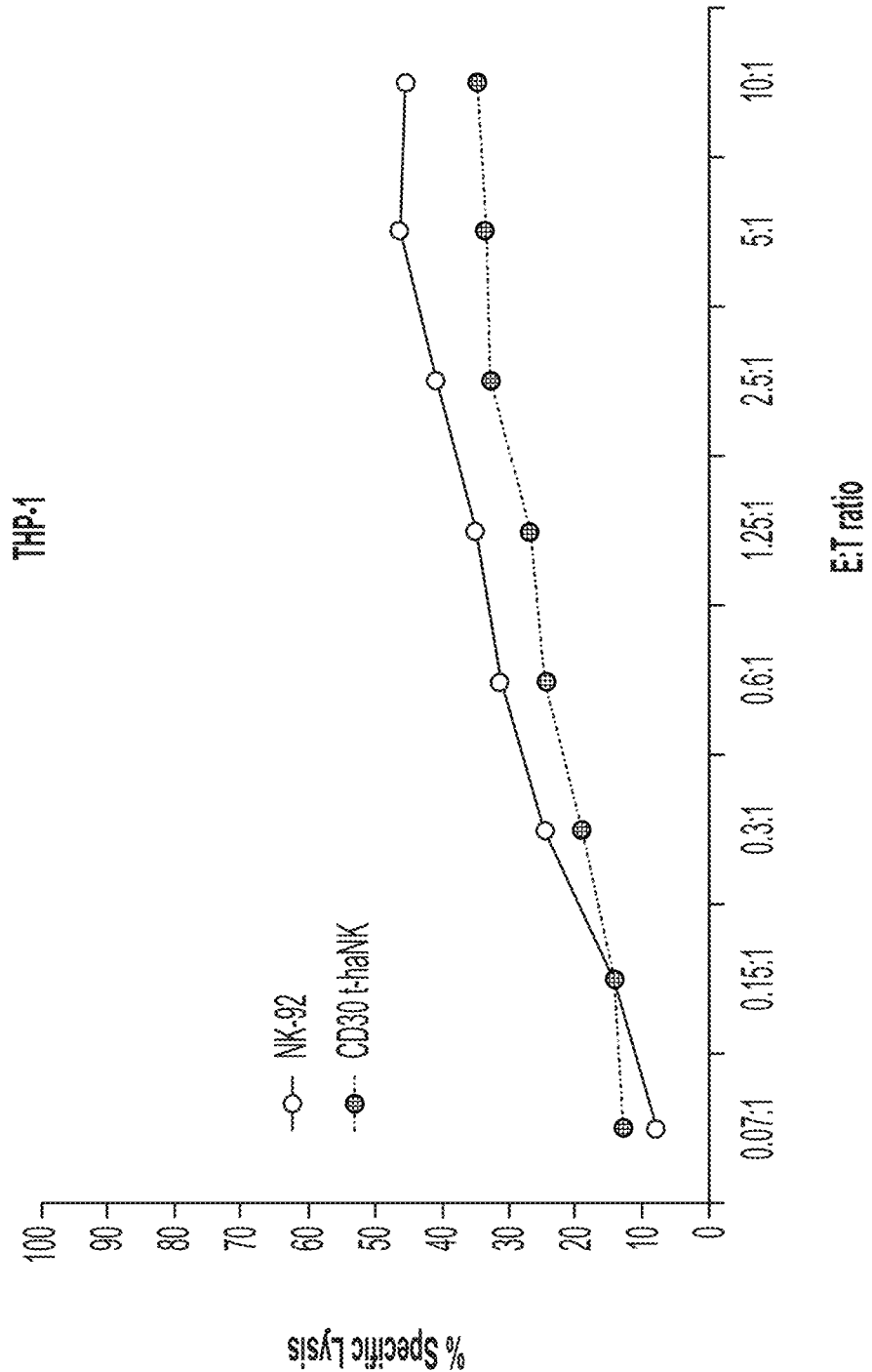
FIG. 52 shows exemplary results for CAR mediated cytotoxicity of CD30.CAR-t-haNK cells.
Figure 53:
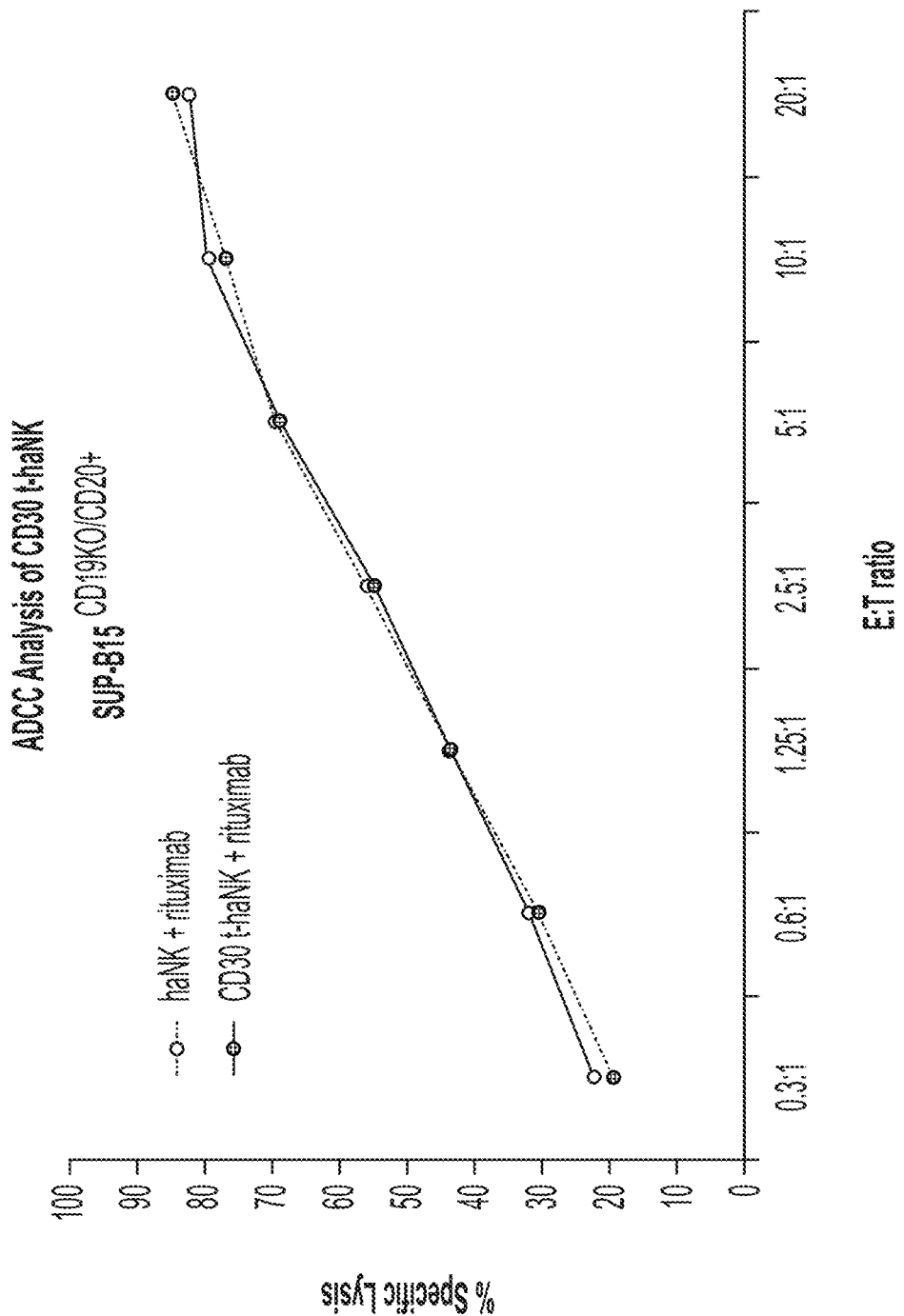
FIG. 53 shows exemplary results for ADCC of CD30.CAR-t-haNK cells.

In this example, the inventors constructed a $1^{st}$ generation CARs with a FcεRIγ signaling domain that included an anti-CD30 scFv coupled to a CD8 hinge, that in turn was coupled to a CD28 transmembrane domain, which was coupled to a FcεRIγ signaling domain. The so constructed CD30-CAR had a nucleic acid sequence of SEQ ID NO:61.
Expression of the CD30-CAR is demonstrated in the results of FIG. 50, while the results for natural cytotoxicity of the recombinant cells are shown in FIG. 51. CAR mediated cytotoxicity was demonstrated in the results of FIG. 52, while exemplary results for ADCC are shown in the data of FIG. 53.

Example 9: EGFR-CAR with FcεRIγ Signaling Domain

Figure 17:
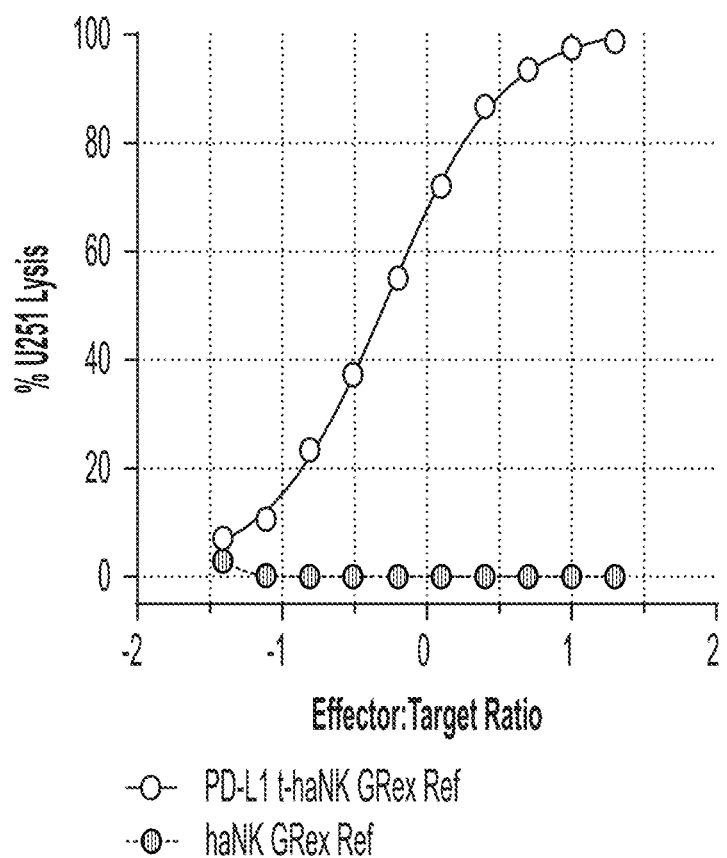
FIG. 17 shows exemplary results for cytotoxicity of PD-L1.CAR-t-haNK cells against U251 cells.
Figure 18:
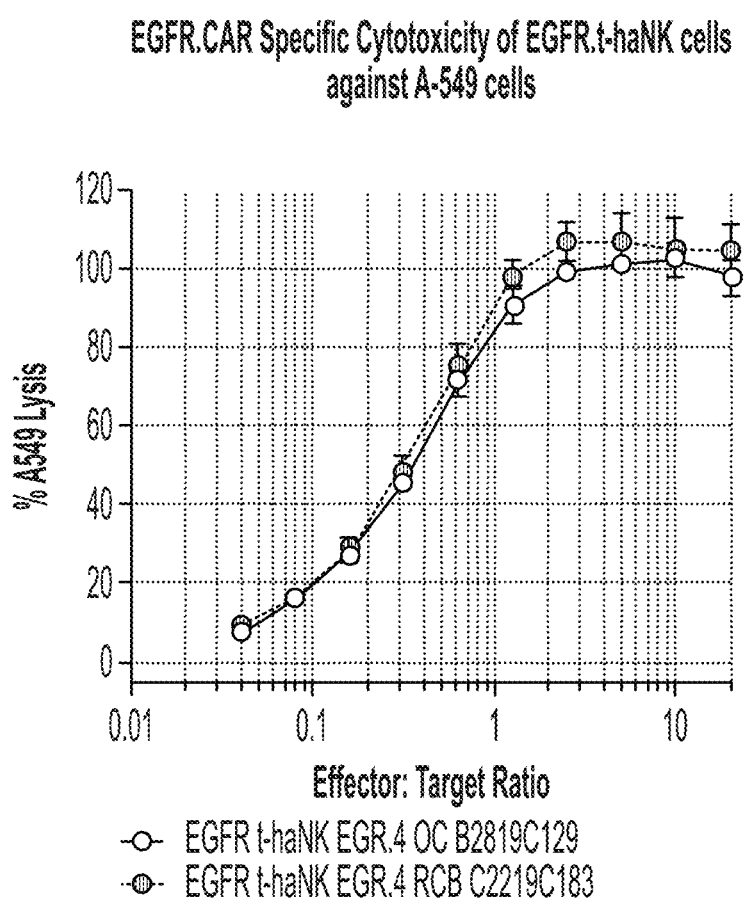
FIG. 18 shows exemplary results for cytotoxicity of EGFR.CAR-t-haNK cells against A-549 cells.
Figure 35:
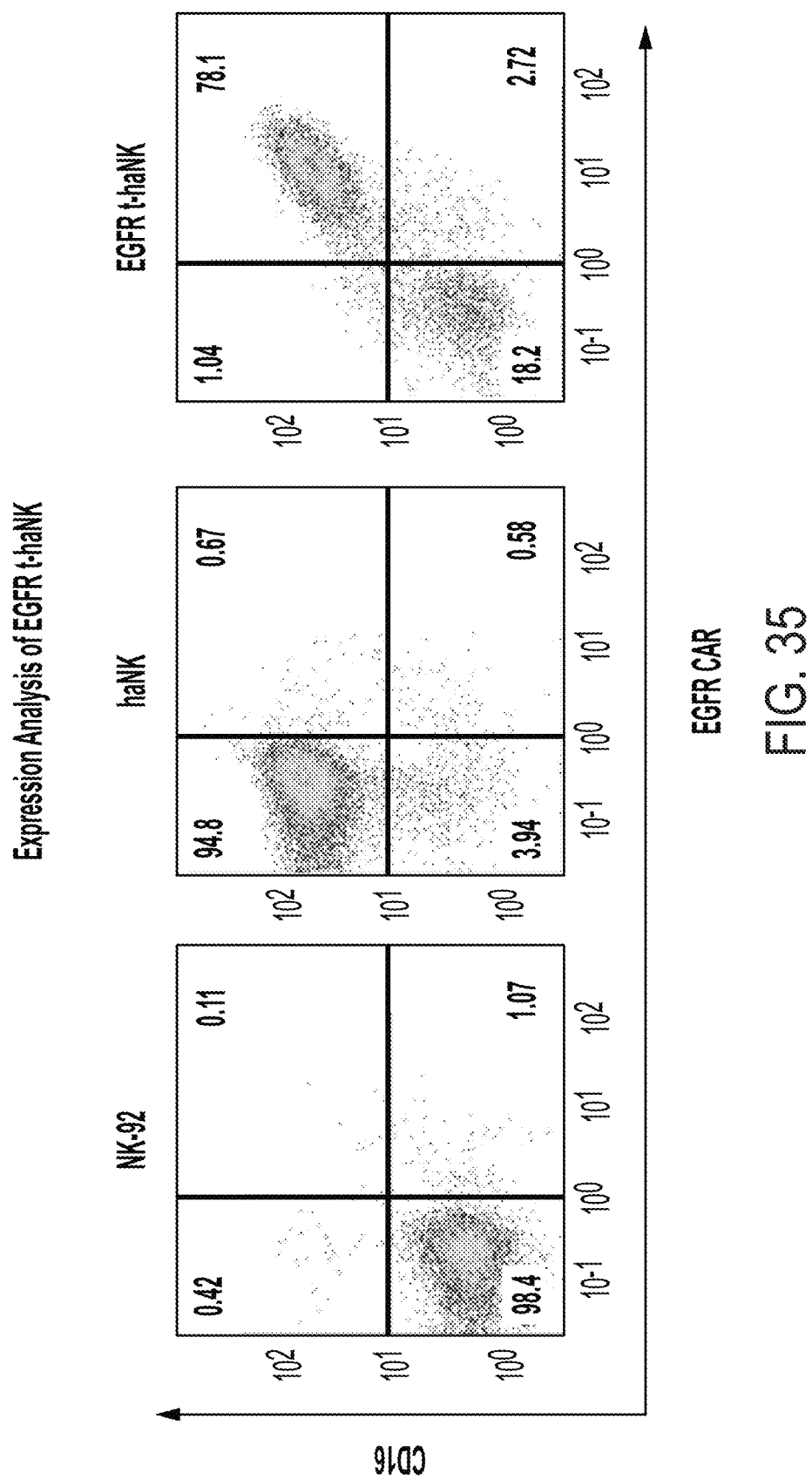
FIG. 35 shows exemplary results for expression of CD16 and EGFR.CAR.
Figure 36:
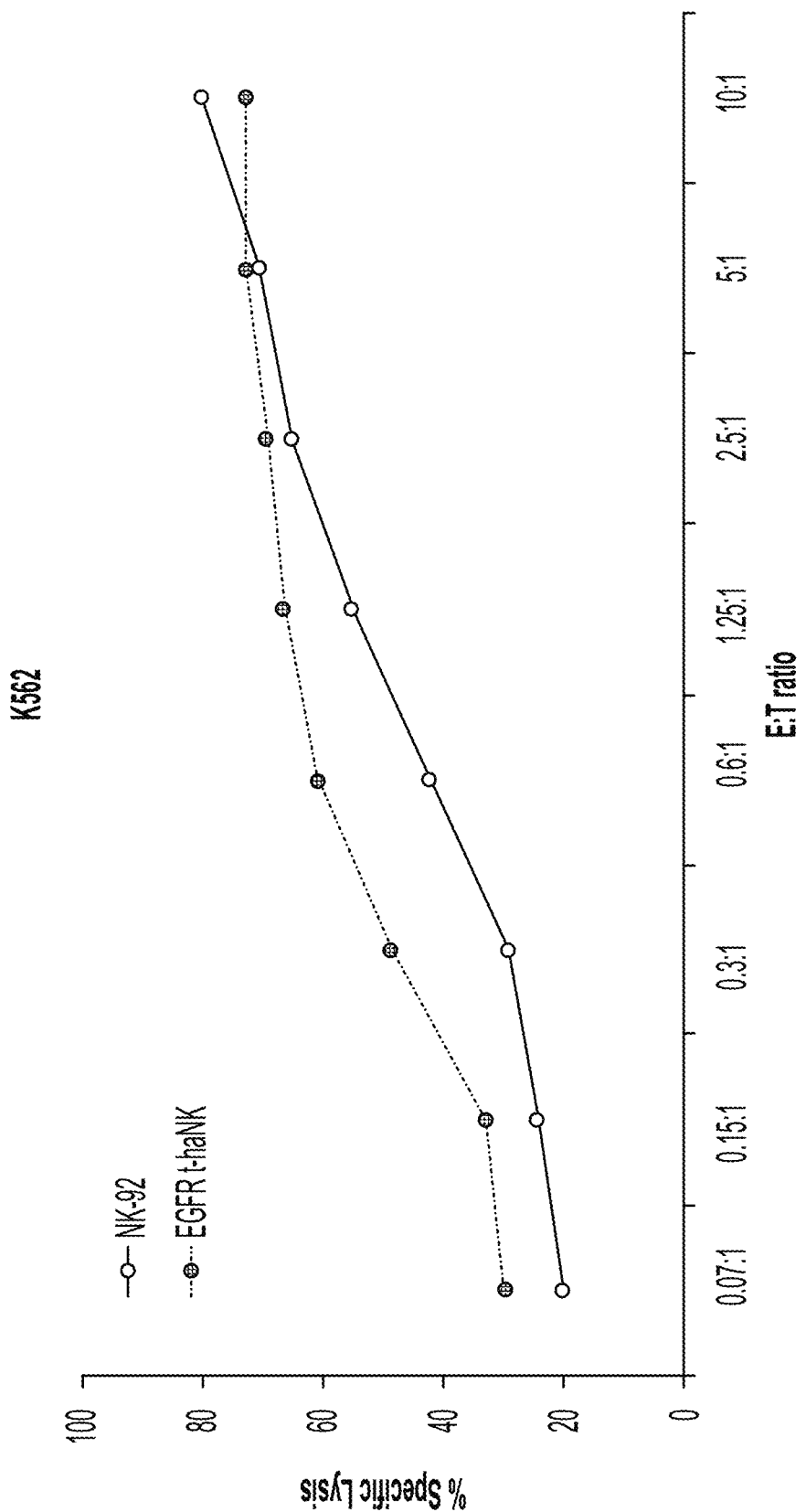
FIG. 36 shows exemplary results for natural cytotoxicity of EGFR.CAR-t-haNK cells.
Figure 37:
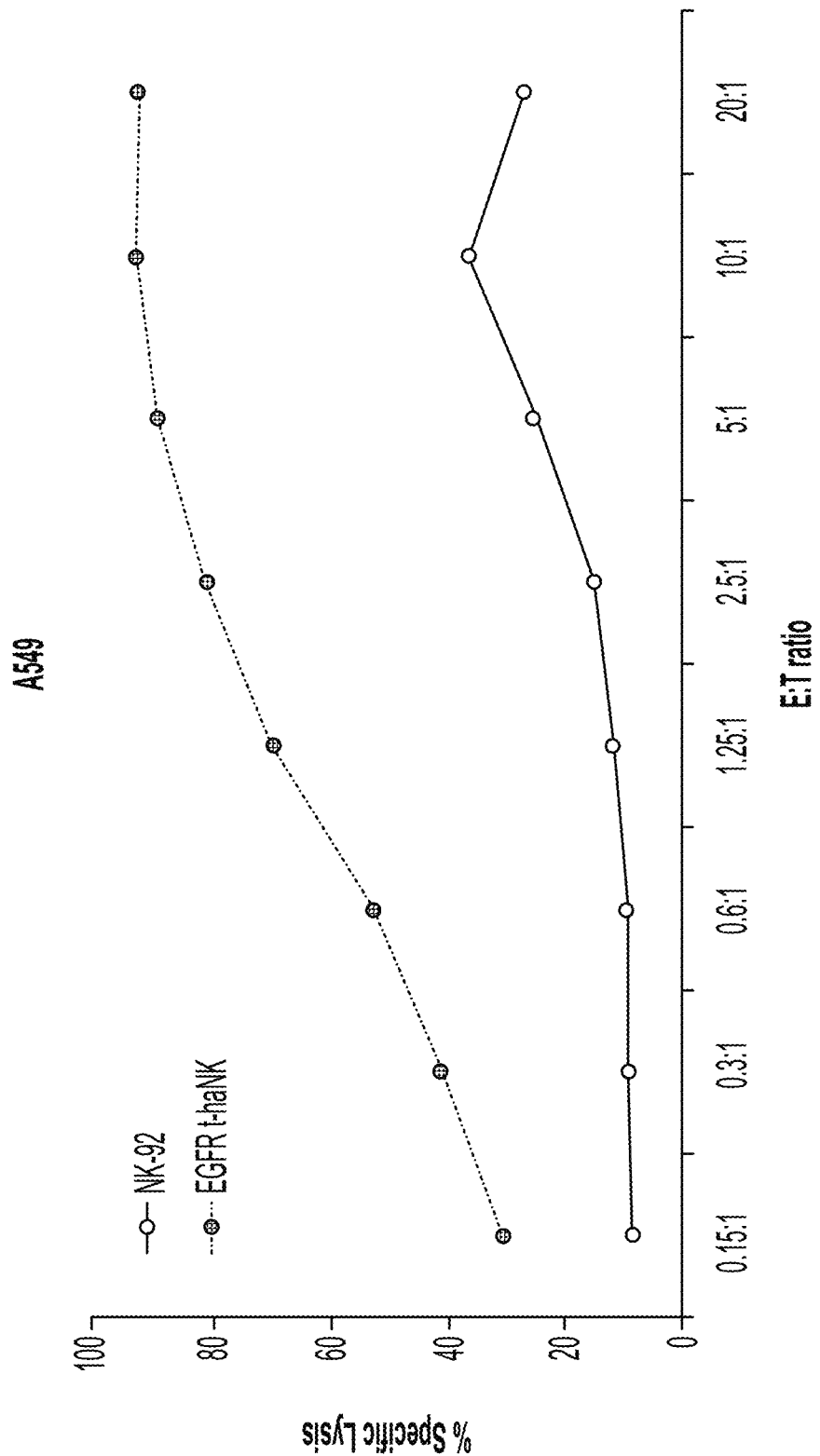
FIG. 37 shows exemplary results for CAR mediated cytotoxicity of EGFR.CAR-t-haNK cells.
Figure 38:
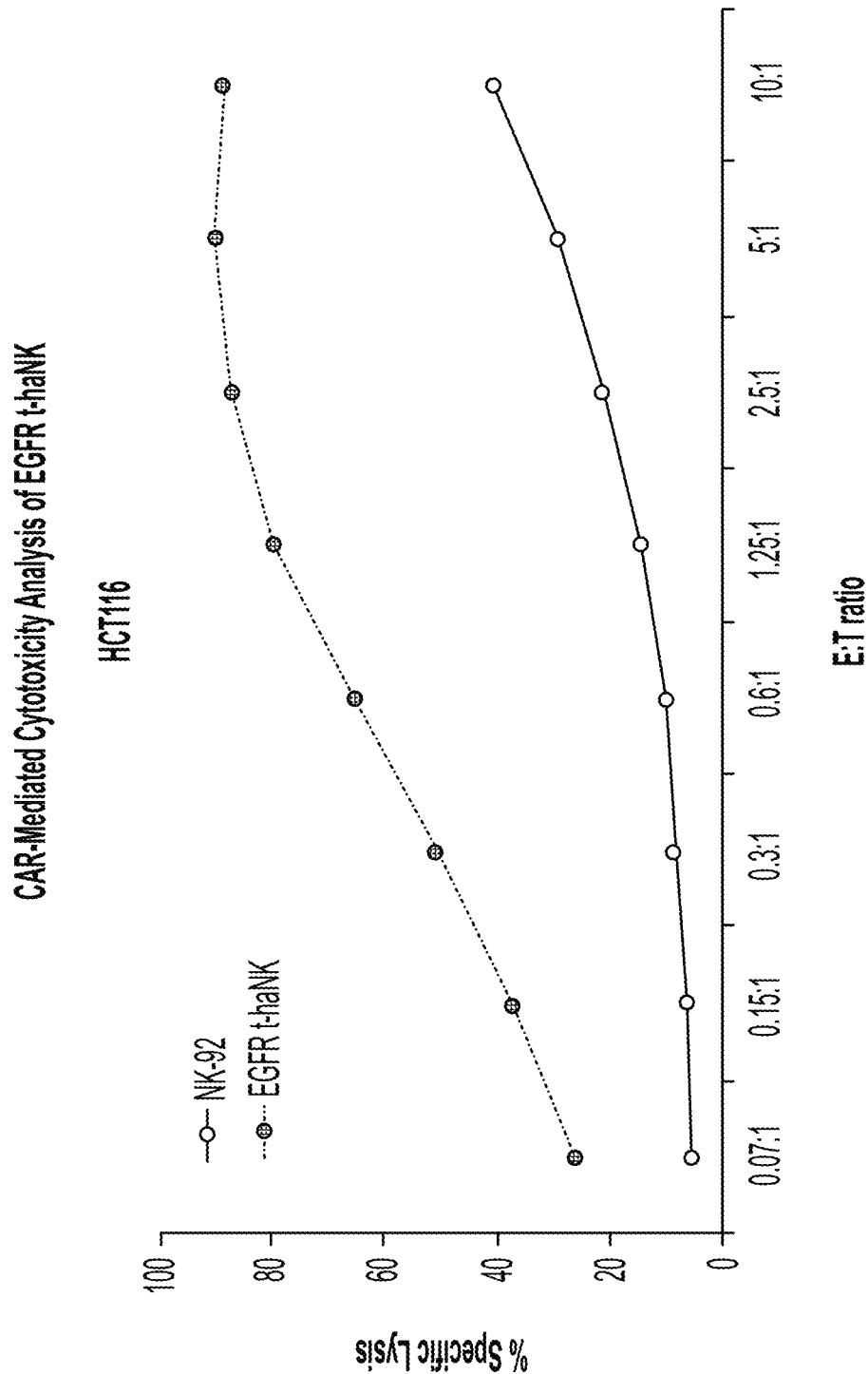
FIG. 38 shows exemplary results for CAR mediated cytotoxicity of EGFR.CAR-t-haNK cells.
Figure 39:
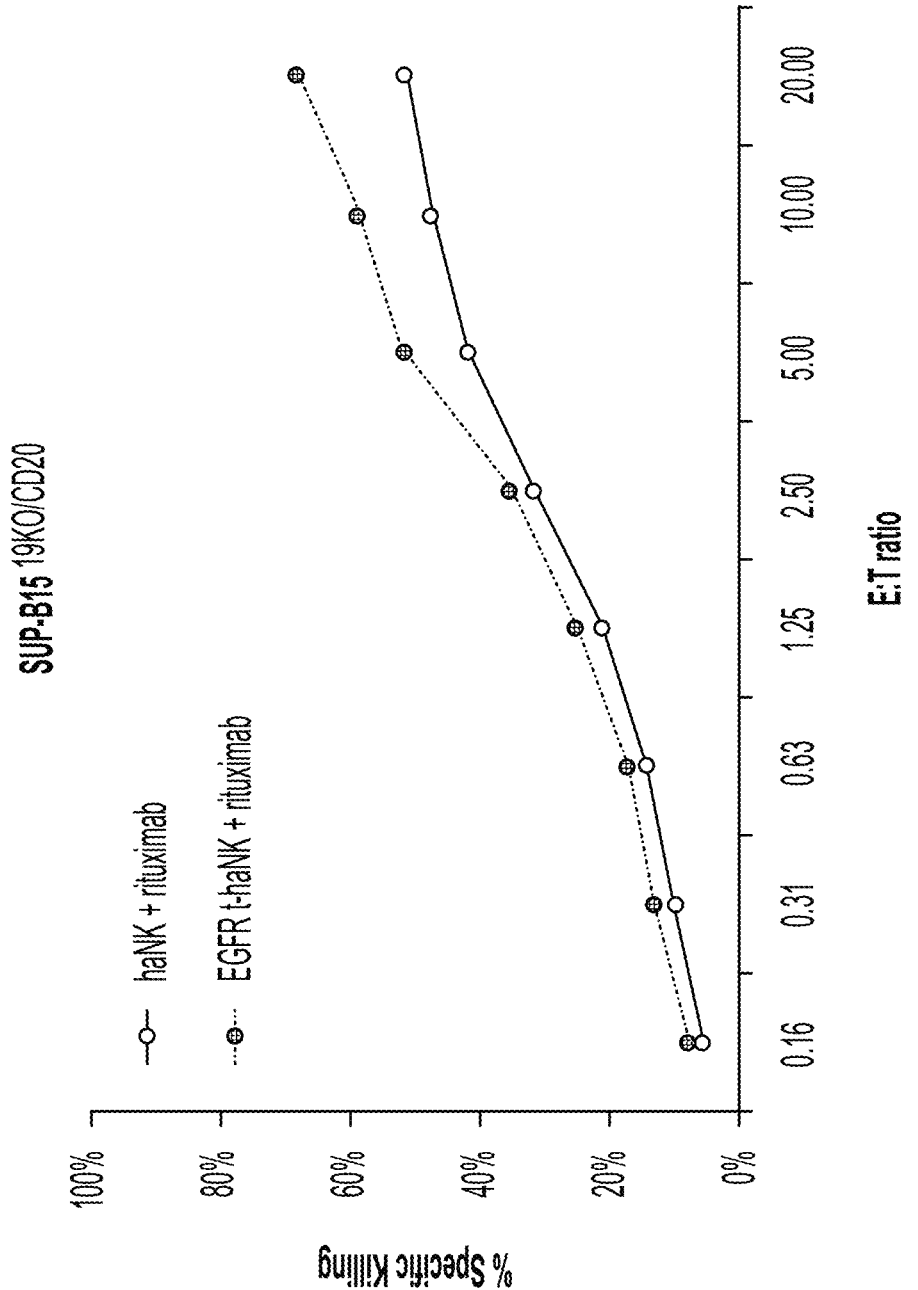
FIG. 39 shows exemplary results for ADCC of EGFR-.CAR-t-haNK cells.

In this example, the inventors constructed a $1^{st}$ generation CARs with a FcεRIγ signaling domain that included an anti-EGFR scFv coupled to a CD8 hinge, that in turn was coupled to a CD28 transmembrane domain, which was coupled to a FcεRIγ signaling domain. The so constructed EGFR-CAR had a nucleic acid sequence of SEQ ID NO:62.
Functionality of the so constructed EGFR.CAR-t-haNK cells was tested against A-549 cells using a standard cytotoxicity assay and exemplary results are shown in FIG. 17. As can be readily seen from the data, the EGFR.CAR-t-haNK cells expressing the CAR with the FcεRIγ signaling domain exhibited significant cytotoxicity against the A-549 target cells. Expression of the EGFR-CAR in the EGFR.CAR-t-haNK cells is shown in FIG. 35, while natural cytotoxicity results are shown in FIG. 36. Exemplary results for CAR mediated cytotoxicity of EGFR.CAR-t-haNK cells are shown in FIG. 37 and FIG. 38, while results for ADCC of EGFR.CAR-t-haNK cells are shown in FIG. 39.

Example 10: IGF1R-CAR with FcεRIγ Signaling Domain

Figure 22:
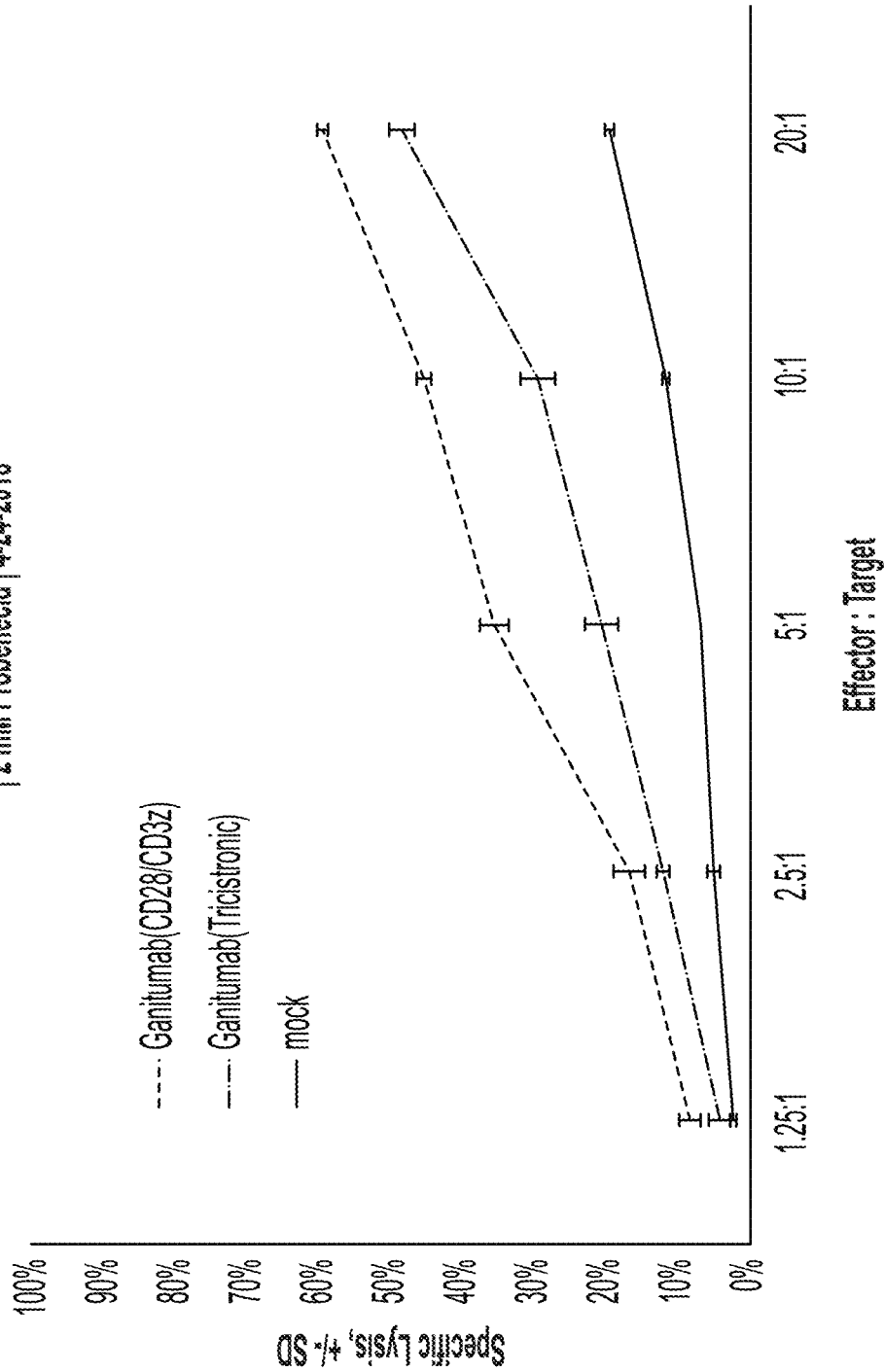
FIG. 22 shows exemplary results for cytotoxicity of IGF1R.CAR-t-haNK cells against MDA-MB-231 cells.
Figure 23:
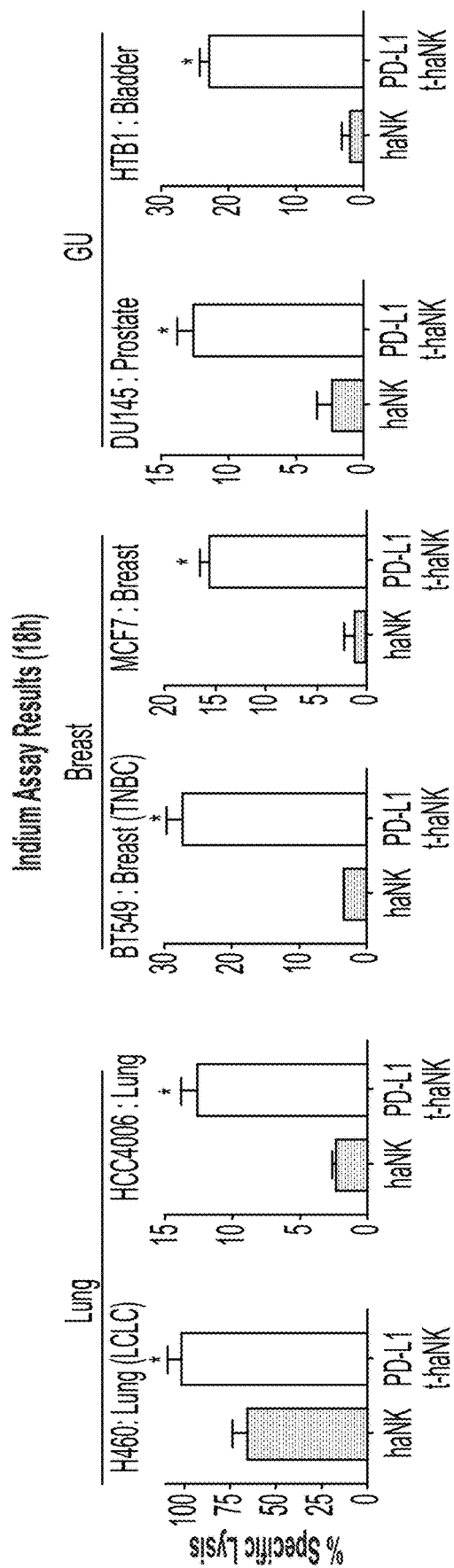
FIG. 23 shows exemplary results for cytotoxicity of PD-L1.CAR-t-haNK cells against a variety of cancer cells.
Figure 65:
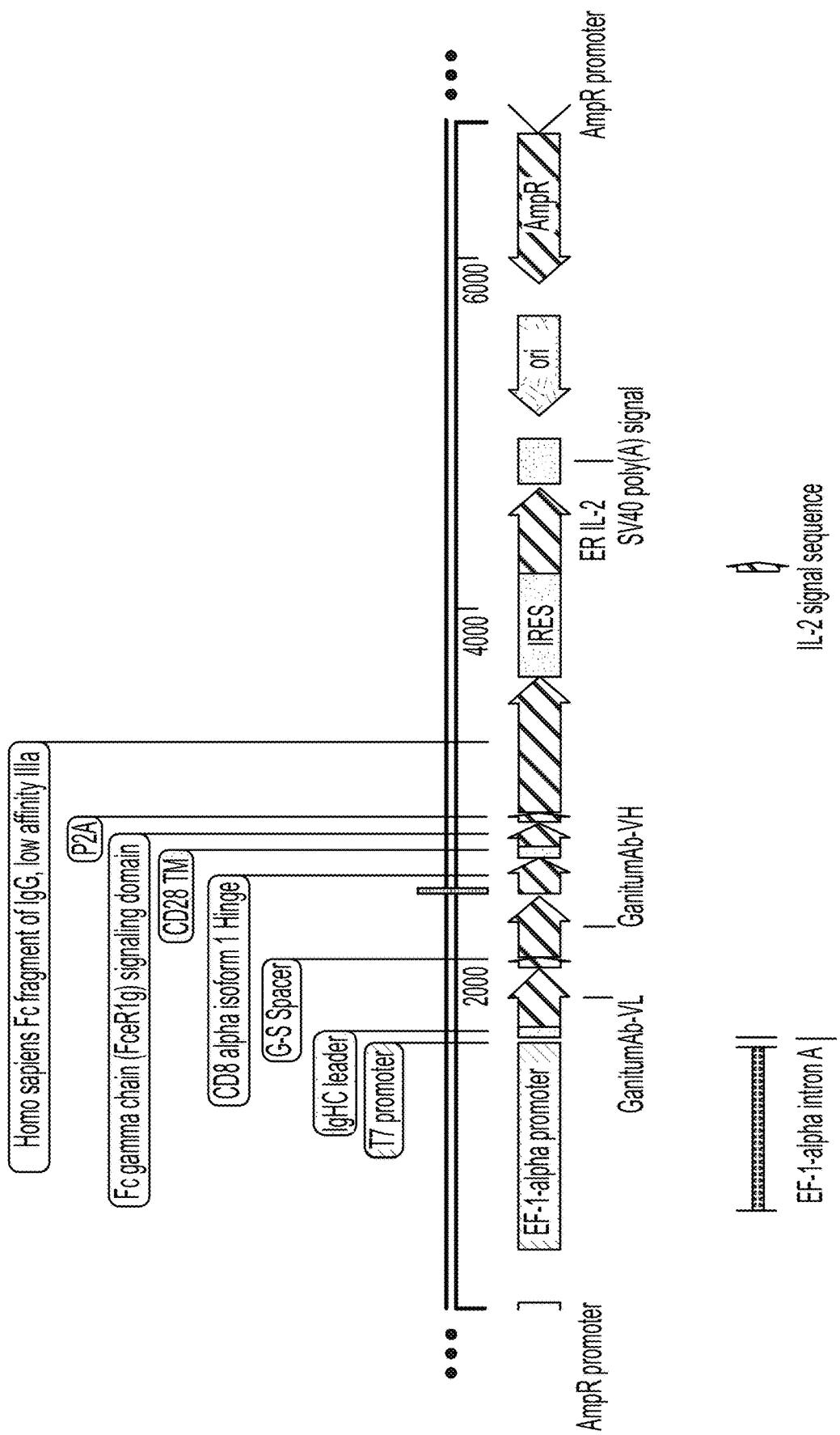
FIG. 65 depicts an exemplary tricistronic construct encoding IGF1R-CAR, CD16, and IL-$2^{ER}$.

In this example, the inventors constructed a $1^{st}$ generation CARs with a FcεRIγ signaling domain that included an anti-IGF1R scFv coupled to a CD8 hinge, that in turn was coupled to a CD28 transmembrane domain, which was coupled to a FcεRIγ signaling domain. The so constructed IGF1R-CAR had a nucleic acid sequence of SEQ ID NO:63, and a tricistronic construct encoding IGF1R-CAR, CD16, and IL-2$^{ER}$ had a nucleic acid sequence of SEQ ID NO:76, which is also schematically illustrated in FIG. 65.
Functionality of the so constructed IGF1R.CAR-t-haNK cells was tested against MDA-MB-231 cells using a standard cytotoxicity assay in comparison with a $2^{nd}$ generation CAR (CD28/CD3z) and exemplary results are shown in FIG. 22. As can be readily seen from the data, the IGF1R.CAR-t-haNK cells expressing the CAR with the FcεRIγ signaling domain exhibited significant and target specific cytotoxicity against the MDA-MB-231 target cells, which was comparable with the cytotoxicity of the $2^{nd}$ generation CAR.

Example 11: CD123-CAR with FcεRIγ Signaling Domain

Figure 48:
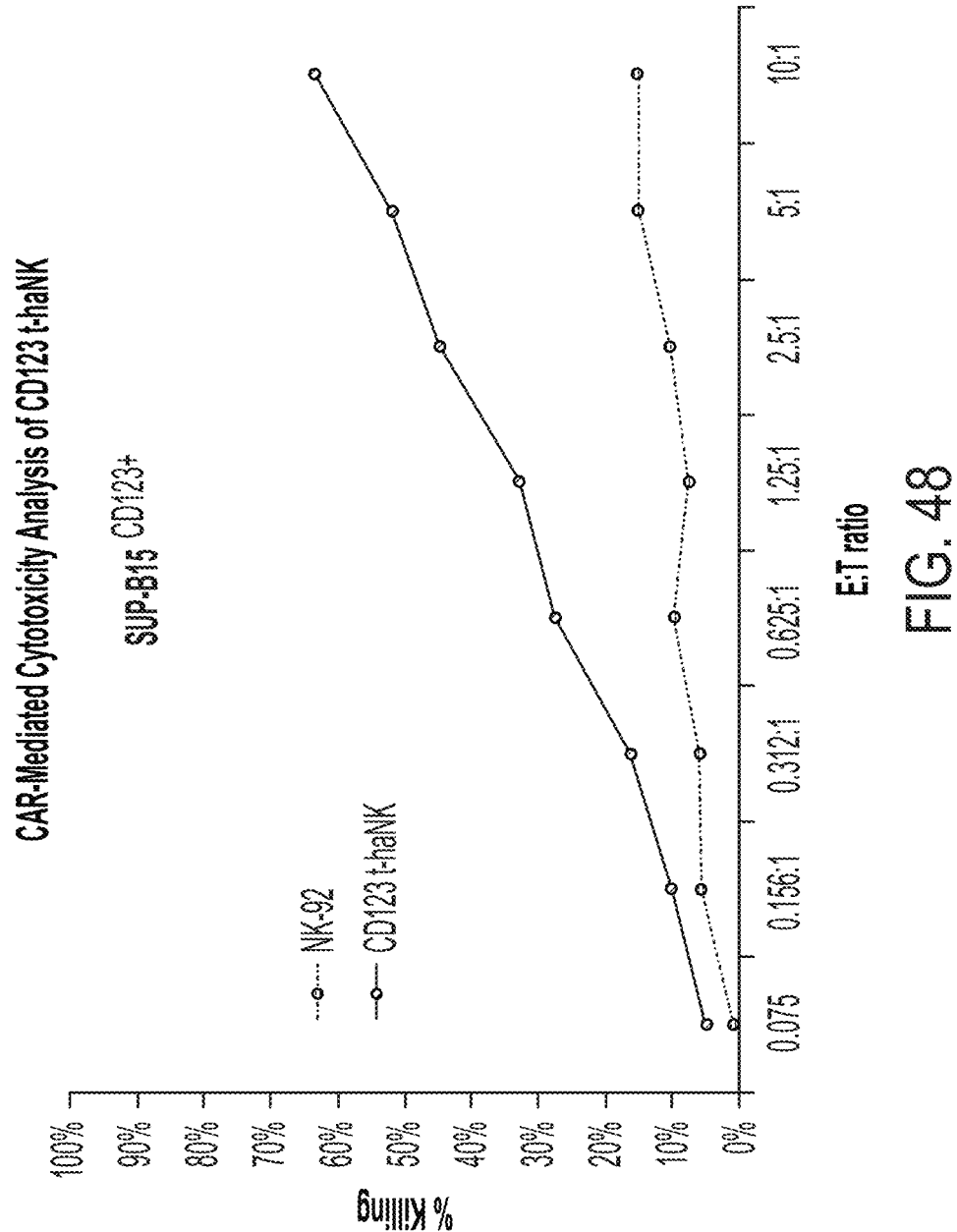
FIG. 48 shows exemplary results for CAR mediated cytotoxicity of CD123.CAR-t-haNK cells.
Figure 49:
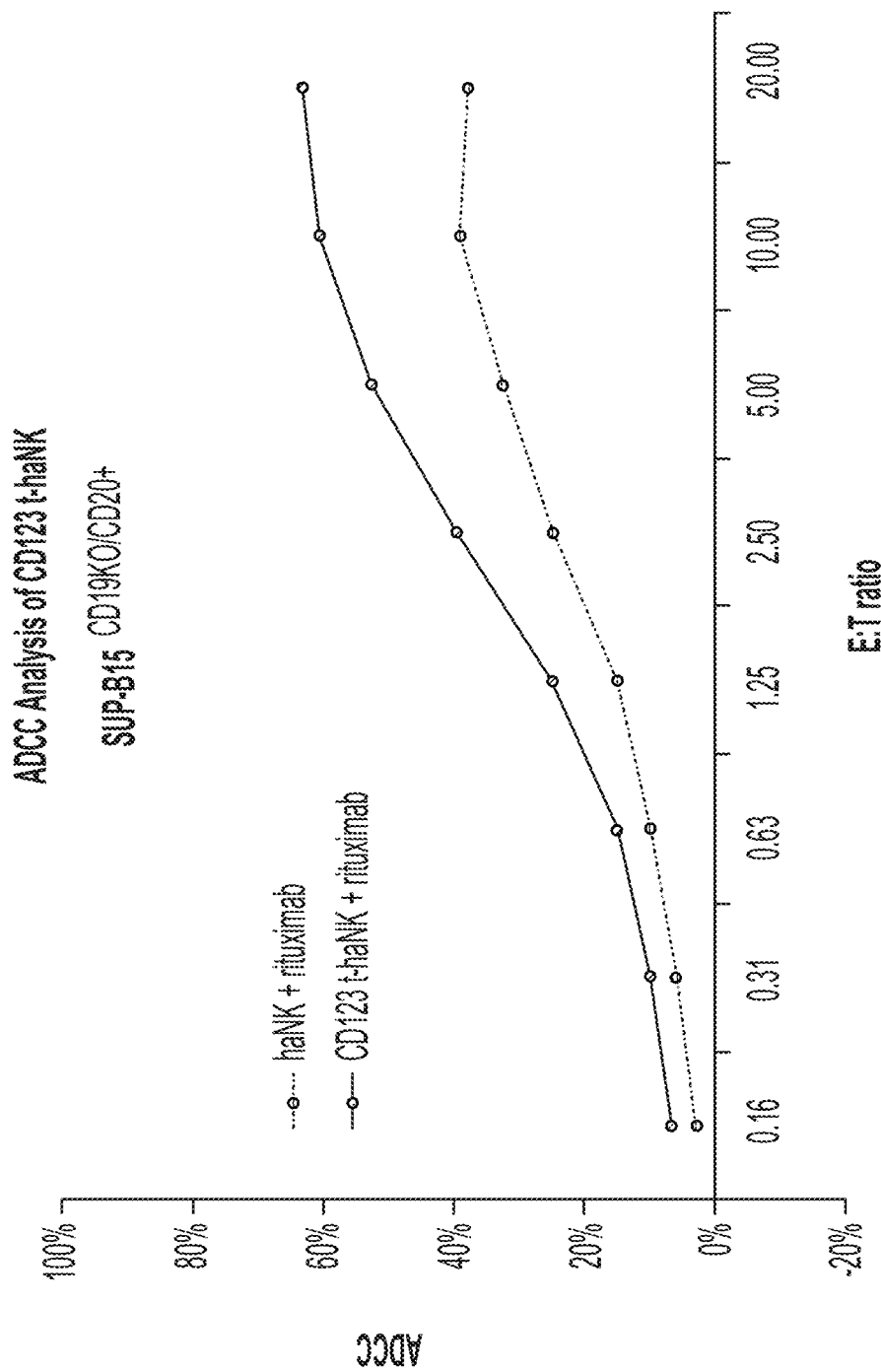
FIG. 49 shows exemplary results for ADCC of CD123.CAR-t-haNK cells.

In this example, the inventors constructed a $1^{st}$ generation CARs with a FcεRIγ signaling domain that included an anti-CD123 scFv coupled to a CD8 hinge, that in turn was coupled to a CD28 transmembrane domain, which was coupled to a FcεRIγ signaling domain. The so constructed CD123-CAR had a nucleic acid sequence of SEQ ID NO:64. Data for the CAR mediated cytotoxicity of the CD123-CAR expressing recombinant NK cells is shown in FIG. 48, and FIG. 49 shows exemplary data for ADCC of CD123-CAR expressing recombinant NK cells.

Example 12: PD-L1-CAR with FcεRIγ Signaling Domain

Figure 16:
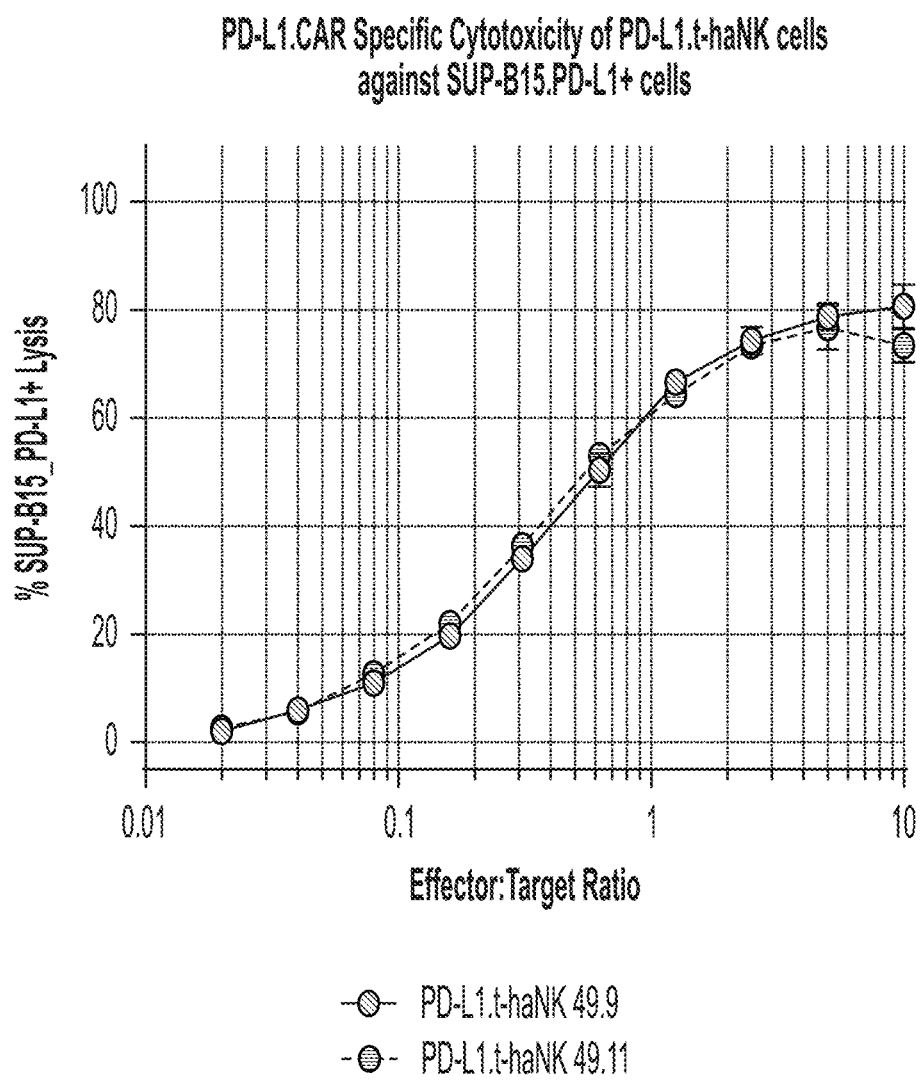
FIG. 16 shows exemplary results for cytotoxicity of PD-L1.CAR-t-haNK cells against SUP-B15.PD-L1+ cells.
Figure 24:
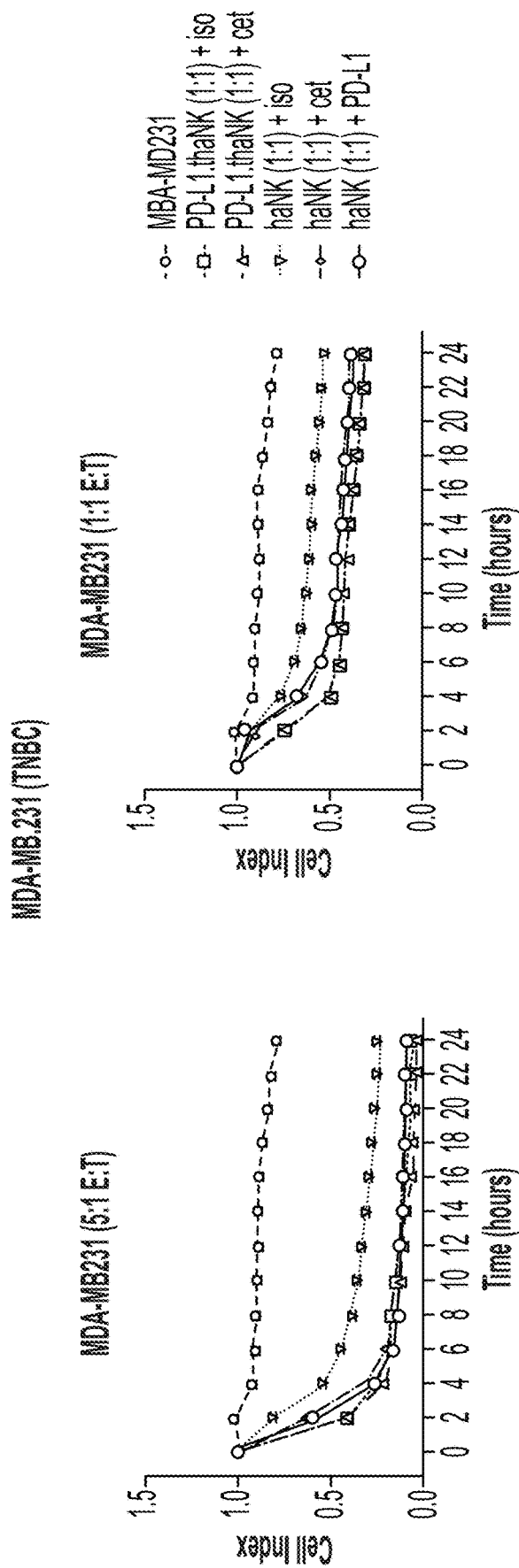
FIG. 24 shows exemplary comparative results for cytotoxicity of PD-L1.CAR-t-haNK cells against MDA-MB-231 cells.

In this example, the inventors constructed a $1^{st}$ generation CARs with a FcεRIγ signaling domain that included an anti-PD-L1 scFv coupled to a CD8 hinge, that in turn was coupled to a CD28 transmembrane domain, which was coupled to a FcεRIγ signaling domain. The so constructed PD-L1-CAR had a nucleic acid sequence of SEQ ID NO:65.
Functionality of the so constructed PD-L1.CAR-t-haNK cells was tested against SUP-B15.PD-L1$^+$ cells using a standard cytotoxicity assay and exemplary results are shown in FIG. 16. As can be readily seen from the data, the PD-L1.CAR-t-haNK cells expressing the CAR with the FcεRIγ signaling domain exhibited significant cytotoxicity against the SUP-B15.PD-L1$^+$ target cells.
Functionality of the so constructed PD-L1.CAR-t-haNK cells was also tested against U251 cells using a standard cytotoxicity assay and exemplary results are shown in FIG. 17 along with non-transfected haNK cells. As can be readily seen from the data, the PD-L1.CAR-t-haNK cells expressing the CAR with the FcεRIγ signaling domain exhibited target specific and significant cytotoxicity against the U251 target cells, whereas the haNK control cells had substantially no cytotoxicity against the same U251 cells.
In still further experiments on target cell specificity with respect to PD-L1, the inventors tested several PD-L1 positive tumor cell lines using the PD-L1.CAR-t-haNK cells along with haNK cells as control for general cytotoxicity. As can be readily seen from FIG. 24, the PD-L1.CAR-t-haNK cells had superior cytotoxicity across a wide variety of tumor cells (lung, breast, genituy tumor cells, and additionally, head and neck small cell cancer, chordoma). Notably, the PD-L1.CAR-t-haNK cells required less than 4 hours for the majority (>85%) of cell killing whereas the control haNK cells required more than 12 hours.
FIG. 24 further illustrates cytotoxicity of the PD-L1.CAR-t-haNK cells against MDA-MB-231 cells as compared to various other control cells (haNK cells as indicated). As can be taken from the data, at a 5:1 E:T ratio, MDA-MB-231 lysis by PD-L1.thaNK was improved by cetuximab, and haNK activity was improved by the addition of cetuximab and a-PD-L1. Plain PD-L1.thank had improved cytotoxic activity compared to haNK and haNK+cetuximab, and plain PD-L1.thank killing was comparable to that of haNK+PD-L1 antibody but PD-L1.thank+cetuximab outperformed haNK+cetuximab and haNK+PD-L1. At a 1:1 E:T ratio, PD-L1.thaNK activity was the same with or without cetuximab, and PD-L1.thaNK significantly outperformed intrinsic and ADCC-mediated killing by hank. haNK activity was improved by the addition of cetuximab and a-PD-L1.

Figure 44:
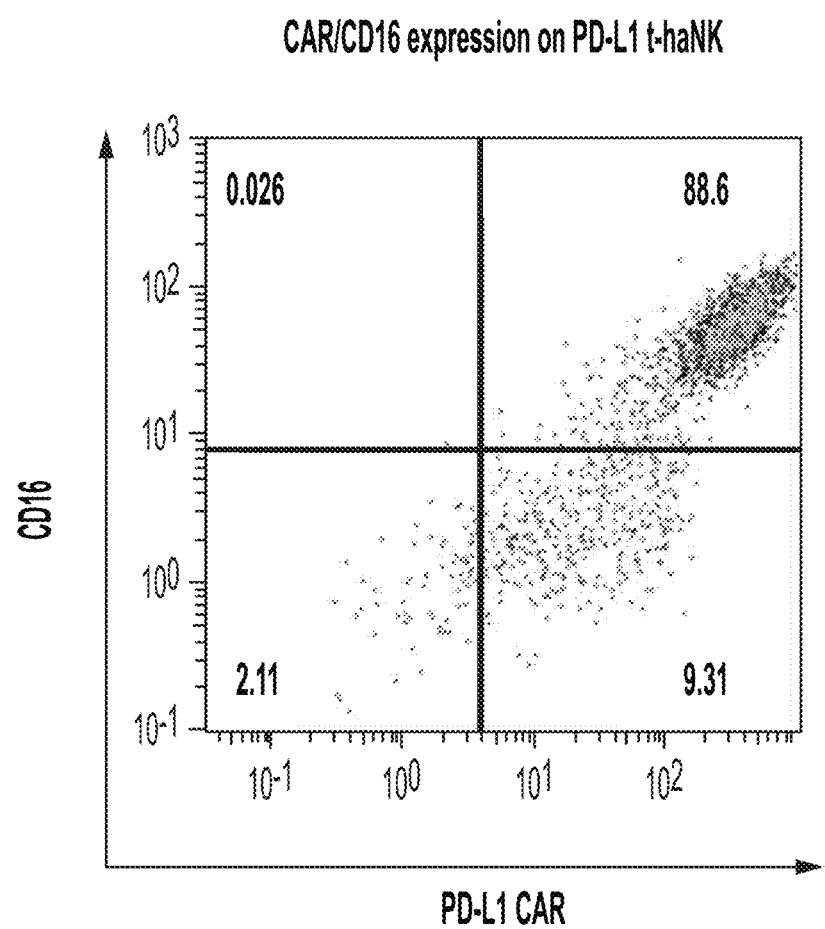
FIG. 44 shows exemplary results expression of CD16 and PD-L1.CAR.
Figure 45:
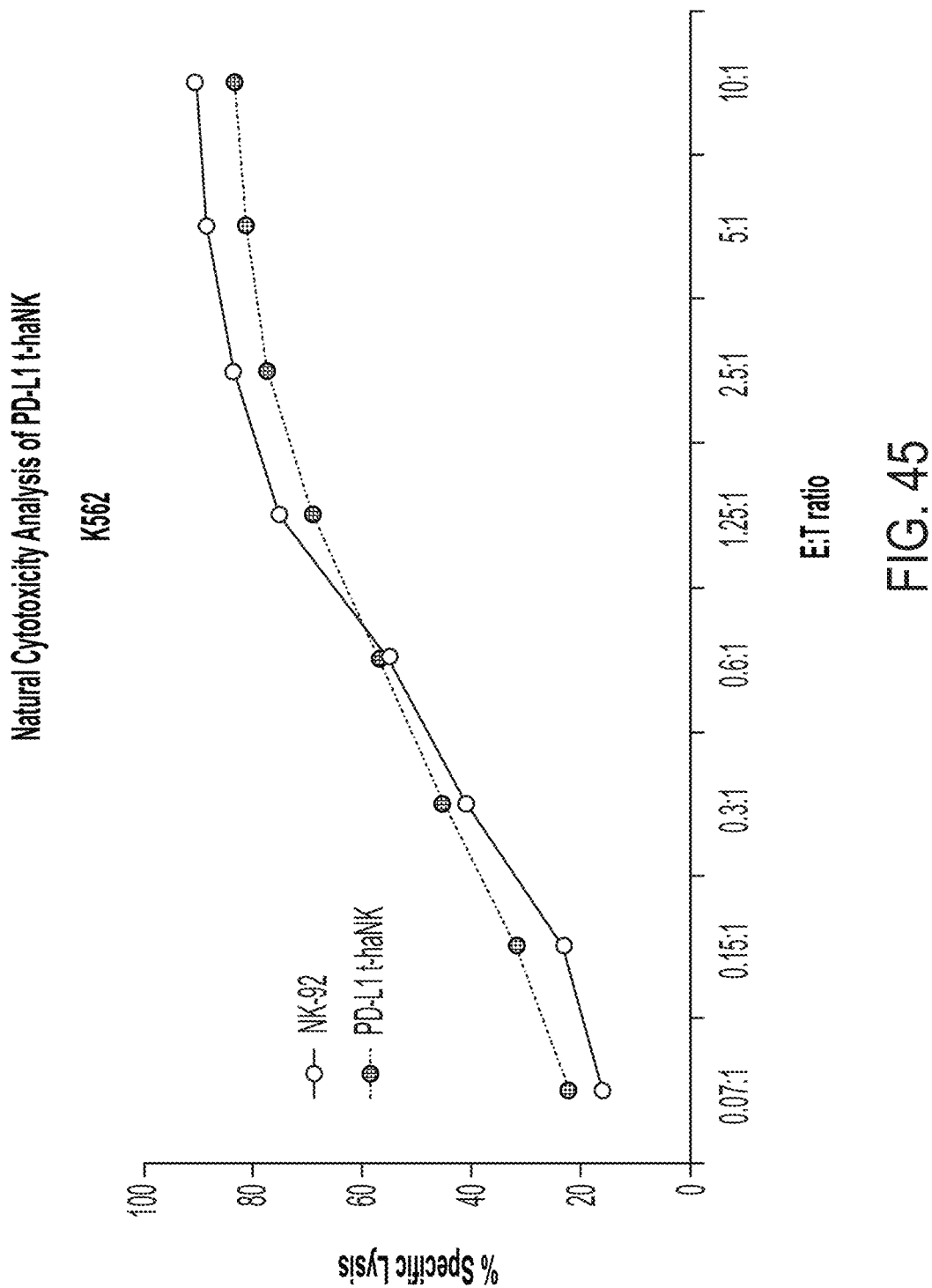
FIG. 45 shows exemplary results for natural cytotoxicity of PD-L1.CAR-t-haNK cells.
Figure 46:
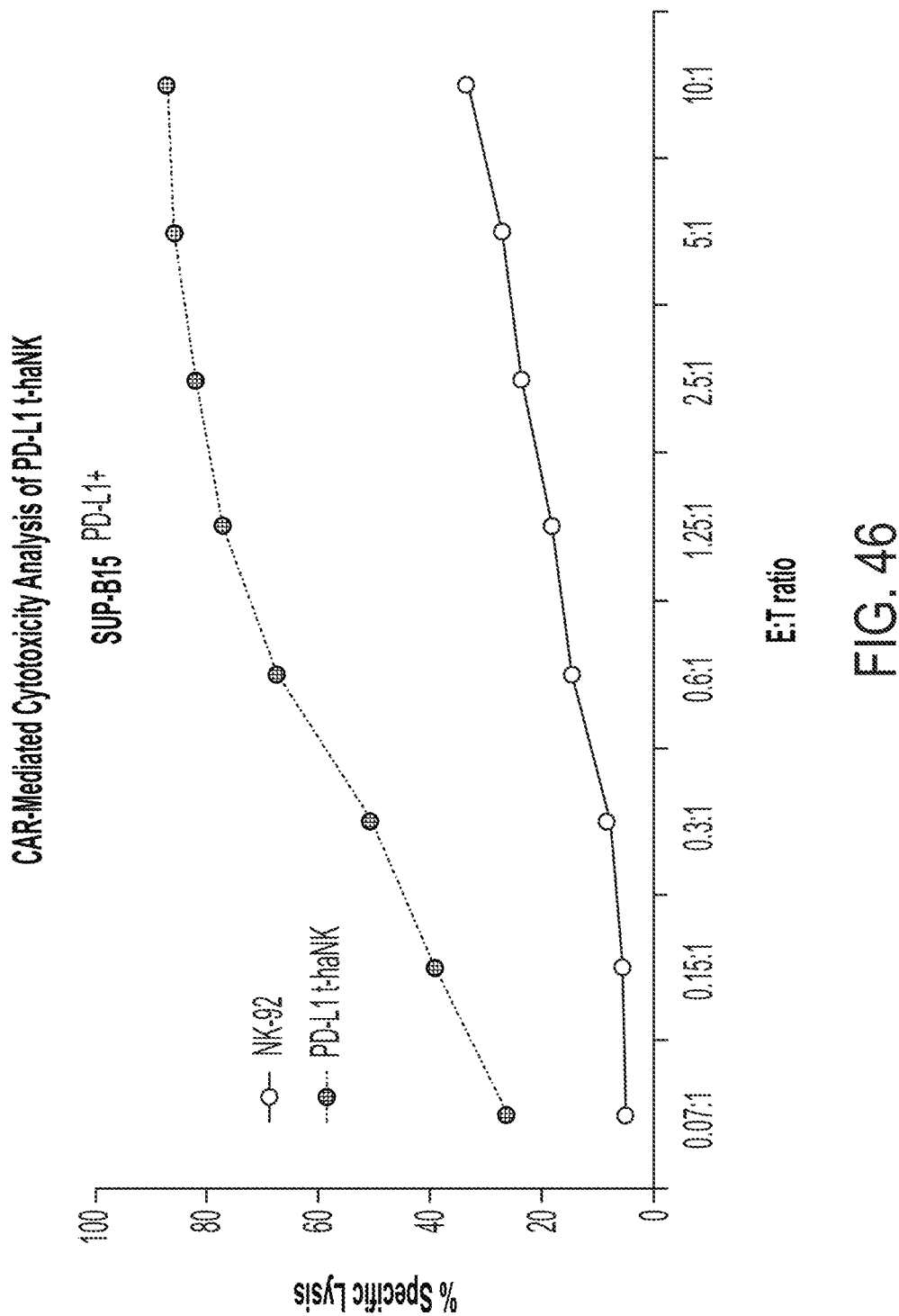
FIG. 46 shows exemplary results for CAR mediated cytotoxicity of PD-L1.CAR-t-haNK cells.
Figure 47:
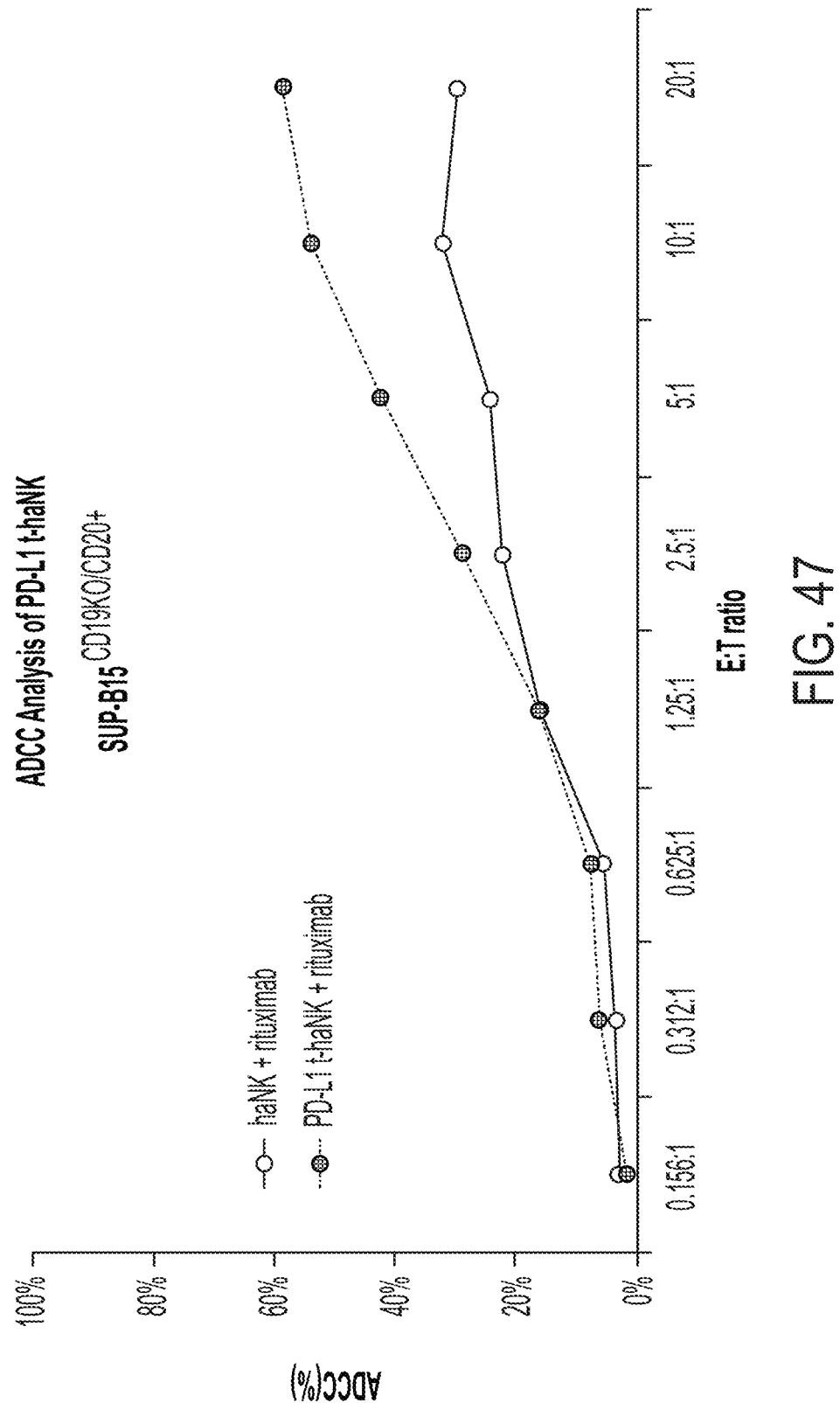
FIG. 47 shows exemplary results for ADCC of PD-L1.CAR-t-haNK cells.

In further experiments, the inventors demonstrated expression of the PD-L1.CAR in PD-L1.CAR-t-haNK cells as is illustrated in FIG. 44. Natural cytotoxicity of the PD-L1.CAR-t-haNK cells is shown in the results of FIG. 45, while results for CAR mediated cytotoxicity are shown in FIG. 46. Exemplary data for ADCC of PD-L1.CAR-t-haNK cells are shown in the graph of FIG. 47.

Example 13: CD33-CAR with FcεRIγ Signaling Domain

In this example, the inventors constructed a $1^{st}$ generation CARs with a FcεRIγ signaling domain that included an anti-HER2 scFv coupled to a CD8 hinge, that in turn was coupled to a CD28 transmembrane domain, which was coupled to a FcεRIγ signaling domain. The so constructed CD33.CAR had a nucleic acid sequence of SEQ ID NO:66.

Figure 15:
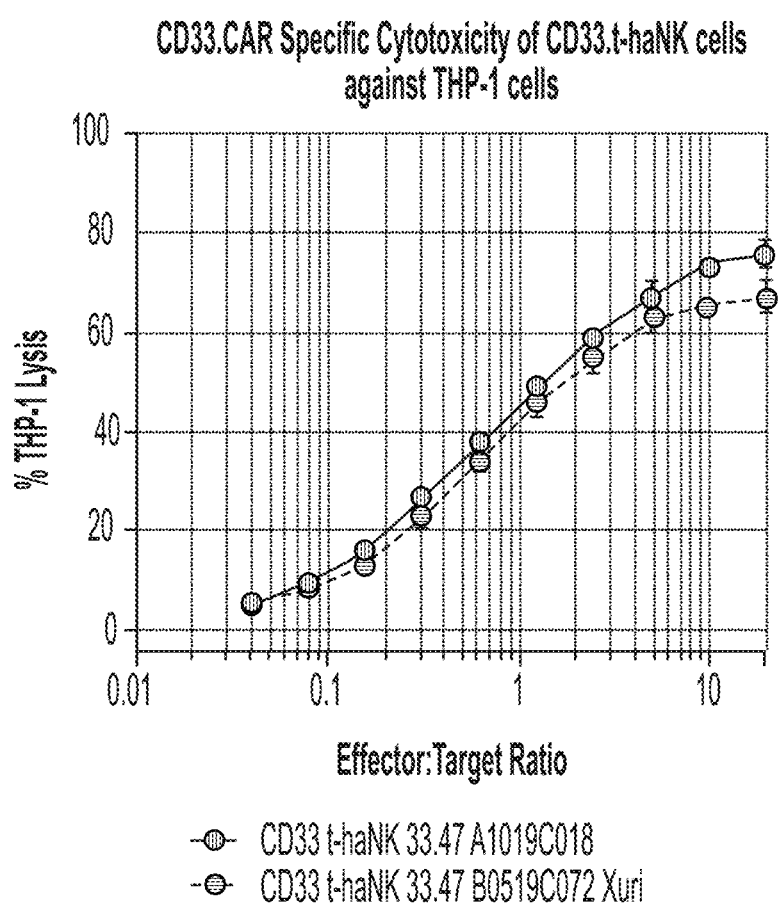
FIG. 15 shows exemplary results for cytotoxicity of CD33.CAR-t-haNK cells against THP-1 cells.
Figure 31:
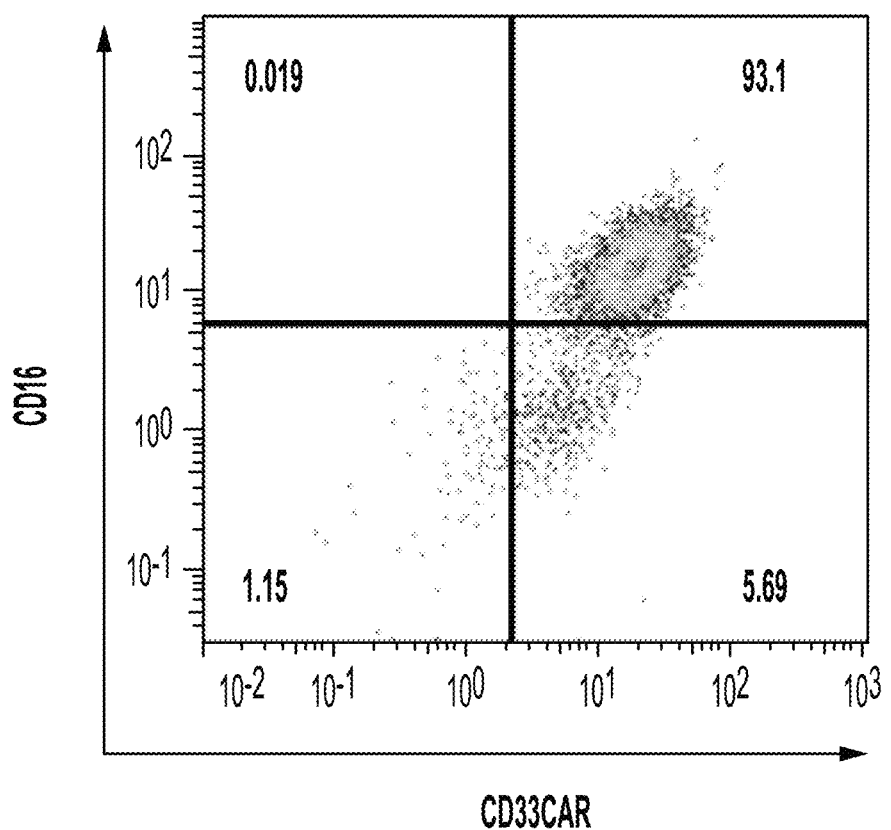
FIG. 31 shows exemplary results for expression of CD16 and CD33.CAR.
Figure 32:
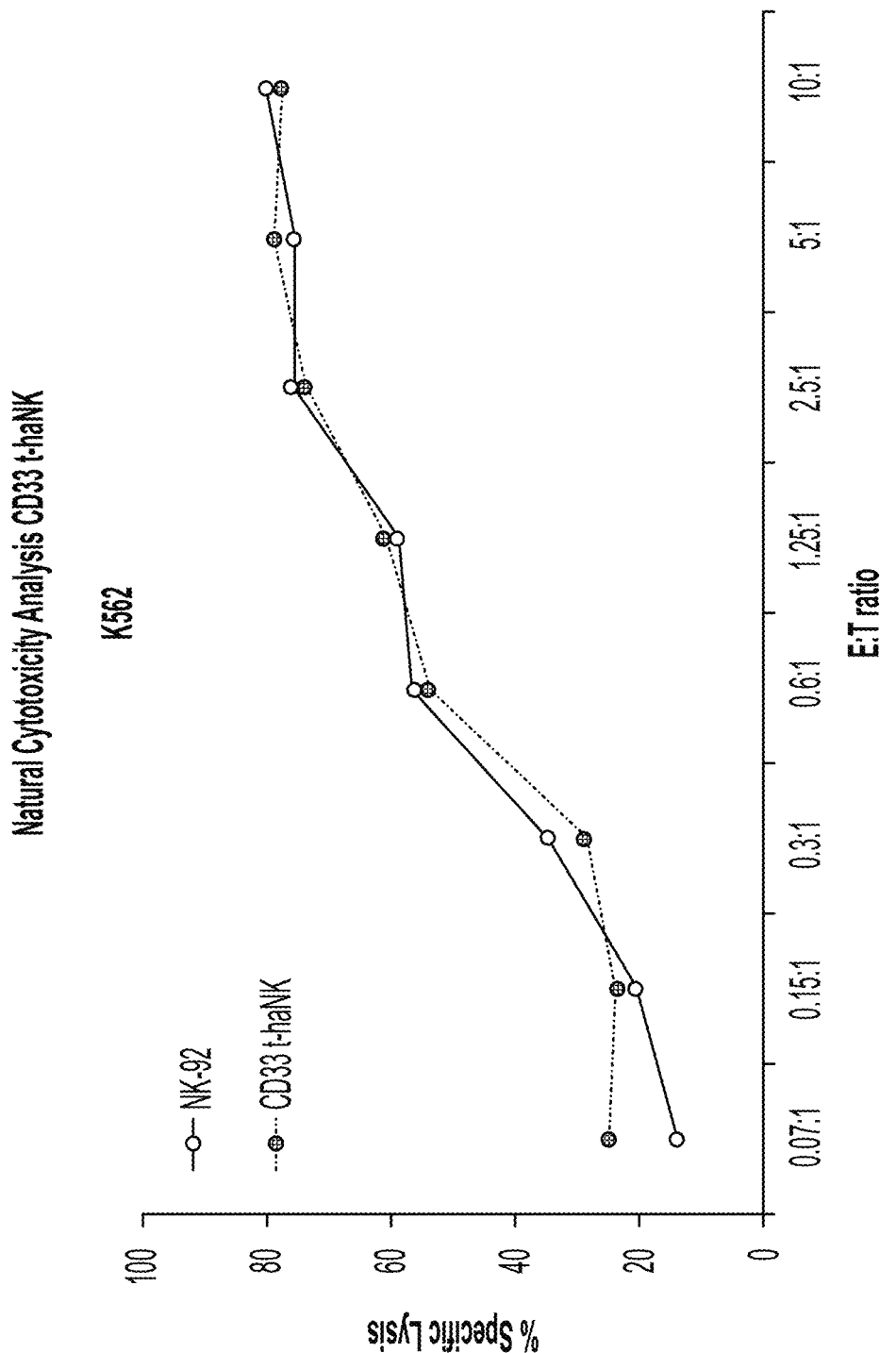
FIG. 32 shows exemplary results for natural cytotoxicity of CD33.CAR-t-haNK cells.
Figure 33:
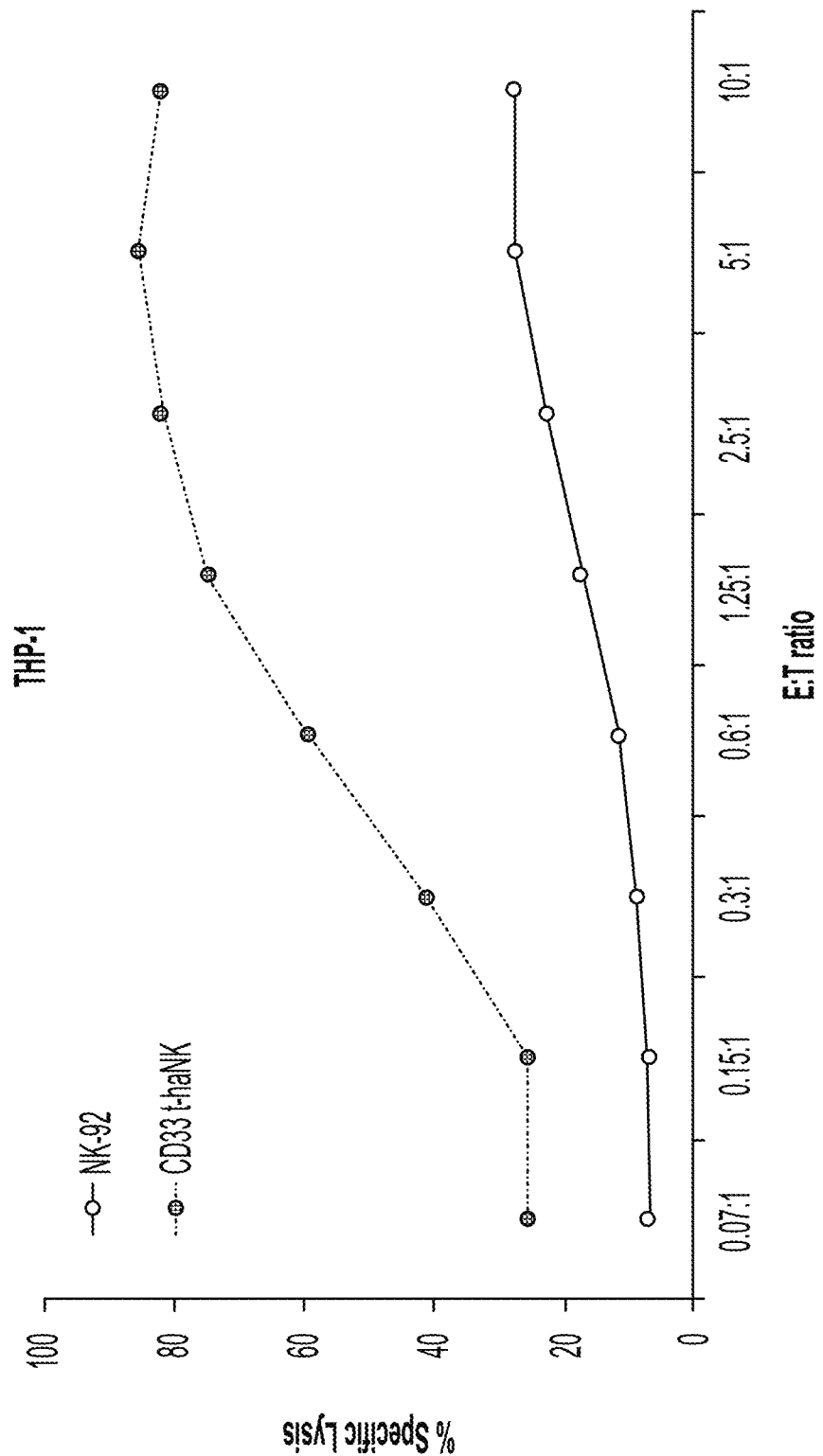
FIG. 33 shows exemplary results for CAR mediated cytotoxicity of CD33.CAR-t-haNK cells.
Figure 34:
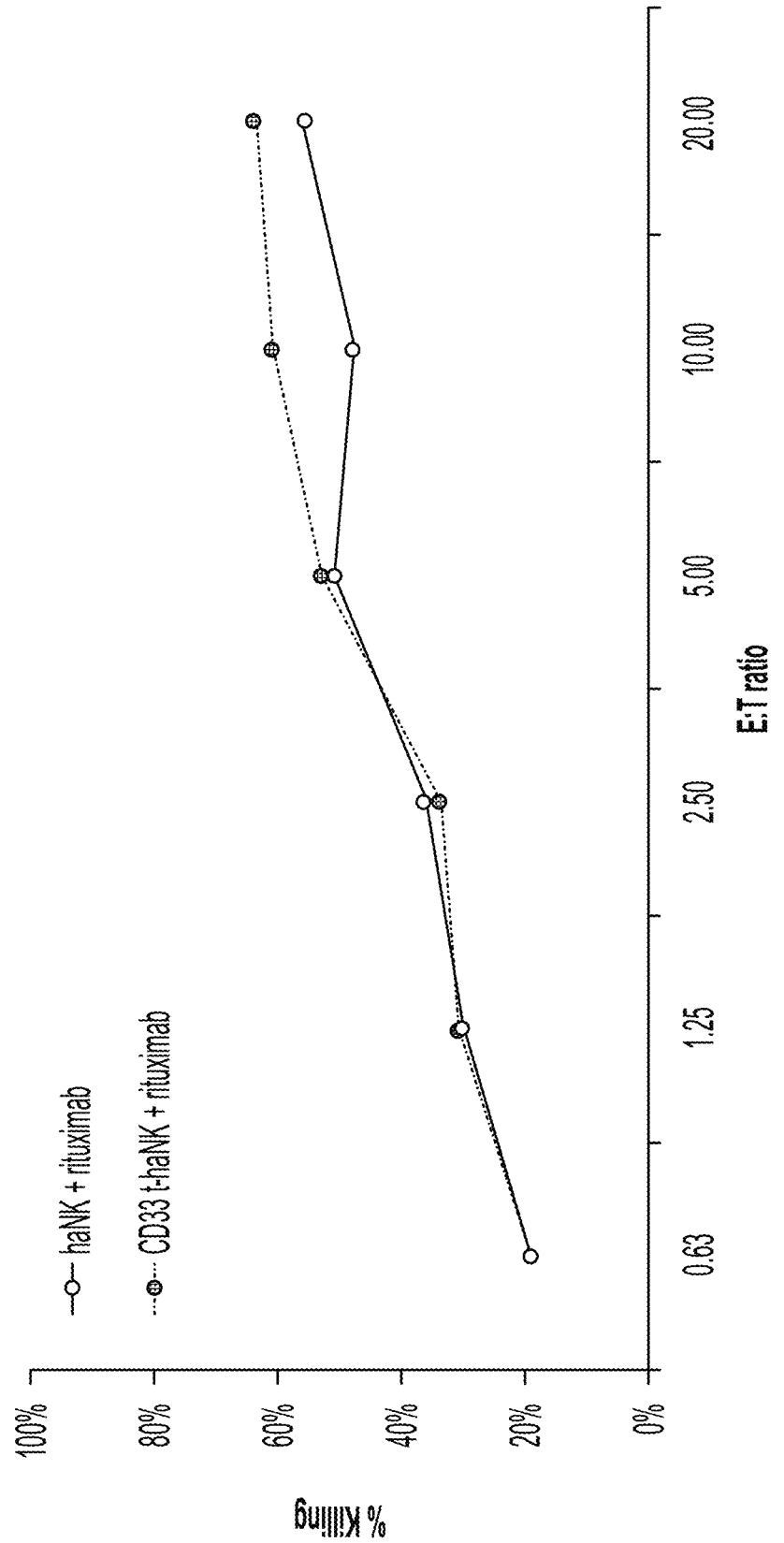
FIG. 34 shows exemplary results for ADCC of CD33.CAR-t-haNK cells.

Functionality of the so constructed CD33.CAR-t-haNK cells was tested against THP-1 cells using a standard cytotoxicity assay and exemplary results are shown in FIG. 15. As can be readily seen from the data, the CD33.CAR-t-haNK cells expressing the CAR with the FcεRIγ signaling domain exhibited significant cytotoxicity against the THP-1 target cells. Further data depicting strong expression of the CD33CAR in NK-92 cells are presented in FIG. 31. Natural cytotoxicity of the CD33.CAR-t-haNK cells against K562 cells is shown in FIG. 32, and FIG. 33 depicts results for CAR mediated cytotoxicity against THP-1 cells. FIG. 34 shows further results for ADCC of CD33.CAR-t-haNK cells against SUP-B15 CD19$^{KO}$/CD20$^+$ with rituximab.

Example 14: 21120-CAR with FcεRIγ Signaling Domain

In this example, the inventors constructed a $1^{st}$ generation CARs with a FcεRIγ signaling domain that included an anti-gp120 scFv coupled to a CD8 hinge, that in turn was coupled to a CD28 transmembrane domain, which was coupled to a FcεRIγ signaling domain. The so constructed gp120-CAR had a nucleic acid sequence of SEQ ID NO:67.

Figure 57:
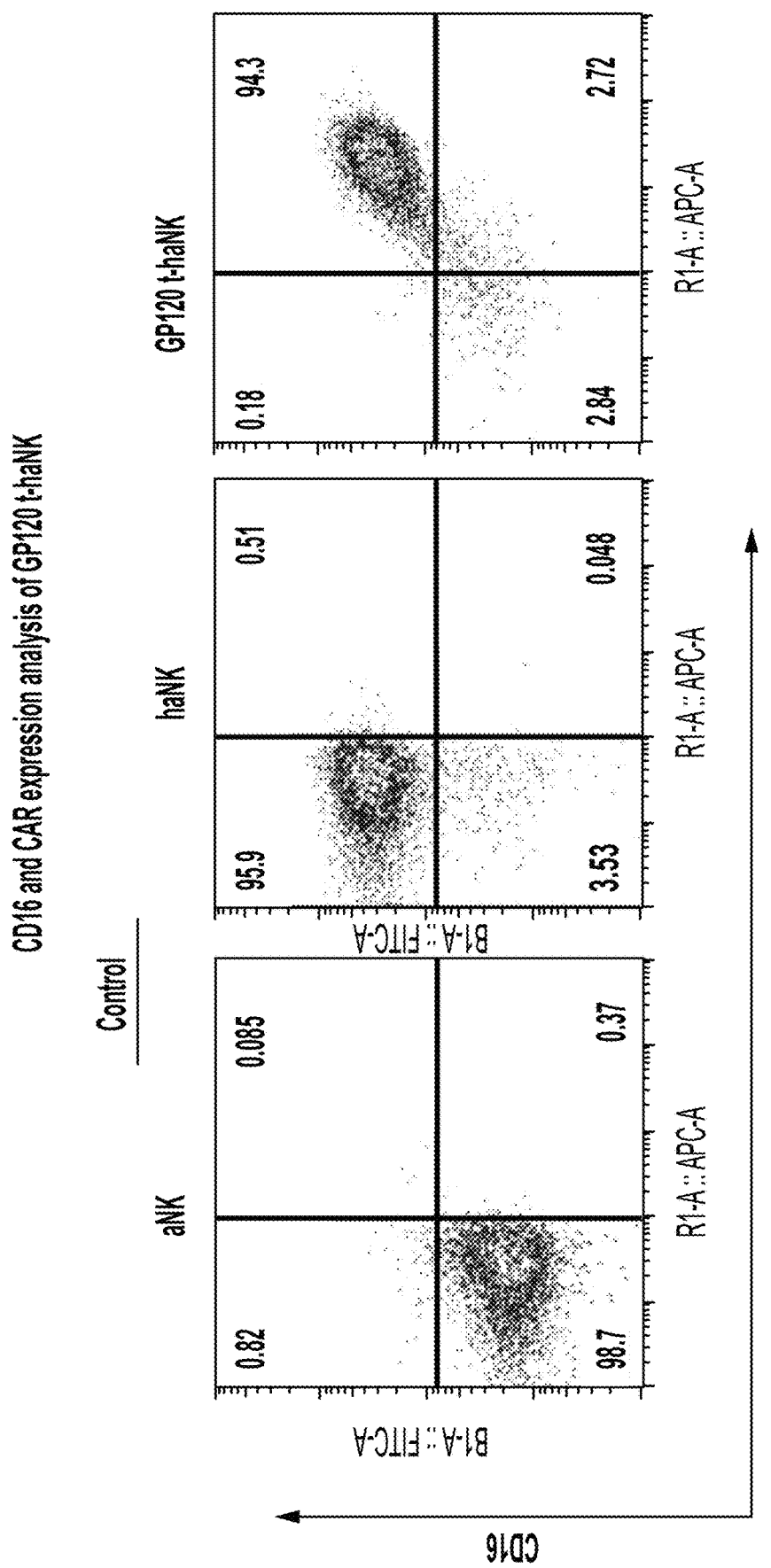
FIG. 57 shows exemplary results for expression of CD16 and gp120.CAR.
Figure 58:
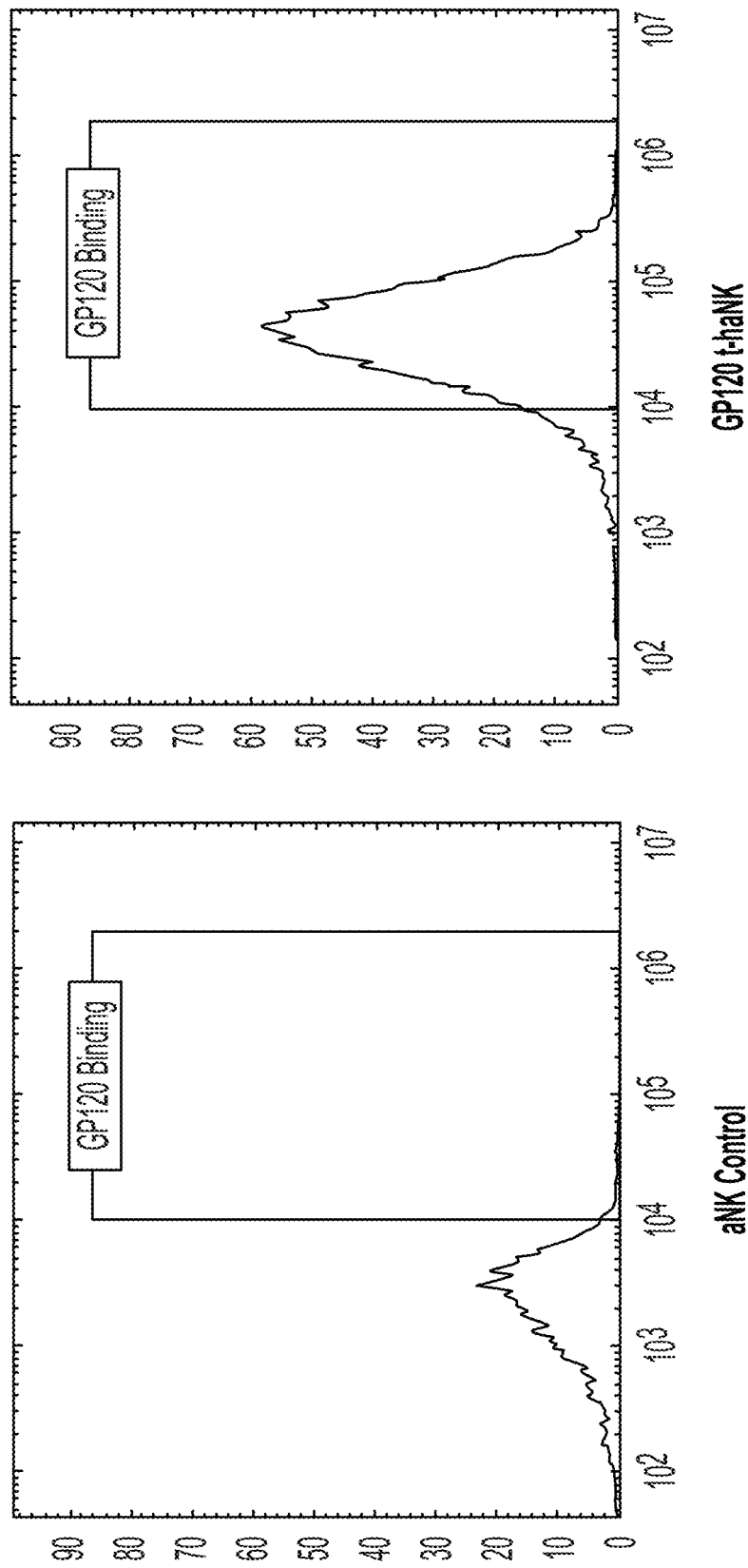
FIG. 58 shows exemplary results for GP120 binding of gp120.CAR-t-haNK cells.
Figure 59:
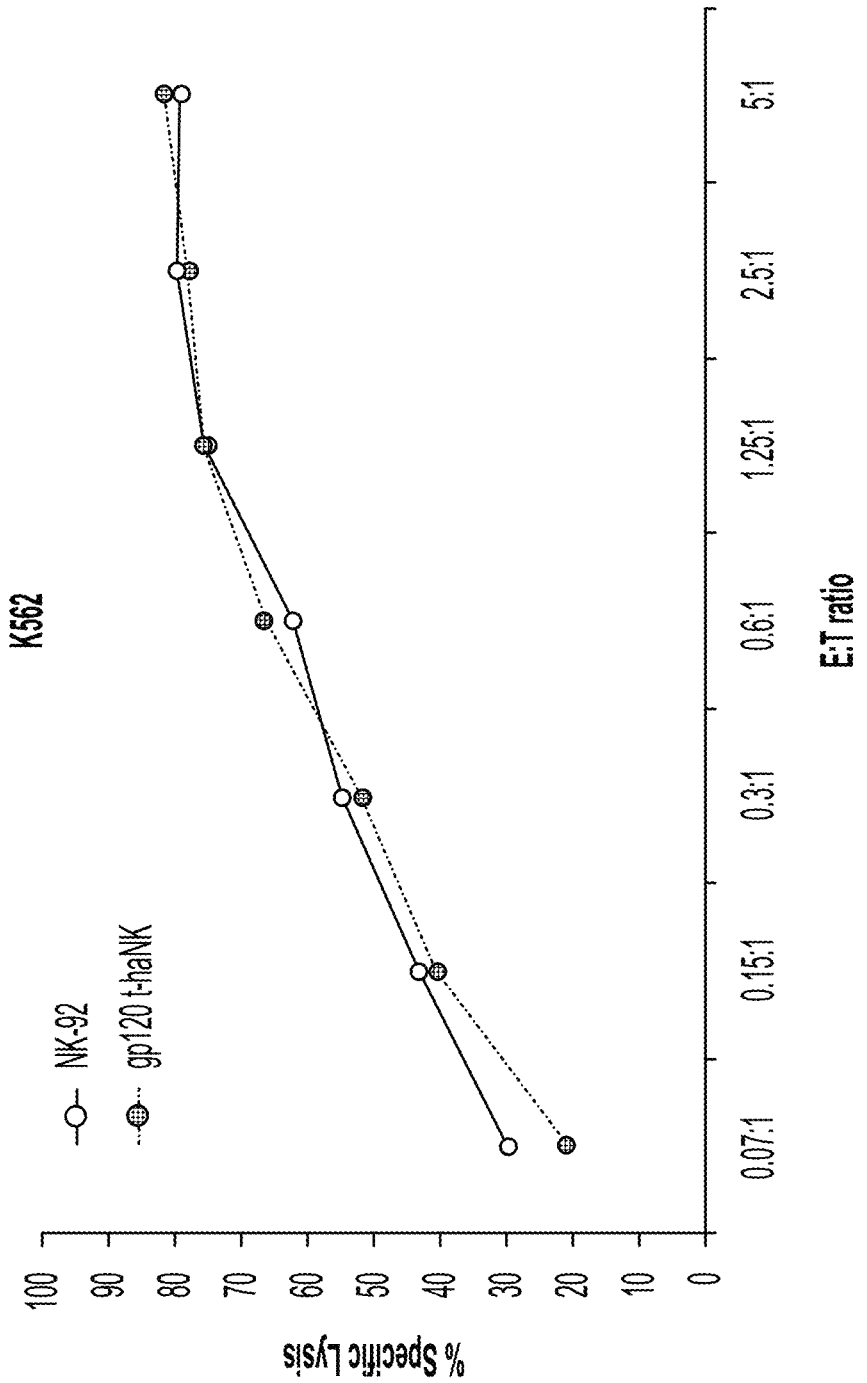
FIG. 59 shows exemplary results for natural cytotoxicity of gp120.CAR-t-haNK cells.
Figure 60:
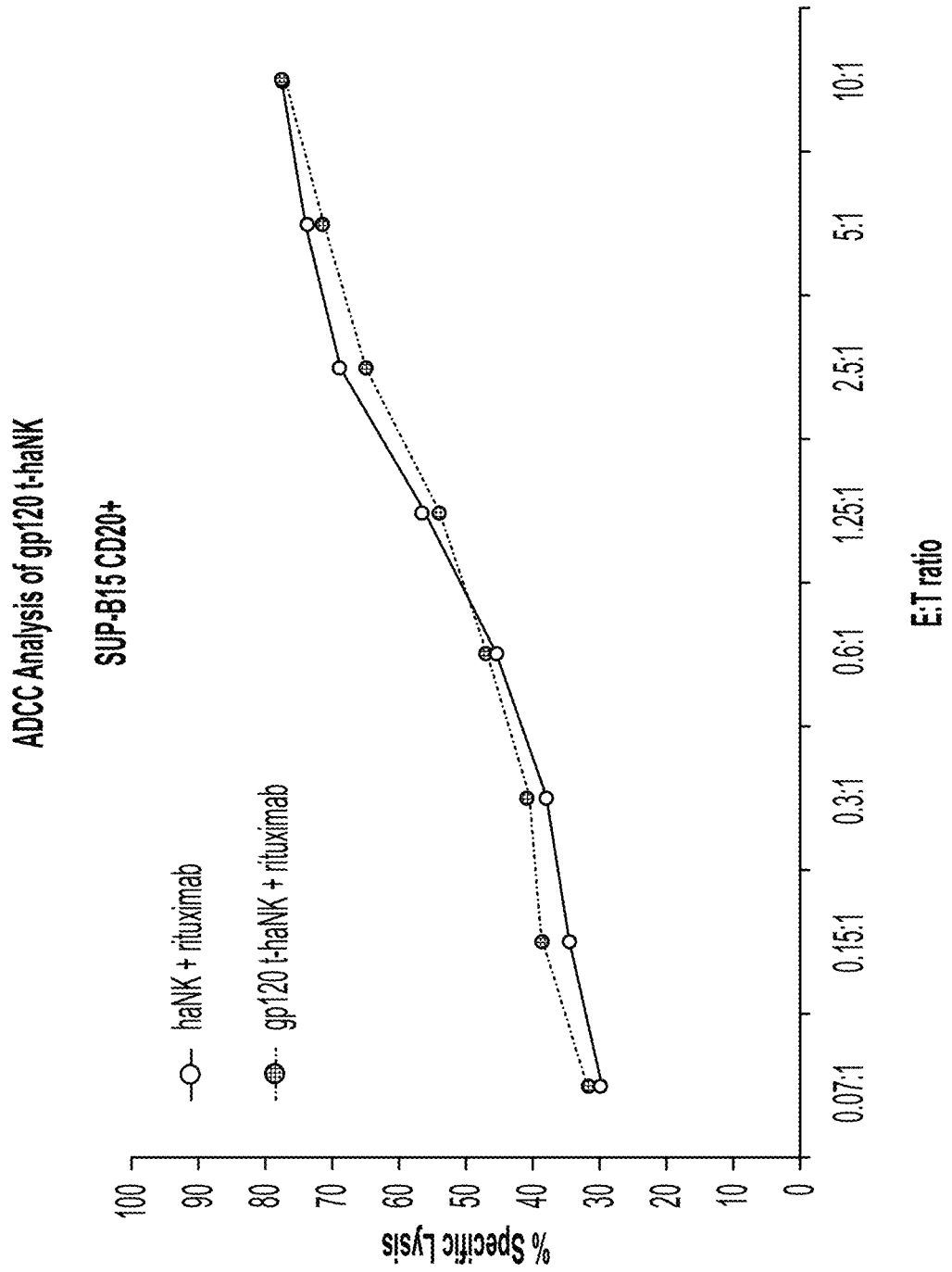
FIG. 60 shows exemplary results for ADCC of gp120.CAR-t-haNK cells.

The inventors further demonstrated that so generated cells expressed significant quantities of CD16 and gp120CAR as can be seen from FIG. 57. Binding of GP120 to the gp120CAR was shown as demonstrated in FIG. 58 versus non-recombinant aNK cells as negative control. Natural cytotoxicity of the so generated cells is shown in FIG. 59, while corresponding ADCC data are shown in FIG. 60.

Example 15: B7-H4-CAR with FcεRIγ Signaling Domain

In this example, the inventors constructed a $1^{st}$ generation CARs with a FcεRIγ signaling domain that included an anti-B7-H4 scFv coupled to a CD8 hinge, that in turn was coupled to a CD28 transmembrane domain, which was coupled to a FcεRIγ signaling domain. The so constructed B7-H4-CAR had a nucleic acid sequence of SEQ ID NO:68.

Example 16: BCMA-CAR with FcεRIγ Signaling Domain

In this example, the inventors constructed a $1^{st}$ generation CARs with a FcεRIγ signaling domain that included an anti-BCMA scFv coupled to a CD8 hinge, that in turn was coupled to a CD28 transmembrane domain, which was coupled to a FcεRIγ signaling domain. The so constructed BCMA-CAR had a nucleic acid sequence of SEQ ID NO:69.

Figure 54:
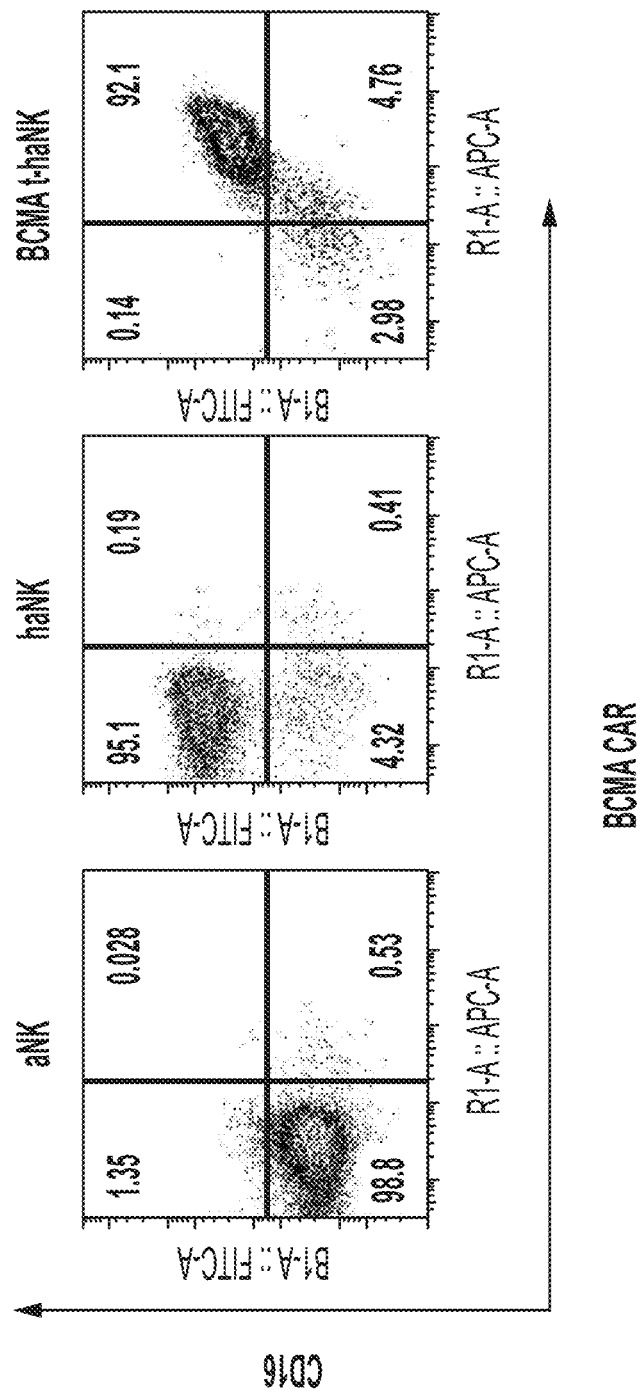
FIG. 54 shows exemplary results for CD16 and BCMA.CAR expression.
Figure 55:
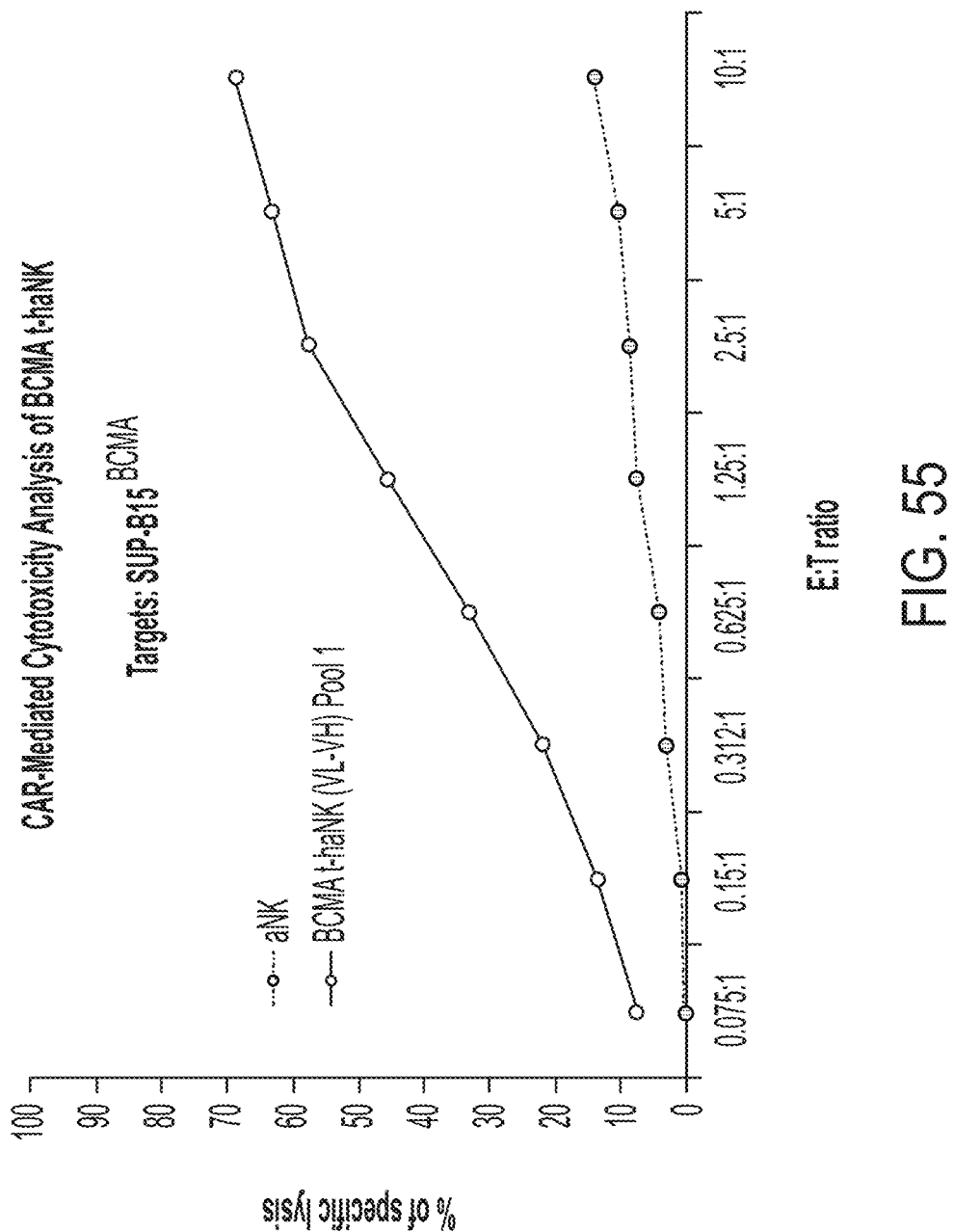
FIG. 55 shows exemplary results for CAR mediated cytotoxicity of BCMA.CAR-t-haNK cells.
Figure 56:
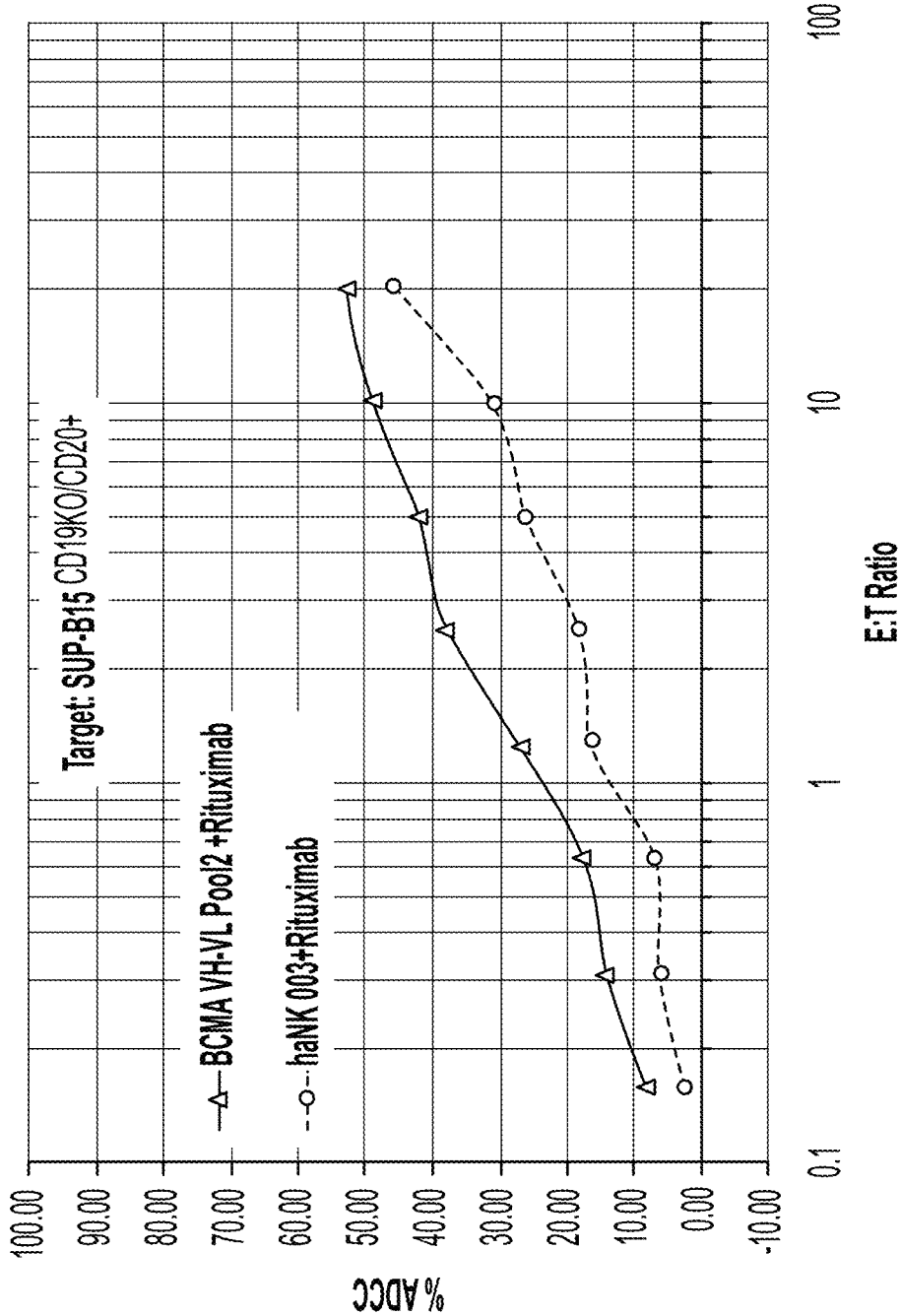
FIG. 56 shows exemplary results for ADCC of BCMA.CAR-t-haNK cells.

BCMA expression was confirmed as is shown in the exemplary results of FIG. 54, and CAR mediated cytotoxicity was demonstrated against target cells as is shown in FIG. 55. Similarly, as can be seen from the results in FIG. 56, recombinant cells had significant ADCC using rituximab as antibody against the target cells.

Example 17: GD2-CAR with FcεRIγ Signaling Domain

In this example, the inventors constructed a $1^{st}$ generation CARs with a FcεRIγ signaling domain that included an anti-GD2 scFv coupled to a CD8 hinge, that in turn was coupled to a CD28 transmembrane domain, which was coupled to a FcεRIγ signaling domain. The so constructed GD2-CAR had a nucleic acid sequence of SEQ ID NO:70.

Example 18: FAP-CAR with FcεRIγ Signaling Domain

Figure 61:
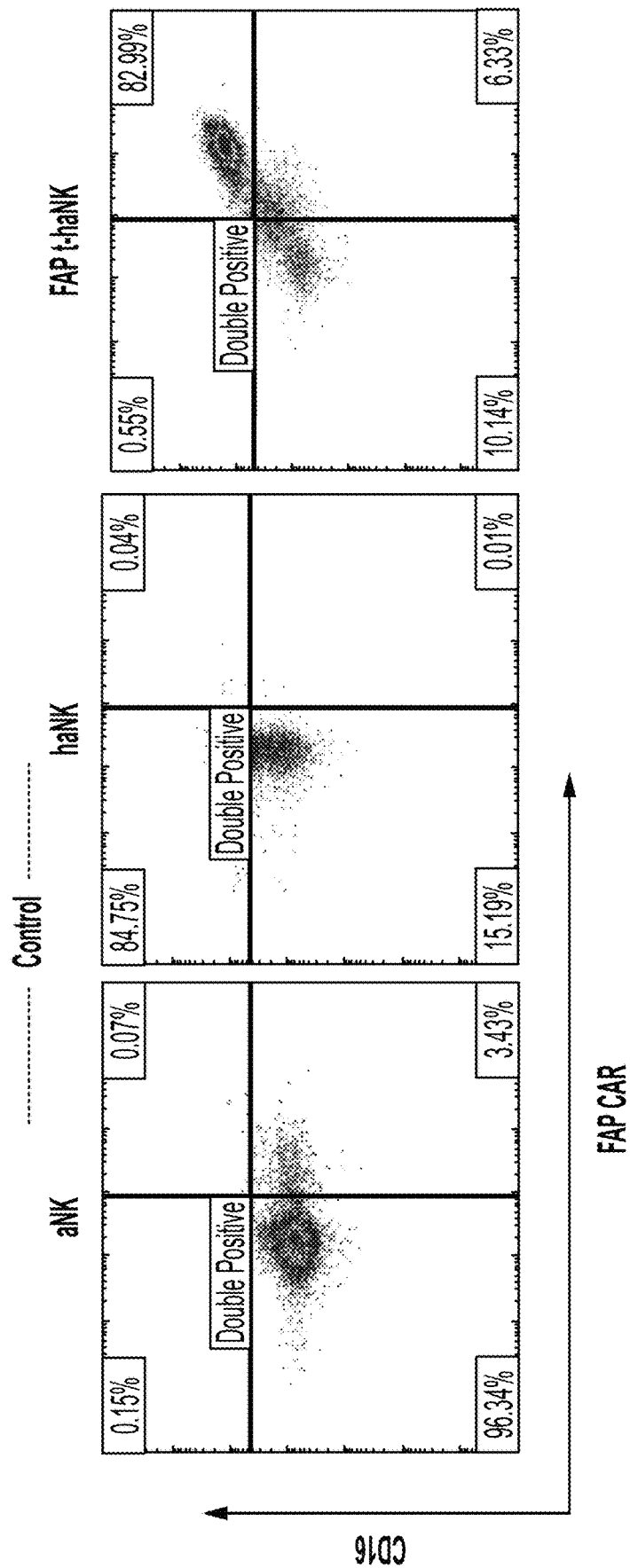
FIG. 61 shows exemplary results for CD16 and FAP.CAR expression.
Figure 62:
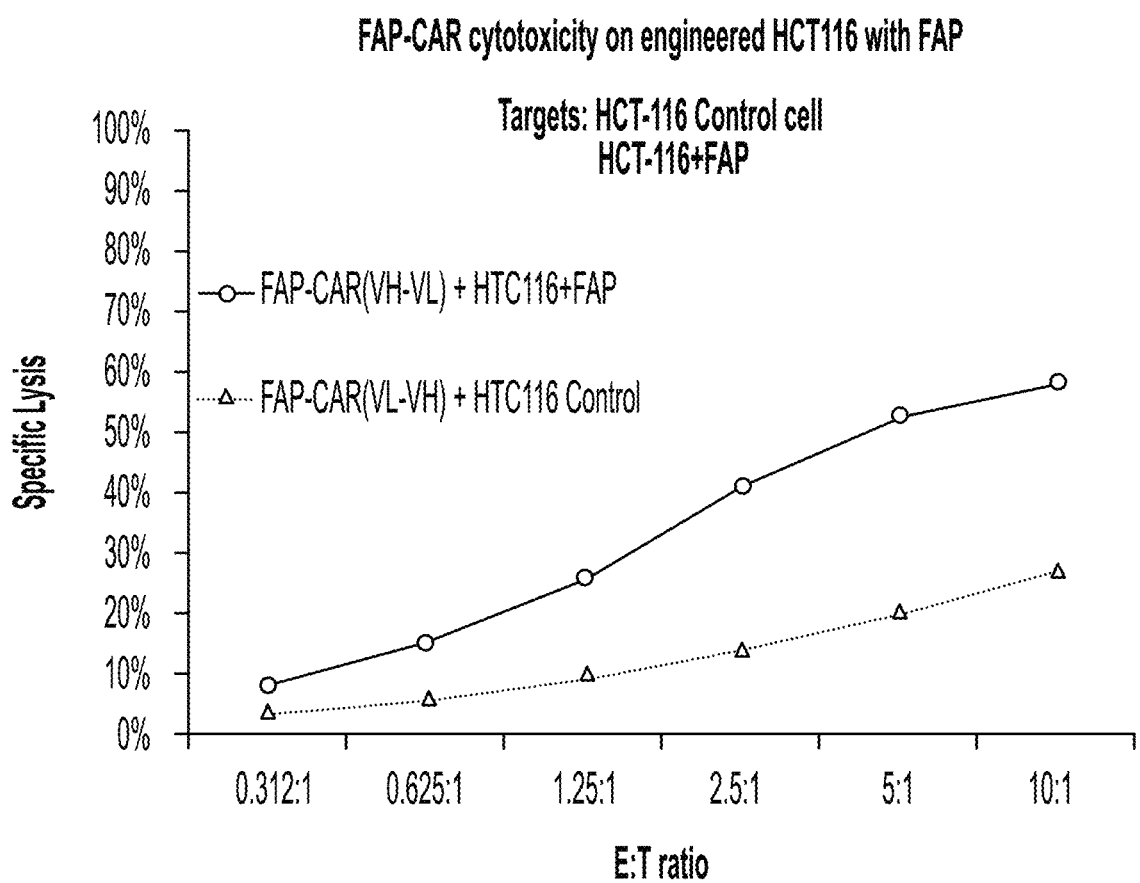
FIG. 62 shows exemplary results for CAR mediated cytotoxicity of FAP.CAR-t-haNK cells.

In this example, the inventors constructed a $1^{st}$ generation CARs with a FcεRIγ signaling domain that included an anti-FAP scFv coupled to a CD8 hinge, that in turn was coupled to a CD28 transmembrane domain, which was coupled to a FcεRIγ signaling domain. The so constructed FAP-CAR had a nucleic acid sequence of SEQ ID NO:71. Expression of the FAP-CAR is shown in the data of FIG. 61, and FAP.CAR cytotoxicity is demonstrated on target cells in the results of FIG. 62.

Example 19: CD20-CAR with FcεRIγ Signaling Domain

In this example, the inventors constructed a $1^{st}$ generation CARs with a FcεRIγ signaling domain that included an anti-CD20 scFv coupled to a CD8 hinge, that in turn was coupled to a CD28 transmembrane domain, which was coupled to a FcεRIγ signaling domain. The so constructed CD20-CAR had a nucleic acid sequence of SEQ ID NO:74.

Figure 29:
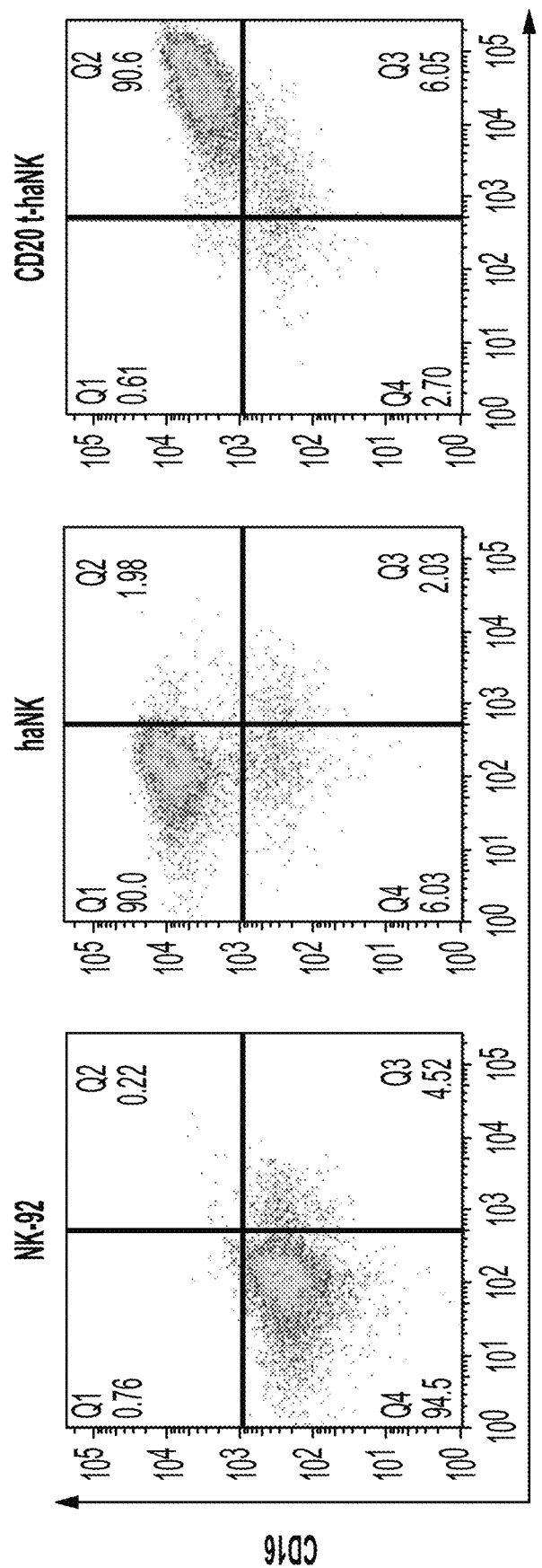
FIG. 29 shows exemplary comparative results for expression of CD16 and CD20.CAR.
Figure 30:
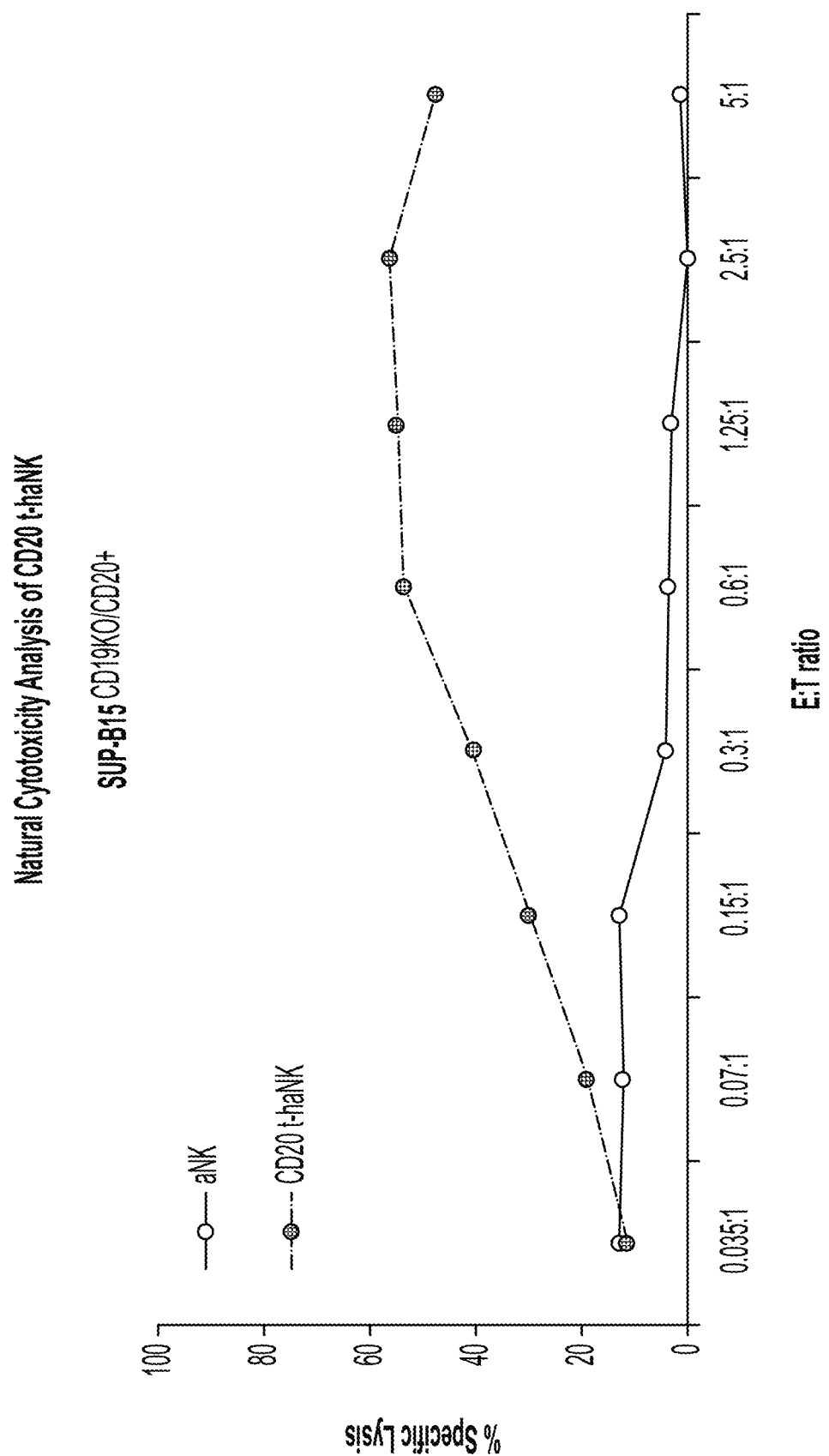
FIG. 30 shows exemplary results for natural cytotoxicity of CD20.CAR-t-haNK cells.

Expression of the CD20 CAR in NK-92 cells is shown in the results of FIG. 29. As can be readily seen, CD20.CAR is expressed strongly in the vast majority of recombinant cells (along with CD16 from the linearized DNA as noted above). FIG. 30 depicts exemplary results for cytotoxicity of the CD20.CAR NK cells against CD20+target cells.

Example 20: CSPG-4-CAR with FcεRIγ Signaling Domain

Figure 63:
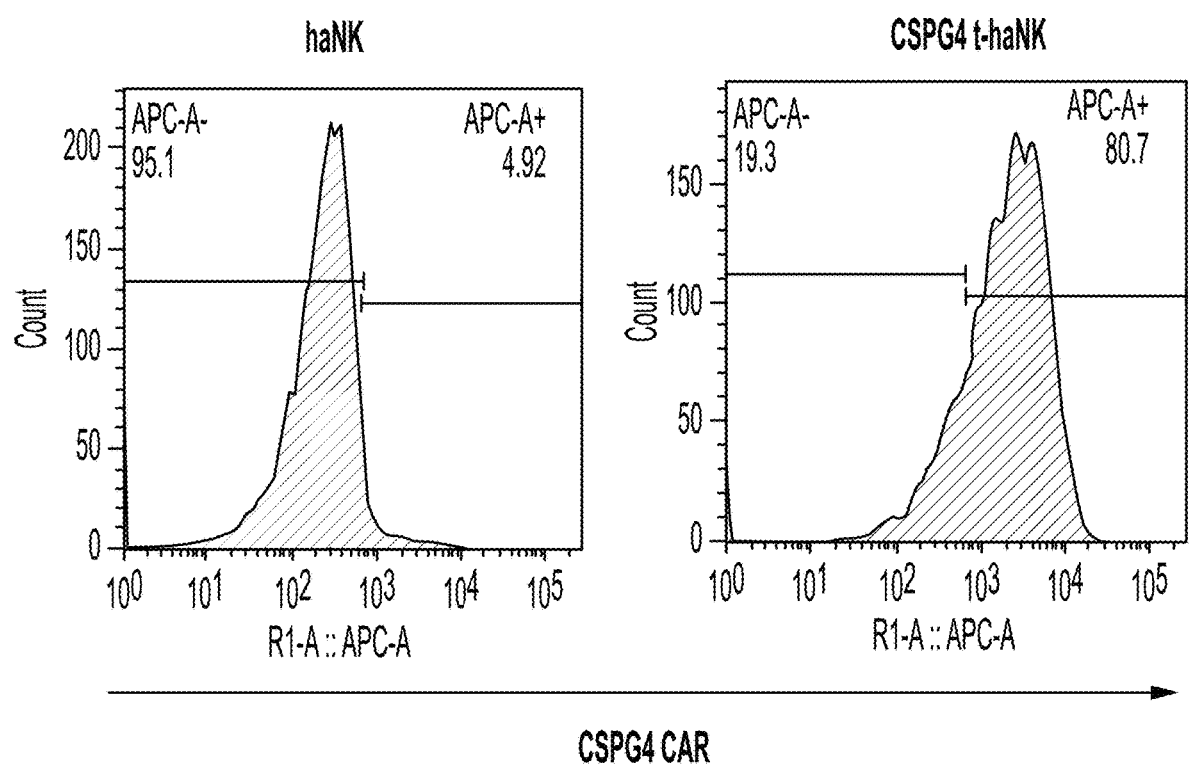
FIG. 63 shows exemplary results for CSPG4 expression in CSPG4.CAR-t-haNK cells.
Figure 64:
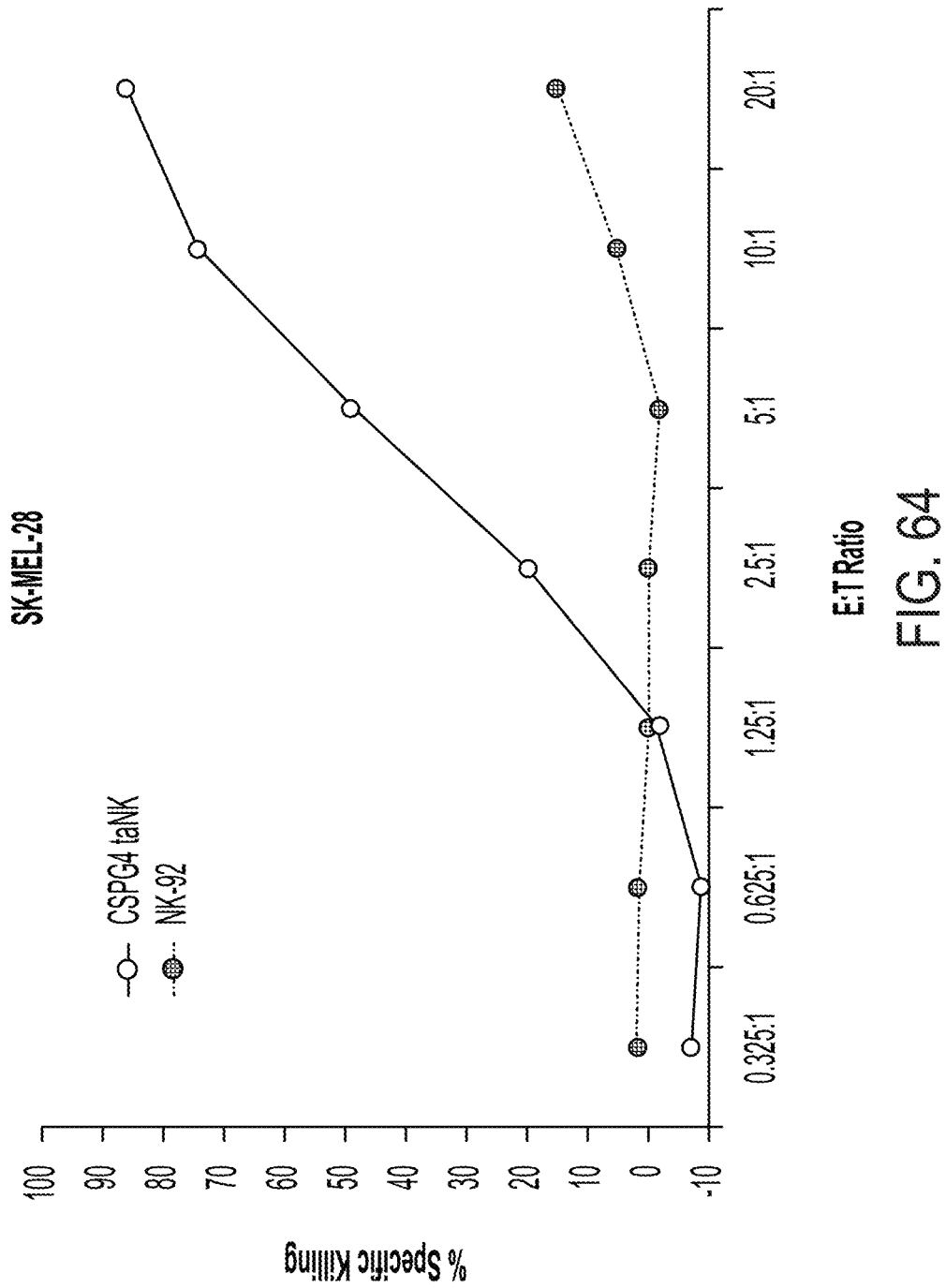
FIG. 64 shows exemplary results for CAR mediated cytotoxicity of CSPG4.CAR-t-haNK cells.

In this example, the inventors constructed a $1^{st}$ generation CARs with a FcεRIγ signaling domain that included an anti-CSPG-4 scFv coupled to a CD8 hinge, that in turn was coupled to a CD28 transmembrane domain, which was coupled to a FcεRIγ signaling domain. The so constructed CSPG-4-CAR had a nucleic acid sequence of SEQ ID NO:75. Expression of the CSPG-4-CAR was confirmed with FACS analysis and exemplary results are shown in FIG. 63. Thusly constructed cells also exhibited significant cytotoxicity as is shown in the exemplary data of FIG. 64.

Example 21: CD19-CAR with FcεRIγ Signaling Domain

In this example, the inventors used the $1^{st}$ generation CARs as described above having a FcεRIγ signaling domain that included an anti-CD19 scFv coupled to a CD8 hinge, that in turn was coupled to a CD28 transmembrane domain, which was coupled to a FcεRIγ signaling domain and transfected NK-92 cells with linearized DNA for functional testing.

Figure 19:
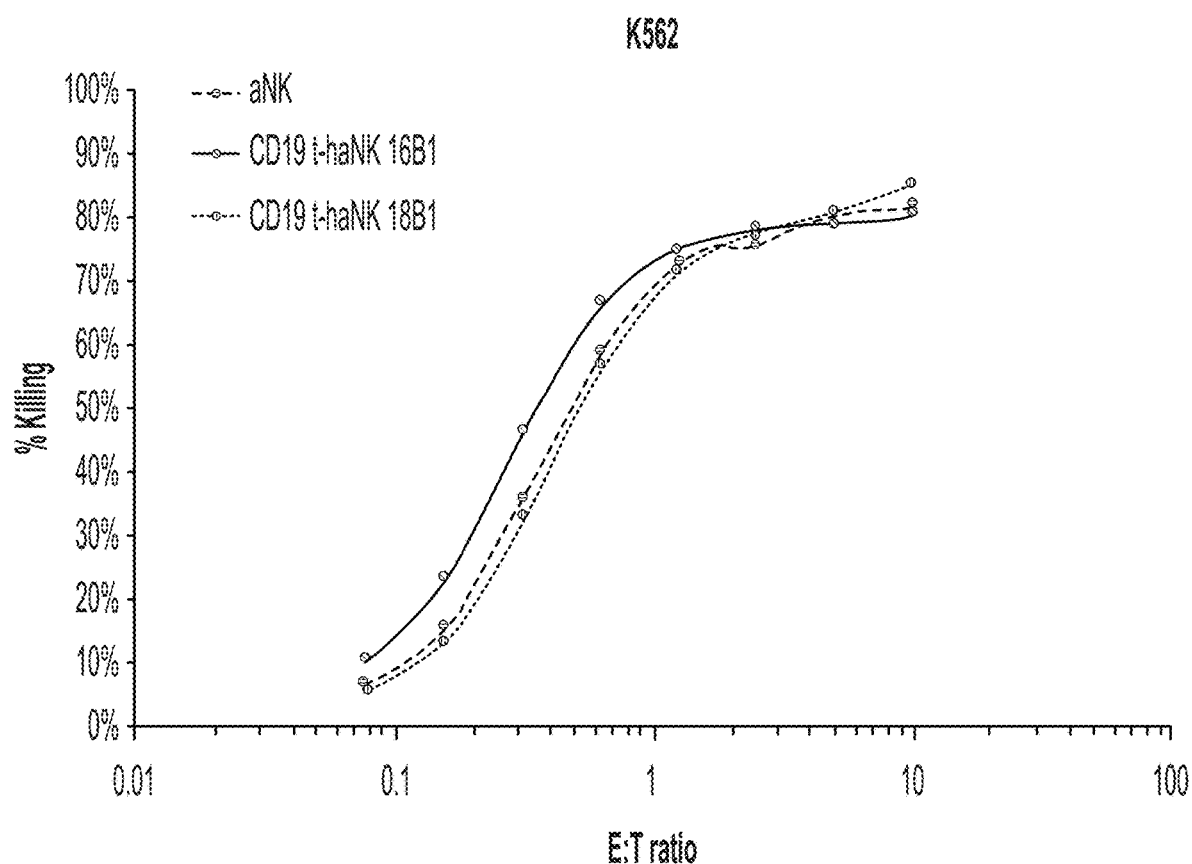
FIG. 19 shows exemplary results for cytotoxicity of CD19.CAR-t-haNK cells against K562 cells.
Figure 20:
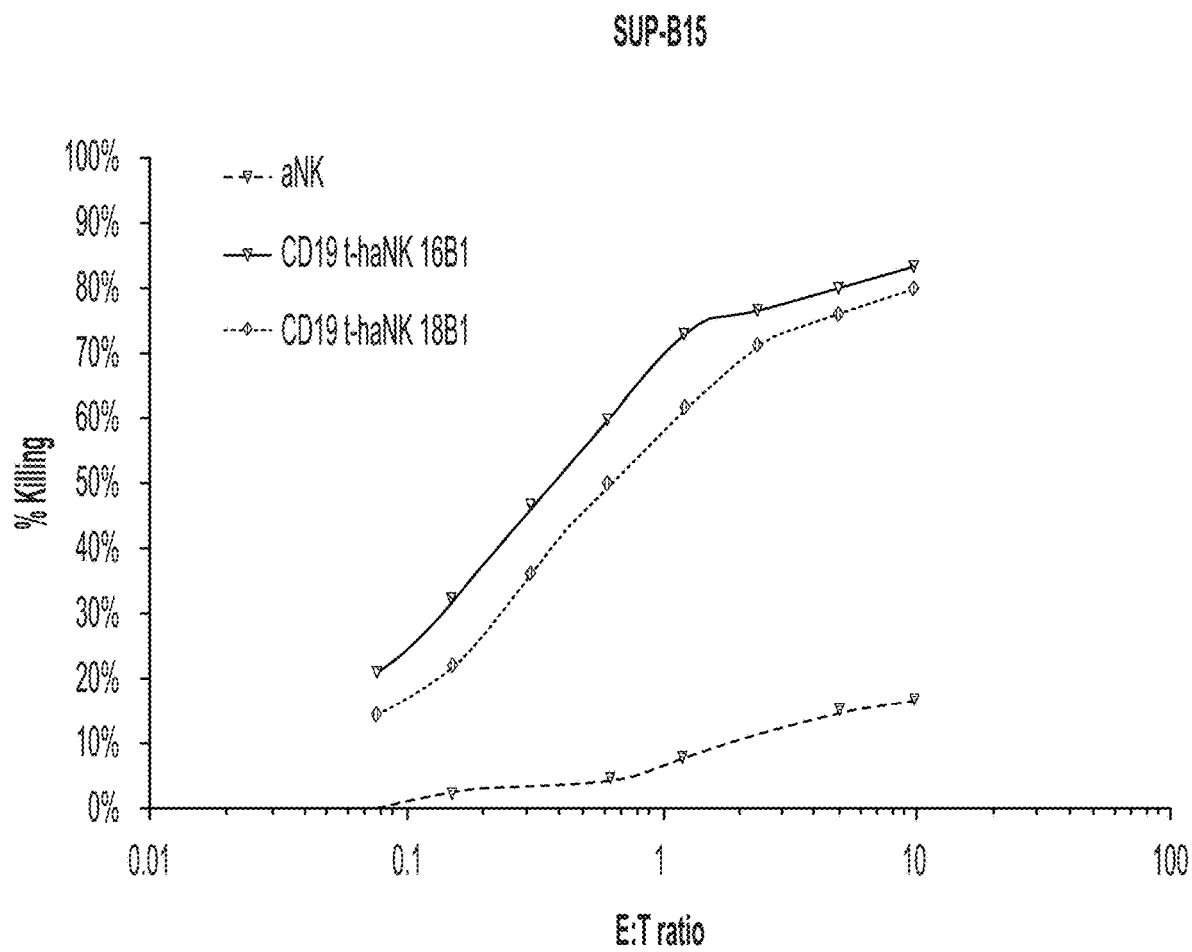
FIG. 20 shows exemplary results for cytotoxicity of CD19.CAR-t-haNK cells against SUP-B15 cells.
Figure 21:
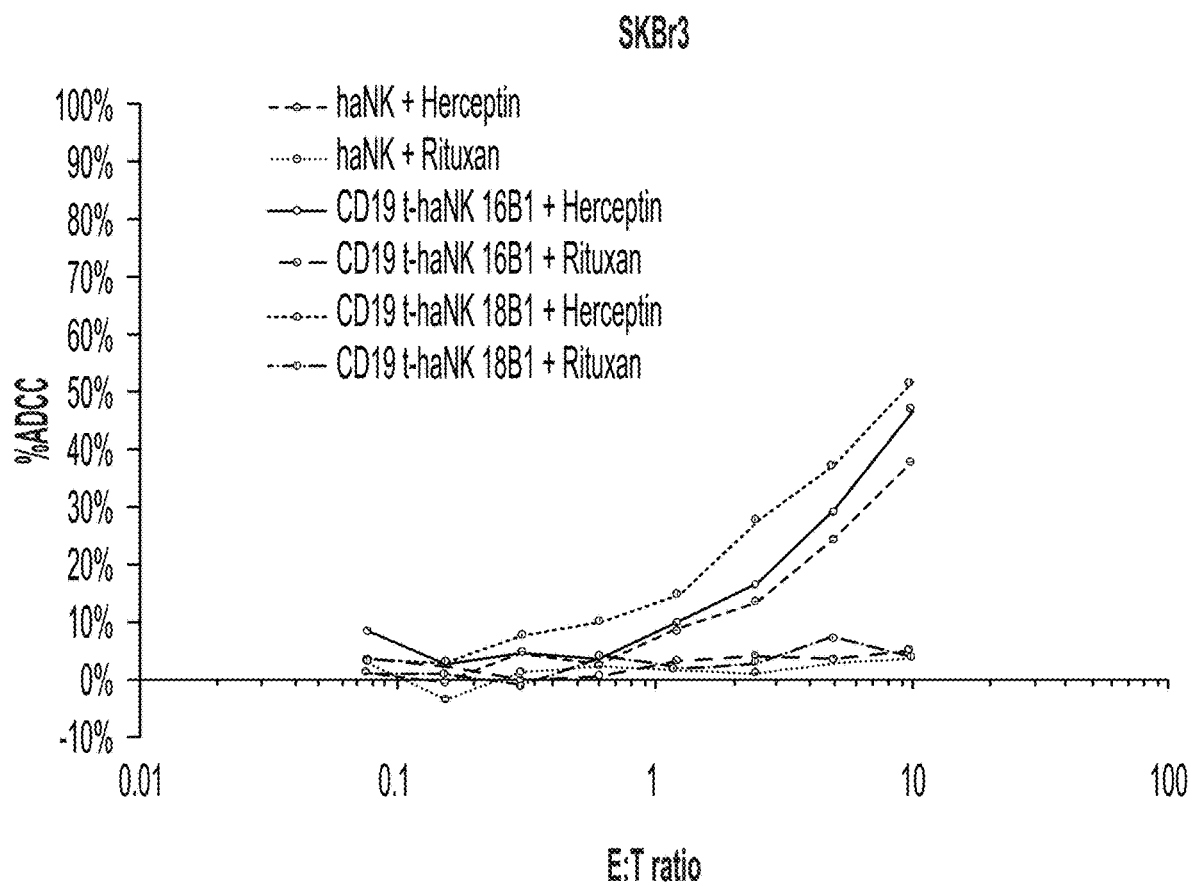
FIG. 21 shows exemplary results for ADCC of CD19.CAR-t-haNK cells against SKBr3 cells.

Functionality of the so constructed CD19.CAR-t-haNK cells was tested against K562 cells for determination of general cytotoxicity using a standard cytotoxicity assay and exemplary results are shown in FIG. 19. As can be readily seen, the CD19.CAR-t-haNK cells expressing the CAR with the FcεRIγ signaling domain exhibited significant cytotoxicity against the K562 target cells. In a further set of experiments, target specific cytotoxicity was determined using SUP-B15 cells in comparison with aNK cells as control, and exemplary results are shown in FIG. 20. Once more, CD19.CAR-t-haNK cells expressing the CAR with the FcεRIγ signaling domain exhibited significant and target specific cytotoxicity. In yet another set of experiments, target specific ADCC was determined using SKBr3 cells using Herceptin and Rituxan as antibodies, and exemplary results are shown in FIG. 21. Again, CD19.CAR-t-haNK cells expressing the CAR with the FcεRIγ signaling domain exhibited significant antibody and target specific ADCC. Notably, doubling times of the recombinant NK cells were substantially the same as aNK cells.

Figure 25:
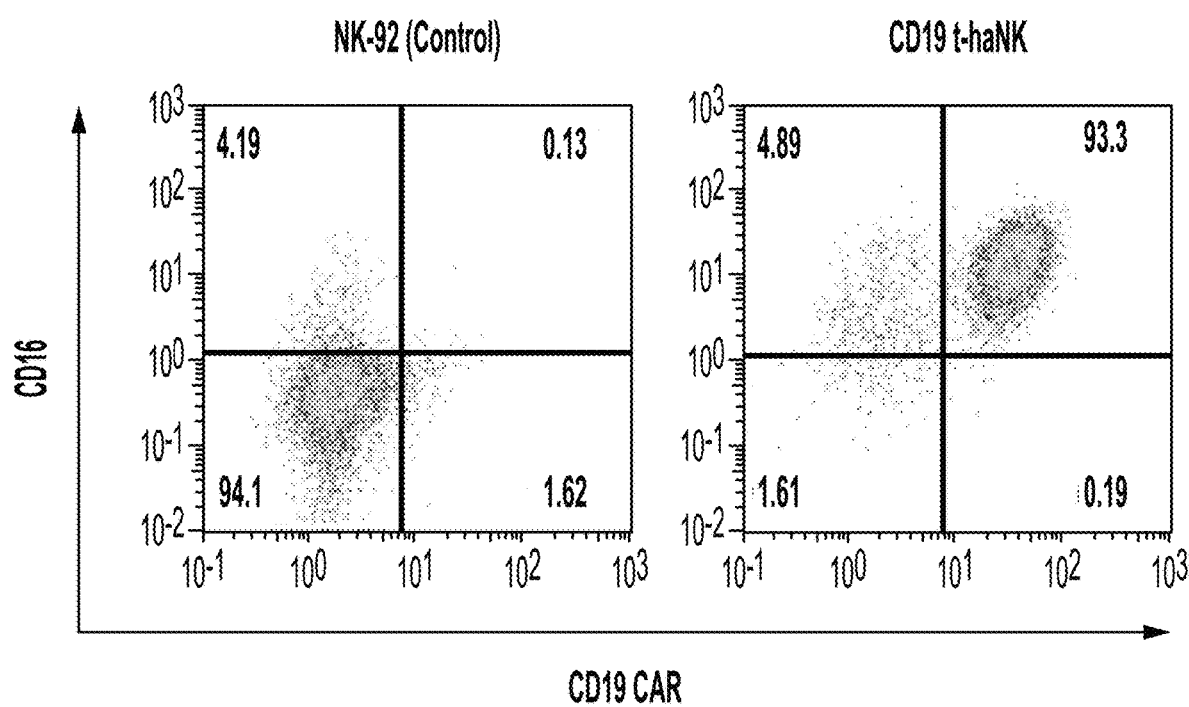
FIG. 25 shows exemplary results expression of CD16 and CD19.CAR.
Figure 26:
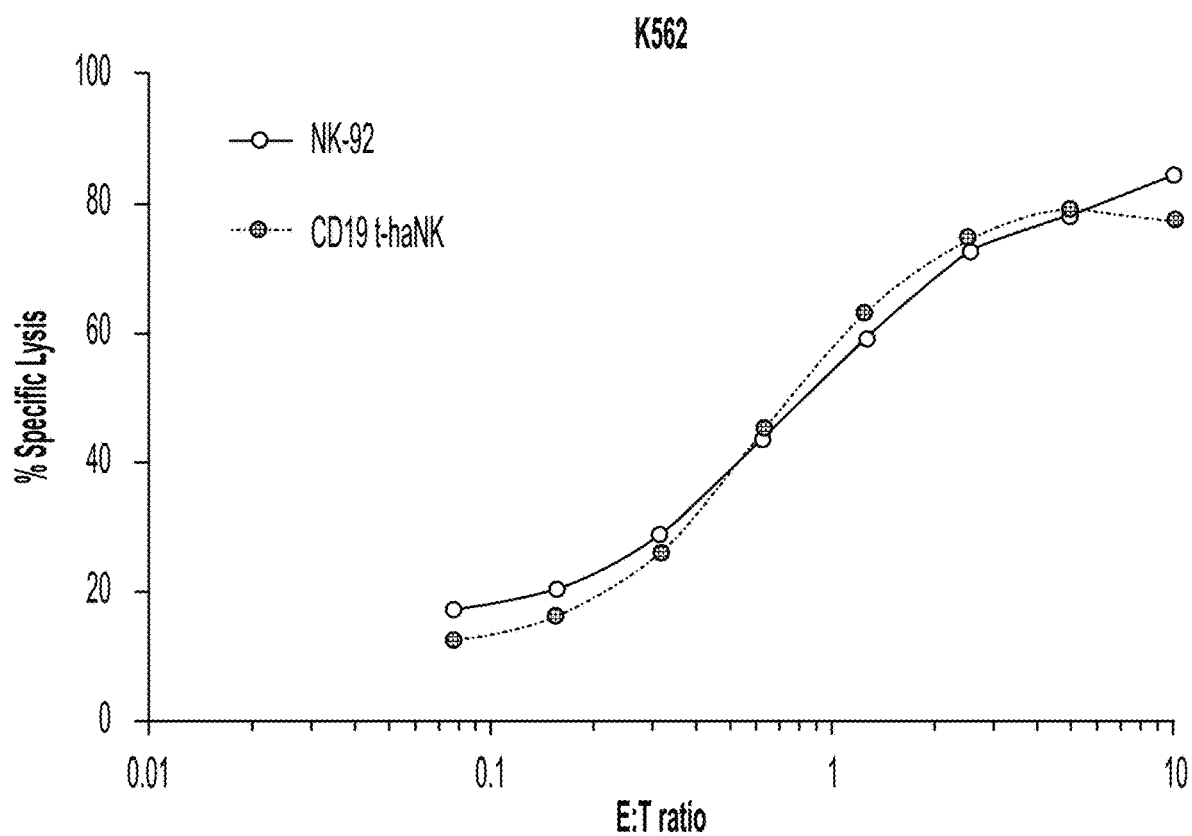
FIG. 26 shows exemplary results for natural cytotoxicity of CD19.CAR-t-haNK cells.
Figure 27:
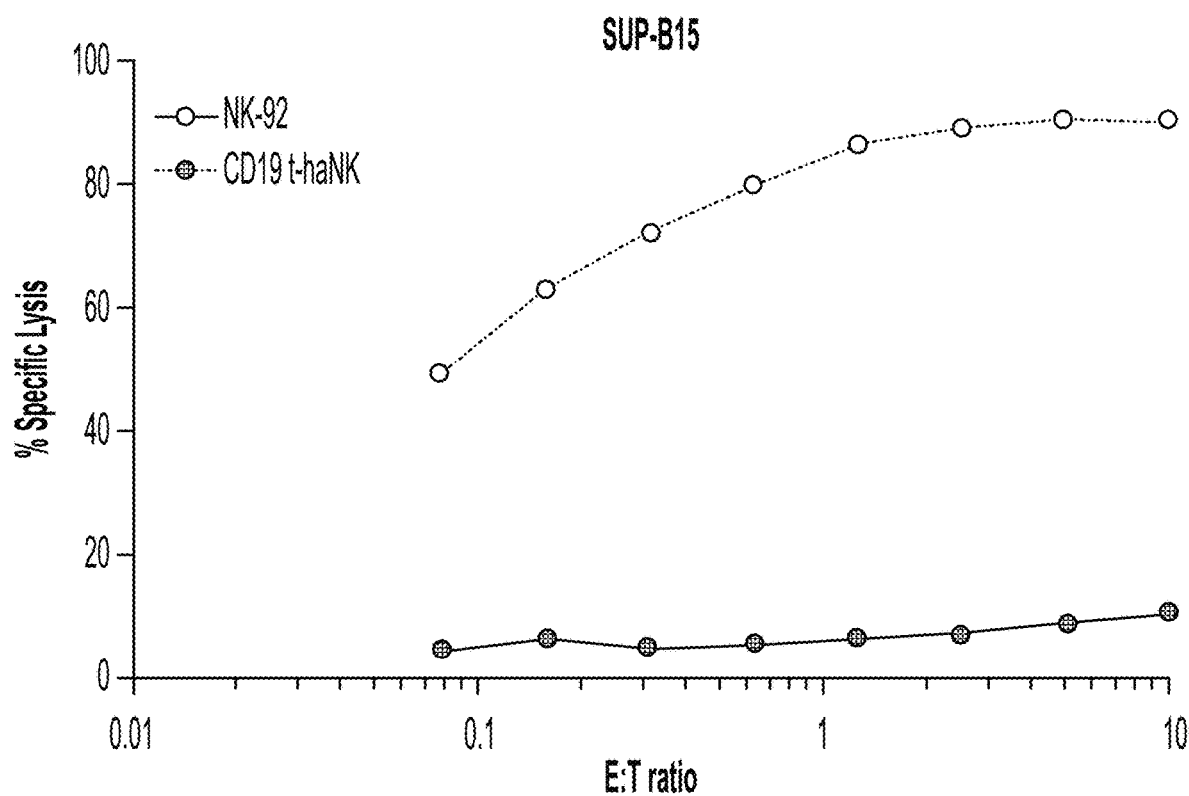
FIG. 27 shows exemplary results for CAR mediated cytotoxicity of CD19.CAR-t-haNK cells.
Figure 28:
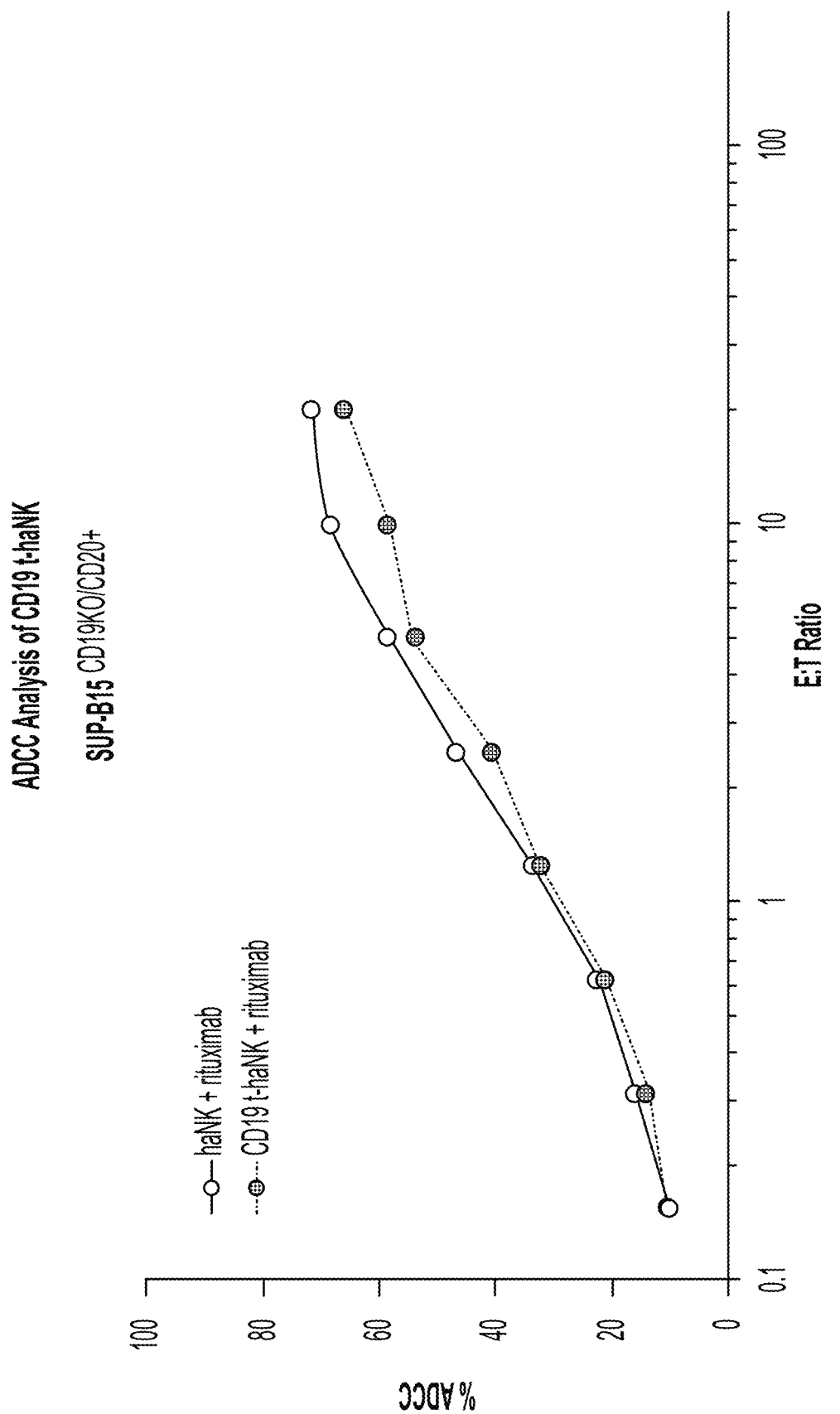
FIG. 28 shows exemplary results for ADCC of CD19.CAR-t-haNK cells.

FIG. 25 exemplarily illustrates CD19.CAR expression from linearized DNA that included a segment encoding CD16 and IL-$2^{ER}$ in NK-92 cells versus control. As can be seen form FIG. 25, the expression was very strong across the vast majority of cells. Additional results for natural cytotoxicity of CD19.CAR t-haNK cells against K562 cells and targeted cytotoxicity against SUP-B15 cells are depicted in FIG. 26 and FIG. 27. Exemplary further results for ADCC of CD19.CAR t-haNK cells against SUP-B15CD19$^{KO}$/CD20+ cells are shown in FIG. 28.

Example 22: Anti-Tumor Activity of PD-L1-Targeting t-haNK Cells in Human Xenograft Models in NSG Mice MDA-MB-231 and HCC827 were used as validated xenograft models that are PD-L1 positive, and efficacy of PD-L1 t-haNK cells in varied formulations, dosing levels, and dosing routes (IV and IT) was evaluated.

Animals: Animal type: NSG mice (JAX), females, 9-10 weeks old; Number of animals for MDA-MB-231 model: 24 (fresh cells), and for HCC827 model: 24 (fresh cells)+6 (cryopreserved cells). Tumor model used the following cell line: MDA-MB-231 (human breast adenocarcinoma) and HCC827 (human lung adenocarcinoma), Route of inoculation was subcutaneous on both flanks, and average tumor burden upon treatment initiation was for MDA-MB-231 about 100 mm$^3$ and for HCC827 about 75-80 mm$^3$.

Treatment articles: Anti-PD-L1 t-haNK, freshly prepared, irradiated, at a concentration: 5E7 cells/mL or 2E7 cells/mL; Vehicle control was X-VIVO™ 10 medium; Method of administration was IV and IT as noted. Dosage for IV NK dosing was 1E7 cells/dose in 200 μL (Freshly prepared cells), 4E6 cells/dose in 200 μL (Cryopreserved cells); for IT NK dosing (fresh cells only) dose was 2.5E6 cells/tumor/dose in 50 μL. Dosing frequency was Twice a week (M/Th or T/F) for 4 consecutive weeks, and first day of dosing was defined as Day 1.

Study design for MDA-MB-231 is in Table 4 below (This study was ended on Day 27, when some animals in Groups A, C and D had reached combined tumor volume of >2000 mm$^3$)

TABLE 4

| Group | N | Tumor model | Treatment | Fresh or Frozen | NK Cell Dose | NK dosing route | Treatment Regimen | Dosing Volume |
|---|---|---|---|---|---|---|---|---|
| A | 6 | MDA-MB-231 SC, bilateral 1 × 10$^6$ | Vehicle | / | / | IV | BIW × 4 weeks | 200 μL |
| B | 6 | | PD-L1 t-haNK | Fresh | 1E7 | IV | BIW × 4 weeks | 200 μL |
| C | 6 | | Vehicle | / | / | IT | BIW × 4 weeks | 50 μL |
| D | 6 | | PD-L1 t-haNK | Fresh | 2.5E6 | IT | BIW × 4 weeks | 50 μL |

Study design for HCC827 is in Table 5 below (This study was ended on Day 29, when surviving animals were re-purposed and transferred to another study).

TABLE 5

| Group | N | Tumor model | Treatment | Fresh or Frozen | NK Cell Dose | NK dosing route | Treatment Regimen | Dosing Volume |
|---|---|---|---|---|---|---|---|---|
| A | 6 | HCC827 SC, bilateral 1 × 10$^6$ | Vehicle | / | / | IV | BIW × 4 weeks | 200 μL |
| B | 6 | | PD-L1 t-haNK | Fresh | 1E7 | IV | BIW × 4 weeks | 200 μL |
| C | 6 | | Vehicle | / | / | IT | BIW × 4 weeks | 50 μL |
| D | 6 | | PD-L1 t-haNK | Fresh | 2.5E6 | IT | BIW × 4 weeks | 50 μL |
| Pilot | 6 | | PD-L1 t-haNK | Frozen | 4E6 | IV | BIW × 4 weeks | 200 μL |

Results: Freshly prepared PD-L1 t-haNK cells (1E7 cells/dose) led to marked and long-lasting tumor growth inhibition in both MDA-MB-231 and HCC827 models MDA-MB-231: tumor stasis: TGI on Day 16: 84% (peak); TGI on Day 26: 79% (last measurement).

HCC827: tumor regression: TGI on Day 16: 120% (peak); TGI on Day 29: 84% (study end).

Cryopreserved PD-L1 t-haNK cells (4E6 cells/dose) also showed statistically significant efficacy in suppressing tumor growth compared to X-VIVO™ 10 media: TGI on Day 26: 60% (peak), and TGI on Day 29: 40% (study end).

Freshly prepared PD-L1 t-haNK cells (1E7 cells/dose) also led to significant reduction of metastatic disease burden in the MDA-MB-231 model as shown in Table 6 below.

TABLE 6

| Group | Mouse | Macroscopic lesions found in: | Overall Summary |
|---|---|---|---|
| A (vehicle) | 1 | Liver, lungs | 100% animals developed metastases in multiple organs |
|  | 2 | Ax LNs, liver, lungs |  |
|  | 3 | Ax LN (left), liver, lungs |  |
|  | 4 | Liver, lungs |  |
|  | 5 | Ax LNs, spleen, liver, lungs |  |
|  | 6 | Ax LNs, liver, lungs |  |
| B (PD-L1 t-haNK) | 1 | None | 50% developed metastasis; all single-organ findings |
|  | 2 | Lungs |  |
|  | 3 | Ax LNs |  |
|  | 4 | None |  |
|  | 5 | Ax LN (left) |  |
|  | 6 | None |  |

The number of visible nodules in liver was in vehicle: 29±9, in the PD-L1 t-haNK group: 0 (P=0.0116 by unpaired 2-tailed t test).

Based on the experiments performed, IV dosing of freshly prepared PD-L1 t-haNK cells at the dosing level of 1E7 cells/dose, twice a week for 4 weeks, showed marked anti-tumor efficacy in both of the subcutaneous xenograft models tested: The treatment resulted in tumor stasis in MDA-MB-231 tumor-bearing mice, with a peak TGI of 84% on Day 16 and an end-of-study TGI of 79% (P<0.0001 for both time points by 2-way ANOVA followed by multiple comparison by Tukey test), and tumor regression in the HCC827 model, with a peak TGI of 120% on Day 16 and an end-of-study TGI of 84% (P<0.0001). IV dosing of cryopreserved PD-L1 t-haNK cells at the dosing level of 4E6 cells/dose, twice a week for 4 weeks, also showed significant therapeutic efficacy in the HCC827 tumor model, reaching a peak TGI of 60% (P<0.0001), and an end-of-study TGI of 40% (P<0.01). IT dosing of freshly prepared PD-L1 t-haNK cells at the dosing level of 2.5E6 cells/dose/tumor, twice a week for 4 weeks, effectively suppressed the growth of HCC827 tumors, resulting in a peak TGI of 70% on Day 20 and an end-of-study TGI of 49% (P<0.001).

Significant adverse reactions were observed for animals that received IV administrations of freshly prepared PD-L1 t-haNK cells (1E7 cells/dose). In contrast to freshly prepared PD-L1 t-haNK cells, cryopreserved cells (dosed at a lower level of 4E6 cells/dose) proved to be safe to the animals after IV administrations. PD-L1 t-haNK cells demonstrated remarkable efficacy in the two subcutaneous tumor models. Cryopreserved cells dosed at the lower 4E6 cells/dose level, also showed significant efficacy in suppressing tumor growth, and proved to be safe for the animals.

Of course, it should be recognized that for all nucleic acid sequences provided herein the corresponding encoded proteins are also expressly contemplated herein. Likewise, for all amino acid sequences, corresponding nucleic acids sequences are also contemplated herein (with any codon usage).

All patent applications, publications, references, and sequence accession numbers cited in the present specification are hereby incorporated by reference in their entirety.

Unless defined otherwise, all technical and scientific terms used herein have the same meaning as commonly understood by one of ordinary skill in the art to which this invention belongs.

In this specification and in the claims that follow, reference will be made to a number of terms that shall be defined to have the following meanings:

The terminology used herein is for the purpose of describing particular embodiments only and is not intended to be limiting of the invention. As used herein, the singular forms "a", "an" and "the" are intended to include the plural forms as well, unless the context clearly indicates otherwise.

It is understood that all numerical values described herein (e.g., pH, temperature, time, concentration, amounts, and molecular weight, including ranges) include normal variation in measurements encountered by one of ordinary skill in the art. Thus, numerical values described herein include variation of +/−0.1 to 10%, for example, +/−0.1%, 0.5%, 1%, 2%, 3%, 4%, 5%, 6%, 7%, 8%, 9%, or 10%. It is to be understood, although not always explicitly stated, that all numerical designations may be preceded by the term "about." Thus, the term about includes variation of +/−0.1 to 10%, for example, +/−0.1%, 0.5%, 1%, 2%, 3%, 4%, 5%, 6%, 7%, 8%, 9%, or 10% of the numerical value. It is also to be understood, although not always explicitly stated, that the reagents described herein are merely exemplary and that equivalents of such are known in the art.

As will be understood by one skilled in the art, for any and all purposes, particularly in terms of providing a written description, all ranges disclosed herein include the end points of the range, and include all values between the end points of the range. All ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

It is also to be understood, although not always explicitly stated, that the reagents described herein are merely exemplary and that equivalents of such are known in the art.

"Optional" or "optionally" means that the subsequently described event or circumstance can or cannot occur, and that the description includes instances where the event or circumstance occurs and instances where it does not.

The term "comprising" is intended to mean that the compositions and methods include the recited elements, but not excluding others. "Consisting essentially of," when used to define compositions and methods, shall mean excluding other elements of any essential significance to the combination. For example, a composition consisting essentially of the elements as defined herein would not exclude other elements that do not materially affect the basic and novel characteristic(s) of the claimed invention. "Consisting of" shall mean excluding more than trace amount of other ingredients and substantial method steps recited. Embodiments defined by each of these transition terms are within the scope of this disclosure.

As used herein, "immunotherapy" refers to the use of NK-92 cells, modified or unmodified, naturally occurring or modified NK cell or T-cell, whether alone or in combination, and which are capable of inducing cytotoxicity when contacting a target cell.

As used herein, "natural killer (NK) cells" are cells of the immune system that kill target cells in the absence of a specific antigenic stimulus, and without restriction according to major histocompatibility complex (MHC) class. Target cells may be tumor cells or cells harboring a virus. NK cells are characterized by the presence of CD56 and the absence of CD3 surface markers.

The term "endogenous NK cells" is used to refer to NK cells derived from a donor (or the patient), as distinguished from the NK-92 cell line. Endogenous NK cells are generally heterogeneous populations of cells within which NK cells have been enriched. Endogenous NK cells may be intended for autologous or allogeneic treatment of a patient.

The term "NK-92" refers to natural killer cells derived from the highly potent unique cell line described in Gong et al. (1994), rights to which are owned by NantKwest (hereafter, "NK-92™ cells"). The immortal NK cell line was originally obtained from a patient having non-Hodgkin's lymphoma. Unless indicated otherwise, the term "NK-92™" is intended to refer to the original NK-92 cell lines as well as NK-92 cell lines that have been modified (e.g., by introduction of exogenous genes). NK-92™ cells and exemplary and non-limiting modifications thereof are described in U.S. Pat. Nos. 7,618,817; 8,034,332; 8,313,943; 9,181,322; 9,150,636; and published U.S. application Ser. No. 10/008,955, all of which are incorporated herein by reference in their entireties, and include wild type NK-92™ NK-92™-CD16, NK-92™-CD16-7, NK-92™-CD16-ζ, NK-92™-CD16(F176V), NK-92™MI, and NK-92™CI. NK-92 cells are known to persons of ordinary skill in the art, to whom such cells are readily available from NantKwest, Inc.

The term "aNK" refers to an unmodified natural killer cells derived from the highly potent unique cell line described in Gong et al. (1994), rights to which are owned by NantKwest (hereafter, "aNK™ cells"). The term "haNK" refers to natural killer cells derived from the highly potent unique cell line described in Gong et al. (1994), rights to which are owned by NantKwest, modified to express CD16 on the cell surface (hereafter, "CD16+NK-92™ cells" or "haNK® cells"). In some embodiments, the CD16+NK-92™ cells comprise a high affinity CD16 receptor on the cell surface. The term "taNK" refers to natural killer cells derived from the highly potent unique cell line described in Gong et al. (1994), rights to which are owned by NantKwest, modified to express a chimeric antigen receptor (hereafter, "CAR-modified NK-92™ cells" or "taNK® cells"). The term "t-haNK" refers to natural killer cells derived from the highly potent unique cell line described in Gong et al. (1994), rights to which are owned by NantkWest, modified to express CD 16 on the cell surface and to express a chimeric antigen receptor (hereafter, "CAR-modified CD16+NK-92™ cells" or "t-haNK™ cells"). In some embodiments, the t-haNK™ cells express a high affinity CD16 receptor on the cell surface.

A "modified NK-92 cell" refers to an NK-92 cell that expresses an exogenous gene or protein, such as an Fc receptor, a CAR, a cytokine (such as IL-2 or IL-12), and/or a suicide gene. In some embodiments, the modified NK-92 cell comprises a vector that encodes for a transgene, such as an Fc receptor, a CAR, a cytokine (such as IL-2 or IL-12), and/or a suicide gene. In one embodiment, the modified NK-92 cell expresses at least one transgenic protein.

As used herein, "non-irradiated NK-92 cells" are NK-92 cells that have not been irradiated. Irradiation renders the cells incapable of growth and proliferation. It is envisioned that the NK-92 cells will be irradiated at the treatment facility or some other point prior to treatment of a patient, since the time between irradiation and infusion should be no longer than four hours in order to preserve optimal activity. Alternatively, NK-92 cells may be prevented from proliferating by another mechanism.

As used herein, "inactivation" of the NK-92 cells renders them incapable of growth. Inactivation may also relate to the death of the NK-92 cells. It is envisioned that the NK-92 cells may be inactivated after they have effectively purged an ex vivo sample of cells related to a pathology in a therapeutic application, or after they have resided within the body of a mammal a sufficient period of time to effectively kill many or all target cells residing within the body. Inactivation may be induced, by way of non-limiting example, by administering an inactivating agent to which the NK-92 cells are sensitive.

As used herein, the terms "cytotoxic" and "cytolytic," when used to describe the activity of effector cells such as NK-92 cells, are intended to be synonymous. In general, cytotoxic activity relates to killing of target cells by any of a variety of biological, biochemical, or biophysical mechanisms. Cytolysis refers more specifically to activity in which the effector lyses the plasma membrane of the target cell, thereby destroying its physical integrity. This results in the killing of the target cell. Without wishing to be bound by theory, it is believed that the cytotoxic effect of NK-92 cells is due to cytolysis.

The term "kill" with respect to a cell/cell population is directed to include any type of manipulation that will lead to the death of that cell/cell population.

The term "Fc receptor" refers to a protein found on the surface of certain cells (e.g., natural killer cells) that contribute to the protective functions of the immune cells by binding to part of an antibody known as the Fc region. Binding of the Fc region of an antibody to the Fc receptor (FcR) of a cell stimulates phagocytic or cytotoxic activity of a cell via antibody-mediated phagocytosis or antibody-dependent cell-mediated cytotoxicity (ADCC). FcRs are classified based on the type of antibody they recognize. For example, Fc-gamma receptors (FCγR) bind to the IgG class of antibodies. FCγRIII-A (also called CD16; SEQ ID NO:20) is a low affinity Fc receptor bind to IgG antibodies and activate ADCC. FCγRIII-A are typically found on NK cells. NK-92 cells do not express FCγRIII-A. Fc-epsilon receptors (FcR) bind to the Fc region of IgE antibodies.

The term "chimeric antigen receptor" (CAR), as used herein, refers to an extracellular antigen-binding domain that is fused to an intracellular signaling domain. CARs can be expressed in T cells or NK cells to increase cytotoxicity. In general, the extracellular antigen-binding domain is a scFv that is specific for an antigen found on a cell of interest. A CAR-expressing NK-92 cell is targeted to cells expressing certain antigens on the cell surface, based on the specificity of the scFv domain. The scFv domain can be engineered to recognize any antigen, including tumor-specific antigens and virus-specific antigens. For example, CD19CAR recognizes CD19, a cell surface marker expressed by some cancers.

The term "tumor-specific antigen" as used herein refers to antigens that are present on a cancer or neoplastic cell but not detectable on a normal cell derived from the same tissue or lineage as the cancer cell. Tumor-specific antigens, as used herein, also refers to tumor-associated antigens, that is, antigens that are expressed at a higher level on a cancer cell as compared to a normal cell derived from the same tissue or lineage as the cancer cell.

The term "virus-specific antigen" as used herein refers to antigens that are present on a virus-infected cell but not detectable on a normal cell derived from the same tissue or lineage as the virus-infected cell. In one embodiment, a virus-specific antigen is a viral protein expressed on the surface of an infected cell.

The terms "polynucleotide", "nucleic acid" and "oligonucleotide" are used interchangeably and refer to a polymeric form of nucleotides of any length, either deoxyribonucleotides or ribonucleotides or analogs thereof. Polynucleotides can have any three-dimensional structure and may perform any function, known or unknown. The following are non-limiting examples of polynucleotides: a gene or gene fragment (for example, a probe, primer, EST or SAGE tag), exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes and primers. A polynucleotide can comprise modified nucleotides, such as methylated nucleotides and nucleotide analogs. If present, modifications to the nucleotide structure can be imparted before or after assembly of the polynucleotide. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any embodiment of this invention that is a polynucleotide encompasses both the double-stranded form and each of two complementary single-stranded forms known or predicted to make up the double-stranded form.

A polynucleotide is composed of a specific sequence of four nucleotide bases: adenine (A); cytosine (C); guanine (G); thymine (T); and uracil (U) for thymine when the polynucleotide is RNA. Thus, the term "polynucleotide sequence" is the alphabetical representation of a polynucleotide molecule.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences.

As used herein, "percent identity" refers to sequence identity between two peptides or between two nucleic acid molecules. Percent identity can be determined by comparing a position in each sequence which may be aligned for purposes of comparison. When a position in the compared sequence is occupied by the same base or amino acid, then the molecules are identical at that position. Homologous nucleotide sequences include those sequences coding for naturally occurring allelic variants and mutations of the nucleotide sequences set forth herein. Homologous nucleotide sequences include nucleotide sequences encoding for a protein of a mammalian species other than humans. Homologous amino acid sequences include those amino acid sequences which contain conservative amino acid substitutions and which polypeptides have the same binding and/or activity. In some embodiments, a homologous amino acid sequence has no more than 15, nor more than 10, nor more than 5 or no more than 3 conservative amino acid substitutions. In some embodiments, a nucleotide or amino acid sequence has at least 60%, at least 65%, at least 70%, at least 80%, or at least 85% or greater percent identity to a sequence described herein. In some embodiments, a nucleotide or amino acid sequence has at least 90%, 91%, 92%, 93%, 94%, 95%, 96%, 97%, 98% or 99% identity to a sequence described herein. Percent identity can be determined by, for example, the Gap program (Wisconsin Sequence Analysis Package, Version 8 for UNIX, Genetics Computer Group, University Research Park, Madison Wis.), using default settings, which uses the algorithm of Smith and Waterman (Adv. Appl. Math., 1981, 2, 482-489). Algorithms suitable for determining percent sequence identity include the BLAST and BLAST 2.0 algorithms, which are described in Altschul et al. (Nuc. Acids Res. 25:3389-402, 1977), and Altschul et al. (J. Mol. Biol. 215:403-10, 1990), respectively. Software for performing BLAST analyses is publicly available through the National Center for Biotechnology Information. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff, Proc. Natl. Acad. Sci. USA 89:10915, 1989) alignments (B) of 50, expectation (E) of 10, M=5, N=−4.

In some embodiments, a nucleic acid sequence is codon optimized for expression in a particular species, for example, a mouse sequence can be codon optimized for expression in humans (expression of the protein encoded by the codon-optimized nucleic acid sequence). Thus, in some embodiments, a codon-optimized nucleic acid sequence has at least 60%, at least 65%, at least 70%, at least 80%, or at least 85% or greater percent identity to a nucleic acid sequence described herein. In some embodiments, a codon-optimized nucleic acid sequence acid sequence has at least 90%, 91%, 92%, 93%, 94%, 95%, 96%, 97%, 98% or 99% identity to a sequence described herein.

The term "express" refers to the production of a gene product (e.g., a protein). The term "transient" when referring to expression means a polynucleotide is not incorporated into the genome of the cell. The term "stable" when referring to expression means a polynucleotide is incorporated into the genome of the cell, or a positive selection marker (i.e., an exogenous gene expressed by the cell that confers a benefit under certain growth conditions) is utilized to maintain expression of the transgene.

The term "cytokine" or "cytokines" refers to the general class of biological molecules which affect cells of the immune system. Exemplary cytokines include but are not limited to interferons and interleukins (IL)—in particular IL-2, IL-12, IL-15, IL-18 and IL-21. In preferred embodiments, the cytokine is IL-2.

As used herein, the term "vector" refers to a non-chromosomal nucleic acid comprising an intact replicon such that the vector may be replicated when placed within a permissive cell, for example by a process of transformation. A vector may replicate in one cell type, such as bacteria, but have limited or no ability to replicate in another cell, such as mammalian cells. Vectors may be viral or non-viral. Exemplary non-viral vectors for delivering nucleic acid include naked DNA; DNA complexed with cationic lipids, alone or in combination with cationic polymers; anionic and cationic liposomes; DNA-protein complexes and particles comprising DNA condensed with cationic polymers such as heterogeneous polylysine, defined-length oligopeptides, and polyethylene imine, in some cases contained in liposomes; and the use of ternary complexes comprising a virus and polylysine-DNA. In one embodiment, the vector is a viral vector, e.g. adenovirus. Viral vectors are well known in the art.

As used herein, the term "targeted," when referring to protein expression, is intended to include, but is not limited to, directing proteins or polypeptides to appropriate destinations in the cell or outside of it. The targeting is typically achieved through signal peptides or targeting peptides, which are a stretch of amino acid residues in a polypeptide chain. These signal peptides can be located anywhere within a polypeptide sequence, but are often located on the N-terminus. Polypeptides can also be engineered to have a signal peptide on the C-terminus. Signal peptides can direct a polypeptide for extracellular section, location to plasma membrane, golgi, endosomes, endoplasmic reticulum, and other cellular compartments. For example, polypeptides with a particular amino acid sequence on their C-terminus (e.g., KDEL) are retained in the ER lumen or transported back the ER lumen.

As used herein, the term "target," when referring to targeting of a tumor, refers to the ability of NK-92 cells to recognize and kill a tumor cell (i.e., target cell). The term "targeted" in this context refers, for example, to the ability of a CAR expressed by the NK-92 cell to recognize and bind to a cell surface antigen expressed by the tumor.

As used herein, the term "transfect" refers to the insertion of nucleic acid into a cell. Transfection may be performed using any means that allows the nucleic acid to enter the cell. DNA and/or mRNA may be transfected into a cell. Preferably, a transfected cell expresses the gene product (i.e., protein) encoded by the nucleic acid.

The term "suicide gene" refers to a transgene that allows for the negative selection of cells expressing that transgene. A suicide gene is used as a safety system, allowing the cells expressing the gene to be killed by introduction of a selective agent. A number of suicide gene systems have been identified, including the herpes simplex virus thymidine kinase (TK) gene, the cytosine deaminase gene, the varicella-zoster virus thymidine kinase gene, the nitroreductase gene, the *Escherichia coli* gpt gene, and the *E. coli* Deo gene (see also, for example, Yazawa K, Fisher W E, Brunicardi F C: Current progress in suicide gene therapy for cancer. World J. Surg. 2002 July; 26(7):783-9). In one embodiment, the suicide gene is the thymidine kinase (TK) gene. The TK gene may be a wild-type or mutant TK gene (e.g., tk30, tk75, sr39tk). Cells expressing the TK protein can be killed using ganciclovir.

What is claimed is:

1. A genetically modified NK cell carrying a non-viral vector encoding a membrane bound recombinant chimeric antigen receptor (CAR),
wherein the CAR comprises in a single polypeptide chain:
an extracellular scFv domain according to SEQ ID NO:51,
a hinge domain,
a transmembrane domain, and
a FcεRIγ signaling domain according to SEQ ID NO:1; and
wherein the NK cell is an NK-92 cell.

2. The genetically modified NK cell of claim 1, wherein the hinge domain comprises a CD8 hinge domain according to SEQ ID NO:6 or SEQ ID NO:45, and/or wherein the transmembrane domain comprises a CD28 transmembrane domain according to SEQ ID NO:7.

3. The genetically modified NK cell of claim 1, further carrying a membrane bound recombinant CD16.

4. The genetically modified NK cell of claim 1, further comprising a recombinant cytokine with an endoplasmic retention sequence.

5. The genetically modified NK cell of claim 1, wherein the CAR comprises in a single polypeptide chain: an extracellular scFv domain according to SEQ ID NO:51, a hinge domain according to SEQ ID NO:6 or SEQ ID NO:45, a transmembrane domain according to SEQ ID NO:7, and a FcεRIγ signaling domain according to SEQ ID NO:1.

6. A genetically modified NK cell, comprising:
a recombinant nucleic acid encoding a chimeric antigen receptor (CAR), wherein the recombinant nucleic acid is a transfected plasmid;
wherein the NK cell is an NK-92 cell;
wherein the CAR comprises in a single polypeptide chain an extracellular binding domain according to SEQ ID NO:51, a hinge domain, a transmembrane domain, and a FcεRIγ signaling domain according to SEQ ID NO:1.

7. The genetically modified NK cell of claim 6, wherein the recombinant nucleic acid is an RNA.

8. The genetically modified NK cell of claim 7, wherein the RNA is a polycistronic RNA that further encodes a CD16 and/or a cytokine with an endoplasmic retention sequence.

9. The genetically modified NK cell of claim 6, wherein the extracellular binding domain comprises a scFv.

10. The genetically modified NK cell of claim 6, wherein the extracellular binding domain specifically binds to a tumor-specific antigen, a tumor associated antigen, or a patient- and tumor-specific antigen.

11. The genetically modified NK cell of claim 10, wherein the tumor-specific antigen is PD-L1.

12. The genetically modified NK cell of claim 6, wherein the hinge domain and/or the transmembrane domain comprise a CD8 hinge domain and/or a CD28 transmembrane domain.

13. A method of treating cancer in a patient in need thereof, comprising administering to the patient a therapeutically effective amount of the genetically modified NK cells of claim 1, thereby treating the cancer.

14. The method of claim 13, further comprising a step of administering at least one additional therapeutic entity selected from the group consisting of a viral cancer vaccine, a bacterial cancer vaccine, a yeast cancer vaccine, N-803, an antibody, a stem cell transplant, and a tumor targeted cytokine.

15. The method of claim 13, wherein the cancer is selected from leukemia, acute lymphocytic leukemia, acute myelocytic leukemia, chronic leukemias, chronic myelocytic (granulocytic) leukemia, chronic lymphocytic leukemia, polycythemia vera, lymphomas, Hodgkin's disease, non-Hodgkin's disease, multiple myeloma, Waldenstrom's macroglobulinemia, heavy chain disease, solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyo sarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma and retinoblastoma.

16. A method of treating a viral infection in a patient in need thereof, comprising administering to the patient a therapeutically effective amount of the genetically modified NK cells of claim 1, thereby treating the viral infection.

17. The method of claim 16, further comprising administering an antiviral drug.

* * * * *